(12) United States Patent
Downes et al.

(10) Patent No.: US 7,647,217 B2
(45) Date of Patent: Jan. 12, 2010

(54) STRUCTURE OF THE FARNESOID X RECEPTOR LIGAND BINDING DOMAIN AND METHODS OF USE THEREFOR

(75) Inventors: Michael R Downes, San Diego, CA (US); Mark A. Verdicia, New York, NY (US); Joseph P. Noel, San Diego, CA (US); Ronald M. Evans, La Jolla, CA (US); Lindsey J. Bowman, San Diego, CA (US); Marianne Bowman, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 266 days.

(21) Appl. No.: 10/535,042

(22) PCT Filed: Nov. 14, 2003

(86) PCT No.: PCT/US03/36548

§ 371 (c)(1),
(2), (4) Date: Jan. 9, 2006

(87) PCT Pub. No.: WO2004/046323

PCT Pub. Date: Jun. 3, 2004

(65) Prior Publication Data

US 2006/0194949 A1    Aug. 31, 2006

Related U.S. Application Data

(60) Provisional application No. 60/426,665, filed on Nov. 15, 2002, provisional application No. 60/426,668, filed on Nov. 15, 2002.

(51) Int. Cl.
*G06G 7/58* (2006.01)
*C07K 14/00* (2006.01)

(52) U.S. Cl. ................................. 703/11; 530/350

(58) Field of Classification Search .................. None
See application file for complete search history.

(56) References Cited

U.S. PATENT DOCUMENTS

6,184,353 B1    2/2001   Evans
2004/0137518 A1*   7/2004   Lambert et al. .............. 435/7.1

OTHER PUBLICATIONS

Flower D.R., 2002, Drug Design Cutting Edge Approaches, The Royal Society of Chemistry, p. 21-27.*
Hegyi et al., The Relationship between Protein Structure and Function: a Comprehensive Survey with Application to the Yeast Genome., J Mol Biol (1999) 288:147-164.*

(Continued)

*Primary Examiner*—David J Steadman
*Assistant Examiner*—Alexander D Kim
(74) *Attorney, Agent, or Firm*—Foley & Lardner LLP; Stephen E. Reiter

(57) ABSTRACT

The present invention provides compositions comprising the ligand binding domain (LBD) of a farnesoid X receptor (FXR) in crystalline form. In alternative embodiments, the LBD of FXR is complexed with a ligand therefor. There are provided high resolution structures of FXR complexed with a novel high affinity agonist, fexaramine. The discovered structure of a FXR LBD provides the first three-dimensional view of the structural basis for FXR ligand binding. The present invention further provides a computer for producing a three-dimensional representation of FXR or a complex thereof, and a computer for determining at least a portion of the structure coordinates of FXR or a complex thereof. The present invention further provides methods of using this structural information to predict molecules capable of binding to FXR; to identify compounds with agonist, antagonist or partial agonist activity for FXR; and to determine whether a test compound is capable of binding to the LBD of FXR. The present invention further provides compositions comprising compounds identified by such invention methods.

3 Claims, 7 Drawing Sheets

OTHER PUBLICATIONS

McKinney, Multifunctional Receptor Model for Dioxin and Related Compound Toxic Action: Possible Thyroid Hormone-Responsive Effector-Linked Site., Environmental Health Perspectives, 1989, vol. 82, pp. 323-336.*

Blumberg and Evans (1998). Orphan nuclear receptors—new ligands and new possibilities. Genes Dev. 12(20), 3149-55.

Blumberg et al. (1998). SXR, a novel steroid and xenobiotic-sensing nuclear receptor. Genes Dev. 12(20), 3195-3205.

Chiang (2002) Bile Acid regulation of gene expression: roles of nuclear hormone receptors. Endocr Rev. 23(4), 443-463.

Egea et al. (2000). Crystal structure of the human RXRa ligand-binding domain to its natural ligand: 9-cis retinoic acid EMBO J. 19, 2592-2601.

Evans RM. (1988) The steroid and thyroid hormone receptor superfamily. Science. 240(4854), 889-895.

Forman et al. (1995). Identification of a nuclear receptor that is activated by farnesol metabolites. Cell 81, 687-693.

Goodwin et al (2000). A regulatory cascade of the nuclear receptors FXR, SHP-1, and LRH-1 represses bile acid biosynthesis. Mol Cell. 6(3), 517-526.

Grober et al., (1999) Identification of a bile acid-responsive element in the human ileal bile acid-binding protein gene. J Biol Chem. 274(42), 29749-54.

Jez et al. (2000) Dissection of malonyl-coenzyme A decarboxylation from polyketide formation in the reaction mechanism of a plant polyketide synthase. Biochemistry 39, 890-902.

Kast et al. (2002). Regulation of multidrug resistance-associated protein 2 (ABCC2) by the nuclear receptors pregnane X receptor, farnesoid X-activated receptor, and constitutive androstane receptor. J Biol Chem. 277(4), 2908-15.

Laffitte et al. (2000). Identification of the DNA binding specificity and potential target genes for the farnesoid X-activated receptor. J Biol Chem. 275(14), 10638-47.

Lattman, Use of the rotation and translation functions. *Meth. Enzymol.* 115:55-77 (1985).

Makishima et al, (1999) Identification of a nuclear receptor for bile acids. Science. 284(5418), 1362-5.

McPherson, Crystallization of proteins from polyethylene glycol. *J. Biol. Chem.* 251:6300-6303 (1976).

Nicolaou et al. (2000). Natural product-like combinatorial libraries based on privileged structures. 1. General principles and solid-phase synthesis of benzopyrans. J. Am. Chem. Soc. 122, 9939-9953 (2000).

Nicolaou et al. (2000). Natural product-like combinatorial libraries based on privileged structures. 2. Construction of a 10 000-membered benzopyran library by directed split-and-pool chemistry using nanoKans and optical encoding. J. Am. Chem. Soc. 122, 9954-9967 (2000).

Nicolaou et al. (2000). Natural product-like combinatorial libraries based on privileged structures. 3. The "Libraries from Libraries" principle for diversity enhancement of benzopyran libraries. J. Am. Chem. Soc. 122, 9968-9976 (2000).

Parks et al. (1999). Bile acids: natural ligands for an orphan nuclear receptor. Science. 284(5418). 1365-8.

Pellicciari et al. (2002). 6-alpha-ethyl-chenodeoxycholic acid (6-ECDCA), a potent and selective FXR agonist endowed with anticholestatic activity. J Med Chem. 45(17), 3569-72.

Rochel et al. (2000). The Crystal Structure of the Nuclear Receptor for Vitamin D Bound to its Natural Ligand. Mol Cell 5, 173-179.

Sinal et al. (2000). Targeted disruption of the nuclear receptor FXR/BAR impairs bile acid and lipid homeostasis. Cell: 102(6), 731-44.

Stehlin et al. (2001). X-ray structure of the orphan nuclear receptor RORbeta ligand-binding domain in the active conformation. EMBO J. 20(21), 5822-31.

Urizar et al (2000). The farnesoid X-activated receptor mediates bile acid activation of phospholipid transfer protein gene expression. J Biol Chem. 275(50), 39313-7.

Urizar et al. (2002). A natural product that lowers cholesterol as an antagonist ligand for FXR. Science. 296(5573), 1703-6.

Wang et al. (1999) Endogenous bile acids are ligands for the nuclear receptor FXR/BAR. Mol Cell. 3(5), 543-53.

Watkins et al. (2001). The Human Nuclear Xenobiotic Receptor PXR: Structural Determinants of Directed Promiscuity, Science, 292, 2329-2333.

Xu et al. (2001). Structural determinants of ligand binding selectivity between the peroxisome proliferator-activated receptors. Proc Natl Acad Sci U S A. 98(24), 13919-24.

* cited by examiner

A
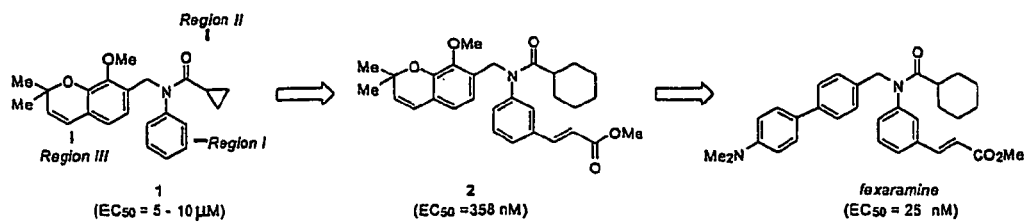
B
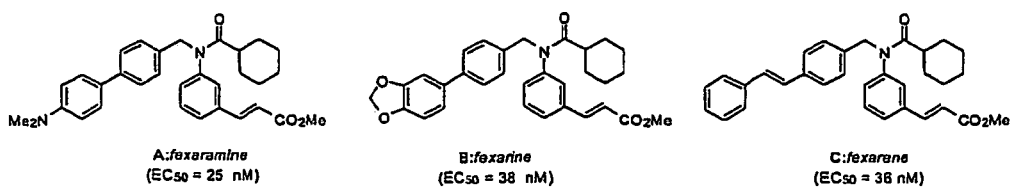
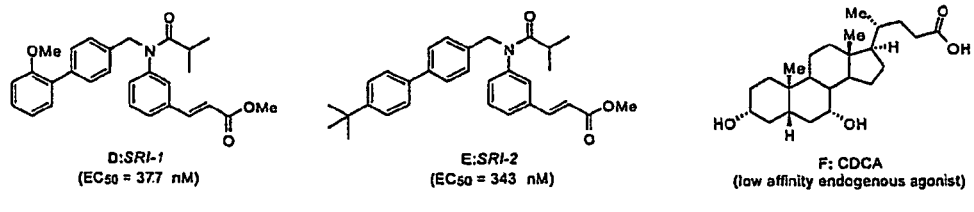
C
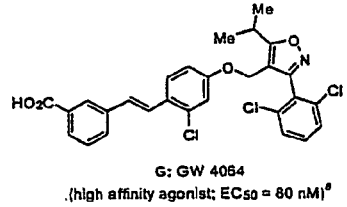
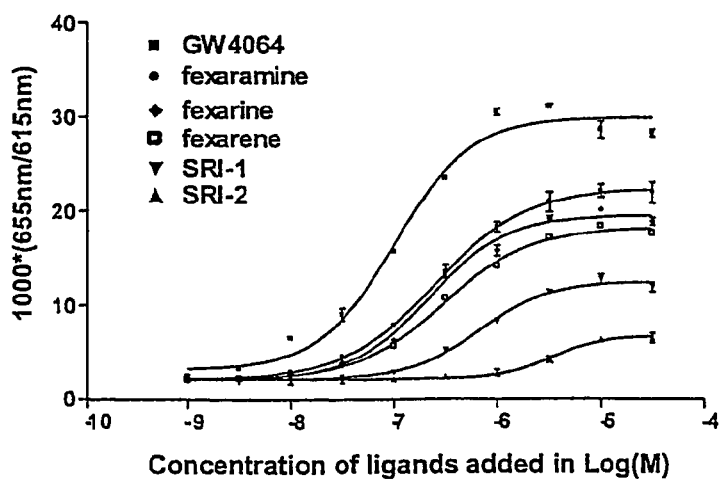
FIG. 1

| Accession Number | Gene Description | Fold Change | + or - |
|---|---|---|---|
| NM_014045 | apolipoprotein E | 252.89 | - |
| NM_003564 | transgelin 2 | 47.07 | - |
| NM_002693 | polymerase (RNA) II (DNA directed) | 45.72 | - |
| NM_001909 | cathepsin D (lysosomal aspartyl protease) | 42.49 | - |
| NM_054013 | MGAT4B | 20.06 | - |
| NM_010945 | WD repeat domain 18 | 19.03 | - |
| NM_005354 | jun D proto-oncogene | 16.87 | - |
| NM_001015 | ribosomal protein S11 | 14.50 | + |
| NM_002014 | FK506 binding protein 5 | 13.73 | - |
| NM_006278 | sialyltransferase 4C | 13.70 | + |
| NM_005354 | jun D proto-oncogene | 11.48 | - |
| NM_005313 | glucose regulated protein, 58kD | 9.03 | - |
| NM_031991 | polypyrimidine tract binding protein 1 | 8.83 | - |
| NM_001023 | ribosomal protein S20 | 8.58 | + |
| NM_006579 | emopamil binding protein (sterol isomerase) | 7.95 | + |
| NM_001467 | glucose-6-phosphatase, transport protein 1 | 7.85 | - |
| NM_003715 | SNARE protein | 7.59 | + |
| NM_017463 | pre-B-cell leukemia transcription factor 2 | 7.49 | + |
| NM_016504 | ribosomal protein L27 | 7.17 | + |
| NM_016315 | CED-6 protein | 7.10 | + |
| NM_001754 | runt-related transcription factor 1 | 6.69 | + |
| NM_001951 | E2F transcription factor 5, p130-binding | 6.52 | + |
| NM_014927 | kinase suppressor of ras | 6.49 | + |
| NM_133280 | FCAR (CD89) | 6.45 | + |
| NM_025170 | hypothetical protein FLJ12987 | 6.41 | - |
| NM_001656 | ADP-ribosylation factor domain protein 1 | 6.21 | + |
| AK023918 | novel | 5.94 | + |
| NM_006672 | SLC22A7 | 5.41 | + |
| XP_166583 | biliverdin reductase A (BLVRA) | 5.30 | + |
| AL159276 | Novel | 5.28 | + |
| NM_013369 | DNA (cytosine-5-)-methyltransferase 3 beta | 5.23 | + |
| NM_131836 | SIM2 | 5.04 | + |
| NM_007514 | SLC7A2 | 4.64 | - |
| NM_002693 | polymerase (RNA) II (DNA directed) gamma 2 | 4.85 | + |
| AI596398 | KIAA0576 protein | 4.61 | + |
| NM_004072 | chemokine-like receptor 1 | 4.40 | + |
| NM_006237 | POU domain, class 4, transcription factor 1 | 4.00 | + |
| NM_000369 | thyroid stimulating hormone receptor | 3.58 | + |
| NM_003317 | thyroid transcription factor 1 | 3.54 | - |
| NM_012443 | sperm associated antigen 6 | 3.46 | + |

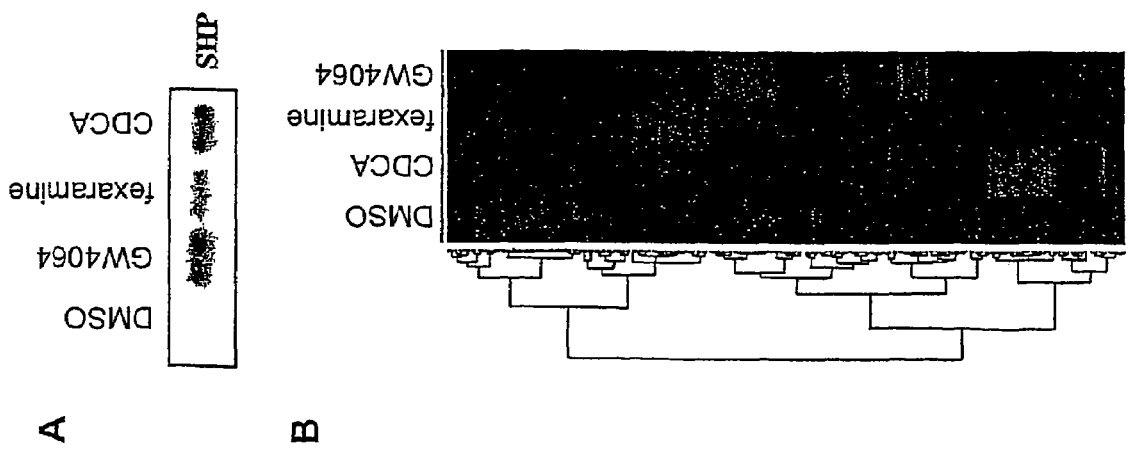

FIG. 6

SEQUENCE LISTING

<160> NUMBER OF SEQ ID NOS: 6

<210> SEQ ID NO 1
<211> LENGTH: 476
<212> TYPE: PRT

<213> ORGANISM: Homo sapiens

<400> SEQUENCE: 1

```
Met Gly Ser Lys Met Asn Leu Ile Glu His Ser His Leu Pro Thr Thr
  1               5                  10                  15

Asp Glu Phe Ser Phe Ser Glu Asn Leu Phe Gly Val Leu Thr Glu Gln
             20                  25                  30

Val Ala Gly Pro Leu Gly Gln Asn Leu Glu Val Glu Pro Tyr Ser Gln
         35                  40                  45

Tyr Ser Asn Val Gln Phe Pro Gln Val Gln Pro Gln Ile Ser Ser Ser
     50                  55                  60

Ser Tyr Tyr Ser Asn Leu Gly Phe Tyr Pro Gln Gln Pro Glu Glu Trp
 65                  70                  75                  80

Tyr Ser Pro Gly Ile Tyr Glu Leu Arg Arg Met Pro Ala Glu Thr Leu
                 85                  90                  95

Tyr Gln Gly Glu Thr Glu Val Ala Glu Met Pro Val Thr Lys Lys Pro
            100                 105                 110

Arg Met Gly Ala Ser Ala Gly Arg Ile Lys Gly Asp Glu Leu Cys Val
        115                 120                 125

Val Cys Gly Asp Arg Ala Ser Gly Tyr His Tyr Asn Ala Leu Thr Cys
    130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
            180                 185                 190

Leu Ala Glu Cys Met Tyr Thr Gly Leu Leu Thr Glu Ile Gln Cys Lys
        195                 200                 205

Ser Lys Arg Leu Arg Lys Asn Val Lys Gln His Ala Asp Gln Thr Val
    210                 215                 220

Asn Glu Asp Ser Glu Gly Arg Asp Leu Arg Gln Val Thr Ser Thr Thr
225                 230                 235                 240

Lys Ser Cys Arg Glu Lys Thr Glu Leu Thr Pro Asp Gln Gln Thr Leu
                245                 250                 255

Leu His Phe Ile Met Asp Ser Tyr Asn Lys Gln Arg Met Pro Gln Glu
            260                 265                 270

Ile Thr Asn Lys Ile Leu Lys Glu Glu Phe Ser Ala Glu Glu Asn Phe
        275                 280                 285

Leu Ile Leu Thr Glu Met Ala Thr Asn His Val Gln Val Leu Val Glu
    290                 295                 300

Phe Thr Lys Lys Leu Pro Gly Phe Gln Thr Leu Asp His Glu Asp Gln
305                 310                 315                 320

Ile Ala Leu Leu Lys Gly Ser Ala Val Glu Ala Met Phe Leu Arg Ser
                325                 330                 335

Ala Glu Ile Phe Asn Lys Lys Leu Pro Ser Gly His Ser Asp Leu Leu
            340                 345                 350

Glu Glu Arg Ile Arg Asn Ser Gly Ile Ser Asp Glu Tyr Ile Thr Pro
        355                 360                 365

Met Phe Ser Phe Tyr Lys Ser Ile Gly Glu Leu Lys Met Thr Gln Glu
    370                 375                 380

Glu Tyr Ala Leu Leu Thr Ala Ile Val Ile Leu Ser Pro Asp Arg Gln
385                 390                 395                 400
```

```
Tyr Ile Lys Asp Arg Glu Ala Val Glu Lys Leu Gln Glu Pro Leu Leu
                405                 410                 415

Asp Val Leu Gln Lys Leu Cys Lys Ile His Gln Pro Glu Asn Pro Gln
                420                 425                 430

His Phe Ala Cys Leu Leu Gly Arg Leu Thr Glu Leu Arg Thr Phe Asn
                435                 440                 445

His His His Ala Glu Met Leu Met Ser Trp Arg Val Asn Asp His Lys
                450                 455                 460

Phe Thr Pro Leu Leu Cys Glu Ile Trp Asp Val Gln
465                 470                 475

<210> SEQ ID NO 2
<211> LENGTH: 472
<212> TYPE: PRT
<213> ORGANISM: Homo sapiens

<400> SEQUENCE: 2

Met Gly Ser Lys Met Asn Leu Ile Glu His Ser His Leu Pro Thr Thr
 1               5                  10                  15

Asp Glu Phe Ser Phe Ser Glu Asn Leu Phe Gly Val Leu Thr Glu Gln
                20                  25                  30

Val Ala Gly Pro Leu Gly Gln Asn Leu Glu Val Glu Pro Tyr Ser Gln
                35                  40                  45

Tyr Ser Asn Val Gln Phe Pro Gln Val Gln Pro Gln Ile Ser Ser Ser
             50                  55                  60

Ser Tyr Tyr Ser Asn Leu Gly Phe Tyr Pro Gln Gln Pro Glu Glu Trp
65                  70                  75                  80

Tyr Ser Pro Gly Ile Tyr Glu Leu Arg Arg Met Pro Ala Glu Thr Leu
                85                  90                  95

Tyr Gln Gly Glu Thr Glu Val Ala Glu Met Pro Val Thr Lys Lys Pro
                100                 105                 110

Arg Met Gly Ala Ser Ala Gly Arg Ile Lys Gly Asp Glu Leu Cys Val
                115                 120                 125

Val Cys Gly Asp Arg Ala Ser Gly Tyr His Tyr Asn Ala Leu Thr Cys
130                 135                 140

Glu Gly Cys Lys Gly Phe Phe Arg Arg Ser Ile Thr Lys Asn Ala Val
145                 150                 155                 160

Tyr Lys Cys Lys Asn Gly Gly Asn Cys Val Met Asp Met Tyr Met Arg
                165                 170                 175

Arg Lys Cys Gln Glu Cys Arg Leu Arg Lys Cys Lys Glu Met Gly Met
                180                 185                 190

Leu Ala Glu Cys Leu Leu Thr Glu Ile Gln Cys Lys Ser Lys Arg Leu
                195                 200                 205

Arg Lys Asn Val Lys Gln His Ala Asp Gln Thr Val Asn Glu Asp Ser
210                 215                 220

Glu Gly Arg Asp Leu Arg Gln Val Thr Ser Thr Thr Lys Ser Cys Arg
225                 230                 235                 240

Glu Lys Thr Glu Leu Thr Pro Asp Gln Gln Thr Leu Leu His Phe Ile
                245                 250                 255

Met Asp Ser Tyr Asn Lys Gln Arg Met Pro Gln Glu Ile Thr Asn Lys
                260                 265                 270

Ile Leu Lys Glu Glu Phe Ser Ala Glu Glu Asn Phe Leu Ile Leu Thr
                275                 280                 285

Glu Met Ala Thr Asn His Val Gln Val Leu Val Glu Phe Thr Lys Lys
                290                 295                 300
```

```
Leu Pro Gly Phe Gln Thr Leu Asp His Glu Asp Gln Ile Ala Leu Leu
305                 310                 315                 320

Lys Gly Ser Ala Val Glu Ala Met Phe Leu Arg Ser Ala Glu Ile Phe
                325                 330                 335

Asn Lys Lys Leu Pro Ser Gly His Ser Asp Leu Leu Glu Glu Arg Ile
            340                 345                 350

Arg Asn Ser Gly Ile Ser Asp Glu Tyr Ile Thr Pro Met Phe Ser Phe
        355                 360                 365

Tyr Lys Ser Ile Gly Glu Leu Lys Met Thr Gln Glu Glu Tyr Ala Leu
    370                 375                 380

Leu Thr Ala Ile Val Ile Leu Ser Pro Asp Arg Gln Tyr Ile Lys Asp
385                 390                 395                 400

Arg Glu Ala Val Glu Lys Leu Gln Glu Pro Leu Leu Asp Val Leu Gln
                405                 410                 415

Lys Leu Cys Lys Ile His Gln Pro Glu Asn Pro Gln His Phe Ala Cys
            420                 425                 430

Leu Leu Gly Arg Leu Thr Glu Leu Arg Thr Phe Asn His His His Ala
        435                 440                 445

Glu Met Leu Met Ser Trp Arg Val Asn Asp His Lys Phe Thr Pro Leu
    450                 455                 460

Leu Cys Glu Ile Trp Asp Val Gln
465                 470

<210> SEQ ID NO 3
<211> LENGTH: 229
<212> TYPE: PRT
<213> ORGANISM: Homo sapiens

<400> SEQUENCE: 3

Glu Leu Thr Pro Asp Gln Gln Thr Leu Leu His Phe Ile Met Asp Ser
1               5                   10                  15

Tyr Asn Lys Gln Arg Met Pro Gln Glu Ile Thr Asn Lys Ile Leu Lys
                20                  25                  30

Glu Glu Phe Ser Ala Glu Glu Asn Phe Leu Ile Leu Thr Glu Met Ala
            35                  40                  45

Thr Asn His Val Gln Val Leu Val Glu Phe Thr Lys Lys Leu Pro Gly
        50                  55                  60

Phe Gln Thr Leu Asp His Glu Asp Gln Ile Ala Leu Leu Lys Gly Ser
65                  70                  75                  80

Ala Val Glu Ala Met Phe Leu Arg Ser Ala Glu Ile Phe Asn Lys Lys
                85                  90                  95

Leu Pro Ser Gly His Ser Asp Leu Leu Glu Glu Arg Ile Arg Asn Ser
            100                 105                 110

Gly Ile Ser Asp Glu Tyr Ile Thr Pro Met Phe Ser Phe Tyr Lys Ser
        115                 120                 125

Ile Gly Glu Leu Lys Met Thr Gln Glu Glu Tyr Ala Leu Leu Thr Ala
    130                 135                 140

Ile Val Ile Leu Ser Pro Asp Arg Gln Tyr Ile Lys Asp Arg Glu Ala
145                 150                 155                 160

Val Glu Lys Leu Gln Glu Pro Leu Leu Asp Val Leu Gln Lys Leu Cys
                165                 170                 175

Lys Ile His Gln Pro Glu Asn Pro Gln His Phe Ala Cys Leu Leu Gly
            180                 185                 190

Arg Leu Thr Glu Leu Arg Thr Phe Asn His His His Ala Glu Met Leu
```

```
                195                 200                 205
Met Ser Trp Arg Val Asn Asp His Lys Phe Thr Pro Leu Leu Cys Glu
    210                 215                 220

Ile Trp Asp Val Gln
225

<210> SEQ ID NO 4
<211> LENGTH: 305
<212> TYPE: PRT
<213> ORGANISM: Homo sapiens

<400> SEQUENCE: 4

Lys Leu Ser Glu Glu Gln Gln Arg Ile Ile Ala Ile Leu Leu Asp Ala
  1               5                  10                  15

His His Lys Thr Tyr Asp Pro Thr Tyr Ser Asp Phe Cys Gln Phe Arg
             20                  25                  30

Pro Pro Val Arg Val Asn Asp Gly Gly Gly Ser His Pro Ser Arg Pro
         35                  40                  45

Asn Ser Arg His Thr Pro Ser Phe Ser Gly Asp Ser Ser Ser Ser Cys
     50                  55                  60

Ser Asp His Cys Ile Thr Ser Ser Asp Met Met Asp Ser Ser Ser Phe
 65                  70                  75                  80

Ser Asn Leu Asp Leu Ser Glu Glu Asp Ser Asp Pro Ser Val Thr
                 85                  90                  95

Leu Glu Leu Ser Gln Leu Ser Met Leu Pro His Leu Ala Asp Leu Val
                100                 105                 110

Ser Tyr Ser Ile Gln Lys Val Ile Gly Phe Ala Lys Met Ile Pro Gly
            115                 120                 125

Phe Arg Asp Leu Thr Ser Glu Asp Gln Ile Val Leu Leu Lys Ser Ser
        130                 135                 140

Ala Ile Glu Val Ile Met Leu Arg Ser Asn Glu Ser Phe Thr Met Asp
145                 150                 155                 160

Asp Met Ser Trp Thr Cys Gly Asn Gln Asp Tyr Lys Tyr Arg Val Ser
                165                 170                 175

Asp Val Thr Lys Ala Gly His Ser Leu Glu Leu Ile Glu Pro Leu Ile
            180                 185                 190

Lys Phe Gln Val Gly Leu Lys Lys Leu Asn Leu His Glu Glu Glu His
        195                 200                 205

Val Leu Leu Met Ala Ile Cys Ile Val Ser Pro Asp Arg Pro Gly Val
    210                 215                 220

Gln Asp Ala Ala Leu Ile Glu Ala Ile Gln Asp Arg Leu Ser Asn Thr
225                 230                 235                 240

Leu Gln Thr Tyr Ile Arg Cys Arg His Pro Pro Gly Ser His Leu
                245                 250                 255

Leu Tyr Ala Lys Met Ile Gln Lys Leu Ala Asp Leu Arg Ser Leu Asn
            260                 265                 270

Glu Glu His Ser Lys Gln Tyr Arg Cys Leu Ser Phe Gln Pro Glu Cys
        275                 280                 285

Ser Met Lys Leu Thr Pro Leu Val Leu Glu Val Phe Gly Asn Glu Ile
    290                 295                 300

Ser
305

<210> SEQ ID NO 5
<211> LENGTH: 293
```

```
<212> TYPE: PRT
<213> ORGANISM: Homo sapiens

<400> SEQUENCE: 5

Gly Leu Thr Glu Glu Gln Arg Met Met Ile Arg Glu Leu Met Asp Ala
 1               5                  10                  15

Gln Met Lys Thr Phe Asp Thr Thr Phe Ser His Phe Lys Asn Phe Arg
            20                  25                  30

Leu Pro Gly Val Leu Ser Ser Gly Cys Glu Leu Pro Glu Ser Leu Gln
        35                  40                  45

Ala Pro Ser Arg Glu Glu Ala Ala Lys Trp Ser Gln Val Arg Lys Asp
    50                  55                  60

Leu Cys Ser Leu Lys Val Ser Leu Gln Leu Arg Gly Glu Asp Gly Ser
65                  70                  75                  80

Val Trp Asn Tyr Lys Pro Pro Ala Asp Ser Gly Gly Lys Glu Ile Phe
                85                  90                  95

Ser Leu Leu Pro His Met Ala Asp Met Ser Thr Tyr Met Phe Lys Gly
            100                 105                 110

Ile Ile Ser Phe Ala Lys Val Ile Ser Tyr Phe Arg Asp Leu Pro Ile
        115                 120                 125

Glu Asp Gln Ile Ser Leu Leu Lys Gly Ala Ala Phe Glu Leu Cys Gln
130                 135                 140

Leu Arg Phe Asn Thr Val Phe Asn Ala Glu Thr Gly Thr Trp Glu Cys
145                 150                 155                 160

Gly Arg Leu Ser Tyr Cys Leu Glu Asp Thr Ala Gly Gly Phe Gln Gln
                165                 170                 175

Leu Leu Leu Glu Pro Met Leu Lys Phe His Tyr Met Leu Lys Lys Leu
            180                 185                 190

Gln Leu His Glu Glu Glu Tyr Val Leu Met Gln Ala Ile Ser Leu Phe
        195                 200                 205

Ser Pro Asp Arg Pro Gly Val Leu Gln His Arg Val Val Asp Gln Leu
    210                 215                 220

Gln Glu Gln Phe Ala Ile Thr Leu Lys Ser Tyr Ile Glu Cys Asn Arg
225                 230                 235                 240

Pro Gln Pro Ala His Arg Phe Leu Phe Leu Lys Ile Met Ala Met Leu
                245                 250                 255

Thr Glu Leu Arg Ser Ile Asn Ala Gln His Thr Gln Arg Leu Leu Arg
            260                 265                 270

Ile Gln Asp Ile His Pro Phe Ala Thr Pro Leu Met Gln Glu Leu Phe
        275                 280                 285

Gly Ile Thr Gly Ser
        290

<210> SEQ ID NO 6
<211> LENGTH: 240
<212> TYPE: PRT
<213> ORGANISM: Homo sapiens

<400> SEQUENCE: 6

Thr Ser Ser Ala Asn Glu Asp Met Pro Val Glu Arg Ile Leu Glu Ala
 1               5                  10                  15

Glu Leu Ala Val Glu Pro Lys Thr Glu Thr Tyr Val Glu Ala Asn Met
            20                  25                  30

Gly Leu Asn Pro Ser Ser Pro Asn Asp Pro Val Thr Asn Ile Cys Gln
        35                  40                  45
```

-continued

```
Ala Ala Asp Lys Gln Leu Phe Thr Leu Val Glu Trp Ala Lys Arg Ile
    50              55              60

Pro His Phe Ser Glu Leu Pro Leu Asp Asp Gln Val Ile Leu Leu Arg
65              70              75              80

Ala Gly Trp Asn Glu Leu Leu Ile Ala Ser Phe Ser His Arg Ser Ile
                85              90              95

Ala Val Lys Asp Gly Ile Leu Leu Ala Thr Gly Leu His Val His Arg
            100             105             110

Asn Ser Ala His Ser Ala Gly Val Gly Ala Ile Phe Asp Arg Val Leu
        115             120             125

Thr Glu Leu Val Ser Lys Met Arg Asp Met Gln Met Asp Lys Thr Glu
    130             135             140

Leu Gly Cys Leu Arg Ala Ile Val Leu Phe Asn Pro Asp Ser Lys Gly
145             150             155             160

Leu Ser Asn Pro Ala Glu Val Glu Ala Leu Arg Glu Lys Val Tyr Ala
            165             170             175

Ser Leu Glu Ala Tyr Cys Lys His Lys Tyr Pro Glu Gln Pro Gly Arg
            180             185             190

Phe Ala Lys Leu Leu Leu Arg Leu Pro Ala Leu Arg Ser Ile Gly Leu
        195             200             205

Lys Cys Leu Glu His Leu Phe Phe Phe Lys Leu Ile Gly Asp Thr Pro
    210             215             220

Ile Asp Thr Phe Leu Met Glu Met Leu Glu Ala Pro His Gln Met Thr
225             230             235             240
```

STRUCTURE OF THE FARNESOID X RECEPTOR LIGAND BINDING DOMAIN AND METHODS OF USE THEREFOR

FIELD OF THE INVENTION

The present invention relates to the three-dimensional structure of farnesoid X receptors (FXR). In a particular aspect, the invention relates to compositions comprising the ligand binding domain of a FXR in crystalline form, as described by structure coordinates obtained by X-ray crystallography, and computers utilizing such structure coordinates to provide information regarding the ligand binding domain of FXRs and ligands therefor. In another aspect, the invention relates to methods of utilizing such structure coordinates for modeling of known and putative FXR ligands.

BACKGROUND OF THE INVENTION

Structural biology provides an important tool for the detailed characterization of proteins at the molecular level. This molecular approach can lead to a more complete understanding not only of a protein itself, for example, but also helps characterize the interactions between a ligand-binding protein and its known ligands and/or putative binding partners. The nuclear hormone receptor farnesoid X receptor (FXR) functions as a bile acid sensor by responding to physiological levels of a variety of bile acid ligands and coordinating the control and maintenance of lipid homeostasis. Elucidation of the three-dimensional structure, and in particular, the structure of the ligand binding domain involved in binding bile acids, can assist in studies of the function and physical properties of FXR.

An essential function of the liver and the intestine in vertebrates is to maintain lipid homeostasis within the body through tight regulation of the acquisition, synthesis and metabolism of cholesterol (Chawla et al. (2000). "Don't know much bile-ology". Cell. 103, 1-4). Excess cholesterol is either converted into bile acids in the liver, or undergoes biliary excretion in the intestine and is disposed of in the stool (Chiang (2002) Bile Acid regulation of gene expression: roles of nuclear hormone receptors. Endocr Rev. 23(4), 443-63). The nuclear hormone receptor (NHR) farnesoid X receptor (FXR, also known as NRIH4) is involved in the regulation of both of these metabolic processes. FXR is expressed in the liver and intestine as well as other cholesterol rich tissues such as the adrenal gland. Knockout mice deficient in FXR expression display defects in bile acid (BA) homeostasis when exposed to dietary stresses, including elevated serum BA, reduced bile acid pools, and reduced fecal BA secretion (Sinal et al. (2000). Targeted disruption of the nuclear receptor FXR/BAR impairs bile acid and lipid homeostasis. Cell: 102(6), 731-44). In the liver, the rate-limiting step for the conversion of excess cholesterol into bile acids is catalyzed by the cytochrome p450 gene, cholesterol 7alpha-hydroxylase (CYP7A1). A second cytochrome p450 gene, sterol 12 alpha-hydroxylase (CYP8B) is a key enzyme for regulating the cholic acid (CA)/chenodeoxycholic acid (CDCA) ratio in bile acid biosynthesis (Kerr et al., (2002) Loss of nuclear receptor SHP impairs but does not eliminate negative feedback regulation of bile acid synthesis. Dev Cell. 2(6), 713-20; Wang et al. (2002) Redundant pathways for negative feedback regulation of bile acid production. Dev Cell. 2(6), 721-31). In mammals these genes are indirectly regulated by FXR via the NHR homologue gene SHP (small heterodimer partner) (Lu et al. (2000). Molecular basis for feedback regulation of bile acid synthesis by nuclear receptors. Mol Cell. 6(3), 507-15; Goodwin et al (2000). A regulatory cascade of the nuclear receptors FXR, SHP-1, and LRH-1 represses bile acid biosynthesis. Mol Cell. 6(3), 517-26).

Physiological concentrations of specific BAs bind and activate FXR, the most potent being CDCA a major primary bile acid found in human bile (Makishima et al, (1999) Identification of a nuclear receptor for bile acids. Science. 284(5418), 1362-5; Parks et al. (1999). Bile acids: natural ligands for an orphan nuclear receptor. Science. 284(5418). 1365-8, and Wang et al. (1999) Endogenous bile acids are ligands for the nuclear receptor FXR/BAR. Mol Cell. 3(5), 543-53). This activation enables FXR to act as a transcriptional sensor for bile acids (BAs), repressing the transcriptional expression of both CYP7A and CYP8B genes by increasing the levels of the inhibitory nuclear receptor SHP. SHP is a promiscuous inhibitory heterodimer partner of NHRs that suppresses the transcriptional activity of a large number of NHRs. However, its ability to bind and inhibit the liver receptor homologue (LRH-1) a NHR required for CYP7A gene expression, indirectly allows FXR to exert its influence on cholesterol homeostasis (Lu et al., (2000), supra; Goodwin et al., (2000), supra). Additionally, BA activation of FXR positively regulates the expression of genes involved in the excretion and transportation of BAs including intestinal bile acid-binding protein (IBABP), bile salt export pump (BSEP) and canalichur multi-specific organic anion transporter (cMOAT) (Chiang (2002), supra). Thus, this receptor plays a key physiological role in the regulation of lipid homeostasis.

FXR belongs to a superfamily of ligand-inducible transcription factors involved in a wide array of biological functions including development, differentiation and homeostasis. The family members share two structurally-conserved domains; a central, highly conserved DNA binding domain (DBD) that targets the receptor to specific DNA sequences, termed hormone response elements, and a ligand binding domain (LBD) that binds small lipophilic hormones (Evans R M. (1988) The steroid and thyroid hormone receptor superfamily. Science. 240(4854), 889-95). The LBD functions as the regulating molecular switch. Binding of the appropriate hormone to the LBD causes a conformational change that results in the release of bound co-repressor proteins and the recruitment of co-activator proteins that culminates in the activation of transcriptional target genes. This regulation of NHR transcription factors by small lipophilic hormones makes this gene family an ideal target for chemical biology to identify novel chemical activators (Blumberg and Evans (1998). Orphan nuclear receptors-new ligands and new possibilities. Genes Dev. 12(20), 3149-55). FXR senses BA levels and mediates the repression of genes that convert excess cholesterol into bile BAs as well as the induction of BA transport genes makes FXR an attractive pharmaceutical target. The availability of potent synthetic agonists for FXR, and an understanding of how various binding agents interact with the ligand binding domain of FXR is a critical step required for the validation of FXR as a drug target and the elaboration of the functions of FXR.

SUMMARY OF THE INVENTION

The present invention provides the first high-resolution crystal structure determinations of a farnesoid X receptor (FXR) in its active state. Specifically disclosed herein is the ligand binding domain of FXR bound with a novel FXR agonist termed fexaramine, which is structurally distinct from known natural bile acid (BA) ligands. Accordingly, the invention provides a structural basis for understanding FXR ligand binding, and provides further knowledge of the physical properties of this receptor. The present invention uses molecular modeling at the atomic level, to elucidate FXR-ligand interactions.

According to one aspect of the present invention, there are provided compositions comprising the ligand binding domain (LBD) of a FXR, and complexes thereof with ligands, in crystalline form. The invention further provides the structure coordinates of FXR complexed with fexaramine as determined by X-ray crystallography.

According to another aspect of the present invention, there is provided a computer for producing a three-dimensional representation of a FXR molecule or molecular complex or a homologue thereof, based on such FXR structure coordinates, or a portion thereof sufficient to define the points of interaction between a FXR LBD and a ligand therefor.

According to yet another aspect of the present invention, there is provided a computer for determining at least a portion of the structure coordinates corresponding to X-ray diffraction data obtained from a FXR molecule or molecular complex or a homologue thereof.

According to still another aspect of the present invention, there are provided methods of using the high-resolution crystal structure determinations of a farnesoid X receptor (FXR) in its active state. Specifically disclosed herein are methods of using the structure of the ligand binding domain (LBD) of FXR bound with a novel FXR agonist. Accordingly, the invention provides a structural basis for understanding FXR ligand binding, and provides further knowledge of the physical properties of this receptor. The present invention uses molecular modeling at the atomic level, to elucidate FXR-ligand interactions. By determining high-resolution x-ray crystal structures of a FXR complexed with a synthetic ligand, the present invention provides a more complete understanding of FXR structure and provides a molecular explanation of how both natural and modified or synthetic BAs interact with the receptor.

According to a further aspect of the present invention, there are provided methods of predicting a molecule capable of binding to a FXR molecule. Such methods comprise modeling a test molecule that potentially interacts with the LBD of FXR, wherein the LBD is defined by a plurality of structure coordinates of the LBD of FXR. The structure coordinates of FXR are derived from X-ray diffraction data obtained from crystals of a FXR molecule or molecular complex or a homologue of said FXR molecule or molecular complex. In preferred embodiments, the structure coordinates correspond to the LBD of FXR complexed with the high affinity ligand fexaramine as described herein.

According to further aspects of the present invention, there are provided methods of identifying a compound with agonist, antagonist, or partial agonist activity for a FXR molecule. Such methods comprise modeling test compound using FXR structure coordinates. Also provided are compositions of compounds identified by such methods.

According to yet another aspect of the present invention, there are provided methods of determining whether a test compound is capable of binding to the LBD of a FXR molecule by analyzing and comparing points of interaction between the LBD and one or more FXR ligand(s), with points of interaction between the LBD and the test compound. In preferred embodiments, the test compound is a bile acid.

BRIEF DESCRIPTION OF THE FIGURES

FIGS. 1A-1C collectively depict the activation of FXR by a variety of putative ligands.

FIG. 1A depicts the selected regions of interest of prototypical structure lead compounds 1 used for further FXR ligand binding analysis. Region I denotes the right-hand aromatic system; Region II denotes the acyl group region; and Region III denotes the left-hand benzopyran ring system. Compound 2 was produced by systematic optimization of regions I and II. The novel compound termed fexaramine was discovered from a final 94-membered combinatorial library of region III.

FIG. 1B illustrates the structures of lead compounds (and their $EC_{50}$ values in a cell-based assay) selected for further biological evaluation as FXR agonists. Compound A is fexaramine ($EC_{50}$=25 nM), compound B is fexarine ($EC_{50}$=38 nM), compound C is fexarene ($EC_{50}$=36 nM), compound D is SRI-1 ($EC_{50}$=377 nM), and compound E is SRI-2 ($EC_{50}$=343 nM). The identified compounds (A-E) are structurally distinct from known FXR agonists. Compound F is CDCA, a biological low affinity endogenous agonist; and compound G is GW4064 ($EC_{50}$=80 nM), a high affinity agonist.

FIG. 1C shows that the identified compounds fexaramine, fexarine, fexarene, SRI-1 and SRI-2 are agonist ligands for FXR in vitro. A FRET ligand-binding assay was carried out in agonist mode with GW4064 used as the control ligand. Increasing amounts of the compounds were added as indicated. Binding reactions contained 8 nM Europium labeled GST-FXR ligand-binding domain fusion protein and 16 nM allophycocyanin-labeled SRC-1 receptor binding peptide. Results are expressed at 1000*(665 nm/615 nm).

FIG. 2A with a minimal TK promoter, FIG. 2B with a TK-ECRE*6 promoter, FIG. 2C with a TK-ER8*2 promoter, FIG. 2D with HIBABP promoter, FIG. 2E with a hPLTP promoter, or FIG. 2 with a FhMRP-2 promoter. Increasing amounts (1 nM to 1 µM of the compounds fexaramine, fexarine, fexarene, SRI-1, SRI-2 and GW4064 were added to the cells 24 hours post-transfection. Activation of the luciferase reporter gene was measured in relative light units (with β-galactosidase activity as a control for transfection efficiency) and presented as normalized luciferase units. Ligand response data were derived from triplicate points from two independent experiments and represented as the mean±SE (n=6).

FIG. 3A shows the results of cells containing the MH2004 promoter-reporter construct that contains four GALA binding sites with pCMXGAL4-FXR LBD chimeric expression construct, treated with increasing amounts of the compounds fexaramine, fexarine, fexarene, SRI-1, SRI-2 and GW4064. FIG. 3B shows the results of MH2004 promoter-reporter construct with pCMXGAL4-FXR LBD/RXRα constructs, treated with increasing amounts of the compounds fexaramine, fexarine, fexarene, SRI-1, SRI-2 and GW4064. FIGS. 3C-3E show the results of CV-1 cells transiently transfected with the indicated reporter constructs, treated with either DMSO or 10 µM of the compounds fexaramine (3C), fexarine (3D), fexarene (3E). Reporter activity was normalized to the internal control and the data plotted as fold activation relative to untreated cells. All transfections contained CMX-βgal as an internal control.

FIG. 4A shows the respective RNAs expressed in HT29 stable cells cultured until confluence. 20 µg total RNA isolated using Trizol (Invitrogen) was used for Northern blot analysis. cDNA probes for mouse FXR and human IBABP were prepared and hybridized to the blot. Blots were normalized by β-actin expression.

FIGS. 4B and 4C show IBABP RNA expressed in HT29 stable cells that were cultured until confluence and then treated overnight with increasing amounts of CDCA (4B), GW4064 (4C) as indicated. 20 µg total RNA was isolated using Trizol (Invitrogen) and used for Northern blot analysis. cDNA probe for human IBABP was prepared and hybridized to the blot. Blots were normalized by β-actin expression.

FIG. 4D shows IBABP RNA expressed in HT29-FXRFL stable cells that were cultured until confluence and then treated overnight with increasing amounts of the FXR ligands fexaramine, fexarine or fexarene as indicated. 20 µg total RNA was isolated using Trizol (Invitrogen) and used for Northern blot analysis. cDNA probe for human IBABP was prepared and hybridized to the blot. Blots were normalized by β-actin expression.

FIG. 4E shows various FXR target molecule RNAs expressed in HEPG2-FXRFL stable cells that were cultured until confluence and then treated overnight with increasing amounts of FXR ligands fexaramine, fexarine, fexarene SRI-1, SRI-2, GW4064 (10 nM, 100 nM, 1 µM, 10 µM) and CDCA (10 µM, 25 µM, 50 µM, 100 µM). 20 µg total RNA was isolated using Trizol (Invitrogen) and used for Northern blot analysis. cDNA probes for human PLTP, SHP, MRP-2 and BSEP were prepared and hybridized to the blot. Blots were normalized by 36B4 expression as shown.

FIG. 5A shows SHP RNA expression in ligand-treated primary mouse hepatocytes obtained from Cedera scientific and cultured in the appropriate medium. Twenty-four hours after delivery, hepatocytes were treated for 6 or 12 hours with either vehicle alone or 100 µM CDCA, 10 µM fexaraime, or 10 µM GW4064, as indicated. 10 µg total RNA was isolated using Trizol (Invitrogen) and used for Northern blot analysis. The probe for human SHP was prepared and hybridized to the blot. To ensure constant loading of total RNA to the blot, GAPDH was also hybridized as a control.

FIG. 5B is a clustergram of genes changed by FXR agonist treatment. Genes were identified using a paired Student's T-test and DMSO treatment as the control group. 222 transcripts were identified meeting a criteria of a change of at least 0.005 and a fold change with respect to DMSO of 2. Data was imported into Cluster and the genes were subjected to hierarchal clustering. The output was visualized using Treeview to monitor changes.

FIG. 5C is a table of genes changed by FXR agonist treatment

FIGS. 6A-6E collectively illustrate the three-dimensional structure of the ligand-binding domain of human farnesoid X receptor (FXR).

FIG. 6A is a three-dimensional representation of residues 248 to 270 and 286 to 476 of hFXR that were crystallized and examined in complex with the high affinity agonist, fexaramine. The α-helices are shown as ribbons and the ligand is shown within the ligand binding region within a transparent van der Waals surface. The structural elements are numbered according to the canonical structure for the LBD of nuclear receptors.

FIG. 6B is a sequence alignment of the ligand binding domains of four human nuclear receptors, FXR (SEQ ID NO: 3), VDR (SEQ ID NO: 4), SXR (SEQ ID NO: 5), and RXRα (SEQ ID NO: 6). The secondary structural elements of the hFXR-LBD are shown above the FXR sequence.

FIG. 6C is a close-up of the first set of points of interaction between the FXR LBD and fexaramine. The hexyl group protrudes out into solution while making weak van der Waals contact with two side chains; I339 and L344. The fexaramine carbonyl oxygen makes two hydrogen bonds, one with H298 and another with S336. The methyl ester aliphatic chain makes van der Waals contacts with Met294, Leu352 and I356. No charged interactions are seen in contact with the methyl ester moiety itself.

In accordance with the present invention, the crystal structure of the LBD of FXR complexed with fexaramine has been refined to 1.78 Å resolution. FXR LBD/fexaramine crystals belong to space group $P2_12_12_1$ with one molecule per asymmetric unit (52.9% solvent). Unit cell dimensions are about a=36.656 Å, b=56.776 Å, c=117.646 Å, $\alpha=\beta=\gamma=90.0°$. The complete structure coordinates for the X-ray diffraction data set are set forth in Appendix 1 (comprising residues 248-270 and 286-475 of SEQ ID NO:1).

FIG. 6E is a close-up of a proposed model for binding of the natural ligand CDCA by FXR. CDCA was modeled upon the orientation of fexaramine with its hydroxyl groups pointed towards Y365 and H451 to accommodate hydrogen bonding. This positions the CDCA carboxyl group into the same orientation as the fexaramine hexyl group, suggesting that it protrudes from the protein or makes contacts with the insertion domain region. Glycine and taurine bile acid conjugates could be accommodated by this orientation.

Figure 7:
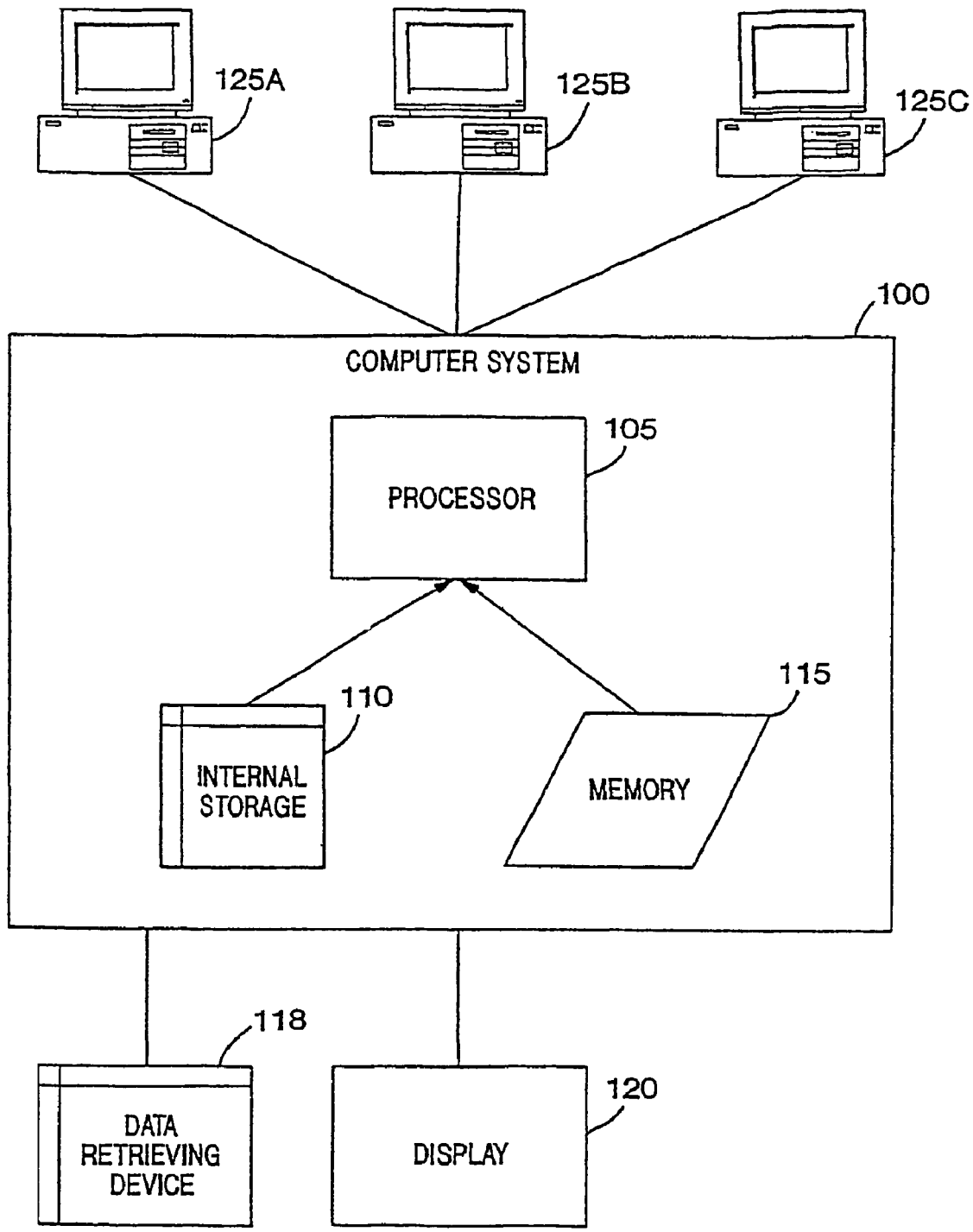

FIG. 7 shows an example of a computer system in block diagram form.

DETAILED DESCRIPTION OF THE INVENTION

In accordance with the present invention, there are provided compositions comprising the ligand binding domain (LBD) of a farnesoid X receptor (FXR) in crystalline form. In accordance with a preferred embodiment of the present invention, there are provided high-resolution structures of FXR LBD complexed with a high affinity ligand, fexaramine, as described herein. The structure of a FXR LBD presented herein provides the first three-dimensional view of the structural basis for ligand binding between FXR and natural, modified and synthetic ligands therefor.

In accordance with the present invention, the crystal structure of the LBD of FXR complexed with fexaramine has been refined to 1.78 Å resolution. FXR LBD/fexaramine crystals belong to space group $P2_12_12_1$ with one molecule per asymmetric unit (52.9% solvent). Unit cell dimensions are about a=36.656 Å, b=56.776 Å, c=117.646 Å, $\alpha=\beta=\gamma=90.0°$. The complete structure coordinates for the X-ray diffraction data set are set forth in Appendix 1.

One aspect of the invention resides in obtaining the FXR LBD in crystalline form, of sufficient quality to determine the three-dimensional structure of the protein by X-ray diffraction methods. X-ray crystallography is a method of solving the three-dimensional structures of molecules. The structure of a molecule is calculated from X-ray diffraction patterns using a crystal as a diffraction grating. Three-dimensional structures of protein molecules arise from crystals grown from a concentrated solution of that protein. The process of X-ray crystallography can include the following steps:
  (a) synthesizing and isolating a FXR LBD polypeptide;
  (b) growing a crystal from a solution comprising the polypeptide with or without a ligand, or ligand analog; and
  (c) collecting X-ray diffraction patterns from the crystals, determining unit cell dimensions and symmetry, determining electron density, fitting the amino acid sequence of the polypeptide to the electron density, and refining the structure.

The term "crystalline form" refers to a crystal formed from a solution comprising a purified polypeptide corresponding to all or part of FXR. In preferred embodiments, a crystalline form may also be formed from a purified polypeptide corresponding to all or part of FXR in a complex with one or more additional known or putative ligand molecules, or other known or putative molecules capable of binding to FXR or an FXR homologue, such as natural, synthetic, or modified bile acids.

In accordance with another embodiment of the present invention, there are provided methods utilizing structure coordinates obtained by X-ray crystallography of crystals comprising the ligand binding domain (LBD) of a farnesoid X receptor (FXR). In accordance with a preferred aspect of this embodiment of the present invention, the methods utilize information obtained from high-resolution structures of FXR LBD complexed with a high affinity ligand fexaramine as described herein. The structure of a FXR LBD presented herein provides the first three-dimensional view of the structural basis for ligand binding between FXR and natural, modified and synthetic ligands therefor.

According to one aspect of the present invention, there are provided methods of predicting a molecule capable of binding to a farnesoid X receptor (FXR) molecule, said method comprising: modeling a test molecule that potentially interacts with the ligand binding domain of said FXR molecule, wherein said ligand binding domain is defined by a plurality of structure coordinates of the ligand binding domain of a FXR molecule or a fragment thereof, and wherein said structure coordinates are derived from X-ray diffraction data obtained from crystals of said FXR molecule or molecular complex or a homologue of said FXR molecule or molecular complex.

FXR was first reported by Forman et al., (1995). Identification of a nuclear receptor that is activated by farnesol metabolites. Cell 81:687-693. This receptor is a protein having a relative molecular mass of approximately 54,000 Daltons, and is a vertebrate transcription factor regulated by intracellular metabolites. The receptor is activated by certain farnesoids, i.e., farnesol itself and compounds derived from, and/or similar in structure to, farnesol. These farnesoids include farnesol, farnesal, farnesyl acetate, farnesoic acid, geranylgeraniol, and juvenile hormone III.

FXR polypeptides contemplated for use in the practice of the present invention can be characterized by reference to the unique tissue distribution thereof. Thus, expression of FXR polypeptides is restricted to the liver, gut, adrenal gland and kidney, all tissues known to have a significant flux through the mevalonate pathway. U.S. Pat. No. 6,184,353 to Evans et al., which is hereby incorporated by reference herein in its entirety, describes the characteristics of a murine FXR protein.

Presently preferred human FXR polypeptides contemplated for use in the practice of the present invention can be characterized as having substantially the same amino acid sequence as SEQ ID NO:1, a representative human FXR (see below). Especially preferred FXR polypeptides contemplated for use in the practice of the present invention are those which have the same amino acid sequence as SEQ ID NO:1, or a fragment thereof. The LBD of SEQ ID NO:1 corresponds to approximately C-terminal amino acid residues 248-476. An alternative human FXR polypeptide for use in the methods of the present invention is provided as SEQ ID NO:2 (see below). The LBD of SEQ ID NO:2 corresponds to approximately C-terminal amino acid residues 244-472, and is identical to the LBD of SEQ ID NO:1.

```
                                                                    SEQ ID NO:1
Human FXR amino acid sequence (Q96RI1)
    1 MGSKMNLIEH SHLPTTDEFS FSENLFGVLT EQVAGPLGQN LEVEPYSQYS NVQFPQVQPQ

61 ISSSSYYSNL GFYPQQPEEW YSPGIYELRR MPAETLYQGE TEVAEMPVTK KPRMGASAGR

122 IKGDELCVVC GDRASGYHYN ALTCEGCKGF FRRSITKNAV YKCKNGGNCV MEMYMRRKCQ

181 ECRLRKCKEM GMLAECMYTG LLTEIQCKSK RLRKNVKQHA DQTVNEDSEG RDLRQVTSTT

241 KSCREKTELT PDQQTLLHFI MDSYNKQRMP QEITNKILKE EFSAEENFLI LTEMATNHVQ

301 VLVEFTKKLP GFQTLDHEDQ IALLKGSAVE AMFLRSAEIF NKKLPSGHSD LLEERIRNSG

361 ISDEYITPMF SFYKSIGELK MTQEEYALLT AIVILSPDRQ YIKDREAVEK LQEPLLDVLQ

421 KLCKIHQPEN PQHFACLLGR LTELRTFNHH HAEMLMSWRV NDHKFTPLLC EIWDVQ

SEQ ID NO:2
Human FXR amino acid sequence (AAB08017)
    1 MGSKMNLIEH SHLPTTDEFS FSENLFGVLT EQVAGPLGQN LEVEPYSQYS NVQFPQVQPQ

61 ISSSSYYSNL GFYPQQPEEW YSPGIYELRR MPAETLYQGE TEVAEMPVTK KPRMGASAGR

121 IKGDELCVVC GDRASGYHYN ALTCEGCKGF FRRSITKNAV YKCKNGGNCV MDMYMRRKCQ

181 ECRLRKCKEM GMLAECLLTE IQCKSKRLRK NVKQHADQTV NEDSEGRDLR QVTSTTKSCR

241 EKTELTPDQQ TLLHFIMDSY NKQRMPQEIT NKILDEEFSA EENFLILTEM ATNHVQVLVE

301 FTKKLPGFQT LDHEDQIALL KGSAVEAMFL RSAEIFNKKL PSGHSDLLEE RIRNSGISDE

361 YITPMFSFYK SIGELKMTQE EYALLTAIVI LSPDRQYIKD REAVEKLQEP LLDVLQKLCK

421 IHQPENPQHF ACLLGRLTEL RTFNHHHAEM LMSWRVNDHK FTPLLCEIWD VQ
```

The phrase "substantially the same" is used herein in reference to amino acid sequences that have slight and non-consequential sequence variations from the actual sequences disclosed herein. Species which are "substantially the same" as the reference sequence are considered to be equivalent to the disclosed sequences and as such are within the scope of the appended claims. The amino acid sequences of FXRs of a variety of species are readily available to one of skill in the art using public databases, such as through the National Center for Biotechnology Information (NCBI) at the National library of Medicine (NLM), accessible on the World Wide Web (www) at the URL "ncbi.nlm.nih.gov".

An FXR homologue as used herein, refers to a FXR molecule that has the same ligand binding properties as the FXR molecule identified in SEQ ID NO:1.

Alternatively, a farnesoid activated receptor polypeptides contemplated for use in the practice of the present invention can be characterized by:

(1) being responsive to the presence of farnesoid(s) to regulate the transcription of associated gene(s);

(2) having a relative molecular mass of about 54,000 Daltons; and (3) having a DNA binding domain of about 66 amino acids with 9 Cys residues, wherein said DNA binding domain has:
   (a) about 81% amino acid identity with the DNA binding domain of the *Drosophila* ecdysone receptor,
   (b) about 56% amino acid identity with the DNA binding domain of VDR, and
   (c) about 45% amino acid identity with the DNA binding domain of hGR.

FXR polypeptides contemplated for use in the practice of the present invention can be further characterized by: having a ligand binding domain of about 220 amino acids, wherein said ligand binding domain has:
   (a) about 33% amino acid identity, and about 59% amino acid similarity, with the ligand binding domain of the *Drosophila* ecdysone receptor,
   (b) about 32% amino acid identity with the ligand binding domain of VDR, and
   (c) about 26% amino acid identity with the ligand binding domain of hGR.

FXR polypeptides contemplated for use in the present invention include those derived from vertebrates, mammals, murine species, humans, and the like.

The amino acid sequence of a contemplated FXR contains several features that are consistent as being a member of the nuclear receptor superfamily. The region spanning about amino acid residues 124-289 contains several invariant amino acids, including 4 cysteine residues that are characteristic of the DNA binding domain (DBD) of all nuclear hormone receptors. The DBD of a murine FXR is most similar to the DBD of the insect ecdysone receptor (EcR). These receptors share about 81% amino acid sequence identity within their DBDs.

In addition, the carboxy-terminal LBD of nuclear receptors is a complex region encoding subdomains for ligand binding, dimerization and transcriptional activation. Analysis of the carboxy terminal region of a murine FXR indicates that it possesses only about 33% sequence identity (59% similarity) with the corresponding region of the ecdysone receptor. Within this region, significant similarity is confined to regions involved in receptor dimerization (see, e.g., Forman and Samuels (1990) *Mol. Endocrinol.* 4:1293-1301), including the Ti subdomain (48% identity), heptad repeats 4-6 (50% identity) and heptad 9 (75% identity). In addition, the last 22 amino acids, which possess transcriptional activation functions in other receptors (see Danielian et al., *EMBO J.* 11:1025-1033 (1992)), are 42% identical among FXR and EcR. These structural similarities indicate that FXR is a member of the nuclear receptor superfamily.

As used herein, the phrase "amino acid sequence similarity" refers to sequences which have amino acid substitutions which do not change the inherent chemical properties of the subject polypeptide. Thus, amino acid sequences wherein an acidic residue is replaced with another acidic residue, or wherein a basic residue is replaced with another basic residue, or wherein a neutral residue is replaced with another neutral residue, retain a high degree of similarity with respect to the original sequence, notwithstanding the fact that the sequences are no longer identical.

The term "ligand" as used herein refers to a molecule that is capable of binding to a FXR polypeptide or portion thereof. The term "agonist" as used herein refers to a molecule that binds to and activates a receptor polypeptide or portion thereof. The term "antagonist" as used herein refers to a molecule that attenuates the effect of an agonist. The term "partial agonist" as used herein refers to an agonist that is incapable of producing maximal activation of a receptor, as compared to a full agonist, at any concentration.

Ligands that are suitable for use in the methods and compositions of the invention include, but are not limited to, bile acids (natural, modified or synthetic) and related compounds such as CDCA (chenodeoxycholic acid), GCDCA (glycochenodeoxycholic acid), TCDCA (taurochenodeoxycholic acid), GCA (glycocholic acid), TCA (taurocholic acid), DCA (deoxycholic acid), LCA (lithocholic acid), DHCA (dehydrocholic acid), UDCA (ursodeoxycholic acid) and CA (cholic acid).

Bile acids are derivatives of cholesterol synthesized in the hepatocyte. Cholesterol, ingested as part of the diet or derived from hepatic synthesis is converted into the bile acids cholic and chenodeoxycholic acids, which are then conjugated to an amino acid (glycine or taurine) to yield the conjugated form that is actively secreted into cannaliculi. Bile acids are facial amphipathic, that is, they contain both hydrophobic (lipid soluble) and polar (hydrophilic) faces. The cholesterol-derived portion of a bile acid has one face that is hydrophobic (that with methyl groups) and one that is hydrophilic (that with the hydroxyl groups); the amino acid conjugate is polar and hydrophilic.

Any compounds that are capable of binding to the LBD of FXR can also be used in methods and compositions of the present invention. In a presently preferred embodiment, the ligand is selected from the group consisting of fexaramine, fexarine, fexarene and GW4064, the structures of which are presented in FIG. 1. An endogenous agonist, such as the bile acid CDCA can also be crystallized and/or modeled according the methods of the present invention. Additional bile acids and other ligands are described in, for example, Makishima et al. (1999), supra. Methods and compositions described herein can also employ coactivators and corepressors with which FXR interacts.

Any test compound can be tested for its ability to regulate or modulate transcription-activating effects of a farnesoid activated receptor polypeptide using the following exemplary method. Host cells containing a FXR LBD, or transfected with a FXR LBD expression construct, may be transfected with a target reporter construct encoding a reporter protein, such as luciferase. When cells containing both a FXR LBD and a reporter construct as below are contacted with a test compound that has agonist activity, expression of the reporter protein is activated, and the reporter is detected. When cells containing both a FXR LBD and a reporter construct as below are contacted with a known agonist in addition to a test compound that has antagonist activity, the level of expression of the reporter protein is decreased relative to the level of expression in the presence of the known agonist alone. When cells containing both a FXR LBD and a reporter construct as below are contacted with a test compound that has partial agonist activity, the level of expression of the reporter protein is decreased relative to the level of expression in the presence of a known agonist, even at the highest concentrations of the compound that is a partial agonist The reporter construct in this exemplary system comprises: (a) a promoter that is operable in said cell, (b) a hormone response element that is responsive to the DNA binding domain of the receptor (FXR DBD if native or alternative DBD if FXR is chimeric), and (c) DNA encoding a reporter protein, wherein said reporter protein-encoding DNA segment is operatively linked to said promoter for transcription of said DNA segment, and wherein said promoter is operatively linked to said hormone response element for activation thereof.

Other molecules are also capable of binding to a FXR polypeptide or portion thereof. Such molecules include any compound that can interact with the ligand binding domain of a FXR themselves, or prevent access of another molecule to the ligand binding domain of a FXR by binding to FXR at another location, for example, small chemical compounds (natural, modified or synthetic), drugs, other polypeptides or proteins, antibodies, nucleic acids, or the like.

Test molecules or test compounds may be developed de novo, or from a known ligand of FXR, such as a bile acid (natural, modified or synthetic). Test molecules may also be developed using a computer algorithm to predict a three-dimensional representation of the test molecule interacting with a FXR based upon a three-dimensional representation of A FXR molecule or fragment thereof.

According to another aspect of the present invention, there are provided methods of identifying a compound with agonist activity for a farnesoid X receptor (FXR) molecule, said method comprising:
(a) modeling a test compound that potentially interacts with the ligand binding domain of said FXR molecule or a fragment thereof, wherein said ligand binding domain is defined by a plurality of structure coordinates of the ligand binding domain of a FXR molecule or a fragment thereof,
    wherein said plurality of structure coordinates are derived from X-ray diffraction data obtained from crystals of said FXR molecule or molecular complex or a homologue of said FXR molecule or molecular complex; and
(b) determining the ability of said test compound to activate said FXR molecule.

According to another aspect of the present invention, there are provided methods of identifying a compound with antagonist activity for a farnesoid X receptor (FXR) molecule, said method comprising:
(a) modeling a test compound that potentially interacts with the ligand binding domain of said FXR molecule or a fragment thereof, wherein said ligand binding domain is defined by a plurality of structure coordinates of the ligand binding domain of a FXR molecule or a fragment thereof,
wherein said plurality of structure coordinates are derived from X-ray diffraction data obtained from crystals of said FXR molecule or molecular complex or a homologue of said FXR molecule or molecular complex; and
(b) determining the ability of said test compound to modulate the activity of said FXR molecule in the presence of a known FXR agonist According to another aspect of the present invention, there are provided methods of identifying a compound with partial agonist activity for a farnesoid X receptor (FXR) molecule, said method comprising:
(a) modeling a test compound that potentially interacts with the ligand binding domain of said FXR molecule or a fragment thereof, wherein said ligand binding domain is defined by a plurality of structure coordinates of the ligand binding domain of a FXR molecule or a fragment thereof,
    wherein said plurality of structure coordinates are derived from X-ray diffraction data obtained from crystals of said FXR molecule or molecular complex or a homologue of said FXR molecule or molecular complex; and
(b) determining the ability of said test compound to modulate the activity of said FXR molecule in the optional presence of a known FXR agonist.

Any agonist of FXR or potential agonist may be used in such methods. Typically, a test compound exhibiting antagonist activity tested in combination with a known agonist will decrease the level of activity or activation of FXR as compared to the level of activity or activation of FXR in the presence of the agonist alone. Typically, a test compound exhibiting partial agonist activity will not activate FXR to the same level as a known agonist, regardless of the concentrations tested.

In preferred embodiments, said plurality of structure coordinates are set forth in Appendix 1, or a portion thereof sufficient to define the points of interaction between said ligand binding domain and a ligand therefor.

Also provided are compositions of compounds identified by such methods, as well as pharmaceutical compositions comprising such compounds and a pharmaceutically acceptable carrier therefor.

According to the present invention, a FXR polypeptide comprising the LBD of FXR can be synthesized and isolated using methods that are well known in the art. Nucleic acid sequences encoding a FXR or a portion thereof can be produced by the methods described herein, or any alternative methods available to the skilled artisan. In designing the nucleic acid sequence of interest, it may be desirable to reengineer the gene for improved expression in a particular expression system. For example, it has been shown that many bacterially derived genes do not express well in plant systems. In some cases, plant-derived genes do not express well in bacteria. This phenomenon may be due to the non-optimal G+C content and/or A+T content of the gene relative to the expression system being used. For example, the very low G+C content of many bacterial genes results in the generation of sequences mimicking or duplicating plant gene control sequences that are highly A+T rich. The presence of A+T rich sequences within the genes introduced into plants (e.g., TATA box regions normally found in promoters) may result in aberrant transcription of the gene(s). In addition, the presence of other regulatory sequences residing in the transcribed mRNA (e.g., polyadenylation signal sequences (AAUAAA) or sequences complementary to small nuclear RNAs involved in pre-mRNA splicing) may lead to RNA instability. Therefore, one goal in the design of genes is to generate nucleic acid sequences that have a G+C content that affords mRNA stability and translation accuracy for a particular expression system.

Due to the plasticity afforded by the redundancy of the genetic code (i.e., many amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. Therefore, in reengineering genes for expression, one may wish to determine the codon bias of the organism in which the gene is to be expressed. The usage of codons for genes of a particular organism can be determined by analyzing such genes that have been deposited in GenBank or other databases containing nucleotide sequence information. After determining the bias thereof, the new gene sequence can be analyzed for restriction enzyme sites as well as other sites that could affect transcription such as exon:intron junctions, polyA addition signals, or RNA polymerase termination signals.

Genes encoding a FXR polypeptide comprising the LBD of FXR can be placed in an appropriate vector, depending on the artisan's interest, and can be expressed using a suitable expression system. An expression vector, as is well known in the art, typically includes elements that permit replication of said vector within the host cell and may contain one or more phenotypic markers for selection of cells containing said gene. The expression vector will typically contain sequences that control expression such as promoter sequences, ribosome-binding sites, and translational initiation and termination sequences. Expression vectors may also contain elements such as subgenomic promoters, a repressor gene or various activator genes. The artisan may also choose to include nucleic acid sequences that result in secretion of the gene product, movement of said product to a particular organelle such as a plant plastid (see, e.g., U.S. Pat. Nos. 4,762,785; 5,451,513 and 5,545,817, which are incorporated by reference herein) or other sequences that increase the ease of peptide purification, such as an affinity tag.

A wide variety of expression control sequences are useful in expressing the gene encoding the polypeptide when operably linked thereto. Such expression control sequences include, for example, the early and late promoters of SV40 for animal cells, the lac system, the trp system, major operator and promoter systems of phage S, and the control regions of coat proteins, particularly those from RNA viruses in plants. In *E. coli*, a useful transcriptional control sequence is the T7 RNA polymerase binding promoter, which can be incorporated into a pET vector as described by Studier et al., Meth. Enzymol. 185:60-89 (1990), which is incorporated by reference herein.

For expression, a desired gene should be operably linked to the expression control sequence and maintain the appropriate reading frame to permit production of the desired polypeptide. Any of a wide variety of well-known expression vectors are of use in the practice of the present invention. These include, for example, vectors comprising segments of chromosomal, non-chromosomal and synthetic DNA sequences such as those derived from SV40, bacterial plasmids including those from *E. coli* such as col E1, pCR1, pBR322 and derivatives thereof, pMB9, wider host range plasmids such as RP4, phage DNA such as phage S, NM989, M13, and other such systems as described by Sambrook et al., (MOLECULAR CLONIG, A LABORATORY MANUAL, $2^{nd}$ Ed. (1989) Cold Spring Harbor Laboratory Press), which is incorporated by reference herein.

A wide variety of host cells are available for expressing polypeptides of the present invention. Such host cells include, for example, bacteria such as *E. coli, Bacillus* and *Streptomyces*, fungi, yeast, animal cells, plant cells, insect cells, and the like. Preferred embodiments of the present invention include FXR polypeptides comprising the LBD of FXR that are expressed in *E. coli* with a histidine tag to facilitate purification.

Once a polypeptide of the present invention is expressed, the protein obtained therefrom can be isolated or purified so that structural analysis, modeling, and/or biochemical analysis can be performed, as exemplified herein. The nature of the protein obtained can be dependent on the expression system used. For example, genes, when expressed in mammalian or other eukaryotic cells, may contain latent signal sequences that may result in glycosylation, phosphorylation, or other post-translational modifications, which may or may not alter function. Therefore, a preferred embodiment of the present invention is the expression of FXR genes or portions thereof in *E. coli* cells. Once such proteins are expressed, they can be easily purified using techniques common to the person having ordinary skill in the art of protein biochemistry, such as, for example, techniques described in Colligan et al. (CURRENT PROTOCOLS IN PROTEIN SCIENCE, Chanda, Ed., John Wiley & Sons, Inc., (1997)), which is incorporated by reference herein. Such techniques often include the use of cation-exchange or anion-exchange chromatography, gel filtration-size exclusion chromatography, and the like. Another technique that may be commonly used is affinity chromatography. Affinity chromatography can include the use of antibodies, substrate analogs, or histidine residues (His-tag technology as preferred herein).

By a "substantially pure polypeptide" is meant a polypeptide which has been separated from components which naturally accompany it. Typically, the polypeptide is substantially pure when it is at least 60%, by weight, free from the proteins and naturally-occurring molecules with which it is naturally associated. Preferably, the preparation is at least 75%, more preferably at least 90%, and most preferably at least 99%, by weight, polypeptide of interest. A substantially pure polypeptide may be obtained, for example, by extraction from a natural source; by expression of a recombinant nucleic acid encoding the polypeptide; or by chemically synthesizing the protein. Purity can be measured by any appropriate method (e.g., column chromatography, polyacrylamide gel electrophoresis, by HPLC analysis, and the like).

Once purified, the present invention allows for the characterization of FXR polypeptides comprising the LBD of FXR by crystallization followed by X-ray diffraction. Polypeptide crystallization occurs in solutions where the polypeptide concentration exceeds it solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk media to promote associations that lead to crystallization.

Compounds known as "precipitants" are often used to decrease the solubility of the polypeptide in a concentrated solution by forming an energetically unfavorable precipitating layer around the polypeptide molecules (Weber, *Adv. Prot. Chem.* 41:1-36 (1991)). In addition to precipitants, other materials are sometimes added to the polypeptide crystallization solution. These include buffers to adjust the pH of the solution and salts to reduce the solubility of the polypeptide. Various precipitants are known in the art and include, for example, ethanol, 3-ethyl-2-4 pentanediol, many of the polyglycols, such as polyethylene glycol, and the like.

Commonly used polypeptide crystallization methods include, for example, batch, hanging drop, seed initiation, and dialysis methods. In each of these methods, it is important to promote continued crystallization after nucleation by maintaining a supersaturated solution. In the batch method, the polypeptide is mixed with precipitants to achieve supersaturation, the vessel is sealed, and set aside until crystals appear. In the dialysis method, the polypeptide is retained in a sealed dialysis membrane that is placed into a solution containing precipitant. Equilibration across the membrane increases the polypeptide and precipitant concentrations thereby causing the polypeptide to reach supersaturation levels.

In the preferred hanging drop technique (McPherson, *J. Biol. Chem.* 251:6300-6303 (1976)), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide will form.

Another method of crystallization involves introducing a nucleation site into a concentrated polypeptide solution. Generally, a concentrated polypeptide solution is prepared and a seed crystal of the polypeptide is introduced into this solution. If the concentrations of the polypeptide and of any precipitants are correct, the seed crystal will provide a nucleation site around which a larger crystal forms.

Some proteins may be recalcitrant to crystallization. However, several techniques are available to the skilled artisan. Quite often the removal of polypeptide segments at the amino or carboxy terminal end of the protein is necessary to produce crystalline protein samples. Said procedures involve either the treatment of the protein with one of several proteases including trypsin, chymotrypsin, substilisin, and the like. This treatment often results in the removal of flexible polypeptide segments that are likely to negatively affect crystallization. Alternatively, the removal of coding sequences from the protein's gene facilitates the recombinant expression of shortened proteins that can be screened for crystallization. In preferred embodiments of the present invention, only the LBD of FXR, amino acid residues 248-476 of SEQ ID NO:1, is expressed for crystallization.

The crystals so produced have a wide range of uses. For example, high quality crystals are suitable for X-ray or neutron diffraction analysis to determine the three-dimensional structure of a FXR, to design mutants thereof, to determine ligand binding properties and pharmacokinetics thereof, and the like. In addition, crystallization can serve as a further purification method. In some instances, a polypeptide or protein will crystallize from a heterogeneous mixture into crystals. Isolation of such crystals by methods known in the art, for example, filtration, centrifugation, and the like, followed by redissolving the polypeptide affords a purified solution suitable for use in growing the high-quality crystals needed for diffraction studies. The high-quality crystals may also be dissolved in water and then formulated to provide an aqueous solution having other uses as desired.

Because FXR polypeptides may crystallize in more than one crystal form, the structure coordinates of a FXR or portions thereof, as provided by this invention, are particularly useful to solve the structure of other crystal forms of a FXR polypeptide. Said structure coordinates, as provided herein in Appendix 1, may also be used to solve the structure of FXR homologues or portions thereof.

The structure coordinates disclosed herein may be used to determine the structure of the crystalline form of other proteins with significant amino acid or structural homology to any functional domain of a FXR. One method that may be employed for such purpose is molecular replacement. In this method, the unknown crystal structure, whether it is another crystal form of a FXR, a FXR having a mutation of one or more amino acid position(s), or the crystal of some other protein with significant sequence and/or structural homology to a FXR, may be determined using the coordinates provided herein. This method provides structural information for the unknown crystal in sufficient detail for further evaluation, and is more efficient than attempting to determine such information ab initio. In addition, this method can be used to determine whether or not a given FXR molecule in question falls within the scope of this invention.

The terms "structure coordinates", "structural coordinates", "atomic coordinates", "data set", "X-ray coordinates" or "X-ray data coordinates" as used herein are interchangeable, and refer to a data set (or portions thereof) that defines the three-dimensional structure of a molecule, for example, as set forth in Appendix 1. In particular, the LBD of FXR can be defined by a particular set of points of interaction between specific amino acid residues of the FXR LBD and a ligand therefor, for example, as illustrated in FIGS. 6C-6E. Amino acid residues of FXR that may be used as reference points of interaction to define the LBD include two or more of Phe288, Leu291, Thr292, Met294, Ala295, His298, Met332, Phe333, Ser336, Ile339, Phe340, Leu344, Leu352, Ile356, Ile361, Tyr365, Met369, Phe370, Tyr373, His451, Met454, Leu455, Trp458, Phe465, Leu469, and Trp473.

In preferred embodiments, crystals of the LBD of FXR complexed with the high affinity agonist fexaramine belong to space group $P2_12_12_1$ with unit cell dimensions of about a=37 Å, b=57 Å, c=117 Å, and $\alpha=\beta=\gamma=90°$. The data sets are derived from mathematical equations related to the patterns obtained on diffraction of a monochromatic beam of X-rays by the atoms (scattering centers) of a protein molecule in crystal form. The diffraction data are used to calculate an electron density map of the repeating unit of the crystal cell. Structure coordinates can be slightly modified and still render nearly identical three-dimensional structures. A measure of a unique set of structure coordinates is the root-mean-square (r.m.s.) deviation of the resulting structure. Structure coordinates that render three-dimensional structures that deviate from one another by an r.m.s. deviation of less than about 1.5 Å may be viewed as identical since they have little effect on the overall structure, and would not significantly alter the nature of binding associations. Furthermore, those of skill in the art understand that a set of coordinates for a polypeptide or portion thereof, is a relative set of points that define the three-dimensional shape of said polypeptide or portion thereof. As such, it is possible that an entirely different set of structure coordinates could define a similar or identical shape. Hence, the structure coordinates set forth in Appendix 1 are not limited to the express values set forth therein.

X-ray crystallography can elucidate the three-dimensional structure of crystalline forms according to the invention. Typically, the first characterization of crystalline forms by X-ray crystallography can determine the unit cell shape and its orientation in the crystal. The term "unit cell" refers to the smallest and simplest volume element of a crystal that is completely representative of the unit of pattern of the crystal. The dimensions of the unit cell are defined by six numbers: dimensions a, b and c and angles $\alpha$, $\beta$ and $\gamma$. A crystal can be viewed as an efficiently packed array of multiple unit cells. Detailed descriptions of crystallographic terms are provided in Hahn, THE INTERNATIONAL TABLES FOR CRYSTALLOGRAPHY, VOLUME A, 4th Ed., Kluwer Academic Publishers (1996); and Shmueli, THE NATIONAL TABLES FOR CRYSTALLOGRAPHY, VOLUME B, 1st Ed., Kluwer Academic Publishers. The term "space group" refers to the symmetry of a unit cell. In a space group designation (e.g., P2) the capital letter indicates the lattice type and the other symbols represent symmetry operations that can be carried out on the unit cell without changing its appearance.

The term "selenomethionine substitution" refers to the method of producing a chemically modified form of a protein crystal. The protein is expressed by bacteria in media that is depleted in methionine and supplement with selenomethionine. Selenium is thereby incorporated into the crystal in place of methionine sulfurs. The location(s) of selenium is(are) determined by X-ray diffraction analysis of the crystal. This information is used to generate the phase information used to construct a three-dimensional structure of the protein.

"Heavy atom derivatization" refers to a method of producing a chemically modified form of a protein crystal. In practice, a crystal is soaked in a solution containing heavy atom salts or organometallic compounds, e.g., lead chloride, gold thiomalate, thimerosal, uranyl acetate, and the like, which can diffuse through the crystal and bind to the protein's surface. Locations of the bound heavy atoms can be determined by X-ray diffraction analysis of the soaked crystal. This information is then used to construct phase information which can then be used to construct three-dimensional structures of the enzyme as described in Blundel and Johnson, PROTEIN CRYSTALLOGRAPHY, Academic Press (1976), which is incorporated by reference herein.

The knowledge obtained from X-ray diffraction patterns can be used in the determination of the three-dimensional structure of the binding sites of other homologous polypeptides. This is achieved through the use of commercially available software known in the art that is capable of generating three-dimensional graphical representations of molecules or portions thereof from a set of structure coordinates. The binding domain can also be predicted by various computer models. Based on the structural X-ray coordinates of the solved structure, mutations and variants of the solved structure can also be designed.

According to another aspect of the present invention, there is provided a computer method for producing a three-dimensional representation of a FXR molecule or molecular complex or a homologue of said molecule or molecular complex, wherein said molecule or molecular complex or a homologue of said molecule or molecular complex comprises a LBD defined by structure coordinates obtained from X-ray diffraction data obtained from crystals of said FXR molecule of molecular complex or a homologue thereof. Said computer comprises:

(i) a computer-readable data storage medium comprising a data storage material encoded with computer-readable data, wherein said data comprises X-ray diffraction data obtained from crystals of said FXR molecule or molecular complex or a homologue of said FXR molecule or molecular complex;

(ii) a working memory for storing instructions for processing said computer-readable data;

(ii) a central-processing unit coupled to said working memory and to said computer-readable data storage medium for processing said computer-machine readable data into said three-dimensional representation; and (iv) a display coupled to said central-processing unit for displaying said three-dimensional representation.

Figure 6:
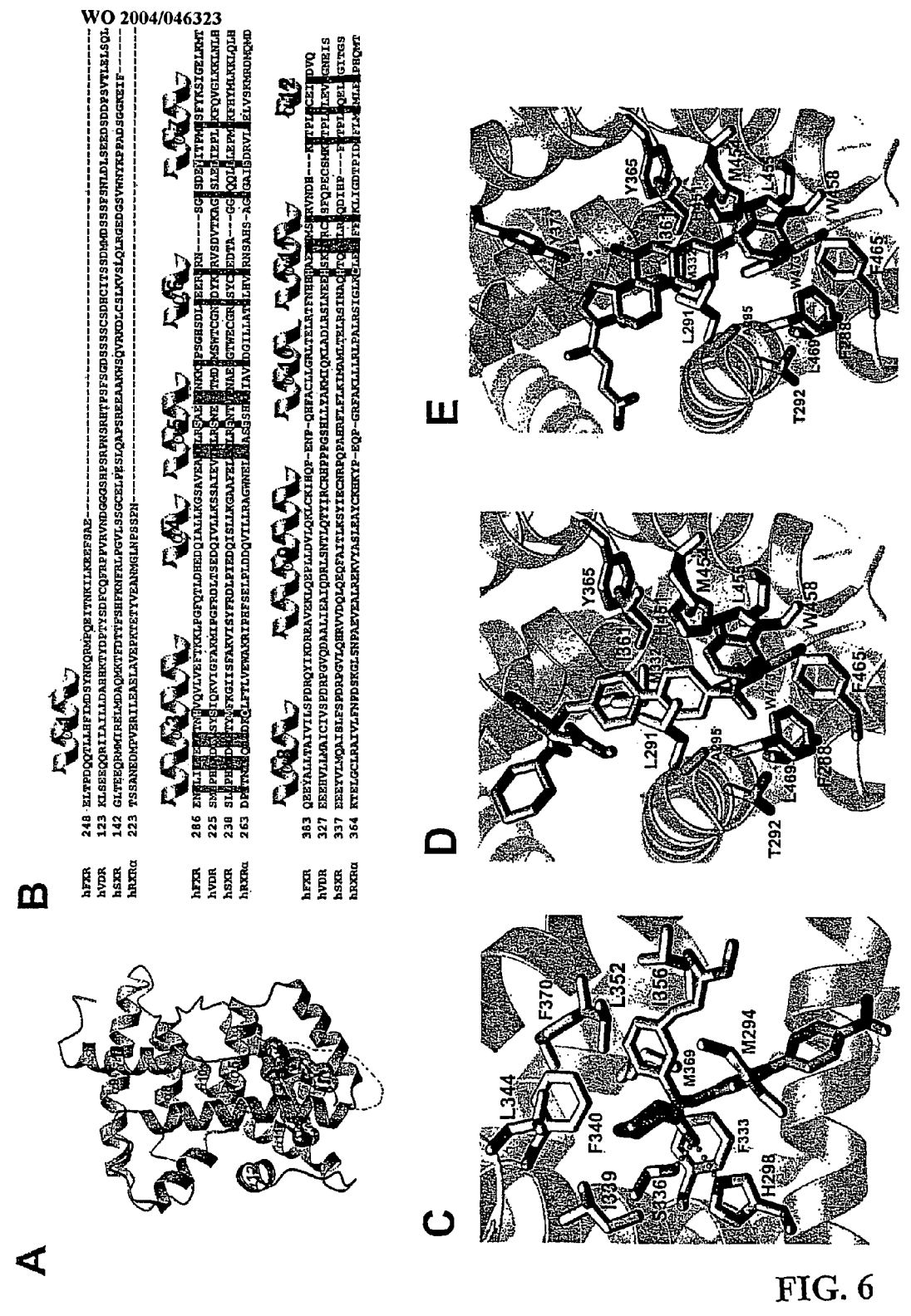

In preferred embodiments, the structure coordinates are set forth in Appendix 1, or a portion thereof sufficient to define the points of interaction between said LBD and a ligand therefor. The points of interaction can be one or more amino acid residues of the LBD which come into contact with or proximity with a molecule capable of binding the FXR LBD, as illustrated in FIG. 6.

The term "molecular complex" as used herein refers to a FXR polypeptide or portion thereof combined with one or more additional molecules. For example, in preferred embodiments, the contemplated molecular complex comprises the FXR LBD together with a high affinity agonist, such as, for example, fexaramine, fexarene, ortho-fluoro-fexarene, and the like.

According to another aspect of the present invention, there is provided a computer for determining at least a portion of the structure coordinates corresponding to X-ray diffraction data obtained from a FXR molecule or molecular complex or a homologue of said FXR molecule or molecular complex, said computer comprising:

(i) a computer-readable data storage medium comprising a data storage material encoded with machine-readable data, wherein said data comprises at least a portion of the structure coordinates of Appendix 1;

(ii) a computer-readable data storage medium comprising a data storage material encoded with computer-readable data, wherein said data comprises X-ray diffraction data obtained from said FXR molecule or molecular complex or a homologue of said FXR molecule or molecular complex;

(iii) a working memory for storing instructions for processing said computer-readable data of (i) and (ii);

(iv) a central-processing unit coupled to said working memory and to said computer-readable data storage medium of (i) and (ii) for performing a Fourier transform of the machine readable data of (i) and for processing said computer-readable data of (ii) into structure coordinates; and (v) a display coupled to said central-processing unit for displaying said structure coordinates of said molecule or molecular complex.

The term "computer" as used herein can be composed of a central processing unit (for example, the Pentium III from Intel Corporation, or similar processor from Sun, Motorola, Compaq, AMD or International Business Machines, and the like), a working memory which may be random-access memory or core memory, mass storage memory (for example, one or more floppy disk drives, compact disk drives or magnetic tape containing data recorded thereon), at least one display terminal, at least one keyboard and accompanying input and output devices and connections therefor. The computer typically includes a mechanism for processing, accessing and manipulating input data. A skilled artisan can readily appreciate that any one of the currently available computer systems are suitable. It should also be noted that the computer can be linked to other computer systems in a network or wide area network to provide centralized access to the information contained within the computer.

Contemplated input devices for entering machine readable data include, for example, telephone modem lines, cable modems, CD-ROMs, a keyboard or disk drives. The computer may advantageously include or be programmed with appropriate software for reading the data from the data storage component or input device, for example computational programs for use in rational drug design that are described in detail below. Contemplated output devices include conventional systems known in the art, for example, display terminals, printers, or disk drives for further storage of output.

Embodiments of the invention include systems (e.g., internet based systems), particularly computer systems which store and manipulate the coordinate and sequence information described herein. One example of a computer system 100 is illustrated in block diagram form in FIG. 7. As used herein, "a computer system" refers to the hardware components, software components, and data storage components used to analyze the coordinates and sequences such as those set forth in Appendix 1. The computer system 100 typically includes a processor for processing, accessing and manipulating the sequence data. The processor 105 can be any well-known type of central processing unit, such as, for example, the Pentium III from Intel Corporation, or similar processor from other suppliers such as Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM and one or more internal data storage devices 110, such as a hard drive and/or other computer readable media having data recorded thereon. In some embodiments, the computer system 100 further includes one or more data retrieving device(s) 118 for reading the data stored on the internal data storage devices 110.

The data retrieving device 118 may represent, for example, a floppy disk drive, a compact disk drive, a magnetic tape drive, a modem capable of connection to a remote data storage system (e.g., via the internet), and the like. In some embodiments, the internal data storage device 110 is a removable computer readable medium such as a floppy disk, a compact disk, a magnetic tape, and the like, containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125*a-c* in a network or wide area network to provide centralized access to the computer system 100.

Software for accessing and processing the coordinate and sequences of Appendix 1, (such as search tools, compare tools, and modeling tools etc.) may reside in main memory 115 during execution.

Computer programs are widely available that are capable of carrying out the activities necessary to model structures and substrates using the crystal structure information provided herein. Examples include, but are not limited to, the computer programs listed below:

Catalyst Databases™—an information retrieval program accessing chemical databases such as BioByte Master File, Derwent WDI and ACD;

Catalyst/HYPO™—generates models of compounds and hypotheses to explain variations of activity with the structure of drug candidates;

Ludi™—fits molecules into the active site of a protein by identifying and matching complementary polar and hydrophobic groups;

Leapfrog™—"grows" new ligands using an algorithm with parameters under the control of the user.

In addition, various general purpose machines may be used with programs written in accordance with the teachings herein, or it may be more convenient to construct more specialized apparatus to perform the operations. However, preferably this is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

"Molecular replacement" refers to generating a preliminary model of a polypeptide whose structure coordinates are unknown, by orienting and positioning a molecule whose structure coordinates are known within the unit cell of the unknown crystal so as to best account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, *Meth. Enzymol.* 115:55-77 (1985); Rossmann, M G., ed., THE MOLECULAR REPLACEMENT METHOD (1972), Int. Sci. Rev. Ser. No. 13, Gordon & Breach, New York). Using structure coordinates of the FXR LBD provided herein, molecular replacement may be used to determine the structure coordinates of a crystalline mutant, homologue, or a different crystal form of a FXR LBD.

In accordance with this invention, a FXR polypeptide, or a portion thereof such as the LBD, may be crystallized in association or complex with any known or putative ligands. The crystal structures of a series of such complexes may then be solved by molecular replacement and compared with that of a native FXR molecule. Potential sites for modification within the FXR molecule or a corresponding ligand may thus be identified based on the points of interaction between a ligand and the LBD of FXR. This information provides an additional tool for determining the most efficient binding interactions, for example, increased hydrophobic interactions, between FXR and a putative chemical entity or compound, even before any synthesis or modifications are performed.

All of the complexes referred to above may be studied using well-known X-ray diffraction techniques as described herein, and may be refined versus 2-3 Å resolution X-ray data to an R value of about 0.20 or less using computer software, such as X-PLOR (Yale University, 1992, distributed by Molecular Simulations, Inc.). See, e.g., Blundel & Johnson, supra; Methods in Enzymology, vol. 114 and 115, H. W. Wyckoff et al., eds., Academic Press (1985). This information may thus be used to optimize known classes of FXR binding agents or ligand, such as natural bile acids, and to design, modify and/or synthesize novel classes of FXR ligands.

The modeling or design of compounds or ligands that bind to and/or modulate a FXR polypeptide according to the invention generally involves consideration of two factors. First, the compound or molecule must be capable of physically and structurally associating with a FXR molecule. Non-covalent molecular interactions important in the association of a FXR with a putative ligand include hydrogen bonding, van der Waals and hydrophobic interactions, and the like.

Second, the compound or molecule must be able to assume a conformation that allows it to associate with a FXR molecule. Although certain portions of the compound or molecule will not directly participate in this association, those portions may still influence the overall conformation of the molecule. This, in turn, may have a significant impact on affinity with the receptor. Such conformational requirements include the overall three-dimensional structure and orientation of the compound or molecule in relation to all or a portion of the binding site, e.g., LBD or any potential accessory binding sites, or the spacing between functional groups of a compound or molecule comprising several chemical entities that directly interact with FXR.

The term "modeling" as used herein, refers to analysis of the interaction of FXR and a known or test compound or molecule by utilizing a computer generated representation of the molecules, as opposed to physical molecules.

The potential binding of a test compound with a FXR may be analyzed prior to its actual synthesis and testing by the use of computer modeling techniques. If the theoretical structure of the given compound suggests insufficient interaction and association between it and FXR, synthesis and testing of the compound may be obviated. However, if computer modeling indicates a strong interaction, the molecule may then be tested for its ability to bind to FXR. Methods of assaying for FXR activity are known in the art (as identified and discussed herein). Methods for assaying the effect of a potential binding agent can be performed in the presence of a known binding agent of FXR. For example, the effect of the potential binding agent can be assayed by measuring the ability of the potential binding agent to compete with a known binding agent.

A test compound may be computationally evaluated and designed by means of a series of steps in which chemical entities or fragments are screened and selected for their ability to associate with the individual binding pockets or other areas of FXR associated with ligand binding. In particular, the ability to form points of interaction with the approximately 25 amino acid residues of the LBD identified earlier and depicted in FIG. 6 can be assessed.

One skilled in the art may use one of several methods to predict a molecule capable of binding to FXR and to screen test compounds for their ability to associate with a FXR and more particularly with the individual binding pockets or LBD of a FXR polypeptide. This process may begin by visual inspection of, for example, the LBD on the computer screen based on structure coordinates obtained derived from X-ray diffraction data obtained from crystals of FXR, such as those provided in Appendix 1. Selected fragments or chemical entities may then be positioned in a variety of orientations, or docked, within an individual binding pocket of the FXR LBD. Docking may be accomplished using software such as Quanta and Sybyl, followed by energy minimization and molecular dynamics with standard molecular mechanics forcefields, such as CHARMM and AMBER.

Specialized computer programs may also assist in the process of selecting fragments or chemical entities at this stage. These include:

1. GRID (Goodford, P. J., "A Computational Procedure for Determining Energetically Favorable Binding Sites on Biologically Important Macromolecules", J. Med. Chem., 28, pp. 849-857 (1985)). GRID is available from Oxford University, Oxford, UK.
2. MCSS (Miranker, A. and M. Karplus, "Functionality Maps of Binding Sites: A Multiple Copy Simultaneous Search Method." Proteins: Structure. Function and Genetics, 11, pp. 29-34 (1991)). MCSS is available from Molecular Simulations, Burlington, Mass.
3. AUTODOCK (Goodsell, D. S. and A. J. Olsen, "Automated Docking of Substrates to Proteins by Simulated Annealing", Proteins: Structure. Function, and Genetics, 8, pp. 195-202 (1990)). AUTODOCK is available from Scripps Research Institute, La Jolla, Calif.
4. DOCK (Kuntz, I. D. et al., "A Geometric Approach to Macromolecule-Ligand Interactions", J. Mol. Biol., 161, pp. 269-288 (1982)). DOCK is available from University of California, San Francisco, Calif.

Once suitable chemical entities or fragments have been selected, they can be assembled into a single compound that is a candidate ligand. Assembly may be performed by visual inspection of the relationship of the fragments to each other on the three-dimensional image displayed on a computer screen in relation to the structure coordinates of the FXR molecule as set forth in Appendix 1. This would be followed by manual model building using software such as Quanta or Sybyl.

Useful programs to aid one of skill in the art in connecting the individual chemical entities or fragments include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182-196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992)).
3. HOOK (available from Molecular Simulations, Burlington, Mass.).

In addition to the method of building or identifying a ligand in a stepwise fashion one fragment or chemical entity at a time as described above, FXR ligands may be designed as a whole or "de novo" using either an empty LBD site or optionally including some portion(s) of a known ligand(s). These methods include:

1. LUDI (Bohm, H.-J., "The Computer Program LUDI: A New Method for the De Novo Design of Enzyme Inhibitors", J. Comp. Aid. Molec. Design, 6, pp. 61-78 (1992)). LUDI is available from Biosym Technologies, San Diego, Calif.
2. LEGEND (Nishibata, Y. and A. Itai, Tetrahedron, 47, p. 8985 (1991)). LEGEND is available from Molecular Simulations, Burlington, Mass.
3. LeapFrog (available from Tripos Associates, St Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33, pp. 883-894 (1990). See also, Navia, M. A, and M. A, Murcko, "The Use of Structural Information in Drug Design", Current Opinions in Structural Biology, 2, pp. 202-210 (1992).

Once a test compound or binding agent has been designed or selected by the above methods, the efficiency with which that compound may bind to a FXR may be tested and optimized by computational evaluation.

A compound designed or selected as a putative ligand may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the binding agent and FXR when the ligand is bound to the FXR, preferably make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., 1992); AMBER, version 4.0 (P. A. Kollman, University of California at San Francisco, 1994); QUANTA/CHARMM (Molecular Simulations, Inc., Burlington, Mass. 1994); and Insight II/Discover (Biosysm Technologies Inc., San Diego, Calif., 1994). These programs may be implemented, for example, using a Silicon Graphics workstation, IRIS 4D/35 or IBM RISC/6000 workstation model 550. Other hardware systems and software packages will be known to those skilled in the art of which the speed and capacity are continually modified.

Other molecular modeling techniques may also be employed in accordance with this invention. For exemplary reviews and techniques, see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)]

In another embodiment of the present invention, the crystal structure and structure coordinates may be employed for the design of novel therapeutics. The transactivating capability of FXR on multiple target genes can be modified in new ways with novel compounds identified herein.

Bile acid synthesis is a major pathway for cholesterol disposal and thus represents a potential therapeutic target pathway for the treatment of hypercholesterolemia. FXR acts as a bile acid receptor and biological sensor for the regulation of bile acid biosynthesis. FXR is known to regulate cholesterol metabolism in two ways: (1) chenodeoxycholic acid (CDCA), a primary bile acid, binds directly to and activates FXR, which then mediates the feedback suppression by bile acids of cholesterol 7 alpha-hydroxylase (CYP7A1), the rate-limiting enzyme in bile acid biosynthesis from cholesterol; and (2) FXR participates in the activation of intestinal bile acid binding protein (IBABP), which is involved in the enterohepatic circulation of bile acids. Thus FXR constitutes a potential therapeutic target that can be modulated to enhance the removal of cholesterol from the body. Novel compounds identified by the methods presented herein provide a new tool for regulating or modulating FXR function.

Furthermore, FXR is known to in turn activate a series of target genes. In particular FXR functions as a heterodimer with the 9-cis-retinoic acid receptor (RXR). A number of target DNA binding sequences that would be present in target genes have recently been identified. A consensus sequence has been determined, which contains an inverted repeat of the sequence AGGTCA with a 1-base pair spacing (IR-1) (Laffitte et al. (2000) Identification of the DNA binding specificity and potential target genes for the farnesoid X-activated receptor. *J. Biol. Chem.* 275:10638-10647). This sequence was shown to be a high affinity binding site for FXR/RXR in vitro and to confer ligand-dependent transcriptional activation by FXR/RXR to a heterologous promoter in response to a bile acid or synthetic retinoid. Although these studies demonstrated that the FXR/RXR heterodimer binds to the consensus IR-1 sequence with the highest affinity, it was also demonstrated that FXR/RXR can bind to and activate through a variety of elements including IR-1 elements with changes in the core half-site sequence, spacing nucleotide, and flanking nucleotides. In addition, it was shown that FXR/RXR can bind to and transactivate through direct repeats. Therefore, by providing novel ways to modulate FXR function, the present invention in turn provides a method of modulating the function of a variety of target genes that are acted upon by FXR.

A FXR modulating agent or compound identified by the methods of the present invention may be administered with a pharmaceutically-acceptable diluent, carrier, or excipient, in unit dosage form. Conventional pharmaceutical practice may be employed to provide suitable formulations or compositions to administer to a subject suffering from bile acid imbalances, for example. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, oral administration, or the like. Therapeutic formulations may be in the form of liquid solutions or suspensions; for oral administration, formulations may be in the form of tablets, capsules or the like; and for intranasal formulations, in the form of powders, nasal drops, aerosols, or the like.

Methods well known in the art for making formulations are found in, for example, Remington's Pharmaceutical Sciences, 15th ed. Easton: Mack Publishing Co., 1405-1412, 1461-1487 (1975) and The National Formulary XIV, 14th ed. Washington: American Pharmaceutical Association (1975), the contents of which are hereby incorporated by reference. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for IAP modulatory agents include ethylene-vinyl acetate copolymer particles, osmotic pumps, implantable infusion systems, liposomes, and the like. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The following terms are provided to facilitate the reader's understanding of the crystal compositions of FXR provided herein.

"Isolated" refers to a protein or nucleic acid that has been identified and separated from its natural environment. Contaminant components of its natural environment may include enzymes, hormones, and other proteinaceous or non-proteinaceous solutes. In one embodiment, the isolated molecule, in the case of a protein, will be purified to a degree sufficient to obtain at least 15 residues of N-terminal or internal amino acid sequence or to homogeneity by SDS-PAGE under reducing or non-reducing conditions using Coomassie blue or silver stain. In the case of a nucleic acid the isolated molecule will preferably be purified to a degree sufficient to obtain a nucleic acid sequence using standard sequencing methods.

As used herein, "naturally occurring amino acid" and "naturally occurring R-group" includes L-isomers of the twenty amino acids naturally occurring in proteins. Naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specially indicated, all amino acids referred to in this application are in the L-form.

"Unnatural amino acid" and "unnatural R-group" includes amino acids that are not naturally found in proteins. Examples of unnatural amino acids included herein are racemic mixtures of selenocysteine and selenomethionine. In addition, unnatural amino acids include the D or L forms of, for example, nor-leucine, para-nitrophenylalanine, homophenylalanine, para-fluorophenylalanine, 3-amino-2-benzylpropionic acid, homoarginines, D-phenylalanine, and the like.

"R-group" refers to the substituent attached to the α-carbon of an amino acid residue. An R-group is an important determinant of the overall chemical character of an amino acid. There are twenty natural R-groups found in proteins, which make up the twenty naturally occurring amino acids.

"α-carbon" refers to the chiral carbon atom found in an amino acid residue. Typically, four substituents will be covalently bound to said α-carbon including an amine group, a carboxylic acid group, a hydrogen atom, and an R-group. The α-carbon atoms can also be referred to by their crystal structure coordinates as a convenient reference point.

"Positively charged amino acid" and "positively charged R-group" includes any naturally occurring or unnatural amino acid having a side chain, which is positively charged under normal physiological conditions. Examples of positively charged, naturally occurring amino acids include arginine, lysine, histidine, and the like.

"Negatively charged amino acid" and "negatively charged R-group" includes any naturally occurring or unnatural amino acid having a side chain, which is negatively charged under normal physiological conditions. Examples of negatively charged, naturally occurring amino acids include aspartic acid, glutamic acid, and the like.

"Hydrophobic amino acid" and "hydrophobic R-group" includes any naturally occurring or unnatural amino acid that is relatively insoluble in water. Examples of naturally occurring hydrophobic amino acids are alanine, leucine, isoleucine, valine, proline, phenylalanine, tryptophan, methionine, and the like.

"Hydrophilic amino acid" and "hydrophilic R-group" includes any naturally occurring or unnatural amino acid that is relatively soluble in water. Examples of naturally occurring hydrophilic amino acids include serine, threonine, tyrosine, asparagine, glutamine, cysteine, and the like.

"Degenerate variations thereof" refers to changing a gene sequence using the degenerate nature of the genetic code to encode proteins having the same amino acid sequence yet having a different gene sequence. For example, FXRs of the present invention are based on amino acid sequences. Degenerate gene variations thereof can be made encoding the same protein due to the plasticity of the genetic code, as described herein.

"Expression" refers to transcription of a gene or nucleic acid sequence, stable accumulation of nucleic acid, and the translation of that nucleic acid to a polypeptide sequence. Expression of genes also involves transcription of the gene to make RNA, processing of RNA into mRNA in eukaryotic systems, and translation of mRNA into proteins. It is not necessary for the genes to integrate into the genome of a cell in order to achieve expression. This definition in no way limits expression to a particular system or to being confined to cells or a particular cell type and is meant to include cellular, transient, in vitro, in vivo, and viral expression systems in both prokaryotic, eukaryotic cells, and the like.

"Foreign" or "heterologous" genes refers to a gene encoding a protein whose exact amino acid sequence is not normally found in the host cell.

"Promoter" and "promoter regulatory element", and the like, refers to a nucleotide sequence element within a nucleic acid fragment or gene that controls the expression of that gene. These can also include expression control sequences. Promoter regulatory elements, and the like, from a variety of sources can be used efficiently to promote gene expression. Promoter regulatory elements are meant to include constitutive, tissue-specific, developmental-specific, inducible, subgenomic promoters, and the like. Promoter regulatory elements may also include certain enhancer elements or silencing elements that improve or regulate transcriptional efficiency. Promoter regulatory elements are recognized by RNA polymerases, promote the binding thereof, and facilitate RNA transcription.

A polypeptide is a chain of amino acids, regardless of length or post-translational modification (e.g., glycosylation or phosphorylation). A polypeptide or protein refers to a polymer in which the monomers are amino acid residues, which are joined together through amide bonds. When the amino acids are alpha-amino acids, either the L-optical isomer or the D-optical isomer can be used, the L-isomers being typical. An exemplary FXR polypeptide of the invention is provided as an amino acid sequence set forth in SEQ ID NO:1.

Accordingly, the polypeptides of the invention are intended to cover naturally occurring proteins, as well as those which are recombinantly or synthetically synthesized. Polypeptide or protein fragments are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general polypeptides of the invention include peptides, or full-length protein, that contains substitutions, deletions, or insertions into the protein backbone, that would still have an approximately 70%-90% homology to the original protein over the corresponding portion. A yet greater degree of departure from homology is allowed if like-amino acids, i.e. conservative amino acid substitutions, do not count as a change in the sequence.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of amine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylamine to tyrosine, leucine or methionine; serine to threonine; threonine to serine; tryptophan to tyrosine; tyrosine to tryptophan or phenylalanine; valine to isoleucine or leucine, and the like. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture, and so on.

The term "variant" refers to polypeptides modified at one or more amino acid residues yet still retain the biological activity of a FXR polypeptide. Variants can be produced by any number of means known in the art, including, for example, methods such as, for example, error-prone PCR, shuffling, oligonucleotide-directed mutagenesis, assembly PCR, sexual PCR mutagenesis, and the like, as well as any combination thereof. Variants of FXR may also be FXR proteins, or isoforms or homologues naturally found in other species.

By "substantially identical" is meant a polypeptide or nucleic acid exhibiting at least 50%, preferably 60%, more preferably 70%, more preferably 80%, more preferably 85%, more preferably 90%, and most preferably 95% homology to a reference amino acid or nucleic acid sequence.

Sequence homology and identity are often measured using sequence analysis software (e.g., Sequence Analysis Software Package of the Genetics Computer Group, University of Wisconsin Biotechnology Center, 1710 University Avenue, Madison, Wis. 53705). The term "identity" in the context of two or more nucleic acids or polypeptide sequences, refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. The term "homology" in the context of two or more nucleic acids or polypeptide sequences, refers to two or more sequences or subsequences that are homologous or have a specified percentage of amino acid residues or nucleotides that are homologous when compared and aligned for maximum correspondence over a comparison window or designated region as measured using any number of sequence comparison algorithms or by manual alignment and visual inspection. Programs as mentioned above allow for amino acid substitutions with similar amino acids matches by assigning degrees of homology to determine a degree of homology between the sequences being compared.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2-482 (1981), by the homology alignment algorithm of Needleman & Wunsch, J. Mol. Biol. 48:443 (1970), by the search for similarity method of Person & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, accessible on the world wide web (www) at the URL "weber.u.Washington.edu/~roach/human_genome_progress 2.html") (Gibbs, 1995). Several databases containing genomic information annotated with some functional information are maintained by different organization, and are accessible via the internet on the world wide wed (www), for example, at the URL "tigr.org/tdb"; "genetics.wisc.edu"; "genome-www.stanford.edu/~ball"; "hiv-web.lanl.gov"; "ncbi.nlm.nih.gov"; "ebi.ac.uk"; "Pasteur.fr/other/biology"; and "genome.wi.mit.edu".

One example of a useful algorithm is BLAST and BLAST 2.0 algorithms, which are described in Altschul et al., Nucl. Acids Res. 25:3389-3402 (1977), and Altschul et al., J. Mol. Biol. 215:403-410 (1990), respectively. Software for performing BLASE analyses is publicly available through the National Center for Biotechnology Information on the world wide web (www) at the URL "ncbi.nlm.nih.gov". This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAT program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see. Henikoff & Henikoff, Proc. Natl. Acad. Sc. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445 (1992); Henikoff and Henikoff, Proteins 17:49-61 (1993)). Less preferably, the PAM or PAM250 matrices may also be used (see, e.g., Schwartz and Dayhoff, eds., *Matrices for Detecting Distance Relationships: Atlas of Protein Sequence and Structure*, Washington: National Biomedical Research Foundation (1978)). BLAST programs are accessible through the U.S. National Library of Medicine, e.g., accessible on the world wide web (www) at ncbi.nlm.nih.gov.

The parameters used with the above algorithms may be adapted depending on the sequence length and degree of homology studied. In some embodiments, the parameters may be the default parameters used by the algorithms in the absence of instructions from the user.

A detailed description of FXR LBD structure is provided below as a preferred embodiment of the invention.

The crystal structure of the ligand binding domain (LBD) of human FXR (hFXR, amino acids 248-476 of SEQ ID NO:1) in complex with the novel potent agonist identified herein, fexaramine was determined to 1.78 Å resolution. The hFXR LBD adopts a 12 alpha helix bundle as seen in all NHR LBD structures (RXRα (Egea et al. (2000). Crystal structure of the human RXRa ligand-binding domain to its natural ligand: 9-cis retinoic acid EMBO J. 19, 2592-2601), PXR/SXR (Watkins et al. (2001). The Human Nuclear Xenobiotic Receptor PXR: Structural Determinants of Directed Promiscuity, Science, 292, 2329-2333), PPARγ (Xu et al. (2001). Structural determinants of ligand binding selectivity between the peroxisome proliferator-activated receptors. Proc Natl Acad Sci USA. 98(24), 13919-24) and RORβ (Stehlin et al. (2001). X-ray structure of the orphan nuclear receptor ROR-beta ligand-binding domain in the active conformation. EMBO J. 20(21), 5822-31; see FIGS. 6A and 6B). The most significant difference between FXR and other NHRs (RXR, VDR and PPARs) is in the replacement of the β-turn found following helix 5 with a more pronounced helix 6 (see FIG. 6A). Also, the 15-residue insertion region between helices 1 and 3 is completely disordered in the FXR crystal structure (see FIGS. 6A and B). RXRα, which most closely resembles FXR in both primary sequence and length of the insertion region, has an additional helix (helix 2) in this position in the absence of ligand that unfolds upon binding of 9-cis retinoic acid (Egea et al. (2000, supra). This region of RXRα has been proposed to act as a "molecular spring" that accommodates the large conformational movements of helix 3 upon ligand binding. The insertion region may serve a similar role in hFXR, facilitating helix 3 rearrangements upon ligand binding. In the PPARs, this region contains a helix 2 and is the proposed ligand access site for the binding pocket. In SXR (Watkins et al (2001), supra) and VDR (Rochel et al. (2000). The Crystal Structure of the Nuclear Receptor for Vitamin D Bound to its Natural Ligand. Mol Cell 5, 173-179) the insertion domain region is significantly longer (see FIG. 6B). Analysis of root mean square deviations (RMSD) between the apo and ligand bound structures of SXR and VDR revealed no significant differences, suggesting that a shorter insertion domain region may be responsible for regulating large rearrangements of helix 3.

Significantly, the activation function-2 domain (AF2 or helix 12), essential for transcriptional activation of the receptor is packed against the body of FXR, positioned between helices 3 and 4 (see FIG. 6A). This dosed or active conformation is a signature feature that enables stable interactions between NHRs and their co-activator accessory protein partners (Xu et al. (2001), supra). By homology with NHR LBD structures, the LXXLL co-activator binding sequence would interact with the hydrophobic pocket formed between helices 3, 4, 5, and 12 that interacts with the hydrophobic face of the LXXLL helix located within co-activator proteins.

The ligand-binding cavity of the hFXR LBD is predominantly hydrophobic in nature and is formed by about 25 amino acids (see FIGS. 6C and 6D). The binding pocket has a volume of 726 $Å^3$ which is smaller than that seen in SXR ($1150 Å^3$) (Watkins et al. (2001), supra), but larger than that of RXRα ($439 Å^3$) (Egea et al. (2000), supra; see FIG. 6E). The fexaramine is sequestered between a helices 3 and 7 and makes significant contacts with helices 5, 6, 11 and 12 (see FIG. 6B).

Interactions between FXR and fexaramine can be divided into two sets. The first set stabilizes the hexyl ring and the first benzene ring as well as the methyl ester moieties. The hexyl group makes minimal van der Waals contacts with Ile339 and Leu344 (helix 5), while Phe333 helix 5) and Met369 and Phe370 (helix 7) create a hydrophobic surface behind fexaramine's central nitrogen and single benzyl group. Met294 (helix 3) as well as Leu352 and Ile356 (helix 6) stabilize the aliphatic linker between the first benzene ring and the methyl ester moiety (see FIG. 6C). The methyl ester itself occupies a neutral groove between helices 3 and 6 and is stabilized by two hydrogen bonds from the NE2 proton of His298 (helix 3) and the hydroxyl of Ser336 (helix 5) to the amide carbonyl oxygen of fexaramine.

The second set of interactions stabilizes the biaryl rings and the dimethyl amine moiety. Phe288, Leu291, Thr292, and Ala295 (helix 3) form a hydrophobic surface on one side, while Ile361 (helix 6 and loop 7) and His451, Met454, Leu455, and Trp458 (helix 11) form a hydrophobic surface on the other side of fexaramine's double ring structure. Phe465 (helix 11 and loop 12) and Leu469 and Trp473 (helix 12) bridge the hydrophobic surface from the helix 11 region to helix 3 creating a deep hydrophobic pocket that is filled by the biaryl moiety (see FIG. 6E).

Thus, some combination of at least two of these amino acid residues in particular, and/or the structure coordinates corresponding thereto, can be used to define the points of interaction between a known or putative ligand or molecule capable of binding to FXR, and a FXR molecule.

The present invention provides novel chemical tools that activate FXR in a highly potent and specific fashion. Fexaramine was identified by utilization of a cell-based assay to screen a combinatorial library of approximately 10000 benzopyran compounds. The original compounds were discovered from the screen-activated FXR in the low μM range and were unique in chemical structure. Once discovered, these compounds were then systematically optimized to subsequently elucidate a high affinity agonist for FXR, termed fexaramine. The compound is chemically distinct from other synthetic and physiological agonists previously reported for FXR. Intensive structure activity analysis of this compound determined that the 3-methylcinnamate moiety in region I in addition to the cyclohexyl amide unit in region II are optimal for FXR agonist activity. Addition of a biaryl amine subunit at region III was necessary to achieve the maximal efficacy on FXR.

Characterization of fexaramine was undertaken and reported using both in vitro and in vivo assays. In vitro assays established that fexaramine and related ligands robustly recruited the co-activator SRC-1 peptide to FXR in a manner comparable to that of GW4064. Rigorous analysis of cell based in vivo assays with FXR response elements (ECRE and ERA) and natural promoters of known target genes IBABP, PLTP and MRP-2 showed that these ligands could potently activate FXR in a concentration-dependent manner. When tested in cross reactivity experiments the fexaramine class of ligands showed no activity against a diverse range of other nuclear hormone receptors. Unlike the fexaramine class of compounds, GW4064 required the accessory protein RXR to achieve maximal efficacy in the chimeric GAL4DBD-FXR-LBD protein. This suggests that the in vivo binding of GW4064 to FXR may recognize the FXR/RXR heterodimer preferentially. Induction of known target genes in both intestinal and liver cell systems demonstrated the usefulness of the identified compounds in studying FXR target genes. In intestinal cells treatment with fexaramine robustly induced the IBABP gene in a concentration dependent manner with efficacy similar to GW4064. Likewise, in the HEPG2 liver cell system, strong induction of target genes SHP, PLTP BSEP and MRP-2 was achieved at comparable concentrations of fexaramine and GW4064.

The specificity and efficacy of fexaramine allowed for a more detailed investigation of FXR target genes. Gene profiling of primary liver hepatocytes treated with three chemically distinct classes of FXR agonists revealed surprisingly little overlap. This exemplifies the difficulties of investigating NHR function using a ligand present at high physiological concentrations, and highlights the need for specific synthetic ligands. However, high affinity synthetic compounds tailored for the target protein may have non-specific effects on other pathways. This potential cross-reactivity may necessitate the development of multiple synthetic ligands to accurately discern receptor pathways and physiological relevance.

The crystal structure of FXR complexed with fexaramine allowed modeling of CDCA with a high degree of confidence into the ligand-binding pocket of FXR. This model provides a molecular explanation for the selectivity of BAs on FXR and highlighted the importance of position and orientation of the hydroxyl groups (position 7 and 3) in binding affinity. Specifically, this model provides a rationale for the beneficial effects of UDCA in the treatment of primary biliary cirrhosis. Although UDCA has two hydroxyl groups to potentially form hydrogen bonds with FXR in the ligand-binding cavity, their trans configuration create a more open ligand-binding pocket that would destabilize helix 12 and thereby inhibit activation of the receptor.

The present invention integrates chemical, genetic, and structural approaches to the analysis of FXR. In doing so, the present invention provides valuable and novel chemical tools to study the function of the receptor and also elucidates how FXR interacts with physiological natural and synthetic ligands at the molecular level.

The invention will now be described in greater detail by reference to the following non-limiting examples.

EXAMPLE 1

Identification and Development of Novel Small Molecule Ligands for FXR

Expression and Reporter Constructs

The expression plasmids pCMX, pCMX-LacZ, pCMX-mFXRFL, pCMX-hRXRFL, pCMX-GALDBD-rFXRLBD and other pCUX-GALDBD-NR LBDs (hRXRα, hPPARαγδ, mPXR, hPXR, hLXRα, HTRβ, hRARβ, mCAR, mERR3 and hVDR) have been described elsewhere (Blumberg et al. (1998). SXR, a novel steroid and xenobiotic-sensing nuclear receptor. Genes Dev. 12(20), 3195-205). The reporter plasmids pMH2004-TK-luc, pTKECRE*6-luc, pTKER-8*2-luc and pMRP-2-luc also have been described elsewhere. The hPLTP-luc promoter was kindly provided by Dr Dennis Dowhan and the hIBABP-luc promoter was created from a plasmid provided by Dr Philippe Besnard.

Standard PCR amplifications of the LBD of human FXR (residues 248 to 476) and sub-cloning techniques were used to generate pGEX Glutathione-s-transferase (GST) and pHIS8-3 (Jez et al. (2000) Dissection of malonyl-coenzyme A decarboxylation from polyketide formation in the reaction mechanism of a plant polyketide synthase. Biochemistry 39, 890-902) prokaryote protein expression vectors. DNA fragments containing hFXR aa248 to 476 were cloned into the BamHI site of pGEX-hFXR, while the cloning sites NcoI and BamHI sites were used in pHIS8-3.

The retroviral plasmids were constructed by cloning FXRFL, FXR-AF2 and VP16 FXR cDNAs into the BamHI site of the established pBABE retroviral backbone vector. Viral extracts were established using published procedures and used to infect HT29 colon cells which, after exposure for 24 hours, were selected by addition of 4 µg/ml of the drug puromycin. Cells that survived this selection procedure were then pooled and analyzed for the expression of the FXR gene.

All constructs were verified by double-stranded sequencing to confirm identity and reading frame. Detailed information regarding each construct is available upon request.

For transfection of these constructs, monkey CV-1 HEPG2 and HEK293T cells were grown in DMEM supplemented with 10% FBS, 50 U/ml penicillin G, and 50 µg/ml streptomycin sulfate at 37° C. in 7% CO2. CV-1 cells (60%-70% confluence, 48-well plate) were cotransfected with 16.6 ng of the appropriate expression vector, 100 ng of reporter plasmid, and 100 ng of pCMX-LacZ in 200 µl of DMEM containing 10% FBS by the N-[1-(2,3-dioleoyloxy)propyl]-N,N,N-trimethylammonium methylsulfate (DOTAP)-mediated procedure. After 24 hr, the medium was replaced, and cells were harvested and assayed for luciferase activity 36-48 hr after transfection. The luciferase activity was normalized to the level of β-galactosidase activity. Each transfection was performed in triplicate and repeated at least three times.

Solid Phase Synthesis of Small Molecule Ligands

The synthesis of this library was carried out on solid phase in a parallel fashion as summarized in the diagram below. Thus, Boc-protected cinnamic acid 1 was immobilized on Merrifield resin through the action of $Cs_2CO_3$ to afford conjugate 2. The Boc group was removed from this resin by treatment with 20% TFA (for abbreviations see the legend of diagram below) in $CH_2Cl_2$ and the resultant resin-bound amine was reductively alkylated with 4-bromobenzaldehyde in the presence of $NaCNBH_3$ to yield amino resin 3. Resin 3 was acylated with one of three acyl groups to give amide or urea resins 4. The acylated resins (4) were then subjected to either a Heck coupling [$Pd_2(dba)_3$, P(o-tol)$_3$, Et$_3$N] with thirteen substituted styrenes or a Suzuki coupling [Pd(PPh$_3$)$_4$, $Cs_2CO_3$] with eighteen boronic acids to yield stilbene resins 5 and biaryl resins 6, respectively. Cleavage of the resulting compounds from resins 5 and 6 with NaOMe yielded methyl cinnamates 7 and 8. Analysis of the library by LCMS after purification showed the average purity of these compounds to be >95%.

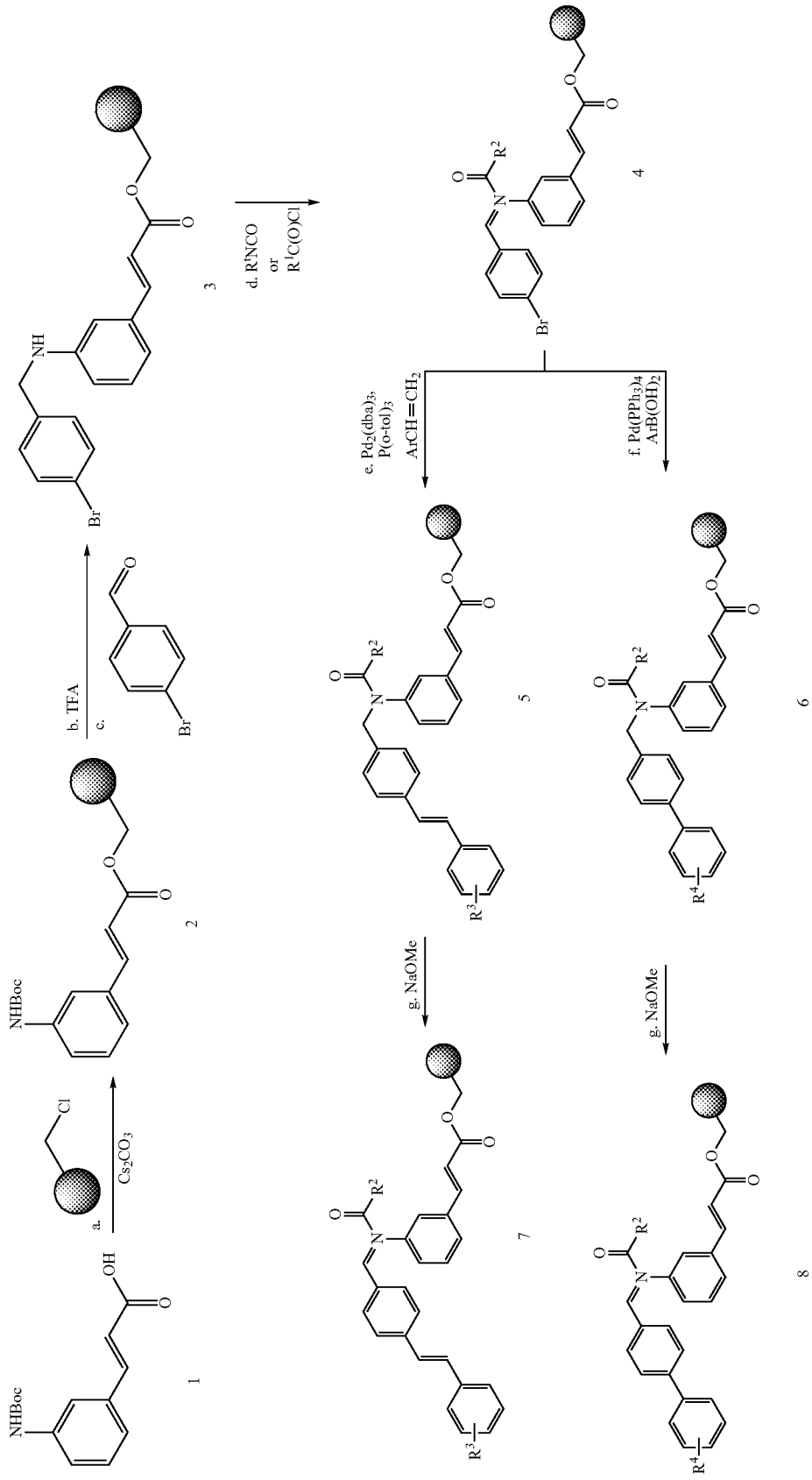

Solid phase synthesis of a 94-membered focused library of biaryl and stilbene cinnamates was as follows: Reagents and conditions: (a) 2.0 equiv of 3, 1.0 equiv of Merrifield Resin (0.91 mmol/g), 2.0 equiv of $Cs_2CO_3$, 0.5 equiv of TBAI, DMF, 55° C., 24 h; (b) 20% TFA in CH2Cl2, 25° C., 1 h; (c) 10.0 equiv of 4-bromobenzaldehyde, 0.05 equiv of AcOH, THF:MeOH (2:1), 25° C., 1 h; then, 8.0 equiv of NaCNBH3, THF:MeOH (2:1), 25° C., 2 h; (d) for R1COCl: 30.0 equiv of R1COCl, 40.0 equiv of Et3N, 1.0 equiv of 4-DMAP, CH2Cl2, 25° C., 12 h; for $R^1$NCO, 30.0 equiv of R1NCO, 40.0 equiv of Et3N, 1.0 equiv of 4-DMAP, DMF, 65° C., 60 h; (e) 8.0 equiv of styrene, 10.0 equiv of Et3N, 0.5 equiv of Pd2(dba)3, 1.5 equiv of P(o-tol)3, DMF, 90° C., 48 h; (f) 5.0 equiv of boronic acid, 3.0 equiv Cs2CO3, 0.5 equiv of $Pd(PPh_3)_4$, DMF, 90° C., 24 h; (g) 10.0 equiv of NaOMe, Et2O:MeOH (10:1), 25° C., 20 min. AcOH=acetic acid; 4-DMAP=4-dimethylaminopyridine; DMF=N,N-dimethylformamide; Et=ethyl; Me=methyl; Pd(PPh3)4=tetrakis(triphenylphosphine)palladium(0); Pd2(dba)3=tris(dibezylideneacetone)dipalladium(0); P(o-tol)3=tri-o-tolylphosphine; TBAI=tetrabutylammonium iodide; TEA=triethylamine; TFA=trifluoroacetic acid; THF=tetrahydrofuran.

Screening for FXR Ligands

To discover novel small molecule ligands for FXR, a constructed combinatorial library of approximately 10 000 benzopyran compounds was screened using a cell-based assay in a 384 well format (Nicolaou et al. (2000). Natural product-like combinatorial libraries based on privileged structures. 1. General principles and solid-phase synthesis of benzopyrans. J. Am. Chem. Soc. 122, 9939-9953; Natural product-like combinatorial libraries based on privileged structures. 2. Construction of a 10000-membered benzopyran library by directed split-and-pool chemistry using nanokans and optical encoding. J. Am. Chem. Soc. 122, 9954-9967; and Natural product-like combinatorial libraries based on privileged structures. 3. The "libraries from libraries" principle for diversity enhancement of benzopyran libraries. J. Am. Chem. Soc. 122, 9968-9976). This cell-based screen was based on the co-transfection of an expression vector containing the full-length FXR receptor with a reporter vector. The reporter vector contains a hormone response element under a minimal eukaryotic promoter driving a luciferase reporter gene. The initial screen identified several lead compounds, possessing activities ranging from 5-10 μM and whose prototypical structure (1) is shown in FIG. 1A. Lead compounds were re-tested and checked for cross-reactivity for the retinoid X receptor (RXR), the heterodimeric partner of FXR. None of the identified compounds had the ability to bind or activate RXR.

Systematic optimization of regions I and II of the prototypical structure through multiple rounds of screening using smaller "focused" chemical libraries defined the requisite features of these domains for high affinity binding to FXR. Specifically, incorporation of the 3-methylcinnamate moiety in region I and the cyclohexyl amide unit in region II resulted in a more than 10-fold enhancement in the potency, as demonstrated by compound 2 ($EC_{50}$=358 nM) (FIG. 1A). Preliminary exploration of region III suggested that replacement of the parent benzopyran unit with styrenyl and biaryl moieties within this latter scaffold (2) would yield compounds with even higher potency. This intelligence gathering was then used to design and synthesize on a solid support a focused library of 94 new compounds for further optimization.

Screening of the synthesized compound library led to the discovery of several highly potent ligands including (see FIG. 1); A [coined fexaramine: $EC_{50}$=25 nM], B [coined fexarine: $EC_{50}$=38 nM] and C [coined fexarene: $EC_{50}$=36 nM], as well as many lower affinity compounds such as D [coined SRI-1: $EC_{50}$=377 nM] and E [coined SRI-2: $EC_{50}$=343 nM], the structures of which are shown in FIG. 1B. Furthermore, these compounds are structurally distinct from the known natural and synthetic ligands for FXR; the BA chenodeoxycholic acid (CDCA) and GW4064 shown in FIG. 1B F and G. GW4064 exhibited $EC_{50}$ values of approximately 90 nM, comparable to the known values.

EXAMPLE 2

Activation of FXR by Novel Compounds

To determine if the compounds identified as ligands could promote the association of FXR with co-activators in vitro, a fluorescence resonance energy transfer (FRET)-based coactivator binding assay was employed (see, for example, Makishima et al. (1999), supra; Urizar et al. (2002). A natural product that lowers cholesterol as an antagonist ligand for FXR. Science. 296(5573), 1703-6). This assay relies on an agonist-induced interaction between the nuclear receptor and its coactivator bringing two fluorogenic partners together resulting in the nuclear receptor ligand-dependent FRET. Specific recruitment of a peptide containing the receptor binding domain of the steroid receptor co-activator SRC-1 (LXXLL) to the FXR ligand-binding domain was only observed in the presence of the agonists fexaramine, fexarine, fexarene, SRI-1, SRI-2 and GW4064 (see FIG. 1C). GW4064 demonstrated the strongest recruitment with an $EC_{50}$ value of 100 nM followed by fexaramine ($EC_{50}$ 255 nM), fexarine ($EC_{50}$ 222 nM), and fexarene ($EC_{50}$≈255 nM). Weaker recruitment is seen with compounds SRI-1 and SRI-2.

The ability of these compounds to activate the receptor in a number of different cell-based reporter gene assays was then determined. The recently identified high affinity non-steroidal synthetic compound GW4064 was used as a control in these experiments. CV-1 cells were transiently transfected with an expression plasmid for mouse FXR and human RXR with a thymidine kinase (minimal promoter reporter vector containing either no copies or six copies of the ecdysone response element (ECRE), a well-characterized FXR response element (FXRE). In addition, two copies of the recently identified FXRE everted repeat separated by 8 nucleotides (ER-8) was also studied (see, for example, Laffitte et al. (2000). Identification of the DNA binding specificity and potential target genes for the farnesoid X-activated receptor. J Biol. Chem. 275(14), 10638-47; Kast et al. (2002). Regulation of multidrug resistance-associated protein 2 (ABCC2) by the nuclear receptors pregnane X receptor, farnesoid X-activated receptor, and constitutive androstane receptor. J Biol Chem. 277(4), 2908-15).

Figure 2:
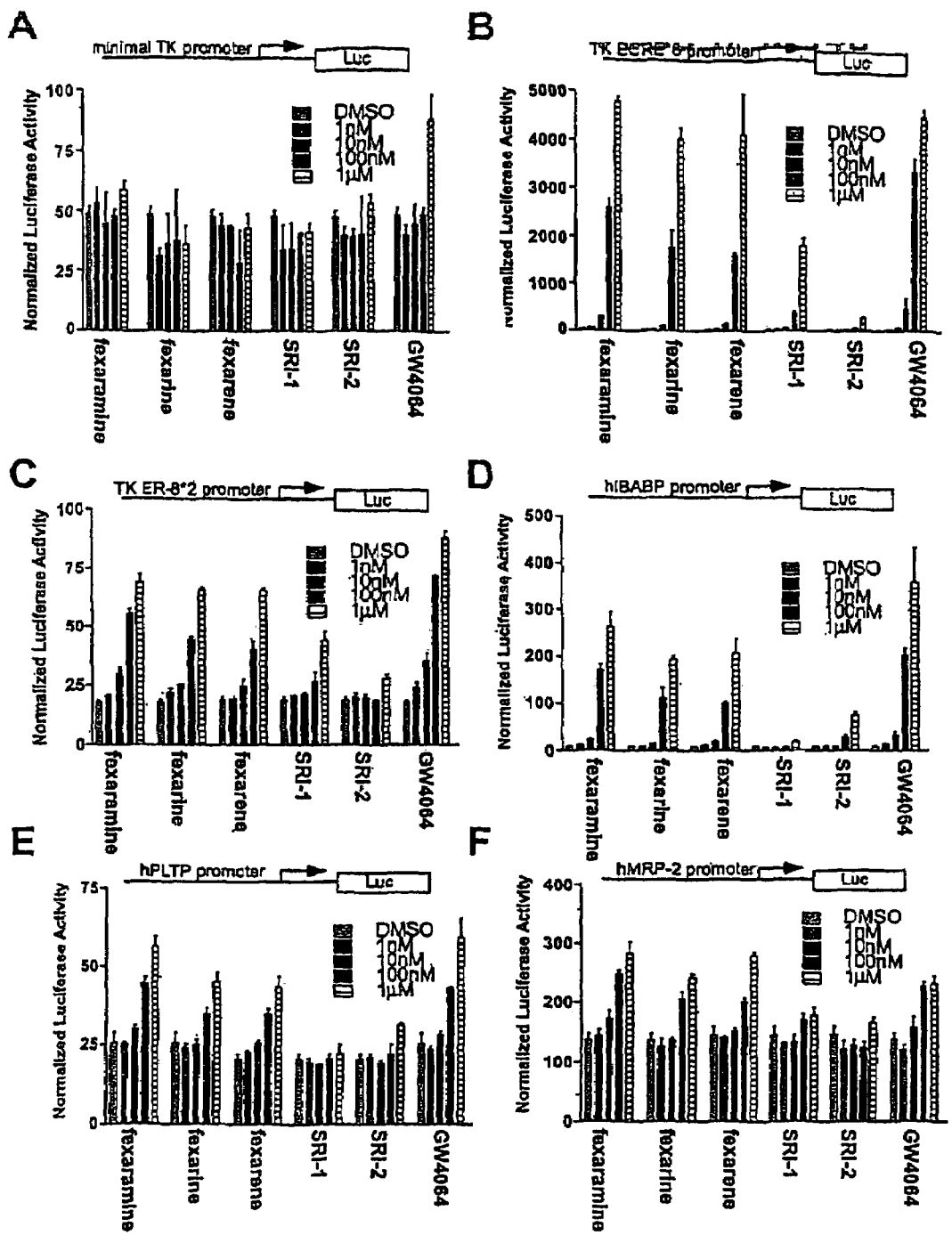
FIGS. 2A-2F collectively show the results of ligand activation of CV-1 cells co-transfected with FXR constructs pCMX-mFXR and pCMX-hRXR and a luciferase reporter gene containing various promoters as follows.

The cells were then treated with increasing concentrations of fexaramine, fexarine, fexarene, SRI-1, SRI-2 or GW4064. The results depicted in FIGS. 2B and C show that fexaramine, fexarine, fexarene and GW4064 showed robust activation of both of the FXREs (ECRE 100-fold; ER-8 4-fold) with a maximal activity achieved at 1 μM (concentrations higher than 1 μM were tested but produced no more activity). The compounds SRI-1 and SRI-2, although structurally similar to fexaramine, showed little or no activity. Novel compounds identified above showed no activity on the minimal TK promoter. However, GW4064 displayed a weak activity (less than 2 fold) on this promoter (see FIG. 2A). Similar results were found in a variety of different cell types including liver cells (HEPG2) and kidney cells (HEK 293).

Having demonstrated that the newly identified compounds could robustly activate multiple copies of FXREs linked to a TK minimal promoter, the ability of the compounds to activate natural promoters of known FXR targets in a transient transfection cell-based assay was examined. For this study, the following gene promoters were used: intestinal bile acid binding protein (IBABP; see, for example, Grober et al. (1999). Identification of a bile acid-responsive element in the human ileal bile acid-binding protein gene. Involvement of the farnesoid X receptor/9-is-retinoic acid receptor heterodimer. J Biol Chem. 274(42), 29749-54>, phospholipid transfer protein (PLTP) (Urizar et al (2000). The farnesoid X-activated receptor mediates bile acid activation of phospholipid transfer protein gene expression. J Biol Chem. 275 (50), 39313-7) and multidrug resistance related protein 2 (MRP-2) (Kast et al. (2002), supra), which are all well characterized targets of FXR. The natural promoters of both the IBABP and PLTP genes contain one copy of an inverted repeat with a one base spacing (IR-1) while MRP-2 contains an ER-8 element. The results obtained, shown in FIGS. 2 D (hIBABP promoter), 2E (hPLTP promoter) and 2F (hMRP-2 promoter), were similar to experiments with multiple FXRE copies with maximum efficacy of the fexaramine, fexarine, fexarene and GW4064 compounds observed at 1 µM, while SRI-1 and SRI-2 showed little or no activity. The most robust activation (28-fold) was seen on the IBABP promoter. Less robust (2-3 fold) but specific activation was observed on the PLTP and MRP-2 promoters.

EXAMPLE 3

Cross Reactivity of FXR Ligands with Other Nuclear Receptors

Figure 3:
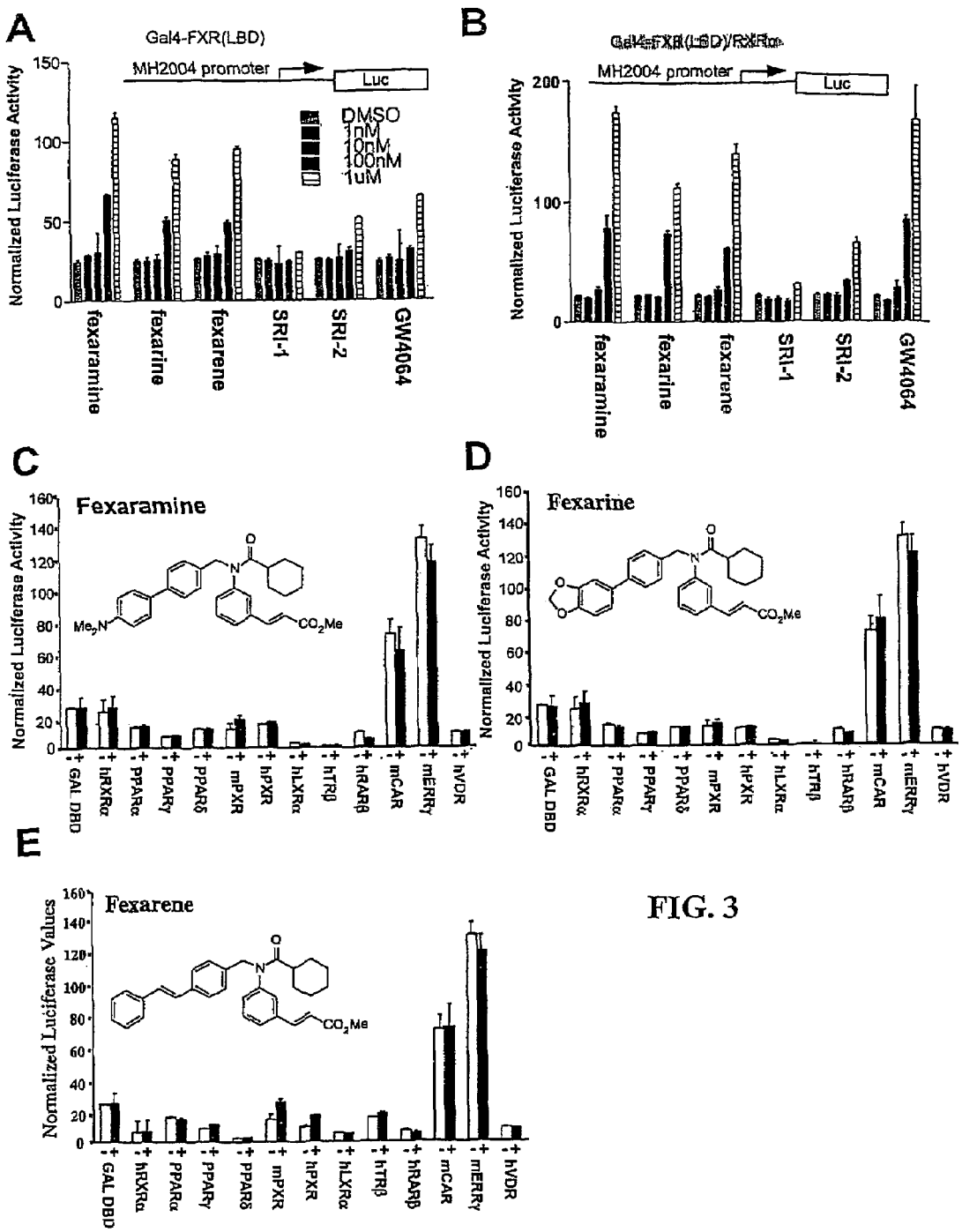
FIGS. 3A-3E collectively show the results of ligand activation of CV-1 cells co-transfected with a luciferase reporter gene with a variety of receptor expression constructs.

Cell-based transcriptional activation assays using chimeric nuclear hormone receptor (NHR) constructs were established to measure the selectivity of the compounds to FXR relative to other NHRs (Forman et al. (1995). Identification of a nuclear receptor that is activated by farnesol metabolites. Cell 81, 687-693). These assays used fusion proteins with the yeast GAL4 DNA binding domain connected to the ligand-binding domain (LBD) of NHRs. These constructs were co-transfected with a thymidine kinase C minimal promoter reporter vector containing four copies of the GAL4 binding site. Titration experiments were then performed using the identified compounds. FIGS. 3A and 3B show that fexaramine, fexarine, fexarene and GW4064 all activate the chimeric FXR construct in the presence and absence of RXR. Interestingly, fexaramine, fexarine, fexarene are more efficacious ligands for FXR than GW4064 in the absence of RXR suggesting some difference between the mechanism of activation between the two classes of compounds. Addition of RXR had no effect on the activation potential of fexaramine, fexarine, fexarene in this assay. Compounds SRI-1 and SRI-2 again showed little or no activity consistent with previous results.

In this assay fexaramine, fexarine and fexarene were highly selective for FXR. No activity was observed on other chimeric NHR constructs including hRXRα, hPPARαγδ, mPXR, hPXR, hLXRα, hTRβ, hRARβ, mCAR, mERR3 and hVDR (see FIGS. 3C-3E).

EXAMPLE 4

Induction of FXR Target Genes by Novel Compounds

RNA Isolation and Northern Blot Hybridization

HepG2 or HT29-derived cell lines were typically cultured in medium containing superstripped FBS for 24 hr before the addition of a ligand or DMSO (vehicle) for an additional 24-48 hr. Total RNA was isolated using TRIzol reagent and was resolved (10 µg/lane) on a 1% agarose, 2.2 M formaldehyde gel, transferred to a nylon membrane (Hybond N+; Amersham Biosciences, Inc.), and cross-linked to the membrane with UV light.

cDNA probes were radiolabeled with [α-$^{32}$P]dCTP using the highprime labeling kit (Amersham Biosciences, Inc.). Membranes were hybridized using the QuikHyb hybridization solution (Stratagene, La Jolla, Calif.) according to the manufacturer's protocol. Blots were normalized for variations of RNA loading by hybridization to a control probe, either, 18 S ribosomal cDNA, or the ribosomal protein 36B4. The RNA levels were quantitated using a PhosphorImager (ImageQuant software; Molecular Dynamics, Inc., Sunnyvale, Calif.) in addition to being exposed to X-ray film.

RNA Analysis of FXR Target Genes

The liver and the intestinal system are the major areas where FXR plays a role in the induction of specific gene targets in response to bile acid (BA) concentrations. To establish that the identified compounds are effective in studying the function of FXR in these systems, the compounds were examined for their ability to induce characterized gene targets. In addition to the ability to induce characterized gene targets, invention compounds are also useful for identification of gene targets for FXR, i.e., genes which are modulated (i.e., induced or repressed) by FXR.

Figure 4:
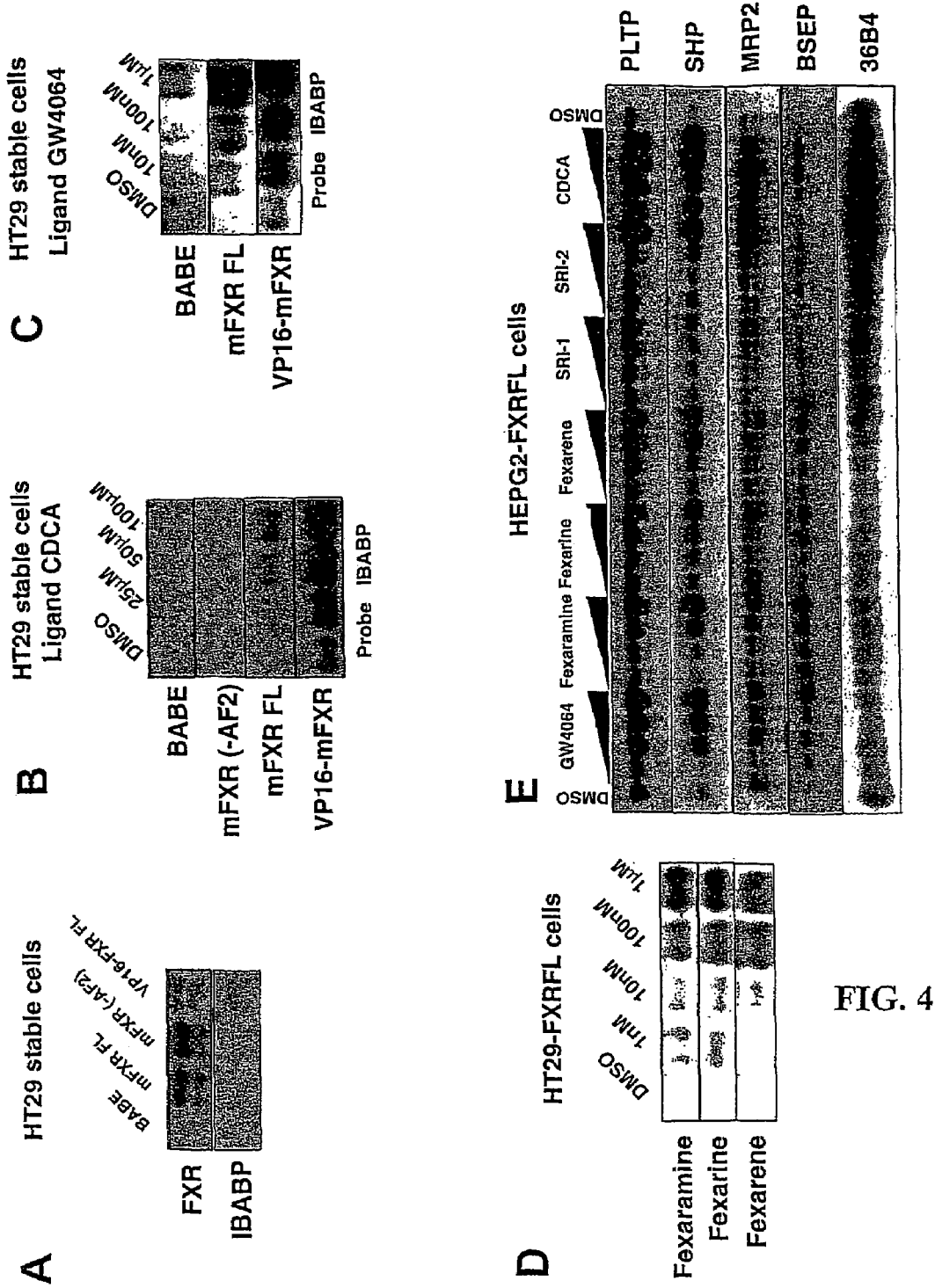
FIGS. 4A-4E collectively show levels of various RNAs expressed in cells containing FXR receptors, in some cases treated with FXR ligands.

Human colon cells HT29 (FXR null until differentiated) were infected with retroviral vectors that expressed either FXR constructs and the puromycin-resistant gene or the puromycin-resistant gene alone. Puromycin resistant cells were isolated and pooled cell populations were propagated that harbored either the vector alone (HT29-BABE), overexpressed FXR full length (HT29-FXRFL), a non-functional FXR truncated at the AF2 region (HT29-FXR-AF2), or a constitutively active FXR that has the VP16 activation domain fused N-terminal of the protein (HT29-VP16-FXR). Confirmation of the successful establishment of the different stable cell lines was established via northern blot analysis of FXR message levels in the cells (see FIG. 4A).

HT29-BABE lines do not express FXR while the stable cell lines expressed the exogenous FXR message. To test the ability of these cell lines to induce FXR target genes total RNA was isolated from cells treated overnight with increasing amounts of CDCA or GW4064. Northern blot analysis of the HT29-FXRFL cell line showed robust concentration dependent induction of IBABP mRNA by both CDCA and GW4064 (see FIGS. 4B and 4C). Maximal activation of the IBABP gene by CDCA was observed at 100 µM while only 1 µM of GW4064 was needed to achieve the same level of induction. No induction of IBABP mRNA levels was observed in the HT29-BABE or HT29-FXR-AF2 cell lines. Constitutive expression was seen in the HT29-VP16-FXR and was super-induced by addition of CDCA and GW4064.

These observations verify the usefulness of this colon cell model system for studying the induction of FXR target genes.

The ability of the novel compounds identified herein to induce IBABP gene expression in this cell system was also examined. Total RNA from HT29 stable cells treated overnight with fexaramine, fexarine and fexarene was probed for IBABP gene expression (see FIG. 4D). Fexaramine, fexarine and fexarene all induced expression of the IBABP mRNA in the HT29-FXRFL with similar profiles to that seen for GW4064 (maximal activity at 1 µM concentration). No induction was seen in the HT29-BABE or HT29-FXR-AF2 cell lines, proving the specificity of the compounds. These results demonstrate that the novel compounds of the present invention are effective in studying FXR target genes in an intestinal model cell system.

To demonstrate the usefulness of these compounds in studying FXR function in the liver, a model hepatocyte cell system that expresses the FXR gene was employed (Kast et al. (2002), supra). Confluent HEPG2-FXR cells were treated overnight with increasing concentrations of fexaramine, fexarine, fexarene SRI-1, SRI-2 and the control ligands GW4064 and CDCA. Total RNA was isolated and the expression of the FXR target genes SHP, MRP-2, BSEP and PLTP was measured by Northern blot analysis (see FIG. 4E).

The control ligands CDCA and GW4064 showed similar induction of the target genes to what has been previously reported. Of the novel compounds identified herein, fexaramine was the most effective inducer of target genes, although strong induction was also observed with fexarine and fexarene. In this hepatocyte cell system, maximal activation of FXR target genes by these compounds was achieved at 10 µM, which is similar to the control ligand GW4064. Interestingly, although GW4064 showed slightly better induction of the FXR target genes PLTP and SHP, fexaramine matched GW4064 induced activation of the BSEP and MRP-2 genes. These results demonstrate that these novel compounds can be used to identify and characterize new FXR target genes in the liver and the intestinal cell systems. Differences in efficacy of target gene induction between the liver and the intestinal cell systems may reflect the ability of the liver hepatocytes to mount a xenobotic response or cell specific permeability to the identified compounds. Modification of the ligands to overcome these effects may be made in order to increase the efficacy of these drugs in liver cell systems.

Further evidence that invention compounds can be used to identify and characterize additional FXR gene targets is provided by the large scale screening summarized in Appendix 2 (for genes upregulated by invention compounds) and Appendix 3 (for genes downregulated by invention compounds).

EXAMPLE 5

Gene Profiling of FXR Agonists

Having established fexaramine as a potent FXR specific agonist in two model cell systems, its gene activation profile with CDCA and GW4064 in human primary hepatocytes was then compared. Hepatocytes were treated with DMSO (control group), fexaramine (10 µM), CDCA (100 µM, or GW4064 (10 M and total RNA isolated at 6 and 12-hour time points. Prior to gene profiling experiments the samples were verified by Northern blot analysis for induction of a known FXR target gene SHP (see FIG. 5A). Subsequently, biotinylated cRNAs prepared from mRNA samples were hybridized to duplicate sets of high-density microarrays (U-133A set Affymetrix, Palo Alto, Calif.) to minimize experimental error.

A total of 222 transcripts were identified whose expression changed with respect to DMSO using a paired student's T-test. These genes were then subjected to hierarchal clustering and visualized using the Treeview. The most striking observation was the very unique profiles seen by the different FXR agonists (see FIG. 5B). Relatively few genes were observed whose expression changed with all three agonists. This may, in part, be due to CDCA regulating genes via non-FXR pathways. The recent body of work by Wang et al supports this idea, which demonstrated that BAs mediate repression of the CYP7A in a SHP independent manner through the activation of the xenobiotic receptor PXR or the c-Jun N-terminal kinase JNK (Wang et al. (2002), supra).

In addition, a small subset of genes (see FIG. 5C) were changed over 3-fold by all three FXR ligands. The largest change was seen in the apolipoprotein E gene repression. This result correlates with levels observed in FXR null mice where increases in apoE levels in the VLDL, LDL, and HDL fractions were seen when compared with wild-type mice (Sinal et al. (2000), supra). This list suggests additional roles for FXR in the bilirubin biosynthetic pathway (BLVRA 5-fold), thyroid metabolism (TSHR 3-fold; thyroid transcription factor 1 3-fold) and amino acid transport (SCL7A2 4-fold), as well as other pathways (see also Appendix 2 and Appendix 3). Confirmation of gene induction by FXR agonists of many of the genes reported in this list have been checked by Northern blot analysis as well.

EXAMPLE 6

Crystallographic Elucidation of FXR Structure

The plasmids pGEX or pHIS8-3-hFXR LBD (residues 248 to 476 of SEQ ID NO:1) were transformed into $E.\ coli$ strain BL21 (DE3) (Novagen) and cells were grown at 37° C. to an $O.D._{600}$ of 1.0. Protein expression was induced by adding iso-propyl-thio-galactose (Boehringer Mannheim) at a concentration of 0.1 mM and cells were allowed to grow for 6 hr at 20° C. Bacteria were harvested at 8,000×g at 5° C. and pellets were stored at −70° C. Cell pellets were thawed and resuspended in 50 mM Tris-Ca (pH 8.0), 500 mM NaCl, 10 mM imidazole (pH 8.0), 10% glycerol, 1% Tween 20, and 10 mM β-mercaptoethanol (β-ME) (Sigma) at 4° C.

Resuspended cells were sonicated and lysates were centrifuged at 100,000×g at 4° C. Supernatants were purified by $Ni^{2+}$-chelation chromatography (QIAGEN). Protein sample was eluted in 50 mM Tris-Cl (pH 8.0), 500 mM NaCl, 250 mM imidazole (pH 8.0), 10% glycerol, and 10 mM β-ME. The N-terminal octahistidine tag was removed by thrombin (Sigma) digestion during dialysis against 50 mM Tris (pH 8.0), 500 mM NaCl, and 10 mM dithiotheitol (DTT) at 4° C. for 24 h. The sample was purified over Superdex 200 26/60 gel filtration column (Pharmacia) equilibrated in dialysis/thrombin cleavage buffer. Peak fractions were collected and dialyzed against 5 mM Tris (pH 8.0) 62.5 mM NaCl and 1 mM DTT, concentrated to 15 mg $ml^{-1}$ using Centricon 10 (Amicon), and stored at −70° C. Selenomethionine substituted protein (SeMet) was obtained from $E.\ coli$ grown in minimal media using the methionine pathway inhibition methods (Doublié (1997). Preparation of selenomethionyl proteins for phase determination. Methods Enzymol. 276, 523-530) and was purified similarly to the native sample.

Crystallization and Structure Determination

Complexing of the receptor with the ligand was accomplished by incubating hFXR (15 mg $ml^{-1}$) with fexaramine at a 1:2 molar ratio. Fexaramine was solubilized in dimethylsulfoxide (DMSO) at 10 mM. Crystals of the hFXR-LBD with fexaramine were grown by the hanging drop vapor diffusion methods at 4° C. by mixing 1.0 µl of hFXR-LBD/fexaramine complex with 1.0 µl of a reservoir solution containing 15%-20% PEG 8000, 100 mM HEPES-Na$^+$ (pH 7.5), 0.2 M Mg 1 mM DTT. Crystals of selenomethionine-substituted hFXR-LBD were grown similarly with an increase in DTT concentration to 10 mM. Crystals were stabilized in 10%-15% glycerol, 20% PEG 8000, 0.2 M MgCl$_2$, 100 mM HEPES-Na$^+$ (pH 7.5), and 10 mM DTT and rapidly frozen in a 100K stream of nitrogen gas.

MAD data to 2.1 Å was collected around the Se edge at European Synchrotron Radiation Facility (ESRF, Grenoble, France) on beamline FIP (BM30A). Native data to 1.78 Å was collected at the Stanford Synchrotron Radiation Laboratory, beamline 9-1. All data was processed with DENZO and SCALEPACK (Otwinowski and Minor (1997). Processing of X-ray diffraction data collected in oscillation mode. Methods Enzymol. 276, 307-326). The crystals contain one molecule per asymmetric unit (52.9% solvent) and belong to the space group P2$_1$2$_1$2$_1$ (a=36.656, b=56.776, c=17.646, α=90.0, β=90.0, γ=90.0). Three wavelength MAD data were scaled to the $\lambda_3$ and verified by inspection of both dispersive and anomalous difference. 7 of 9 Se sites were located and MAD phasing was done with SOLVE (Terwilliger and Berendzen (1992). Automated MAD and MIR structure solution. Acta Crystallogr. D 55, 849-861.) and density modification was carried out with RESOLVE (Terwilliger (2000) "Maximum likelihood density modification," Acta Cryst. D56, 965-972).

The initial model was built into the experimental electron density maps displayed in O (Jones et al. (1991) Improved methods for building protein models in electron density maps and the location of errors in these models. Acta Crystallogr. A 47, 110-119). The resulting model was positionally refined against all the high-resolution native data set using the default bulk solvent model in CNS with maximum likelihood targets (Brunger et al. (1998). Crystallography & NMR system: A new software suite for macromolecular structure determination. Acta Crystallogr. D 54, 905-921). The structure of FXR was refined to a R$_{cryst}$ and a R$_{free}$ value of 23.0% and 27.5%, using all data extending to 1.78 Å resolution. The R-factor=$\Sigma |F_{obs} - F_{cake}|/\Sigma F_{obs}$, where summation is over the data used for refinement and the R$_{free}$ was calculated using 5% of the reflection data chosen and excluded from refinement. The model consists of residues 248 to 270 and 286 to 475 of human FXR, 1 fexaramine molecule, and 340 water molecules. PROCHECK (Laskowski et al. (1993). PROCHECK: a program to check the stereochemical quality of protein structures. J. Appl. Crystallogr. 26, 283-291) revealed a total of 92% of the residues in the most favored region of the Ramachandran plot and 8% in the additionally allowed region. Main chain and side chain structural parameters were consistently better than average (overall G value of 0.16).

EXAMPLE 7

Modeling Compounds into the FXR LBD Crystallographic Structure

The structure of the activated form of the FXR LBD allowed investigation of how BAs, structurally distinct physiological ligands for FXR, bind and activate the receptor. The bile acid CDCA was initially modeled into the FXR binding pocket by overlaying its steroidal backbone onto the biaryl group in fexaramine (see FIG. 6E). The model suggested that potential hydrogen bonds could occur between CDCA's hydroxyl groups and Tyr365, Tyr373, and His451 in helices 7 and 11. These interactions were subsequently used to refine the modeled orientation of the ligand. In this model, hydrophobic interactions with CDCA are predicted to secure helix 3 in a similar orientation to that seen in the complex with fexaramine.

This model also provides an explanation for the partial activation of FXR by lithocholic acid (LCA) and deoxycholic acid (DCA) (Makishima et al. (1999), supra). These BAs lack one of the two hydroxyl groups (the αOH at position 7) found in CDCA and therefore are predicted to interact significantly only with the helix 7. These BAs would therefore not bridge helix 3 to helix 7 as securely as CDCA, which in turn, would affect the rigidity of helix 12. In addition, although the inhibitory BA ursodeoxycholic acid (UDCA) has two hydroxyl groups, their trans rather than cis relationship would orientate UDCA in a manner that would create a more open ligand-binding pocket. This in turn may force a less than optimal orientation of helix 12 and result in inhibition of the co-activator interaction.

Modeling of the recently identified synthetic BA agonist 6alpha-ethyl-chenodeoxycholic acid 6-ECDCA, onto the positional coordinates for the CDCA model further supports the model and suggests a mechanism for its efficacy (Pellicciari et al. (2002). 6-alpha-ethyl-chenodeoxycholic acid (6-ECDCA), a potent and selective FXR agonist endowed with anticholestatic activity. J Med Chem. 45(17), 3569-72). 6-ECDCA differs from CDCA by an addition of an aliphatic moiety at the 6α position. The ethyl substituent at this position would be predicted to fit snugly into a hydrophobic pocket formed by Met332 and Phe333 from helix 5. Furthermore, it was demonstrated that either a methyl substituent or a bulkier group at this position reduced efficacy (Pellicciari et al. (2002), supra). This model would predict that a methyl substituent would not be not as effective as an ethyl group because it does not fill the hydrophobic pocket as well as the ethyl group and therefore would not maximize binding energy through an increase in contact surface resulting in a loss of efficacy. Bulkier substituents would also be unfavorable, as they would surpass the 0.3 Å limit allowed for in overlap before Van der Waals contacts would become energetically unfavorable.

Fexaramine is a much stronger activator of FXR than even its most potent natural ligand. This potency appears to be mediated by two mechanisms. First, the fexaramine methyl ester group provides a significant number of contacts with helix 3 that are absent in our model of CDCA binding. The methyl ester aliphatic chain effectively bridges helix 3 with helix 6 through van der Waals contacts. FXR further stabilizes helix 3 against the remainder of the structure via interactions between Asn297 from helix 3 and Arg335 from helix 5, in addition to interactions from Asn286 (helix 3) and Arg354 from helix 6. The second mechanism seems to be a function of fexaramine's length. Fexaramine and compounds of similar length such as fexarene and fexarine activate FXR at much lower concentrations than the natural ligands. It appears that the sequential hydrophobic ring structures of these compounds penetrate deeper into the ligand-binding pocket and thereby increase the number of stable contacts. The larger size of fexaramine compared to CDCA (fexaramine has a volume of 461 Å$^3$ and a surface area of 465 Å$^2$; CDCA has a volume of 339 Å$^3$, and a surface area of 319 Å$^2$), more effectively fills the ligand-binding cavity. Analysis of buried surface area in the absence and presence of fexaramine reveals an additional 9 Å$^2$ of buried hydrophobic surface when fexaramine is bound. This corresponds to an increase of approximately 1 kJ/M in stabilizing energy. Fexaramine also appears to make direct contact with helix 12 as well. The increase in stabilization of helix 12 directly influences its rigidity and hence its ability to interact with the co-activator.

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein. The examples provided here are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The disclosure of all publications cited above are expressly incorporated herein by reference, each in its entirety, to the same extent as if each were incorporated by reference individually.

APPENDIX 1

STRUCTURE COORDINATES FOR FXR LBD COMPLEXED WITH FEXARAMINE

```
REMARK Written by O version 6.1.0
REMARK Thu Oct 10 10:35:28 2002
CRYST1   36.656  56.776 117.646  90.00  90.00  90.00
ORIGX1     1.000000  0.000000  0.000000      0.00000
ORIGX2     0.000000  1.000000  0.000000      0.00000
ORIGX3     0.000000  0.000000  1.000000      0.00000
SCALE1     0.027281 -0.000001 -0.000001      0.00000
SCALE2     0.000000  0.017613  0.000000      0.00000
SCALE3     0.000000  0.000000  0.008500      0.00000
```

| ATOM | # | TYPE | RESIDUE | | X | Y | Z | OCC | B | |
|------|---|------|---------|-----|--------|--------|--------|------|-------|---|
| ATOM | 1  | N   | GLU | 248 | -1.300 | 16.662 | 18.408 | 1.00 | 26.06 | 7 |
| ATOM | 2  | CA  | GLU | 248 |  0.018 | 16.006 | 18.347 | 1.00 | 24.32 | 6 |
| ATOM | 3  | CB  | GLU | 248 |  1.089 | 16.982 | 18.816 | 1.00 | 23.43 | 6 |
| ATOM | 4  | CG  | GLU | 248 |  1.214 | 18.242 | 17.971 | 1.00 | 26.14 | 6 |
| ATOM | 5  | CD  | GLU | 248 |  0.206 | 19.376 | 18.316 | 1.00 | 26.65 | 6 |
| ATOM | 6  | OE1 | GLU | 248 | -0.853 | 19.163 | 18.951 | 1.00 | 26.91 | 8 |
| ATOM | 7  | OE2 | GLU | 248 |  0.471 | 20.527 | 17.904 | 1.00 | 28.84 | 8 |
| ATOM | 8  | C   | GLU | 248 |  0.066 | 14.789 | 19.297 | 1.00 | 23.85 | 6 |
| ATOM | 9  | O   | GLU | 248 |  0.952 | 13.973 | 19.208 | 1.00 | 22.37 | 8 |
| ATOM | 10 | N   | LEU | 249 | -0.854 | 14.728 | 20.262 | 1.00 | 22.87 | 7 |
| ATOM | 11 | CA  | LEU | 249 | -0.844 | 13.653 | 21.236 | 1.00 | 22.90 | 6 |
| ATOM | 12 | CB  | LEU | 249 | -1.530 | 14.121 | 22.530 | 1.00 | 23.10 | 6 |
| ATOM | 13 | CG  | LEU | 249 | -0.943 | 15.332 | 23.292 | 1.00 | 23.04 | 6 |
| ATOM | 14 | CD1 | LEU | 249 | -1.713 | 15.572 | 24.612 | 1.00 | 18.74 | 6 |
| ATOM | 15 | CD2 | LEU | 249 |  0.552 | 15.118 | 23.434 | 1.00 | 22.62 | 6 |
| ATOM | 16 | C   | LEU | 249 | -1.679 | 12.497 | 20.693 | 1.00 | 23.78 | 6 |
| ATOM | 17 | O   | LEU | 249 | -2.675 | 12.765 | 20.060 | 1.00 | 22.65 | 8 |
| ATOM | 18 | N   | THR | 250 | -1.294 | 11.253 | 20.952 | 1.00 | 21.78 | 7 |
| ATOM | 19 | CA  | THR | 250 | -2.131 | 10.116 | 20.532 | 1.00 | 21.44 | 6 |
| ATOM | 20 | CB  | THR | 250 | -1.465 |  8.742 | 20.857 | 1.00 | 18.84 | 6 |
| ATOM | 21 | OG1 | THR | 250 | -1.263 |  8.652 | 22.258 | 1.00 | 19.62 | 8 |
| ATOM | 22 | CG2 | THR | 250 | -0.098 |  8.627 | 20.156 | 1.00 | 19.88 | 6 |
| ATOM | 23 | C   | THR | 250 | -3.430 | 10.156 | 21.387 | 1.00 | 22.71 | 6 |
| ATOM | 24 | O   | THR | 250 | -3.542 | 10.917 | 22.374 | 1.00 | 20.79 | 8 |
| ATOM | 25 | N   | PRO | 251 | -4.420 |  9.330 | 21.006 | 1.00 | 21.51 | 7 |
| ATOM | 26 | CD  | PRO | 251 | -4.608 |  8.786 | 19.642 | 1.00 | 22.74 | 6 |
| ATOM | 27 | CA  | PRO | 251 | -5.670 |  9.278 | 21.766 | 1.00 | 23.11 | 6 |
| ATOM | 28 | CB  | PRO | 251 | -6.493 |  8.238 | 20.996 | 1.00 | 20.67 | 6 |
| ATOM | 29 | CG  | PRO | 251 | -6.160 |  8.602 | 19.547 | 1.00 | 20.95 | 6 |
| ATOM | 30 | C   | PRO | 251 | -5.380 |  8.870 | 23.189 | 1.00 | 23.37 | 6 |
| ATOM | 31 | O   | PRO | 251 | -5.977 |  9.431 | 24.134 | 1.00 | 23.44 | 8 |
| ATOM | 32 | N   | ASP | 252 | -4.424 |  7.940 | 23.375 | 1.00 | 22.26 | 7 |
| ATOM | 33 | CA  | ASP | 252 | -4.108 |  7.483 | 24.716 | 1.00 | 22.24 | 6 |
| ATOM | 34 | CB  | ASP | 252 | -3.009 |  6.414 | 24.756 | 1.00 | 24.95 | 6 |
| ATOM | 35 | CG  | ASP | 252 | -3.530 |  4.944 | 24.647 | 1.00 | 27.66 | 6 |
| ATOM | 36 | OD1 | ASP | 252 | -2.631 |  4.061 | 24.671 | 1.00 | 29.71 | 8 |
| ATOM | 37 | OD2 | ASP | 252 | -4.769 |  4.666 | 24.531 | 1.00 | 25.30 | 8 |
| ATOM | 38 | C   | ASP | 252 | -3.571 |  8.679 | 25.555 | 1.00 | 21.99 | 6 |
| ATOM | 39 | O   | ASP | 252 | -3.937 |  8.824 | 26.712 | 1.00 | 21.47 | 8 |
| ATOM | 40 | N   | GLN | 253 | -2.677 |  9.453 | 24.971 | 1.00 | 19.91 | 7 |
| ATOM | 41 | CA  | GLN | 253 | -2.050 | 10.588 | 25.632 | 1.00 | 20.91 | 6 |
| ATOM | 42 | CB  | GLN | 253 | -0.894 | 11.111 | 24.764 | 1.00 | 18.51 | 6 |
| ATOM | 43 | CG  | GLN | 253 |  0.265 | 10.122 | 24.650 | 1.00 | 20.05 | 6 |
| ATOM | 44 | CD  | GLN | 253 |  1.382 | 10.622 | 23.735 | 1.00 | 21.33 | 6 |
| ATOM | 45 | OE1 | GLN | 253 |  1.105 | 11.105 | 22.638 | 1.00 | 18.67 | 8 |
| ATOM | 46 | NE2 | GLN | 253 |  2.640 | 10.535 | 24.126 | 1.00 | 20.72 | 7 |
| ATOM | 47 | C   | GLN | 253 | -3.049 | 11.692 | 25.938 | 1.00 | 21.83 | 6 |
| ATOM | 48 | O   | GLN | 253 | -2.956 | 12.372 | 26.972 | 1.00 | 20.56 | 8 |
| ATOM | 49 | N   | GLN | 254 | -3.987 | 11.862 | 25.047 | 1.00 | 20.43 | 7 |
| ATOM | 50 | CA  | GLN | 254 | -5.019 | 12.868 | 25.236 | 1.00 | 22.66 | 6 |
| ATOM | 51 | CB  | GLN | 254 | -5.973 | 12.874 | 24.057 | 1.00 | 24.24 | 6 |

APPENDIX 1-continued

STRUCTURE COORDINATES FOR FXR LBD COMPLEXED WITH FEXARAMINE

| ATOM | 52 | CG | GLN | 254 | −5.363 | 13.502 | 22.811 | 1.00 | 25.78 | 6 |
|---|---|---|---|---|---|---|---|---|---|---|
| ATOM | 53 | CD | GLN | 254 | −6.374 | 13.651 | 21.684 | 1.00 | 28.28 | 6 |
| ATOM | 54 | OE1 | GLN | 254 | −7.373 | 12.935 | 21.661 | 1.00 | 31.15 | 8 |
| ATOM | 55 | NE2 | GLN | 254 | −6.172 | 14.547 | 20.740 | 1.00 | 27.90 | 7 |
| ATOM | 56 | C | GLN | 254 | −5.789 | 12.561 | 26.519 | 1.00 | 25.16 | 6 |
| ATOM | 57 | O | GLN | 254 | −6.045 | 13.443 | 27.339 | 1.00 | 26.26 | 8 |
| ATOM | 58 | N | THR | 255 | −6.152 | 11.297 | 26.697 | 1.00 | 23.88 | 7 |
| ATOM | 59 | CA | THR | 255 | −6.930 | 10.897 | 27.888 | 1.00 | 25.99 | 6 |
| ATOM | 60 | CB | THR | 255 | −7.467 | 9.474 | 27.762 | 1.00 | 27.10 | 6 |
| ATOM | 61 | OG1 | THR | 255 | −6.402 | 8.543 | 27.765 | 1.00 | 33.09 | 8 |
| ATOM | 62 | CG2 | THR | 255 | −8.276 | 9.258 | 26.486 | 1.00 | 22.32 | 6 |
| ATOM | 63 | C | THR | 255 | −6.077 | 11.004 | 29.160 | 1.00 | 25.75 | 6 |
| ATOM | 64 | O | THR | 255 | −6.566 | 11.405 | 30.223 | 1.00 | 25.60 | 8 |
| ATOM | 65 | N | LEU | 256 | −4.820 | 10.634 | 29.028 | 1.00 | 24.61 | 7 |
| ATOM | 66 | CA | LEU | 256 | −3.852 | 10.712 | 30.136 | 1.00 | 25.14 | 6 |
| ATOM | 67 | CB | LEU | 256 | −2.473 | 10.285 | 29.614 | 1.00 | 29.20 | 6 |
| ATOM | 68 | CG | LEU | 256 | −1.584 | 9.546 | 30.626 | 1.00 | 34.14 | 6 |
| ATOM | 69 | CD1 | LEU | 256 | −2.275 | 8.363 | 31.302 | 1.00 | 33.98 | 6 |
| ATOM | 70 | CD2 | LEU | 256 | −0.317 | 8.968 | 29.977 | 1.00 | 34.33 | 6 |
| ATOM | 71 | C | LEU | 256 | −3.793 | 12.167 | 30.644 | 1.00 | 24.91 | 6 |
| ATOM | 72 | O | LEU | 256 | −3.933 | 12.449 | 31.843 | 1.00 | 24.12 | 8 |
| ATOM | 73 | N | LEU | 257 | −3.593 | 13.073 | 29.698 | 1.00 | 22.63 | 7 |
| ATOM | 74 | CA | LEU | 257 | −3.489 | 14.513 | 29.987 | 1.00 | 21.99 | 6 |
| ATOM | 75 | CB | LEU | 257 | −3.157 | 15.292 | 28.719 | 1.00 | 19.83 | 6 |
| ATOM | 76 | CG | LEU | 257 | −3.122 | 16.802 | 28.945 | 1.00 | 22.40 | 6 |
| ATOM | 77 | CD1 | LEU | 257 | −2.121 | 17.218 | 30.025 | 1.00 | 18.07 | 6 |
| ATOM | 78 | CD2 | LEU | 257 | −2.738 | 17.577 | 27.683 | 1.00 | 21.13 | 6 |
| ATOM | 79 | C | LEU | 257 | −4.808 | 15.056 | 30.543 | 1.00 | 21.92 | 6 |
| ATOM | 80 | O | LEU | 257 | −4.824 | 15.859 | 31.487 | 1.00 | 20.03 | 8 |
| ATOM | 81 | N | HIS | 258 | −5.892 | 14.607 | 29.942 | 1.00 | 23.40 | 7 |
| ATOM | 82 | CA | HIS | 258 | −7.237 | 15.040 | 30.339 | 1.00 | 25.69 | 6 |
| ATOM | 83 | CB | HIS | 258 | −8.314 | 14.293 | 29.553 | 1.00 | 29.97 | 6 |
| ATOM | 84 | CG | HIS | 258 | −9.707 | 14.478 | 30.162 | 1.00 | 33.41 | 6 |
| ATOM | 85 | CD2 | HIS | 258 | −10.443 | 13.693 | 30.993 | 1.00 | 34.61 | 6 |
| ATOM | 86 | ND1 | HIS | 258 | −10.480 | 15.610 | 29.914 | 1.00 | 32.40 | 7 |
| ATOM | 87 | CE1 | HIS | 258 | −11.616 | 15.487 | 30.579 | 1.00 | 35.27 | 6 |
| ATOM | 88 | NE2 | HIS | 258 | −11.609 | 14.350 | 31.228 | 1.00 | 34.65 | 7 |
| ATOM | 89 | C | HIS | 258 | −7.482 | 14.790 | 31.836 | 1.00 | 26.38 | 6 |
| ATOM | 90 | O | HIS | 258 | −7.865 | 15.691 | 32.589 | 1.00 | 25.22 | 8 |
| ATOM | 91 | N | PHE | 259 | −7.261 | 13.566 | 32.284 | 1.00 | 26.46 | 7 |
| ATOM | 92 | CA | PHE | 259 | −7.528 | 13.226 | 33.694 | 1.00 | 28.16 | 6 |
| ATOM | 93 | CB | PHE | 259 | −7.498 | 11.716 | 33.905 | 1.00 | 30.66 | 6 |
| ATOM | 94 | CG | PHE | 259 | −8.829 | 11.079 | 33.506 | 1.00 | 34.91 | 6 |
| ATOM | 95 | CD1 | PHE | 259 | −10.023 | 11.523 | 34.094 | 1.00 | 36.00 | 6 |
| ATOM | 96 | CD2 | PHE | 259 | −8.860 | 10.065 | 32.544 | 1.00 | 37.80 | 6 |
| ATOM | 97 | CE1 | PHE | 259 | −11.247 | 10.966 | 33.700 | 1.00 | 37.55 | 6 |
| ATOM | 98 | CE2 | PHE | 259 | −10.084 | 9.514 | 32.144 | 1.00 | 38.35 | 6 |
| ATOM | 99 | CZ | PHE | 259 | −11.278 | 9.966 | 32.720 | 1.00 | 38.15 | 6 |
| ATOM | 100 | C | PHE | 259 | −6.539 | 13.924 | 34.627 | 1.00 | 27.70 | 6 |
| ATOM | 101 | O | PHE | 259 | −6.864 | 14.275 | 35.770 | 1.00 | 27.66 | 8 |
| ATOM | 102 | N | ILE | 260 | −5.330 | 14.140 | 34.156 | 1.00 | 23.14 | 7 |
| ATOM | 103 | CA | ILE | 260 | −4.344 | 14.817 | 34.994 | 1.00 | 23.49 | 6 |
| ATOM | 104 | CB | ILE | 260 | −2.948 | 14.774 | 34.372 | 1.00 | 23.27 | 6 |
| ATOM | 105 | CG2 | ILE | 260 | −2.001 | 15.819 | 34.986 | 1.00 | 22.34 | 6 |
| ATOM | 106 | CG1 | ILE | 260 | −2.284 | 13.406 | 34.577 | 1.00 | 21.63 | 6 |
| ATOM | 107 | CD1 | ILE | 260 | −0.954 | 13.251 | 33.849 | 1.00 | 24.51 | 6 |
| ATOM | 108 | C | ILE | 260 | −4.798 | 16.258 | 35.233 | 1.00 | 21.79 | 6 |
| ATOM | 109 | O | ILE | 260 | −4.790 | 16.750 | 36.366 | 1.00 | 20.94 | 8 |
| ATOM | 110 | N | MET | 261 | −5.212 | 16.907 | 34.164 | 1.00 | 20.87 | 7 |
| ATOM | 111 | CA | MET | 261 | −5.652 | 18.308 | 34.232 | 1.00 | 23.03 | 6 |
| ATOM | 112 | CB | MET | 261 | −5.854 | 18.867 | 32.830 | 1.00 | 22.66 | 6 |
| ATOM | 113 | CG | MET | 261 | −4.551 | 18.918 | 32.028 | 1.00 | 22.62 | 6 |
| ATOM | 114 | SD | MET | 261 | −3.187 | 19.588 | 32.956 | 1.00 | 21.46 | 16 |
| ATOM | 115 | CE | MET | 261 | −3.583 | 21.246 | 33.464 | 1.00 | 19.31 | 6 |
| ATOM | 116 | C | MET | 261 | −6.954 | 18.440 | 35.030 | 1.00 | 24.15 | 6 |
| ATOM | 117 | O | MET | 261 | −7.162 | 19.406 | 35.770 | 1.00 | 24.54 | 8 |
| ATOM | 118 | N | ASP | 262 | −7.833 | 17.473 | 34.879 | 1.00 | 25.16 | 7 |
| ATOM | 119 | CA | ASP | 262 | −9.110 | 17.508 | 35.598 | 1.00 | 25.45 | 6 |
| ATOM | 120 | CB | ASP | 262 | −9.961 | 16.300 | 35.242 | 1.00 | 26.93 | 6 |
| ATOM | 121 | CG | ASP | 262 | −11.339 | 16.360 | 35.889 | 1.00 | 29.88 | 6 |
| ATOM | 122 | OD1 | ASP | 262 | −11.610 | 15.590 | 36.883 | 1.00 | 28.67 | 8 |
| ATOM | 123 | OD2 | ASP | 262 | −12.221 | 17.185 | 35.441 | 1.00 | 30.00 | 8 |
| ATOM | 124 | C | ASP | 262 | −8.854 | 17.514 | 37.109 | 1.00 | 26.43 | 6 |
| ATOM | 125 | O | ASP | 262 | −9.537 | 18.201 | 37.881 | 1.00 | 24.36 | 8 |
| ATOM | 126 | N | SER | 263 | −7.863 | 16.747 | 37.510 | 1.00 | 25.37 | 7 |
| ATOM | 127 | CA | SER | 263 | −7.504 | 16.640 | 38.925 | 1.00 | 26.08 | 6 |
| ATOM | 128 | CB | SER | 263 | −6.680 | 15.381 | 39.178 | 1.00 | 26.03 | 6 |

APPENDIX 1-continued

STRUCTURE COORDINATES FOR FXR LBD COMPLEXED WITH FEXARAMINE

| ATOM | 129 | OG | SER | 263 | −6.330 | 15.310 | 40.554 | 1.00 | 29.76 | 8 |
|---|---|---|---|---|---|---|---|---|---|---|
| ATOM | 130 | C | SER | 263 | −6.688 | 17.860 | 39.380 | 1.00 | 26.66 | 6 |
| ATOM | 131 | O | SER | 263 | −6.884 | 18.389 | 40.479 | 1.00 | 27.29 | 8 |
| ATOM | 132 | N | TYR | 264 | −5.781 | 18.298 | 38.526 | 1.00 | 25.66 | 7 |
| ATOM | 133 | CA | TYR | 264 | −4.883 | 19.427 | 38.845 | 1.00 | 26.94 | 6 |
| ATOM | 134 | CB | TYR | 264 | −3.816 | 19.584 | 37.750 | 1.00 | 23.84 | 6 |
| ATOM | 135 | CG | TYR | 264 | −2.605 | 20.414 | 38.199 | 1.00 | 26.14 | 6 |
| ATOM | 136 | CD1 | TYR | 264 | −2.442 | 21.726 | 37.735 | 1.00 | 25.63 | 6 |
| ATOM | 137 | CE1 | TYR | 264 | −1.338 | 22.485 | 38.145 | 1.00 | 26.64 | 6 |
| ATOM | 138 | CD2 | TYR | 264 | −1.655 | 19.863 | 39.071 | 1.00 | 26.12 | 6 |
| ATOM | 139 | CE2 | TYR | 264 | −0.552 | 20.623 | 39.482 | 1.00 | 25.98 | 6 |
| ATOM | 140 | CZ | TYR | 264 | −0.394 | 21.935 | 39.020 | 1.00 | 28.14 | 6 |
| ATOM | 141 | OH | TYR | 264 | 0.675 | 22.675 | 39.421 | 1.00 | 28.24 | 8 |
| ATOM | 142 | C | TYR | 264 | −5.642 | 20.781 | 38.976 | 1.00 | 30.53 | 6 |
| ATOM | 143 | O | TYR | 264 | −5.343 | 21.598 | 39.861 | 1.00 | 30.88 | 8 |
| ATOM | 144 | N | ASN | 265 | −6.615 | 20.992 | 38.093 | 1.00 | 32.53 | 7 |
| ATOM | 145 | CA | ASN | 265 | −7.390 | 22.266 | 38.004 | 1.00 | 36.75 | 6 |
| ATOM | 146 | CB | ASN | 265 | −8.413 | 22.173 | 36.882 | 1.00 | 35.41 | 6 |
| ATOM | 147 | CG | ASN | 265 | −7.763 | 22.449 | 35.533 | 1.00 | 36.05 | 6 |
| ATOM | 148 | OD1 | ASN | 265 | −8.381 | 22.235 | 34.498 | 1.00 | 37.43 | 8 |
| ATOM | 149 | ND2 | ASN | 265 | −6.527 | 22.916 | 35.490 | 1.00 | 32.44 | 7 |
| ATOM | 150 | C | ASN | 265 | −8.096 | 22.627 | 39.319 | 1.00 | 40.35 | 6 |
| ATOM | 151 | O | ASN | 265 | −8.468 | 23.796 | 39.540 | 1.00 | 41.97 | 8 |
| ATOM | 152 | N | LYS | 266 | −8.265 | 21.612 | 40.140 | 1.00 | 44.37 | 7 |
| ATOM | 153 | CA | LYS | 266 | −8.838 | 21.756 | 41.487 | 1.00 | 48.45 | 6 |
| ATOM | 154 | CB | LYS | 266 | −9.615 | 20.516 | 41.911 | 1.00 | 47.77 | 6 |
| ATOM | 155 | CG | LYS | 266 | −10.433 | 19.902 | 40.803 | 1.00 | 48.86 | 6 |
| ATOM | 156 | CD | LYS | 266 | −10.904 | 18.501 | 41.152 | 1.00 | 48.08 | 6 |
| ATOM | 157 | CE | LYS | 266 | −11.996 | 18.008 | 40.218 | 1.00 | 48.29 | 6 |
| ATOM | 158 | NZ | LYS | 266 | −12.623 | 16.770 | 40.684 | 1.00 | 48.28 | 7 |
| ATOM | 159 | C | LYS | 266 | −7.712 | 21.866 | 42.490 | 1.00 | 51.12 | 6 |
| ATOM | 160 | O | LYS | 266 | −7.208 | 20.862 | 42.998 | 1.00 | 52.51 | 8 |
| ATOM | 161 | N | GLN | 267 | −7.307 | 23.078 | 42.788 | 1.00 | 53.97 | 7 |
| ATOM | 162 | CA | GLN | 267 | −6.178 | 23.252 | 43.710 | 1.00 | 56.59 | 6 |
| ATOM | 163 | CB | GLN | 267 | −4.953 | 22.820 | 43.018 | 1.00 | 56.46 | 6 |
| ATOM | 164 | CG | GLN | 267 | −3.751 | 22.919 | 43.902 | 1.00 | 57.69 | 6 |
| ATOM | 165 | CD | GLN | 267 | −2.535 | 22.395 | 43.195 | 1.00 | 57.98 | 6 |
| ATOM | 166 | OE1 | GLN | 267 | −2.418 | 21.189 | 43.015 | 1.00 | 57.87 | 8 |
| ATOM | 167 | NE2 | GLN | 267 | −1.626 | 23.238 | 42.766 | 1.00 | 57.72 | 7 |
| ATOM | 168 | C | GLN | 267 | −6.084 | 24.690 | 44.192 | 1.00 | 58.17 | 6 |
| ATOM | 169 | O | GLN | 267 | −6.472 | 25.624 | 43.466 | 1.00 | 59.03 | 8 |
| ATOM | 170 | N | ARG | 268 | −5.445 | 24.867 | 45.372 | 1.00 | 60.05 | 7 |
| ATOM | 171 | CA | ARG | 268 | −5.819 | 26.060 | 46.137 | 1.00 | 61.88 | 6 |
| ATOM | 172 | CB | ARG | 268 | −6.737 | 25.574 | 47.256 | 1.00 | 62.04 | 6 |
| ATOM | 173 | CG | ARG | 268 | −6.982 | 24.074 | 47.104 | 1.00 | 64.49 | 6 |
| ATOM | 174 | CD | ARG | 268 | −7.363 | 23.262 | 48.349 | 1.00 | 67.10 | 6 |
| ATOM | 175 | NE | ARG | 268 | −8.601 | 22.510 | 48.096 | 1.00 | 70.55 | 7 |
| ATOM | 176 | CZ | ARG | 268 | −8.892 | 21.244 | 48.456 | 1.00 | 72.10 | 6 |
| ATOM | 177 | NH1 | ARG | 268 | −8.030 | 20.483 | 49.137 | 1.00 | 72.70 | 7 |
| ATOM | 178 | NH2 | ARG | 268 | −10.068 | 20.653 | 48.165 | 1.00 | 72.00 | 7 |
| ATOM | 179 | C | ARG | 268 | −5.016 | 26.917 | 47.094 | 1.00 | 62.81 | 6 |
| ATOM | 180 | O | ARG | 268 | −4.597 | 26.574 | 48.172 | 1.00 | 64.18 | 8 |
| ATOM | 181 | N | MET | 269 | −4.869 | 28.184 | 46.907 | 1.00 | 63.86 | 7 |
| ATOM | 182 | CA | MET | 269 | −4.433 | 28.750 | 48.138 | 1.00 | 64.43 | 6 |
| ATOM | 183 | CB | MET | 269 | −2.982 | 29.206 | 48.225 | 1.00 | 64.17 | 6 |
| ATOM | 184 | CG | MET | 269 | −2.536 | 29.212 | 49.727 | 1.00 | 65.70 | 6 |
| ATOM | 185 | SD | MET | 269 | −1.401 | 27.918 | 50.212 | 1.00 | 66.13 | 16 |
| ATOM | 186 | CE | MET | 269 | −1.903 | 27.117 | 51.731 | 1.00 | 67.05 | 6 |
| ATOM | 187 | C | MET | 269 | −5.386 | 29.831 | 48.685 | 1.00 | 64.67 | 6 |
| ATOM | 188 | O | MET | 269 | −5.630 | 28.771 | 49.823 | 1.00 | 65.69 | 8 |
| ATOM | 189 | N | PRO | 270 | −5.851 | 30.858 | 49.550 | 1.00 | 64.77 | 7 |
| ATOM | 190 | CD | PRO | 270 | −6.430 | 30.187 | 50.202 | 1.00 | 64.53 | 6 |
| ATOM | 191 | CA | PRO | 270 | −6.434 | 32.160 | 50.320 | 1.00 | 64.23 | 6 |
| ATOM | 192 | CB | PRO | 270 | −7.540 | 31.838 | 51.010 | 1.00 | 64.34 | 6 |
| ATOM | 193 | CG | PRO | 270 | −7.592 | 30.375 | 51.244 | 1.00 | 64.44 | 6 |
| ATOM | 194 | C | PRO | 270 | −6.398 | 33.640 | 49.829 | 1.00 | 64.19 | 6 |
| ATOM | 195 | O | PRO | 270 | −6.136 | 34.046 | 49.116 | 1.00 | 65.06 | 8 |
| ATOM | 196 | OXT | PRO | 270 | −6.539 | 34.261 | 48.697 | 1.00 | 63.72 | 8 |
| TER | | | | | | | | | | |
| ATOM | 1 | CB | ASP | 286 | 0.382 | 33.769 | 65.422 | 1.00 | 54.24 | 6 |
| ATOM | 2 | CG | ASP | 286 | −0.926 | 34.440 | 65.715 | 1.00 | 57.55 | 6 |
| ATOM | 3 | OD1 | ASP | 286 | −1.248 | 35.480 | 65.070 | 1.00 | 59.45 | 8 |
| ATOM | 4 | OD2 | ASP | 286 | −1.632 | 33.905 | 66.602 | 1.00 | 60.19 | 8 |
| ATOM | 5 | C | ASP | 286 | 0.955 | 31.742 | 64.116 | 1.00 | 49.99 | 6 |
| ATOM | 6 | O | ASP | 286 | 0.319 | 31.366 | 63.141 | 1.00 | 49.47 | 8 |
| ATOM | 7 | N | ASP | 286 | 0.793 | 31.628 | 66.627 | 1.00 | 50.96 | 7 |
| ATOM | 8 | CA | ASP | 286 | 0.252 | 32.246 | 65.375 | 1.00 | 51.66 | 6 |

APPENDIX 1-continued

STRUCTURE COORDINATES FOR FXR LBD COMPLEXED WITH FEXARAMINE

| ATOM | 9 | N | GLU | 287 | 2.441 | 32.325 | 64.308 | 1.00 | 47.84 | 7 |
|------|---|---|-----|-----|-------|--------|--------|------|-------|---|
| ATOM | 10 | CA | GLU | 287 | 3.421 | 32.140 | 63.248 | 1.00 | 44.91 | 6 |
| ATOM | 11 | CB | GLU | 287 | 4.797 | 32.529 | 63.756 | 1.00 | 47.08 | 6 |
| ATOM | 12 | CG | GLU | 287 | 5.736 | 32.977 | 62.680 | 1.00 | 50.43 | 6 |
| ATOM | 13 | CD | GLU | 287 | 5.260 | 34.269 | 62.097 | 1.00 | 52.24 | 6 |
| ATOM | 14 | OE1 | GLU | 287 | 5.593 | 35.362 | 62.617 | 1.00 | 56.48 | 8 |
| ATOM | 15 | OE2 | GLU | 287 | 4.493 | 34.201 | 61.143 | 1.00 | 54.23 | 8 |
| ATOM | 16 | C | GLU | 287 | 3.482 | 30.659 | 62.840 | 1.00 | 41.62 | 6 |
| ATOM | 17 | O | GLU | 287 | 3.228 | 30.317 | 61.690 | 1.00 | 39.59 | 8 |
| ATOM | 18 | N | PHE | 288 | 3.899 | 29.811 | 63.793 | 1.00 | 37.52 | 7 |
| ATOM | 19 | CA | PHE | 288 | 3.973 | 28.367 | 63.577 | 1.00 | 34.85 | 6 |
| ATOM | 20 | CB | PHE | 288 | 4.285 | 27.639 | 64.875 | 1.00 | 32.00 | 6 |
| ATOM | 21 | CG | PHE | 288 | 4.337 | 26.175 | 64.724 | 1.00 | 30.44 | 6 |
| ATOM | 22 | CD1 | PHE | 288 | 5.434 | 25.599 | 64.140 | 1.00 | 28.62 | 6 |
| ATOM | 23 | CD2 | PHE | 288 | 3.330 | 25.366 | 65.262 | 1.00 | 30.62 | 6 |
| ATOM | 24 | CE1 | PHE | 288 | 5.577 | 24.224 | 64.090 | 1.00 | 30.42 | 6 |
| ATOM | 25 | CE2 | PHE | 288 | 3.451 | 23.975 | 65.227 | 1.00 | 31.08 | 6 |
| ATOM | 26 | CZ | PHE | 288 | 4.593 | 23.397 | 64.635 | 1.00 | 30.53 | 6 |
| ATOM | 27 | C | PHE | 288 | 2.617 | 27.856 | 63.067 | 1.00 | 33.95 | 6 |
| ATOM | 28 | O | PHE | 288 | 2.549 | 26.952 | 62.239 | 1.00 | 32.05 | 8 |
| ATOM | 29 | N | LEU | 289 | 1.582 | 27.911 | 63.398 | 1.00 | 32.30 | 7 |
| ATOM | 30 | CA | LEU | 289 | 0.168 | 27.754 | 63.062 | 1.00 | 31.78 | 6 |
| ATOM | 31 | CB | LEU | 289 | −0.654 | 28.626 | 64.023 | 1.00 | 33.66 | 6 |
| ATOM | 32 | CG | LEU | 289 | −1.875 | 28.012 | 64.721 | 1.00 | 35.60 | 6 |
| ATOM | 33 | CD1 | LEU | 289 | −1.703 | 26.450 | 64.928 | 1.00 | 37.21 | 6 |
| ATOM | 34 | CD2 | LEU | 289 | −2.049 | 28.729 | 66.088 | 1.00 | 35.17 | 6 |
| ATOM | 35 | C | LEU | 289 | −0.068 | 28.152 | 61.568 | 1.00 | 30.12 | 6 |
| ATOM | 36 | O | LEU | 289 | −0.854 | 27.506 | 60.826 | 1.00 | 28.60 | 8 |
| ATOM | 37 | N | ILE | 290 | 0.384 | 29.641 | 61.314 | 1.00 | 26.28 | 7 |
| ATOM | 38 | CA | ILE | 290 | 0.216 | 30.126 | 59.937 | 1.00 | 27.25 | 6 |
| ATOM | 39 | CB | ILE | 290 | 0.806 | 31.570 | 59.729 | 1.00 | 28.35 | 6 |
| ATOM | 40 | CG2 | ILE | 290 | 0.723 | 31.925 | 58.292 | 1.00 | 29.13 | 6 |
| ATOM | 41 | CG1 | ILE | 290 | 0.020 | 32.604 | 60.520 | 1.00 | 30.90 | 6 |
| ATOM | 42 | CD1 | ILE | 290 | −1.458 | 32.512 | 60.232 | 1.00 | 32.59 | 6 |
| ATOM | 43 | C | ILE | 290 | 0.965 | 29.177 | 58.947 | 1.00 | 23.80 | 6 |
| ATOM | 44 | O | ILE | 290 | 0.414 | 28.781 | 57.911 | 1.00 | 24.53 | 8 |
| ATOM | 45 | N | LEU | 291 | 2.235 | 28.907 | 59.252 | 1.00 | 21.55 | 7 |
| ATOM | 46 | CA | LEU | 291 | 3.088 | 27.981 | 58.477 | 1.00 | 20.53 | 6 |
| ATOM | 47 | CB | LEU | 291 | 4.454 | 27.861 | 59.169 | 1.00 | 18.08 | 6 |
| ATOM | 48 | CG | LEU | 291 | 5.352 | 29.105 | 59.000 | 1.00 | 19.61 | 6 |
| ATOM | 49 | CD1 | LEU | 291 | 6.607 | 28.918 | 59.913 | 1.00 | 20.86 | 6 |
| ATOM | 50 | CD2 | LEU | 291 | 5.784 | 29.237 | 57.523 | 1.00 | 19.68 | 6 |
| ATOM | 51 | C | LEU | 291 | 2.424 | 26.590 | 58.419 | 1.00 | 19.60 | 6 |
| ATOM | 52 | O | LEU | 291 | 2.383 | 25.913 | 57.360 | 1.00 | 18.98 | 8 |
| ATOM | 53 | N | THR | 292 | 1.918 | 26.130 | 59.566 | 1.00 | 19.80 | 7 |
| ATOM | 54 | CA | THR | 292 | 1.254 | 24.812 | 59.623 | 1.00 | 20.09 | 6 |
| ATOM | 55 | CB | THR | 292 | 0.745 | 24.467 | 61.067 | 1.00 | 20.79 | 6 |
| ATOM | 56 | OG1 | THR | 292 | 1.875 | 24.221 | 61.917 | 1.00 | 21.38 | 8 |
| ATOM | 57 | CG2 | THR | 292 | −0.163 | 23.189 | 61.034 | 1.00 | 20.16 | 6 |
| ATOM | 58 | C | THR | 292 | 0.044 | 24.718 | 58.688 | 1.00 | 21.47 | 6 |
| ATOM | 59 | O | THR | 292 | −0.172 | 23.712 | 58.004 | 1.00 | 19.53 | 8 |
| ATOM | 60 | N | GLU | 293 | −0.727 | 25.802 | 58.638 | 1.00 | 21.67 | 7 |
| ATOM | 61 | CA | GLU | 293 | −1.906 | 25.811 | 57.802 | 1.00 | 22.91 | 6 |
| ATOM | 62 | CB | GLU | 293 | −2.698 | 27.072 | 58.070 | 1.00 | 25.01 | 6 |
| ATOM | 63 | CG | GLU | 293 | −4.092 | 27.071 | 57.454 | 1.00 | 31.18 | 6 |
| ATOM | 64 | CD | GLU | 293 | −4.991 | 28.192 | 58.069 | 1.00 | 34.78 | 6 |
| ATOM | 65 | OE1 | GLU | 293 | −6.069 | 28.490 | 57.493 | 1.00 | 36.56 | 8 |
| ATOM | 66 | OE2 | GLU | 293 | −4.619 | 28.767 | 59.127 | 1.00 | 35.69 | 8 |
| ATOM | 67 | C | GLU | 293 | −1.480 | 25.738 | 56.352 | 1.00 | 21.17 | 6 |
| ATOM | 68 | O | GLU | 293 | −2.092 | 25.036 | 55.556 | 1.00 | 18.47 | 8 |
| ATOM | 69 | N | MET | 294 | −0.445 | 26.504 | 56.001 | 1.00 | 20.96 | 7 |
| ATOM | 70 | CA | MET | 294 | 0.049 | 26.446 | 54.632 | 1.00 | 21.46 | 6 |
| ATOM | 71 | CB | MET | 294 | 1.173 | 27.437 | 54.413 | 1.00 | 22.39 | 6 |
| ATOM | 72 | CG | MET | 294 | 0.776 | 28.861 | 54.668 | 1.00 | 25.97 | 6 |
| ATOM | 73 | SD | MET | 294 | 2.260 | 29.945 | 54.657 | 1.00 | 27.73 | 16 |
| ATOM | 74 | CE | MET | 294 | 1.488 | 31.565 | 54.140 | 1.00 | 30.04 | 6 |
| ATOM | 75 | C | MET | 294 | 0.557 | 25.031 | 54.258 | 1.00 | 19.87 | 6 |
| ATOM | 76 | O | MET | 294 | 0.224 | 24.534 | 53.199 | 1.00 | 19.58 | 8 |
| ATOM | 77 | N | ALA | 295 | 1.380 | 24.415 | 55.111 | 1.00 | 18.94 | 7 |
| ATOM | 78 | CA | ALA | 295 | 1.884 | 23.064 | 54.816 | 1.00 | 19.37 | 6 |
| ATOM | 79 | CB | ALA | 295 | 2.788 | 22.619 | 55.888 | 1.00 | 18.19 | 6 |
| ATOM | 80 | C | ALA | 295 | 0.729 | 22.082 | 54.696 | 1.00 | 17.66 | 6 |
| ATOM | 81 | O | ALA | 295 | 0.723 | 21.214 | 53.839 | 1.00 | 16.19 | 8 |
| ATOM | 82 | N | THR | 296 | −0.267 | 22.229 | 55.576 | 1.00 | 18.37 | 7 |
| ATOM | 83 | CA | THR | 296 | −1.419 | 21.336 | 55.580 | 1.00 | 18.66 | 6 |
| ATOM | 84 | CB | THR | 296 | −2.353 | 21.684 | 56.754 | 1.00 | 18.29 | 6 |
| ATOM | 85 | OG1 | THR | 296 | −1.714 | 21.302 | 57.976 | 1.00 | 20.03 | 8 |

APPENDIX 1-continued

STRUCTURE COORDINATES FOR FXR LBD COMPLEXED WITH FEXARAMINE

| ATOM | 86 | CG2 | THR | 296 | −3.659 | 21.011 | 56.629 | 1.00 | 20.09 | 6 |
|------|-----|-----|-----|-----|--------|--------|--------|------|-------|---|
| ATOM | 87 | C | THR | 296 | −2.147 | 21.420 | 54.256 | 1.00 | 17.86 | 6 |
| ATOM | 88 | O | THR | 296 | −2.531 | 20.391 | 53.664 | 1.00 | 18.69 | 8 |
| ATOM | 89 | N | ASN | 297 | −2.332 | 22.638 | 53.780 | 1.00 | 18.24 | 7 |
| ATOM | 90 | CA | ASN | 297 | −2.957 | 22.844 | 52.480 | 1.00 | 19.98 | 6 |
| ATOM | 91 | CB | ASN | 297 | −2.966 | 24.320 | 52.125 | 1.00 | 20.69 | 6 |
| ATOM | 92 | CG | ASN | 297 | −3.544 | 24.558 | 50.764 | 1.00 | 27.62 | 6 |
| ATOM | 93 | OD1 | ASN | 297 | −2.839 | 24.927 | 49.805 | 1.00 | 29.49 | 8 |
| ATOM | 94 | ND2 | ASN | 297 | −4.862 | 24.303 | 50.631 | 1.00 | 31.14 | 7 |
| ATOM | 95 | C | ASN | 297 | −2.123 | 22.081 | 51.404 | 1.00 | 17.67 | 6 |
| ATOM | 96 | O | ASN | 297 | −2.677 | 21.386 | 50.552 | 1.00 | 14.27 | 8 |
| ATOM | 97 | N | HIS | 298 | −0.794 | 22.229 | 51.463 | 1.00 | 17.59 | 7 |
| ATOM | 98 | CA | HIS | 298 | 0.054 | 21.550 | 50.483 | 1.00 | 18.04 | 6 |
| ATOM | 99 | CB | HIS | 298 | 1.512 | 21.952 | 50.615 | 1.00 | 21.15 | 6 |
| ATOM | 100 | CG | HIS | 298 | 1.840 | 23.236 | 49.922 | 1.00 | 22.19 | 6 |
| ATOM | 101 | CD2 | HIS | 298 | 2.341 | 24.404 | 50.396 | 1.00 | 23.65 | 6 |
| ATOM | 102 | ND1 | HIS | 298 | 1.729 | 23.392 | 48.554 | 1.00 | 22.66 | 7 |
| ATOM | 103 | CE1 | HIS | 298 | 2.162 | 24.593 | 48.215 | 1.00 | 23.47 | 6 |
| ATOM | 104 | NE2 | HIS | 298 | 2.541 | 25.231 | 49.310 | 1.00 | 21.08 | 7 |
| ATOM | 105 | C | HIS | 298 | −0.045 | 20.063 | 50.531 | 1.00 | 18.06 | 6 |
| ATOM | 106 | O | HIS | 298 | −0.116 | 19.423 | 49.465 | 1.00 | 20.51 | 8 |
| ATOM | 107 | N | VAL | 299 | −0.043 | 19.491 | 51.716 | 1.00 | 18.80 | 7 |
| ATOM | 108 | CA | VAL | 299 | −0.116 | 18.044 | 51.856 | 1.00 | 18.34 | 6 |
| ATOM | 109 | CB | VAL | 299 | 0.097 | 17.623 | 53.299 | 1.00 | 19.15 | 6 |
| ATOM | 110 | CG1 | VAL | 299 | −0.044 | 16.109 | 53.454 | 1.00 | 19.87 | 6 |
| ATOM | 111 | CG2 | VAL | 299 | 1.461 | 18.029 | 53.717 | 1.00 | 24.63 | 6 |
| ATOM | 112 | C | VAL | 299 | −1.480 | 17.552 | 51.403 | 1.00 | 18.54 | 6 |
| ATOM | 113 | O | VAL | 299 | −1.566 | 16.556 | 50.741 | 1.00 | 15.62 | 8 |
| ATOM | 114 | N | GLN | 300 | −2.567 | 18.260 | 51.740 | 1.00 | 17.99 | 7 |
| ATOM | 115 | CA | GLN | 300 | −3.893 | 17.782 | 51.294 | 1.00 | 19.01 | 6 |
| ATOM | 116 | CB | GLN | 300 | −4.965 | 18.704 | 51.846 | 1.00 | 22.22 | 6 |
| ATOM | 117 | CG | GLN | 300 | −4.915 | 18.952 | 53.352 | 1.00 | 30.87 | 6 |
| ATOM | 118 | CD | GLN | 300 | −5.717 | 17.959 | 54.103 | 1.00 | 34.36 | 6 |
| ATOM | 119 | OE1 | GLN | 300 | −5.795 | 16.804 | 53.706 | 1.00 | 39.66 | 8 |
| ATOM | 120 | NE2 | GLN | 300 | −6.305 | 18.381 | 55.213 | 1.00 | 37.60 | 7 |
| ATOM | 121 | C | GLN | 300 | −4.008 | 17.760 | 49.732 | 1.00 | 18.19 | 6 |
| ATOM | 122 | O | GLN | 300 | −4.536 | 16.819 | 49.136 | 1.00 | 16.90 | 8 |
| ATOM | 123 | N | VAL | 301 | −3.562 | 18.821 | 49.070 | 1.00 | 18.12 | 7 |
| ATOM | 124 | CA | VAL | 301 | −3.638 | 18.831 | 47.622 | 1.00 | 19.51 | 6 |
| ATOM | 125 | CB | VAL | 301 | −3.294 | 20.227 | 47.021 | 1.00 | 22.21 | 6 |
| ATOM | 126 | CG1 | VAL | 301 | −4.198 | 21.283 | 47.562 | 1.00 | 23.03 | 6 |
| ATOM | 127 | CG2 | VAL | 301 | −1.897 | 20.566 | 47.304 | 1.00 | 24.65 | 6 |
| ATOM | 128 | C | VAL | 301 | −2.663 | 17.757 | 47.039 | 1.00 | 18.49 | 6 |
| ATOM | 129 | O | VAL | 301 | −2.937 | 17.159 | 46.019 | 1.00 | 18.00 | 8 |
| ATOM | 130 | N | LEU | 302 | −1.512 | 17.536 | 47.680 | 1.00 | 17.88 | 7 |
| ATOM | 131 | CA | LEU | 302 | −0.612 | 16.471 | 47.208 | 1.00 | 17.22 | 6 |
| ATOM | 132 | CB | LEU | 302 | 0.602 | 16.373 | 48.124 | 1.00 | 17.43 | 6 |
| ATOM | 133 | CG | LEU | 302 | 1.573 | 15.178 | 47.873 | 1.00 | 19.18 | 6 |
| ATOM | 134 | CD1 | LEU | 302 | 2.236 | 15.266 | 46.455 | 1.00 | 18.97 | 6 |
| ATOM | 135 | CD2 | LEU | 302 | 2.669 | 15.147 | 49.046 | 1.00 | 16.64 | 6 |
| ATOM | 136 | C | LEU | 302 | −1.364 | 15.085 | 47.248 | 1.00 | 18.20 | 6 |
| ATOM | 137 | O | LEU | 302 | −1.399 | 14.300 | 46.289 | 1.00 | 16.31 | 8 |
| ATOM | 138 | N | VAL | 303 | −1.888 | 14.763 | 48.416 | 1.00 | 18.28 | 7 |
| ATOM | 139 | CA | VAL | 303 | −2.612 | 13.499 | 48.541 | 1.00 | 17.18 | 6 |
| ATOM | 140 | CB | VAL | 303 | −3.250 | 13.369 | 49.962 | 1.00 | 16.21 | 6 |
| ATOM | 141 | CG1 | VAL | 303 | −4.308 | 12.217 | 49.974 | 1.00 | 17.81 | 6 |
| ATOM | 142 | CG2 | VAL | 303 | −2.131 | 13.205 | 51.020 | 1.00 | 18.44 | 6 |
| ATOM | 143 | C | VAL | 303 | −3.725 | 13.440 | 47.499 | 1.00 | 17.48 | 6 |
| ATOM | 144 | O | VAL | 303 | −3.887 | 12.402 | 46.839 | 1.00 | 17.05 | 8 |
| ATOM | 145 | N | GLU | 304 | −4.509 | 14.511 | 47.322 | 1.00 | 17.74 | 7 |
| ATOM | 146 | CA | GLU | 304 | −5.622 | 14.425 | 46.364 | 1.00 | 20.30 | 6 |
| ATOM | 147 | CB | GLU | 304 | −6.591 | 15.623 | 46.510 | 1.00 | 23.98 | 6 |
| ATOM | 148 | CG | GLU | 304 | −7.226 | 15.679 | 47.913 | 1.00 | 28.15 | 6 |
| ATOM | 149 | CD | GLU | 304 | −7.981 | 14.371 | 48.235 | 1.00 | 29.95 | 6 |
| ATOM | 150 | OE1 | GLU | 304 | −8.899 | 14.034 | 47.482 | 1.00 | 31.97 | 8 |
| ATOM | 151 | OE2 | GLU | 304 | −7.652 | 13.667 | 49.189 | 1.00 | 29.89 | 8 |
| ATOM | 152 | C | GLU | 304 | −5.190 | 14.255 | 44.889 | 1.00 | 20.90 | 6 |
| ATOM | 153 | O | GLU | 304 | −5.820 | 13.527 | 44.082 | 1.00 | 21.49 | 8 |
| ATOM | 154 | N | PHE | 305 | −4.108 | 14.910 | 44.544 | 1.00 | 19.35 | 7 |
| ATOM | 155 | CA | PHE | 305 | −3.651 | 14.820 | 43.183 | 1.00 | 17.57 | 6 |
| ATOM | 156 | CB | PHE | 305 | −2.576 | 15.908 | 42.939 | 1.00 | 17.86 | 6 |
| ATOM | 157 | CG | PHE | 305 | −2.039 | 15.948 | 41.524 | 1.00 | 18.48 | 6 |
| ATOM | 158 | CD1 | PHE | 305 | −2.891 | 16.115 | 40.466 | 1.00 | 18.87 | 6 |
| ATOM | 159 | CD2 | PHE | 305 | −0.672 | 15.850 | 41.285 | 1.00 | 22.41 | 6 |
| ATOM | 160 | CE1 | PHE | 305 | −2.419 | 16.186 | 39.120 | 1.00 | 20.69 | 6 |
| ATOM | 161 | CE2 | PHE | 305 | −0.138 | 15.921 | 39.958 | 1.00 | 23.10 | 6 |
| ATOM | 162 | CZ | PHE | 305 | −1.026 | 16.091 | 38.848 | 1.00 | 22.51 | 6 |

APPENDIX 1-continued

STRUCTURE COORDINATES FOR FXR LBD COMPLEXED WITH FEXARAMINE

| ATOM | 163 | C   | PHE | 305 | −3.059  | 13.436 | 42.989 | 1.00 | 16.51 | 6 |
| ---- | --- | --- | --- | --- | ------- | ------ | ------ | ---- | ----- | - |
| ATOM | 164 | O   | PHE | 305 | −3.325  | 12.755 | 41.979 | 1.00 | 15.12 | 8 |
| ATOM | 165 | N   | THR | 306 | −2.230  | 13.032 | 43.933 | 1.00 | 15.89 | 7 |
| ATOM | 166 | CA  | THR | 306 | −1.542  | 11.705 | 43.868 | 1.00 | 16.43 | 6 |
| ATOM | 167 | CB  | THR | 306 | −0.650  | 11.473 | 45.165 | 1.00 | 15.13 | 6 |
| ATOM | 168 | OG1 | THR | 306 | 0.367   | 12.498 | 45.246 | 1.00 | 14.50 | 8 |
| ATOM | 169 | CG2 | THR | 306 | 0.028   | 10.103 | 45.143 | 1.00 | 16.67 | 6 |
| ATOM | 170 | C   | THR | 306 | −2.495  | 10.526 | 43.667 | 1.00 | 15.78 | 6 |
| ATOM | 171 | O   | THR | 306 | −2.260  | 9.689  | 42.810 | 1.00 | 15.88 | 8 |
| ATOM | 172 | N   | LYS | 307 | −3.596  | 10.486 | 44.420 | 1.00 | 16.48 | 7 |
| ATOM | 173 | CA  | LYS | 307 | −4.516  | 9.371  | 44.300 | 1.00 | 18.55 | 6 |
| ATOM | 174 | CB  | LYS | 307 | −5.601  | 9.465  | 45.401 | 1.00 | 17.71 | 6 |
| ATOM | 175 | CG  | LYS | 307 | −6.581  | 10.619 | 45.227 | 1.00 | 20.71 | 6 |
| ATOM | 176 | CD  | LYS | 307 | −7.339  | 10.932 | 46.549 | 1.00 | 24.94 | 6 |
| ATOM | 177 | CE  | LYS | 307 | −8.366  | 9.878  | 46.684 | 1.00 | 25.72 | 6 |
| ATOM | 178 | NZ  | LYS | 307 | −9.072  | 9.871  | 48.045 | 1.00 | 29.69 | 7 |
| ATOM | 179 | C   | LYS | 307 | −5.157  | 9.282  | 42.905 | 1.00 | 18.63 | 6 |
| ATOM | 180 | O   | LYS | 307 | −5.564  | 8.221  | 42.502 | 1.00 | 21.33 | 8 |
| ATOM | 181 | N   | LYS | 308 | −5.253  | 10.391 | 42.189 | 1.00 | 19.50 | 7 |
| ATOM | 182 | CA  | LYS | 308 | −5.840  | 10.368 | 40.849 | 1.00 | 19.00 | 6 |
| ATOM | 183 | CB  | LYS | 308 | −6.540  | 11.687 | 40.556 | 1.00 | 21.16 | 6 |
| ATOM | 184 | CG  | LYS | 308 | −7.631  | 12.080 | 41.516 | 1.00 | 25.16 | 6 |
| ATOM | 185 | CD  | LYS | 308 | −8.732  | 11.053 | 41.574 | 1.00 | 27.43 | 6 |
| ATOM | 186 | CE  | LYS | 308 | −9.740  | 11.549 | 42.583 | 1.00 | 31.55 | 6 |
| ATOM | 187 | NZ  | LYS | 308 | −10.864 | 10.642 | 42.907 | 1.00 | 33.60 | 7 |
| ATOM | 188 | C   | LYS | 308 | −4.796  | 10.142 | 39.739 | 1.00 | 20.57 | 6 |
| ATOM | 189 | O   | LYS | 308 | −5.170  | 10.129 | 38.545 | 1.00 | 17.08 | 8 |
| ATOM | 190 | N   | LEU | 309 | −3.501  | 10.005 | 40.077 | 1.00 | 19.34 | 7 |
| ATOM | 191 | CA  | LEU | 309 | −2.536  | 9.764  | 38.992 | 1.00 | 20.62 | 6 |
| ATOM | 192 | CB  | LEU | 309 | −1.094  | 9.683  | 39.489 | 1.00 | 19.62 | 6 |
| ATOM | 193 | CG  | LEU | 309 | −0.388  | 11.010 | 39.844 | 1.00 | 21.00 | 6 |
| ATOM | 194 | CD1 | LEU | 309 | −1.298  | 11.787 | 40.514 | 1.00 | 23.97 | 6 |
| ATOM | 195 | CD2 | LEU | 309 | 0.803   | 10.828 | 40.790 | 1.00 | 19.53 | 6 |
| ATOM | 196 | C   | LEU | 309 | −2.828  | 8.475  | 38.224 | 1.00 | 20.21 | 6 |
| ATOM | 197 | O   | LEU | 309 | −3.076  | 7.409  | 38.815 | 1.00 | 18.44 | 8 |
| ATOM | 198 | N   | PRO | 310 | −2.703  | 8.527  | 36.889 | 1.00 | 22.57 | 7 |
| ATOM | 199 | CD  | PRO | 310 | −2.291  | 9.642  | 36.014 | 1.00 | 23.56 | 6 |
| ATOM | 200 | CA  | PRO | 310 | −2.984  | 7.323  | 36.091 | 1.00 | 22.89 | 6 |
| ATOM | 201 | CB  | PRO | 310 | −2.776  | 7.798  | 34.624 | 1.00 | 24.04 | 6 |
| ATOM | 202 | CG  | PRO | 310 | −1.821  | 8.912  | 34.783 | 1.00 | 25.27 | 6 |
| ATOM | 203 | C   | PRO | 310 | −2.096  | 6.158  | 36.485 | 1.00 | 22.58 | 6 |
| ATOM | 204 | O   | PRO | 310 | −0.879  | 6.270  | 36.476 | 1.00 | 21.83 | 8 |
| ATOM | 205 | N   | GLY | 311 | −2.727  | 5.037  | 36.832 | 1.00 | 20.55 | 7 |
| ATOM | 206 | CA  | GLY | 311 | −1.963  | 3.861  | 37.265 | 1.00 | 21.62 | 6 |
| ATOM | 207 | C   | GLY | 311 | −1.642  | 3.820  | 38.757 | 1.00 | 18.98 | 6 |
| ATOM | 208 | O   | GLY | 311 | −1.220  | 2.785  | 39.279 | 1.00 | 18.35 | 8 |
| ATOM | 209 | N   | PHE | 312 | −1.843  | 4.928  | 39.479 | 1.00 | 21.41 | 7 |
| ATOM | 210 | CA  | PHE | 312 | −1.450  | 4.920  | 40.903 | 1.00 | 19.93 | 6 |
| ATOM | 211 | CB  | PHE | 312 | −1.679  | 6.307  | 41.544 | 1.00 | 20.01 | 6 |
| ATOM | 212 | CG  | PHE | 312 | −0.906  | 6.496  | 42.794 | 1.00 | 16.33 | 6 |
| ATOM | 213 | CD1 | PHE | 312 | 0.430   | 6.875  | 42.757 | 1.00 | 18.90 | 6 |
| ATOM | 214 | CD2 | PHE | 312 | −1.507  | 6.270  | 44.029 | 1.00 | 20.84 | 6 |
| ATOM | 215 | CE1 | PHE | 312 | 1.172   | 7.039  | 43.958 | 1.00 | 17.69 | 6 |
| ATOM | 216 | CE2 | PHE | 312 | −0.788  | 6.425  | 45.235 | 1.00 | 19.69 | 6 |
| ATOM | 217 | CZ  | PHE | 312 | 0.560   | 6.817  | 45.182 | 1.00 | 18.11 | 6 |
| ATOM | 218 | C   | PHE | 312 | −2.160  | 3.841  | 41.716 | 1.00 | 21.58 | 6 |
| ATOM | 219 | O   | PHE | 312 | −1.590  | 3.237  | 42.622 | 1.00 | 19.65 | 8 |
| ATOM | 220 | N   | GLN | 313 | −3.348  | 3.539  | 41.367 | 1.00 | 23.23 | 7 |
| ATOM | 221 | CA  | GLN | 313 | −4.014  | 2.563  | 42.216 | 1.00 | 25.13 | 6 |
| ATOM | 222 | CB  | GLN | 313 | −5.525  | 2.588  | 41.921 | 1.00 | 26.97 | 6 |
| ATOM | 223 | CG  | GLN | 313 | −6.130  | 3.954  | 42.336 | 1.00 | 31.32 | 6 |
| ATOM | 224 | CD  | GLN | 313 | −5.793  | 4.264  | 43.792 | 1.00 | 32.76 | 6 |
| ATOM | 225 | OE1 | GLN | 313 | −4.948  | 5.140  | 44.136 | 1.00 | 25.45 | 8 |
| ATOM | 226 | NE2 | GLN | 313 | −6.483  | 3.512  | 44.680 | 1.00 | 36.75 | 7 |
| ATOM | 227 | C   | GLN | 313 | −3.421  | 1.153  | 42.092 | 1.00 | 26.40 | 6 |
| ATOM | 228 | O   | GLN | 313 | −3.775  | 0.256  | 42.850 | 1.00 | 28.47 | 8 |
| ATOM | 229 | N   | THR | 314 | −2.757  | 0.897  | 40.858 | 1.00 | 23.84 | 7 |
| ATOM | 230 | CA  | THR | 314 | −2.207  | −0.476 | 40.645 | 1.00 | 24.52 | 6 |
| ATOM | 231 | CB  | THR | 314 | −1.833  | −0.703 | 39.166 | 1.00 | 23.30 | 6 |
| ATOM | 232 | OG1 | THR | 314 | −0.623  | 0.007  | 38.874 | 1.00 | 22.33 | 8 |
| ATOM | 233 | CG2 | THR | 314 | −2.926  | −0.175 | 38.258 | 1.00 | 24.71 | 6 |
| ATOM | 234 | C   | THR | 314 | −0.904  | −0.784 | 41.458 | 1.00 | 23.15 | 6 |
| ATOM | 235 | O   | THR | 314 | −0.395  | −1.928 | 41.451 | 1.00 | 23.42 | 8 |
| ATOM | 236 | N   | LEU | 315 | −0.335  | 0.221  | 42.125 | 1.00 | 19.70 | 7 |
| ATOM | 237 | CA  | LEU | 315 | 0.916   | 0.005  | 42.855 | 1.00 | 18.48 | 6 |
| ATOM | 238 | CB  | LEU | 315 | 1.645   | 1.361  | 43.069 | 1.00 | 17.29 | 6 |
| ATOM | 239 | CG  | LEU | 315 | 2.054   | 2.194  | 41.830 | 1.00 | 17.40 | 6 |

APPENDIX 1-continued

STRUCTURE COORDINATES FOR FXR LBD COMPLEXED WITH FEXARAMINE

| ATOM | 240 | CD1 | LEU | 315 | 2.693 | 3.602 | 42.217 | 1.00 | 14.19 | 6 |
|------|-----|-----|-----|-----|-------|-------|--------|------|-------|---|
| ATOM | 241 | CD2 | LEU | 315 | 3.069 | 1.301 | 40.990 | 1.00 | 17.25 | 6 |
| ATOM | 242 | C | LEU | 315 | 0.789 | −0.643 | 44.223 | 1.00 | 18.72 | 6 |
| ATOM | 243 | O | LEU | 315 | −0.185 | −0.454 | 44.932 | 1.00 | 20.69 | 8 |
| ATOM | 244 | N | ASP | 316 | 1.826 | −1.349 | 44.616 | 1.00 | 19.50 | 7 |
| ATOM | 245 | CA | ASP | 316 | 1.942 | −1.967 | 45.935 | 1.00 | 19.20 | 6 |
| ATOM | 246 | CB | ASP | 316 | 3.379 | −2.450 | 46.107 | 1.00 | 20.18 | 6 |
| ATOM | 247 | CG | ASP | 316 | 3.698 | −2.794 | 47.540 | 1.00 | 25.37 | 6 |
| ATOM | 248 | OD1 | ASP | 316 | 3.889 | −1.872 | 48.362 | 1.00 | 19.03 | 8 |
| ATOM | 249 | OD2 | ASP | 316 | 3.725 | −4.001 | 47.870 | 1.00 | 25.96 | 8 |
| ATOM | 250 | C | ASP | 316 | 1.640 | −0.813 | 46.969 | 1.00 | 21.35 | 6 |
| ATOM | 251 | O | ASP | 316 | 2.138 | 0.337 | 46.806 | 1.00 | 18.68 | 8 |
| ATOM | 252 | N | HIS | 317 | 0.877 | −1.123 | 48.030 | 1.00 | 19.74 | 7 |
| ATOM | 253 | CA | HIS | 317 | 0.469 | −0.114 | 49.046 | 1.00 | 23.76 | 6 |
| ATOM | 254 | CB | HIS | 317 | −0.545 | −0.735 | 50.037 | 1.00 | 26.00 | 6 |
| ATOM | 255 | CG | HIS | 317 | −1.875 | −1.090 | 49.421 | 1.00 | 30.33 | 6 |
| ATOM | 256 | CD2 | HIS | 317 | −2.992 | −1.617 | 49.978 | 1.00 | 29.44 | 6 |
| ATOM | 257 | ND1 | HIS | 317 | −2.178 | −0.884 | 48.086 | 1.00 | 32.91 | 7 |
| ATOM | 258 | CE1 | HIS | 317 | −3.425 | −1.254 | 47.853 | 1.00 | 32.13 | 6 |
| ATOM | 259 | NE2 | HIS | 317 | −3.936 | −1.704 | 48.986 | 1.00 | 34.72 | 7 |
| ATOM | 260 | C | HIS | 317 | 1.650 | 0.514 | 49.810 | 1.00 | 22.45 | 6 |
| ATOM | 261 | O | HIS | 317 | 1.704 | 1.735 | 50.073 | 1.00 | 22.34 | 8 |
| ATOM | 262 | N | GLU | 318 | 2.615 | −0.277 | 50.210 | 1.00 | 20.95 | 7 |
| ATOM | 263 | CA | GLU | 318 | 3.731 | 0.392 | 50.844 | 1.00 | 21.24 | 6 |
| ATOM | 264 | CB | GLU | 318 | 4.707 | −0.617 | 51.366 | 1.00 | 24.39 | 6 |
| ATOM | 265 | CG | GLU | 318 | 4.078 | −1.508 | 52.430 | 1.00 | 32.15 | 6 |
| ATOM | 266 | CD | GLU | 318 | 4.981 | −2.644 | 52.751 | 1.00 | 35.27 | 6 |
| ATOM | 267 | OE1 | GLU | 318 | 6.173 | −2.389 | 52.981 | 1.00 | 36.95 | 8 |
| ATOM | 268 | OE2 | GLU | 318 | 4.515 | −3.782 | 52.756 | 1.00 | 39.48 | 8 |
| ATOM | 269 | C | GLU | 318 | 4.465 | 1.349 | 49.875 | 1.00 | 21.26 | 6 |
| ATOM | 270 | O | GLU | 318 | 4.956 | 2.426 | 50.290 | 1.00 | 17.47 | 8 |
| ATOM | 271 | N | ASP | 319 | 4.577 | 0.950 | 48.599 | 1.00 | 19.59 | 7 |
| ATOM | 272 | CA | ASP | 319 | 5.313 | 1.796 | 47.654 | 1.00 | 18.68 | 6 |
| ATOM | 273 | CB | ASP | 319 | 5.565 | 1.118 | 46.289 | 1.00 | 18.49 | 6 |
| ATOM | 274 | CG | ASP | 319 | 6.682 | 0.052 | 46.331 | 1.00 | 24.88 | 6 |
| ATOM | 275 | OD1 | ASP | 319 | 7.425 | −0.054 | 47.360 | 1.00 | 23.92 | 8 |
| ATOM | 276 | OD2 | ASP | 319 | 6.785 | −0.672 | 45.300 | 1.00 | 24.68 | 8 |
| ATOM | 277 | C | ASP | 319 | 4.538 | 3.077 | 47.426 | 1.00 | 17.13 | 6 |
| ATOM | 278 | O | ASP | 319 | 5.173 | 4.173 | 47.293 | 1.00 | 15.40 | 8 |
| ATOM | 279 | N | GLN | 320 | 3.190 | 2.968 | 47.441 | 1.00 | 16.62 | 7 |
| ATOM | 280 | CA | GLN | 320 | 2.393 | 4.186 | 47.250 | 1.00 | 15.75 | 6 |
| ATOM | 281 | CB | GLN | 320 | 0.867 | 3.924 | 47.274 | 1.00 | 14.55 | 6 |
| ATOM | 282 | CG | GLN | 320 | 0.250 | 3.078 | 46.102 | 1.00 | 15.80 | 6 |
| ATOM | 283 | CD | GLN | 320 | −1.251 | 2.754 | 46.374 | 1.00 | 18.55 | 6 |
| ATOM | 284 | OE1 | GLN | 320 | −1.639 | 2.464 | 47.530 | 1.00 | 21.01 | 8 |
| ATOM | 285 | NE2 | GLN | 320 | −2.073 | 2.798 | 45.353 | 1.00 | 15.19 | 7 |
| ATOM | 286 | C | GLN | 320 | 2.743 | 5.215 | 48.337 | 1.00 | 15.42 | 6 |
| ATOM | 287 | O | GLN | 320 | 2.917 | 6.407 | 48.047 | 1.00 | 15.10 | 8 |
| ATOM | 288 | N | ILE | 321 | 2.792 | 4.781 | 49.586 | 1.00 | 14.62 | 7 |
| ATOM | 289 | CA | ILE | 321 | 3.085 | 5.717 | 50.641 | 1.00 | 16.80 | 6 |
| ATOM | 290 | CB | ILE | 321 | 2.914 | 5.087 | 52.061 | 1.00 | 17.30 | 6 |
| ATOM | 291 | CG2 | ILE | 321 | 3.411 | 6.037 | 53.174 | 1.00 | 17.43 | 6 |
| ATOM | 292 | CG1 | ILE | 321 | 1.451 | 4.740 | 52.325 | 1.00 | 20.51 | 6 |
| ATOM | 293 | CD1 | ILE | 321 | 0.480 | 5.863 | 52.214 | 1.00 | 20.43 | 6 |
| ATOM | 294 | C | ILE | 321 | 4.515 | 6.223 | 50.489 | 1.00 | 16.01 | 6 |
| ATOM | 295 | O | ILE | 321 | 4.795 | 7.390 | 50.749 | 1.00 | 17.42 | 8 |
| ATOM | 296 | N | ALA | 322 | 5.434 | 5.335 | 50.094 | 1.00 | 15.05 | 7 |
| ATOM | 297 | CA | ALA | 322 | 6.817 | 5.792 | 49.927 | 1.00 | 13.64 | 6 |
| ATOM | 298 | CB | ALA | 322 | 7.705 | 4.636 | 49.571 | 1.00 | 14.95 | 6 |
| ATOM | 299 | C | ALA | 322 | 6.956 | 6.889 | 48.837 | 1.00 | 14.45 | 6 |
| ATOM | 300 | O | ALA | 322 | 7.837 | 7.712 | 48.909 | 1.00 | 14.12 | 8 |
| ATOM | 301 | N | LEU | 323 | 6.129 | 6.838 | 47.798 | 1.00 | 13.09 | 7 |
| ATOM | 302 | CA | LEU | 323 | 6.185 | 7.820 | 46.736 | 1.00 | 12.90 | 6 |
| ATOM | 303 | CB | LEU | 323 | 5.335 | 7.364 | 45.554 | 1.00 | 13.56 | 6 |
| ATOM | 304 | CG | LEU | 323 | 5.872 | 6.173 | 44.746 | 1.00 | 13.89 | 6 |
| ATOM | 305 | CD1 | LEU | 323 | 4.980 | 5.830 | 43.625 | 1.00 | 17.08 | 6 |
| ATOM | 306 | CD2 | LEU | 323 | 7.296 | 6.616 | 44.144 | 1.00 | 16.42 | 6 |
| ATOM | 307 | C | LEU | 323 | 5.596 | 9.141 | 47.294 | 1.00 | 15.12 | 6 |
| ATOM | 308 | O | LEU | 323 | 6.105 | 10.200 | 47.031 | 1.00 | 12.70 | 8 |
| ATOM | 309 | N | LEU | 324 | 4.509 | 9.028 | 48.043 | 1.00 | 14.66 | 7 |
| ATOM | 310 | CA | LEU | 324 | 3.835 | 10.189 | 48.586 | 1.00 | 16.63 | 6 |
| ATOM | 311 | CB | LEU | 324 | 2.600 | 9.738 | 49.393 | 1.00 | 16.39 | 6 |
| ATOM | 312 | CG | LEU | 324 | 1.730 | 10.820 | 50.048 | 1.00 | 17.06 | 6 |
| ATOM | 313 | CD1 | LEU | 324 | 0.796 | 11.523 | 48.959 | 1.00 | 14.93 | 6 |
| ATOM | 314 | CD2 | LEU | 324 | 0.830 | 10.132 | 51.172 | 1.00 | 17.39 | 6 |
| ATOM | 315 | C | LEU | 324 | 4.769 | 10.966 | 49.483 | 1.00 | 16.68 | 6 |
| ATOM | 316 | O | LEU | 324 | 4.963 | 12.164 | 49.335 | 1.00 | 13.80 | 8 |

APPENDIX 1-continued

STRUCTURE COORDINATES FOR FXR LBD COMPLEXED WITH FEXARAMINE

| ATOM | 317 | N   | LYS | 325 | 5.355  | 10.268 | 50.439 | 1.00 | 16.50 | 7  |
|------|-----|-----|-----|-----|--------|--------|--------|------|-------|----|
| ATOM | 318 | CA  | LYS | 325 | 6.249  | 10.950 | 51.356 | 1.00 | 17.35 | 6  |
| ATOM | 319 | CB  | LYS | 325 | 6.574  | 10.007 | 52.549 | 1.00 | 18.02 | 6  |
| ATOM | 320 | CG  | LYS | 325 | 5.337  | 9.621  | 53.416 | 1.00 | 19.36 | 6  |
| ATOM | 321 | CD  | LYS | 325 | 5.733  | 8.612  | 54.460 | 1.00 | 22.22 | 6  |
| ATOM | 322 | CE  | LYS | 325 | 4.597  | 8.289  | 55.400 | 1.00 | 26.08 | 6  |
| ATOM | 323 | NZ  | LYS | 325 | 5.009  | 7.369  | 56.518 | 1.00 | 27.52 | 7  |
| ATOM | 324 | C   | LYS | 325 | 7.579  | 11.456 | 50.669 | 1.00 | 18.31 | 6  |
| ATOM | 325 | O   | LYS | 325 | 8.069  | 12.528 | 50.979 | 1.00 | 17.70 | 8  |
| ATOM | 326 | N   | GLY | 326 | 8.142  | 10.599 | 49.805 | 1.00 | 17.79 | 7  |
| ATOM | 327 | CA  | GLY | 326 | 9.354  | 10.910 | 49.086 | 1.00 | 16.62 | 6  |
| ATOM | 328 | C   | GLY | 326 | 9.145  | 12.181 | 48.210 | 1.00 | 16.82 | 6  |
| ATOM | 329 | O   | GLY | 326 | 10.115 | 12.892 | 47.944 | 1.00 | 15.87 | 8  |
| ATOM | 330 | N   | SER | 327 | 7.904  | 12.479 | 47.802 | 1.00 | 13.98 | 7  |
| ATOM | 331 | CA  | SER | 327 | 7.668  | 13.640 | 46.919 | 1.00 | 13.96 | 6  |
| ATOM | 332 | CB  | SER | 327 | 6.663  | 13.252 | 45.806 | 1.00 | 15.72 | 6  |
| ATOM | 333 | OG  | SER | 327 | 5.352  | 13.032 | 46.367 | 1.00 | 17.33 | 8  |
| ATOM | 334 | C   | SER | 327 | 7.136  | 14.943 | 47.589 | 1.00 | 14.59 | 6  |
| ATOM | 335 | O   | SER | 327 | 7.060  | 15.968 | 46.914 | 1.00 | 12.64 | 8  |
| ATOM | 336 | N   | ALA | 328 | 6.703  | 14.860 | 48.858 | 1.00 | 14.21 | 7  |
| ATOM | 337 | CA  | ALA | 328 | 6.067  | 15.995 | 49.559 | 1.00 | 16.31 | 6  |
| ATOM | 338 | CB  | ALA | 328 | 5.710  | 15.643 | 51.028 | 1.00 | 14.45 | 6  |
| ATOM | 339 | C   | ALA | 328 | 6.755  | 17.348 | 49.512 | 1.00 | 15.67 | 6  |
| ATOM | 340 | O   | ALA | 328 | 6.104  | 18.291 | 49.129 | 1.00 | 16.81 | 8  |
| ATOM | 341 | N   | VAL | 329 | 8.056  | 17.419 | 49.818 | 1.00 | 15.11 | 7  |
| ATOM | 342 | CA  | VAL | 329 | 8.797  | 18.669 | 49.801 | 1.00 | 14.39 | 6  |
| ATOM | 343 | CB  | VAL | 329 | 10.193 | 18.472 | 50.471 | 1.00 | 15.93 | 6  |
| ATOM | 344 | CG1 | VAL | 329 | 10.996 | 19.721 | 50.324 | 1.00 | 14.45 | 6  |
| ATOM | 345 | CG2 | VAL | 329 | 10.006 | 17.992 | 51.946 | 1.00 | 18.03 | 6  |
| ATOM | 346 | C   | VAL | 329 | 8.955  | 19.166 | 48.378 | 1.00 | 15.82 | 6  |
| ATOM | 347 | O   | VAL | 329 | 8.639  | 20.309 | 48.107 | 1.00 | 15.63 | 8  |
| ATOM | 348 | N   | GLU | 330 | 9.390  | 18.308 | 47.441 | 1.00 | 14.35 | 7  |
| ATOM | 349 | CA  | GLU | 330 | 9.523  | 18.808 | 46.081 | 1.00 | 16.61 | 6  |
| ATOM | 350 | CB  | GLU | 330 | 10.155 | 17.784 | 45.127 | 1.00 | 17.85 | 6  |
| ATOM | 351 | CG  | GLU | 330 | 11.579 | 17.359 | 45.457 | 1.00 | 19.53 | 6  |
| ATOM | 352 | CD  | GLU | 330 | 11.904 | 15.959 | 44.863 | 1.00 | 22.28 | 6  |
| ATOM | 353 | OE1 | GLU | 330 | 11.344 | 15.676 | 43.785 | 1.00 | 16.30 | 8  |
| ATOM | 354 | OE2 | GLU | 330 | 12.729 | 15.180 | 45.437 | 1.00 | 18.52 | 8  |
| ATOM | 355 | C   | GLU | 330 | 8.188  | 19.282 | 45.482 | 1.00 | 16.03 | 6  |
| ATOM | 356 | O   | GLU | 330 | 8.184  | 20.319 | 44.811 | 1.00 | 16.48 | 8  |
| ATOM | 357 | N   | ALA | 331 | 7.097  | 18.572 | 45.719 | 1.00 | 15.19 | 7  |
| ATOM | 358 | CA  | ALA | 331 | 5.781  | 18.982 | 45.169 | 1.00 | 16.21 | 6  |
| ATOM | 359 | CB  | ALA | 331 | 4.698  | 17.954 | 45.510 | 1.00 | 18.20 | 6  |
| ATOM | 360 | C   | ALA | 331 | 5.371  | 20.312 | 45.749 | 1.00 | 14.82 | 6  |
| ATOM | 361 | O   | ALA | 331 | 4.797  | 21.166 | 45.056 | 1.00 | 14.73 | 8  |
| ATOM | 362 | N   | MET | 332 | 5.647  | 20.482 | 47.019 | 1.00 | 14.40 | 7  |
| ATOM | 363 | CA  | MET | 332 | 5.303  | 21.728 | 47.667 | 1.00 | 16.90 | 6  |
| ATOM | 364 | CB  | MET | 332 | 5.581  | 21.650 | 49.171 | 1.00 | 16.44 | 6  |
| ATOM | 365 | CG  | MET | 332 | 5.472  | 22.995 | 49.820 | 1.00 | 17.98 | 6  |
| ATOM | 366 | SD  | MET | 332 | 5.578  | 22.728 | 51.691 | 1.00 | 25.41 | 16 |
| ATOM | 367 | CE  | MET | 332 | 7.346  | 22.648 | 51.873 | 1.00 | 20.17 | 6  |
| ATOM | 368 | C   | MET | 332 | 6.067  | 22.929 | 47.045 | 1.00 | 16.28 | 6  |
| ATOM | 369 | O   | MET | 332 | 5.489  | 24.017 | 46.846 | 1.00 | 14.37 | 8  |
| ATOM | 370 | N   | PHE | 333 | 7.363  | 22.737 | 46.759 | 1.00 | 16.46 | 7  |
| ATOM | 371 | CA  | PHE | 333 | 8.120  | 23.802 | 46.113 | 1.00 | 16.88 | 6  |
| ATOM | 372 | CB  | PHE | 333 | 9.651  | 23.556 | 46.190 | 1.00 | 15.57 | 6  |
| ATOM | 373 | CG  | PHE | 333 | 10.225 | 24.020 | 47.513 | 1.00 | 16.37 | 6  |
| ATOM | 374 | CD1 | PHE | 333 | 10.633 | 25.365 | 47.684 | 1.00 | 19.32 | 6  |
| ATOM | 375 | CD2 | PHE | 333 | 10.160 | 23.188 | 48.634 | 1.00 | 16.95 | 6  |
| ATOM | 376 | CE1 | PHE | 333 | 10.946 | 25.890 | 49.008 | 1.00 | 20.18 | 6  |
| ATOM | 377 | CE2 | PHE | 333 | 10.472 | 23.690 | 49.957 | 1.00 | 19.20 | 6  |
| ATOM | 378 | CZ  | PHE | 333 | 10.853 | 25.043 | 50.131 | 1.00 | 18.12 | 6  |
| ATOM | 379 | C   | PHE | 333 | 7.695  | 24.044 | 44.683 | 1.00 | 18.09 | 6  |
| ATOM | 380 | O   | PHE | 333 | 7.646  | 25.172 | 44.251 | 1.00 | 18.76 | 8  |
| ATOM | 381 | N   | LEU | 334 | 7.409  | 22.989 | 43.937 | 1.00 | 17.85 | 7  |
| ATOM | 382 | CA  | LEU | 334 | 6.958  | 23.153 | 42.584 | 1.00 | 18.30 | 6  |
| ATOM | 383 | CB  | LEU | 334 | 6.809  | 21.764 | 42.025 | 1.00 | 18.77 | 6  |
| ATOM | 384 | CG  | LEU | 334 | 7.155  | 21.507 | 40.592 | 1.00 | 26.18 | 6  |
| ATOM | 385 | CD1 | LEU | 334 | 6.960  | 19.943 | 40.217 | 1.00 | 24.92 | 6  |
| ATOM | 386 | CD2 | LEU | 334 | 6.331  | 22.317 | 39.812 | 1.00 | 28.42 | 6  |
| ATOM | 387 | C   | LEU | 334 | 5.598  | 23.904 | 42.579 | 1.00 | 17.11 | 6  |
| ATOM | 388 | O   | LEU | 334 | 5.357  | 24.832 | 41.793 | 1.00 | 15.65 | 8  |
| ATOM | 389 | N   | ARG | 335 | 4.690  | 23.482 | 43.439 | 1.00 | 16.49 | 7  |
| ATOM | 390 | CA  | ARG | 335 | 3.399  | 24.176 | 43.524 | 1.00 | 18.43 | 6  |
| ATOM | 391 | CB  | ARG | 335 | 2.484  | 23.454 | 44.460 | 1.00 | 17.09 | 6  |
| ATOM | 392 | CG  | ARG | 335 | 1.156  | 24.182 | 44.525 | 1.00 | 21.57 | 6  |
| ATOM | 393 | CD  | ARG | 335 | 0.176  | 23.373 | 45.352 | 1.00 | 21.97 | 6  |

APPENDIX 1-continued

STRUCTURE COORDINATES FOR FXR LBD COMPLEXED WITH FEXARAMINE

| ATOM | 394 | NE | ARG | 335 | −1.089 | 24.081 | 45.471 | 1.00 | 27.76 | 7 |
|---|---|---|---|---|---|---|---|---|---|---|
| ATOM | 395 | CZ | ARG | 335 | −1.783 | 24.172 | 46.606 | 1.00 | 28.73 | 6 |
| ATOM | 396 | NH1 | ARG | 335 | −1.319 | 23.581 | 47.717 | 1.00 | 31.14 | 7 |
| ATOM | 397 | NH2 | ARG | 335 | −2.894 | 24.888 | 46.653 | 1.00 | 29.24 | 7 |
| ATOM | 398 | C | ARG | 335 | 3.494 | 25.687 | 43.962 | 1.00 | 19.12 | 6 |
| ATOM | 399 | O | ARG | 335 | 2.788 | 26.537 | 43.441 | 1.00 | 16.26 | 8 |
| ATOM | 400 | N | SER | 336 | 4.312 | 25.980 | 44.978 | 1.00 | 18.56 | 7 |
| ATOM | 401 | CA | SER | 336 | 4.544 | 27.347 | 45.432 | 1.00 | 18.60 | 6 |
| ATOM | 402 | CB | SER | 336 | 5.559 | 27.322 | 46.590 | 1.00 | 18.30 | 6 |
| ATOM | 403 | OG | SER | 336 | 5.002 | 26.665 | 47.691 | 1.00 | 29.88 | 8 |
| ATOM | 404 | C | SER | 336 | 5.188 | 28.112 | 44.234 | 1.00 | 18.04 | 6 |
| ATOM | 405 | O | SER | 336 | 4.893 | 29.303 | 43.988 | 1.00 | 18.32 | 8 |
| ATOM | 406 | N | ALA | 337 | 6.033 | 27.419 | 43.467 | 1.00 | 16.79 | 7 |
| ATOM | 407 | CA | ALA | 337 | 6.676 | 28.097 | 42.346 | 1.00 | 17.46 | 6 |
| ATOM | 408 | CB | ALA | 337 | 7.796 | 27.201 | 41.665 | 1.00 | 18.26 | 6 |
| ATOM | 409 | C | ALA | 337 | 5.643 | 28.541 | 41.331 | 1.00 | 18.29 | 6 |
| ATOM | 410 | O | ALA | 337 | 5.713 | 29.677 | 40.829 | 1.00 | 17.95 | 8 |
| ATOM | 411 | N | GLU | 338 | 4.674 | 27.670 | 41.042 | 1.00 | 19.09 | 7 |
| ATOM | 412 | CA | GLU | 338 | 3.637 | 28.006 | 40.090 | 1.00 | 21.75 | 6 |
| ATOM | 413 | CB | GLU | 338 | 2.759 | 26.775 | 39.807 | 1.00 | 22.98 | 6 |
| ATOM | 414 | CG | GLU | 338 | 1.577 | 27.106 | 38.908 | 1.00 | 27.45 | 6 |
| ATOM | 415 | CD | GLU | 338 | 0.641 | 25.937 | 38.689 | 1.00 | 30.18 | 6 |
| ATOM | 416 | OE1 | GLU | 338 | 0.424 | 25.154 | 39.626 | 1.00 | 34.22 | 8 |
| ATOM | 417 | OE2 | GLU | 338 | 0.081 | 25.793 | 37.564 | 1.00 | 34.98 | 8 |
| ATOM | 418 | C | GLU | 338 | 2.782 | 29.173 | 40.622 | 1.00 | 21.21 | 6 |
| ATOM | 419 | O | GLU | 338 | 2.464 | 30.127 | 39.887 | 1.00 | 21.40 | 8 |
| ATOM | 420 | N | ILE | 339 | 2.432 | 29.119 | 41.898 | 1.00 | 21.45 | 7 |
| ATOM | 421 | CA | ILE | 339 | 1.636 | 30.185 | 42.482 | 1.00 | 21.47 | 6 |
| ATOM | 422 | CB | ILE | 339 | 1.255 | 29.863 | 43.943 | 1.00 | 19.46 | 6 |
| ATOM | 423 | CG2 | ILE | 339 | 0.560 | 31.059 | 44.597 | 1.00 | 18.31 | 6 |
| ATOM | 424 | CG1 | ILE | 339 | 0.321 | 28.655 | 43.994 | 1.00 | 21.28 | 6 |
| ATOM | 425 | CD1 | ILE | 339 | 0.215 | 28.014 | 45.481 | 1.00 | 21.24 | 6 |
| ATOM | 426 | C | ILE | 339 | 2.356 | 31.542 | 42.432 | 1.00 | 22.43 | 6 |
| ATOM | 427 | O | ILE | 339 | 1.744 | 32.541 | 42.102 | 1.00 | 22.81 | 8 |
| ATOM | 428 | N | PHE | 340 | 3.631 | 31.579 | 42.779 | 1.00 | 23.06 | 7 |
| ATOM | 429 | CA | PHE | 340 | 4.365 | 32.829 | 42.746 | 1.00 | 24.91 | 6 |
| ATOM | 430 | CB | PHE | 340 | 5.753 | 32.634 | 43.320 | 1.00 | 27.89 | 6 |
| ATOM | 431 | CG | PHE | 340 | 5.837 | 32.969 | 44.752 | 1.00 | 33.81 | 6 |
| ATOM | 432 | CD1 | PHE | 340 | 5.162 | 32.200 | 45.713 | 1.00 | 34.20 | 6 |
| ATOM | 433 | CD2 | PHE | 340 | 6.534 | 34.126 | 45.155 | 1.00 | 36.42 | 6 |
| ATOM | 434 | CE1 | PHE | 340 | 5.177 | 32.590 | 47.082 | 1.00 | 37.61 | 6 |
| ATOM | 435 | CE2 | PHE | 340 | 6.560 | 34.532 | 46.511 | 1.00 | 38.51 | 6 |
| ATOM | 436 | CZ | PHE | 340 | 5.876 | 33.766 | 47.479 | 1.00 | 37.64 | 6 |
| ATOM | 437 | C | PHE | 340 | 4.498 | 33.429 | 41.364 | 1.00 | 24.41 | 6 |
| ATOM | 438 | O | PHE | 340 | 4.479 | 34.639 | 41.225 | 1.00 | 23.54 | 8 |
| ATOM | 439 | N | ASN | 341 | 4.665 | 32.577 | 40.352 | 1.00 | 23.80 | 7 |
| ATOM | 440 | CA | ASN | 341 | 4.820 | 33.038 | 38.983 | 1.00 | 24.65 | 6 |
| ATOM | 441 | CB | ASN | 341 | 5.600 | 32.001 | 38.121 | 1.00 | 23.93 | 6 |
| ATOM | 442 | CG | ASN | 341 | 7.109 | 32.073 | 38.315 | 1.00 | 22.97 | 6 |
| ATOM | 443 | OD1 | ASN | 341 | 7.755 | 32.970 | 37.793 | 1.00 | 23.91 | 8 |
| ATOM | 444 | ND2 | ASN | 341 | 7.670 | 31.126 | 39.048 | 1.00 | 20.60 | 7 |
| ATOM | 445 | C | ASN | 341 | 3.495 | 33.321 | 38.256 | 1.00 | 25.81 | 6 |
| ATOM | 446 | O | ASN | 341 | 3.414 | 34.302 | 37.509 | 1.00 | 27.47 | 8 |
| ATOM | 447 | N | LYS | 342 | 2.496 | 32.466 | 38.439 | 1.00 | 24.48 | 7 |
| ATOM | 448 | CA | LYS | 342 | 1.247 | 32.608 | 37.700 | 1.00 | 25.08 | 6 |
| ATOM | 449 | CB | LYS | 342 | 0.876 | 31.259 | 37.085 | 1.00 | 22.98 | 6 |
| ATOM | 450 | CG | LYS | 342 | 2.062 | 30.531 | 36.494 | 1.00 | 24.27 | 6 |
| ATOM | 451 | CD | LYS | 342 | 1.647 | 29.193 | 35.945 | 1.00 | 28.99 | 6 |
| ATOM | 452 | CE | LYS | 342 | 0.826 | 29.237 | 34.652 | 1.00 | 27.76 | 6 |
| ATOM | 453 | NZ | LYS | 342 | 1.671 | 29.690 | 33.538 | 1.00 | 27.89 | 7 |
| ATOM | 454 | C | LYS | 342 | 0.031 | 33.147 | 38.416 | 1.00 | 25.41 | 6 |
| ATOM | 455 | O | LYS | 342 | −0.925 | 33.562 | 37.759 | 1.00 | 25.80 | 8 |
| ATOM | 456 | N | LYS | 343 | 0.040 | 33.143 | 39.741 | 1.00 | 25.92 | 7 |
| ATOM | 457 | CA | LYS | 343 | −1.134 | 33.579 | 40.464 | 1.00 | 29.28 | 6 |
| ATOM | 458 | CB | LYS | 343 | −1.684 | 32.396 | 41.289 | 1.00 | 30.55 | 6 |
| ATOM | 459 | CG | LYS | 343 | −2.177 | 31.209 | 40.428 | 1.00 | 34.94 | 6 |
| ATOM | 460 | CD | LYS | 343 | −2.189 | 29.909 | 41.276 | 1.00 | 38.00 | 6 |
| ATOM | 461 | CE | LYS | 343 | −2.844 | 28.710 | 40.539 | 1.00 | 42.13 | 6 |
| ATOM | 462 | NZ | LYS | 343 | −4.264 | 29.048 | 40.111 | 1.00 | 45.88 | 7 |
| ATOM | 463 | C | LYS | 343 | −0.973 | 34.821 | 41.327 | 1.00 | 29.54 | 6 |
| ATOM | 464 | O | LYS | 343 | −1.937 | 35.623 | 41.337 | 1.00 | 30.97 | 8 |
| ATOM | 465 | N | LEU | 344 | 0.186 | 35.012 | 41.973 | 1.00 | 29.12 | 7 |
| ATOM | 466 | CA | LEU | 344 | 0.409 | 36.153 | 42.846 | 1.00 | 30.88 | 6 |
| ATOM | 467 | CB | LEU | 344 | 1.427 | 35.842 | 44.008 | 1.00 | 33.60 | 6 |
| ATOM | 468 | CG | LEU | 344 | 0.966 | 35.142 | 45.315 | 1.00 | 36.84 | 6 |
| ATOM | 469 | CD1 | LEU | 344 | 1.439 | 35.838 | 46.518 | 1.00 | 38.66 | 6 |
| ATOM | 470 | CD2 | LEU | 344 | −0.453 | 35.289 | 45.496 | 1.00 | 37.58 | 6 |

APPENDIX 1-continued

STRUCTURE COORDINATES FOR FXR LBD COMPLEXED WITH FEXARAMINE

| ATOM | 471 | C | LEU | 344 | 1.050 | 37.348 | 42.159 | 1.00 | 29.59 | 6 |
| ATOM | 472 | O | LEU | 344 | 2.090 | 37.211 | 41.470 | 1.00 | 27.82 | 8 |
| ATOM | 473 | N | PRO | 345 | 0.459 | 38.567 | 42.427 | 1.00 | 31.73 | 7 |
| ATOM | 474 | CD | PRO | 345 | −0.782 | 38.971 | 43.119 | 1.00 | 30.83 | 6 |
| ATOM | 475 | CA | PRO | 345 | 1.058 | 39.747 | 41.821 | 1.00 | 32.80 | 6 |
| ATOM | 476 | CB | PRO | 345 | 0.109 | 40.882 | 42.162 | 1.00 | 32.28 | 6 |
| ATOM | 477 | CG | PRO | 345 | −0.663 | 40.499 | 43.278 | 1.00 | 32.28 | 6 |
| ATOM | 478 | C | PRO | 345 | 2.406 | 39.957 | 42.437 | 1.00 | 35.91 | 6 |
| ATOM | 479 | O | PRO | 345 | 2.634 | 39.519 | 43.614 | 1.00 | 35.86 | 8 |
| ATOM | 480 | N | SER | 346 | 3.334 | 40.501 | 41.648 | 1.00 | 39.68 | 7 |
| ATOM | 481 | CA | SER | 346 | 4.637 | 40.670 | 42.251 | 1.00 | 43.69 | 6 |
| ATOM | 482 | CB | SER | 346 | 5.738 | 41.300 | 41.367 | 1.00 | 44.35 | 6 |
| ATOM | 483 | OG | SER | 346 | 5.957 | 40.576 | 40.195 | 1.00 | 45.03 | 8 |
| ATOM | 484 | C | SER | 346 | 4.663 | 41.551 | 43.477 | 1.00 | 46.72 | 6 |
| ATOM | 485 | O | SER | 346 | 5.772 | 41.833 | 43.906 | 1.00 | 49.01 | 8 |
| ATOM | 486 | N | GLY | 347 | 3.864 | 41.890 | 44.052 | 1.00 | 48.86 | 7 |
| ATOM | 487 | CA | GLY | 347 | 3.901 | 42.777 | 45.174 | 1.00 | 51.37 | 6 |
| ATOM | 488 | C | GLY | 347 | 3.693 | 42.029 | 46.475 | 1.00 | 51.01 | 6 |
| ATOM | 489 | O | GLY | 347 | 3.343 | 42.624 | 47.516 | 1.00 | 51.80 | 8 |
| ATOM | 490 | N | HIS | 348 | 2.705 | 41.076 | 46.101 | 1.00 | 49.68 | 7 |
| ATOM | 491 | CA | HIS | 348 | 2.235 | 40.289 | 47.237 | 1.00 | 49.33 | 6 |
| ATOM | 492 | C | HIS | 348 | 3.289 | 39.274 | 47.657 | 1.00 | 49.31 | 6 |
| ATOM | 493 | O | HIS | 348 | 3.321 | 38.722 | 48.607 | 1.00 | 49.10 | 8 |
| ATOM | 494 | CB | HIS | 348 | 0.940 | 39.527 | 46.888 | 1.00 | 50.03 | 6 |
| ATOM | 495 | CG | HIS | 348 | −0.240 | 40.445 | 46.482 | 1.00 | 52.00 | 6 |
| ATOM | 496 | ND1 | HIS | 348 | −0.901 | 41.250 | 47.385 | 1.00 | 20.00 | 7 |
| ATOM | 497 | CD2 | HIS | 348 | −0.836 | 40.652 | 45.285 | 1.00 | 20.00 | 6 |
| ATOM | 498 | CE1 | HIS | 348 | −1.856 | 41.916 | 46.759 | 1.00 | 20.00 | 6 |
| ATOM | 499 | NE2 | HIS | 348 | −1.838 | 41.571 | 45.484 | 1.00 | 20.00 | 7 |
| ATOM | 500 | N | SER | 349 | 4.229 | 39.205 | 46.618 | 1.00 | 48.97 | 7 |
| ATOM | 501 | CA | SER | 349 | 5.367 | 38.283 | 46.822 | 1.00 | 48.03 | 6 |
| ATOM | 502 | CB | SER | 349 | 5.975 | 37.696 | 45.538 | 1.00 | 49.59 | 6 |
| ATOM | 503 | OG | SER | 349 | 5.094 | 36.756 | 44.992 | 1.00 | 52.99 | 8 |
| ATOM | 504 | C | SER | 349 | 6.461 | 38.889 | 47.588 | 1.00 | 46.83 | 6 |
| ATOM | 505 | O | SER | 349 | 6.999 | 38.247 | 48.490 | 1.00 | 45.12 | 8 |
| ATOM | 506 | N | ASP | 350 | 6.808 | 40.129 | 47.266 | 1.00 | 45.53 | 7 |
| ATOM | 507 | CA | ASP | 350 | 7.881 | 40.775 | 48.049 | 1.00 | 44.40 | 6 |
| ATOM | 508 | CB | ASP | 350 | 8.338 | 42.169 | 47.430 | 1.00 | 46.18 | 6 |
| ATOM | 509 | CG | ASP | 350 | 8.245 | 42.222 | 45.811 | 1.00 | 48.32 | 6 |
| ATOM | 510 | OD1 | ASP | 350 | 8.264 | 41.151 | 45.237 | 1.00 | 48.97 | 8 |
| ATOM | 511 | OD2 | ASP | 350 | 8.174 | 43.288 | 45.086 | 1.00 | 49.98 | 8 |
| ATOM | 512 | C | ASP | 350 | 7.358 | 40.943 | 49.512 | 1.00 | 42.08 | 6 |
| ATOM | 513 | O | ASP | 350 | 8.132 | 41.063 | 50.450 | 1.00 | 41.23 | 8 |
| ATOM | 514 | N | LEU | 351 | 6.046 | 41.001 | 49.671 | 1.00 | 40.76 | 7 |
| ATOM | 515 | CA | LEU | 351 | 5.454 | 41.102 | 50.966 | 1.00 | 39.24 | 6 |
| ATOM | 516 | CB | LEU | 351 | 4.040 | 41.556 | 50.828 | 1.00 | 40.26 | 6 |
| ATOM | 517 | CG | LEU | 351 | 3.970 | 43.030 | 51.263 | 1.00 | 43.57 | 6 |
| ATOM | 518 | CD1 | LEU | 351 | 5.191 | 43.868 | 50.777 | 1.00 | 44.27 | 6 |
| ATOM | 519 | CD2 | LEU | 351 | 2.672 | 43.599 | 50.735 | 1.00 | 42.89 | 6 |
| ATOM | 520 | C | LEU | 351 | 5.528 | 39.757 | 51.703 | 1.00 | 38.55 | 6 |
| ATOM | 521 | O | LEU | 351 | 5.700 | 39.682 | 52.916 | 1.00 | 36.15 | 8 |
| ATOM | 522 | N | LEU | 352 | 5.394 | 38.661 | 50.964 | 1.00 | 35.86 | 7 |
| ATOM | 523 | CA | LEU | 352 | 5.479 | 37.336 | 51.587 | 1.00 | 34.36 | 6 |
| ATOM | 524 | CB | LEU | 352 | 4.861 | 36.224 | 50.695 | 1.00 | 36.39 | 6 |
| ATOM | 525 | CG | LEU | 352 | 3.607 | 35.615 | 51.310 | 1.00 | 38.73 | 6 |
| ATOM | 526 | CD1 | LEU | 352 | 2.617 | 36.628 | 51.792 | 1.00 | 40.40 | 6 |
| ATOM | 527 | CD2 | LEU | 352 | 3.022 | 34.774 | 50.199 | 1.00 | 39.17 | 6 |
| ATOM | 528 | C | LEU | 352 | 6.924 | 37.010 | 51.959 | 1.00 | 33.09 | 6 |
| ATOM | 529 | O | LEU | 352 | 7.161 | 36.388 | 52.999 | 1.00 | 31.06 | 8 |
| ATOM | 530 | N | GLU | 353 | 7.879 | 37.476 | 51.155 | 1.00 | 32.12 | 7 |
| ATOM | 531 | CA | GLU | 353 | 9.299 | 37.261 | 51.445 | 1.00 | 34.04 | 6 |
| ATOM | 532 | CB | GLU | 353 | 10.189 | 37.765 | 50.301 | 1.00 | 35.06 | 6 |
| ATOM | 533 | CG | GLU | 353 | 11.677 | 37.679 | 50.629 | 1.00 | 38.80 | 6 |
| ATOM | 534 | CD | GLU | 353 | 12.559 | 38.117 | 49.473 | 1.00 | 41.58 | 6 |
| ATOM | 535 | OE1 | GLU | 353 | 12.415 | 37.601 | 48.369 | 1.00 | 44.58 | 8 |
| ATOM | 536 | OE2 | GLU | 353 | 13.419 | 38.988 | 49.632 | 1.00 | 44.72 | 8 |
| ATOM | 537 | C | GLU | 353 | 9.725 | 37.983 | 52.736 | 1.00 | 34.22 | 6 |
| ATOM | 538 | O | GLU | 353 | 10.557 | 37.493 | 53.513 | 1.00 | 32.47 | 8 |
| ATOM | 539 | N | GLU | 354 | 9.098 | 39.204 | 52.963 | 1.00 | 33.64 | 7 |
| ATOM | 540 | CA | GLU | 354 | 9.410 | 40.097 | 54.063 | 1.00 | 35.11 | 6 |
| ATOM | 541 | CB | GLU | 354 | 8.910 | 41.506 | 53.712 | 1.00 | 37.91 | 6 |
| ATOM | 542 | CG | GLU | 354 | 9.030 | 42.544 | 54.805 | 1.00 | 42.37 | 6 |
| ATOM | 543 | CD | GLU | 354 | 7.846 | 43.504 | 54.803 | 1.00 | 45.04 | 6 |
| ATOM | 544 | OE1 | GLU | 354 | 8.026 | 44.610 | 54.232 | 1.00 | 48.51 | 8 |
| ATOM | 545 | OE2 | GLU | 354 | 6.750 | 43.150 | 55.341 | 1.00 | 44.43 | 8 |
| ATOM | 546 | C | GLU | 354 | 8.697 | 39.549 | 55.277 | 1.00 | 33.30 | 6 |
| ATOM | 547 | O | GLU | 354 | 9.291 | 39.453 | 56.351 | 1.00 | 34.63 | 8 |

APPENDIX 1-continued

STRUCTURE COORDINATES FOR FXR LBD COMPLEXED WITH FEXARAMINE

| ATOM | 548 | N   | ARG | 355 | 7.616  | 38.768 | 55.113 | 1.00 | 31.81 | 7 |
|------|-----|-----|-----|-----|--------|--------|--------|------|-------|---|
| ATOM | 549 | CA  | ARG | 355 | 6.901  | 38.090 | 56.172 | 1.00 | 32.49 | 6 |
| ATOM | 550 | CB  | ARG | 355 | 5.511  | 37.716 | 55.676 | 1.00 | 35.34 | 6 |
| ATOM | 551 | CG  | ARG | 355 | 4.679  | 36.915 | 56.673 | 1.00 | 38.68 | 6 |
| ATOM | 552 | CD  | ARG | 355 | 4.309  | 37.797 | 57.855 | 1.00 | 42.55 | 6 |
| ATOM | 553 | NE  | ARG | 355 | 4.063  | 37.012 | 59.057 | 1.00 | 44.20 | 7 |
| ATOM | 554 | CZ  | ARG | 355 | 5.002  | 36.544 | 59.877 | 1.00 | 46.76 | 6 |
| ATOM | 555 | NH1 | ARG | 355 | 6.306  | 36.764 | 59.656 | 1.00 | 45.35 | 7 |
| ATOM | 556 | NH2 | ARG | 355 | 4.616  | 35.864 | 60.962 | 1.00 | 50.30 | 7 |
| ATOM | 557 | C   | ARG | 355 | 7.651  | 36.842 | 56.615 | 1.00 | 32.79 | 6 |
| ATOM | 558 | O   | ARG | 355 | 7.843  | 36.597 | 57.804 | 1.00 | 31.25 | 8 |
| ATOM | 559 | N   | ILE | 356 | 8.115  | 36.037 | 55.662 | 1.00 | 31.30 | 7 |
| ATOM | 560 | CA  | ILE | 356 | 8.802  | 34.818 | 56.066 | 1.00 | 31.81 | 6 |
| ATOM | 561 | CB  | ILE | 356 | 8.906  | 33.776 | 54.868 | 1.00 | 29.87 | 6 |
| ATOM | 562 | CG2 | ILE | 356 | 10.063 | 34.169 | 53.868 | 1.00 | 29.78 | 6 |
| ATOM | 563 | CG1 | ILE | 356 | 9.220  | 32.361 | 55.437 | 1.00 | 31.98 | 6 |
| ATOM | 564 | CD1 | ILE | 356 | 9.226  | 31.168 | 54.362 | 1.00 | 27.51 | 6 |
| ATOM | 565 | C   | ILE | 356 | 10.205 | 35.055 | 56.638 | 1.00 | 32.66 | 6 |
| ATOM | 566 | O   | ILE | 356 | 10.641 | 34.346 | 57.572 | 1.00 | 30.28 | 8 |
| ATOM | 567 | N   | ARG | 357 | 10.962 | 36.020 | 56.110 | 1.00 | 34.98 | 7 |
| ATOM | 568 | CA  | ARG | 357 | 12.324 | 36.200 | 56.661 | 1.00 | 38.93 | 6 |
| ATOM | 569 | CB  | ARG | 357 | 13.159 | 37.184 | 55.843 | 1.00 | 39.92 | 6 |
| ATOM | 570 | CG  | ARG | 357 | 12.510 | 38.453 | 55.500 | 1.00 | 42.64 | 6 |
| ATOM | 571 | CD  | ARG | 357 | 13.332 | 39.115 | 54.358 | 1.00 | 45.19 | 6 |
| ATOM | 572 | NE  | ARG | 357 | 14.636 | 38.470 | 54.098 | 1.00 | 47.06 | 7 |
| ATOM | 573 | CZ  | ARG | 357 | 14.809 | 37.390 | 53.331 | 1.00 | 47.03 | 6 |
| ATOM | 574 | NH1 | ARG | 357 | 13.744 | 36.855 | 52.769 | 1.00 | 48.06 | 7 |
| ATOM | 575 | NH2 | ARG | 357 | 16.018 | 36.857 | 53.109 | 1.00 | 45.38 | 7 |
| ATOM | 576 | C   | ARG | 357 | 12.088 | 36.712 | 58.082 | 1.00 | 40.92 | 6 |
| ATOM | 577 | O   | ARG | 357 | 12.957 | 36.459 | 58.964 | 1.00 | 43.42 | 8 |
| ATOM | 578 | N   | ASN | 358 | 11.002 | 37.390 | 58.441 | 1.00 | 41.89 | 7 |
| ATOM | 579 | CA  | ASN | 358 | 10.992 | 37.671 | 59.865 | 1.00 | 44.29 | 6 |
| ATOM | 580 | CB  | ASN | 358 | 10.905 | 39.179 | 60.259 | 1.00 | 46.14 | 6 |
| ATOM | 581 | CG  | ASN | 358 | 10.651 | 40.122 | 59.091 | 1.00 | 47.37 | 6 |
| ATOM | 582 | OD1 | ASN | 358 | 11.577 | 40.644 | 58.467 | 1.00 | 48.97 | 8 |
| ATOM | 583 | ND2 | ASN | 358 | 9.374  | 40.390 | 58.818 | 1.00 | 49.43 | 7 |
| ATOM | 584 | C   | ASN | 358 | 9.816  | 36.877 | 60.504 | 1.00 | 45.02 | 6 |
| ATOM | 585 | O   | ASN | 358 | 8.747  | 37.439 | 60.975 | 1.00 | 47.50 | 8 |
| ATOM | 586 | N   | SER | 359 | 10.004 | 35.549 | 60.466 | 1.00 | 43.44 | 7 |
| ATOM | 587 | CA  | SER | 359 | 9.093  | 34.575 | 61.063 | 1.00 | 40.81 | 6 |
| ATOM | 588 | CB  | SER | 359 | 8.335  | 33.776 | 60.022 | 1.00 | 41.60 | 6 |
| ATOM | 589 | OG  | SER | 359 | 9.197  | 32.797 | 59.453 | 1.00 | 39.14 | 8 |
| ATOM | 590 | C   | SER | 359 | 9.934  | 33.552 | 61.867 | 1.00 | 39.57 | 6 |
| ATOM | 591 | O   | SER | 359 | 9.379  | 32.681 | 62.527 | 1.00 | 40.17 | 8 |
| ATOM | 592 | N   | GLY | 360 | 11.257 | 33.644 | 61.822 | 1.00 | 36.41 | 7 |
| ATOM | 593 | CA  | GLY | 360 | 12.063 | 32.691 | 62.550 | 1.00 | 36.02 | 6 |
| ATOM | 594 | C   | GLY | 360 | 12.873 | 31.891 | 61.531 | 1.00 | 35.83 | 6 |
| ATOM | 595 | O   | GLY | 360 | 14.065 | 31.652 | 61.730 | 1.00 | 36.26 | 8 |
| ATOM | 596 | N   | ILE | 361 | 12.254 | 31.521 | 60.407 | 1.00 | 34.21 | 7 |
| ATOM | 597 | CA  | ILE | 361 | 12.982 | 30.741 | 59.391 | 1.00 | 32.82 | 6 |
| ATOM | 598 | CB  | ILE | 361 | 12.060 | 30.426 | 58.203 | 1.00 | 31.34 | 6 |
| ATOM | 599 | CG2 | ILE | 361 | 12.842 | 29.799 | 57.081 | 1.00 | 30.21 | 6 |
| ATOM | 600 | CG1 | ILE | 361 | 10.917 | 29.558 | 58.717 | 1.00 | 30.43 | 6 |
| ATOM | 601 | CD1 | ILE | 361 | 9.860  | 29.175 | 57.726 | 1.00 | 28.64 | 6 |
| ATOM | 602 | C   | ILE | 361 | 14.168 | 31.561 | 58.947 | 1.00 | 32.20 | 6 |
| ATOM | 603 | O   | ILE | 361 | 14.066 | 32.747 | 58.853 | 1.00 | 31.99 | 8 |
| ATOM | 604 | N   | SER | 362 | 15.249 | 30.865 | 58.422 | 1.00 | 32.80 | 7 |
| ATOM | 605 | CA  | SER | 362 | 16.369 | 31.700 | 58.062 | 1.00 | 35.78 | 6 |
| ATOM | 606 | CB  | SER | 362 | 17.628 | 31.137 | 58.707 | 1.00 | 37.94 | 6 |
| ATOM | 607 | OG  | SER | 362 | 18.036 | 29.990 | 57.973 | 1.00 | 40.33 | 8 |
| ATOM | 608 | C   | SER | 362 | 16.616 | 31.780 | 56.571 | 1.00 | 36.80 | 6 |
| ATOM | 609 | O   | SER | 362 | 15.879 | 31.174 | 55.756 | 1.00 | 34.55 | 8 |
| ATOM | 610 | N   | ASP | 363 | 17.755 | 32.570 | 56.446 | 1.00 | 37.56 | 7 |
| ATOM | 611 | CA  | ASP | 363 | 18.328 | 32.538 | 55.124 | 1.00 | 39.66 | 6 |
| ATOM | 612 | CB  | ASP | 363 | 19.507 | 33.511 | 55.002 | 1.00 | 42.07 | 6 |
| ATOM | 613 | CG  | ASP | 363 | 19.120 | 34.788 | 54.334 | 1.00 | 45.41 | 6 |
| ATOM | 614 | OD1 | ASP | 363 | 18.656 | 34.743 | 53.162 | 1.00 | 47.71 | 8 |
| ATOM | 615 | OD2 | ASP | 363 | 19.266 | 35.852 | 54.984 | 1.00 | 48.83 | 8 |
| ATOM | 616 | C   | ASP | 363 | 18.821 | 31.089 | 54.995 | 1.00 | 39.22 | 6 |
| ATOM | 617 | O   | ASP | 363 | 18.580 | 30.256 | 55.861 | 1.00 | 41.99 | 8 |
| ATOM | 618 | N   | GLU | 364 | 19.548 | 30.769 | 53.958 | 1.00 | 38.05 | 7 |
| ATOM | 619 | CA  | GLU | 364 | 19.946 | 29.390 | 53.787 | 1.00 | 36.18 | 6 |
| ATOM | 620 | CB  | GLU | 364 | 20.572 | 28.816 | 55.051 | 1.00 | 39.36 | 6 |
| ATOM | 621 | CG  | GLU | 364 | 21.934 | 28.199 | 54.764 | 1.00 | 45.91 | 6 |
| ATOM | 622 | CD  | GLU | 364 | 22.741 | 27.977 | 56.034 | 1.00 | 49.50 | 6 |
| ATOM | 623 | OE1 | GLU | 364 | 22.208 | 27.315 | 56.953 | 1.00 | 53.22 | 8 |
| ATOM | 624 | OE2 | GLU | 364 | 23.900 | 28.458 | 56.134 | 1.00 | 52.53 | 8 |

APPENDIX 1-continued

STRUCTURE COORDINATES FOR FXR LBD COMPLEXED WITH FEXARAMINE

| ATOM | 625 | C   | GLU | 364 | 18.703 | 28.611 | 53.339 | 1.00 | 31.82 | 6  |
| ---- | --- | --- | --- | --- | ------ | ------ | ------ | ---- | ----- | -- |
| ATOM | 626 | O   | GLU | 364 | 18.831 | 27.751 | 52.487 | 1.00 | 30.82 | 8  |
| ATOM | 627 | N   | TYR | 365 | 17.518 | 28.929 | 53.893 | 1.00 | 28.83 | 7  |
| ATOM | 628 | CA  | TYR | 365 | 16.250 | 28.298 | 53.427 | 1.00 | 27.58 | 6  |
| ATOM | 629 | CB  | TYR | 365 | 15.298 | 28.036 | 54.585 | 1.00 | 25.28 | 6  |
| ATOM | 630 | CG  | TYR | 365 | 14.061 | 27.273 | 54.172 | 1.00 | 22.64 | 6  |
| ATOM | 631 | CD1 | TYR | 365 | 14.118 | 25.899 | 53.916 | 1.00 | 20.67 | 6  |
| ATOM | 632 | CE1 | TYR | 365 | 12.954 | 25.163 | 53.636 | 1.00 | 21.27 | 6  |
| ATOM | 633 | CD2 | TYR | 365 | 12.816 | 27.903 | 54.116 | 1.00 | 20.43 | 6  |
| ATOM | 634 | CE2 | TYR | 365 | 11.625 | 27.191 | 53.824 | 1.00 | 18.96 | 6  |
| ATOM | 635 | CZ  | TYR | 365 | 11.700 | 25.813 | 53.599 | 1.00 | 19.07 | 6  |
| ATOM | 636 | OH  | TYR | 365 | 10.598 | 24.974 | 53.454 | 1.00 | 20.64 | 8  |
| ATOM | 637 | C   | TYR | 365 | 15.512 | 29.263 | 52.448 | 1.00 | 26.08 | 6  |
| ATOM | 638 | O   | TYR | 365 | 15.147 | 28.901 | 51.314 | 1.00 | 24.75 | 8  |
| ATOM | 639 | N   | ILE | 366 | 15.302 | 30.494 | 52.899 | 1.00 | 26.17 | 7  |
| ATOM | 640 | CA  | ILE | 366 | 14.568 | 31.514 | 52.123 | 1.00 | 27.29 | 6  |
| ATOM | 641 | CB  | ILE | 366 | 14.326 | 32.737 | 52.951 | 1.00 | 26.78 | 6  |
| ATOM | 642 | CG2 | ILE | 366 | 13.620 | 33.832 | 52.098 | 1.00 | 26.70 | 6  |
| ATOM | 643 | CG1 | ILE | 366 | 13.508 | 32.332 | 54.189 | 1.00 | 27.76 | 6  |
| ATOM | 644 | CD1 | ILE | 366 | 13.402 | 33.410 | 55.257 | 1.00 | 26.95 | 6  |
| ATOM | 645 | C   | ILE | 366 | 15.214 | 31.909 | 50.810 | 1.00 | 28.05 | 6  |
| ATOM | 646 | O   | ILE | 366 | 14.543 | 31.975 | 49.787 | 1.00 | 28.30 | 8  |
| ATOM | 647 | N   | THR | 367 | 16.519 | 32.153 | 50.839 | 1.00 | 28.47 | 7  |
| ATOM | 648 | CA  | THR | 367 | 17.256 | 32.499 | 49.628 | 1.00 | 27.70 | 6  |
| ATOM | 649 | CB  | THR | 367 | 18.702 | 32.802 | 49.938 | 1.00 | 31.22 | 6  |
| ATOM | 650 | OG1 | THR | 367 | 18.759 | 34.128 | 50.481 | 1.00 | 34.14 | 8  |
| ATOM | 651 | CG2 | THR | 367 | 19.602 | 32.659 | 48.659 | 1.00 | 31.67 | 6  |
| ATOM | 652 | C   | THR | 367 | 17.184 | 31.477 | 48.512 | 1.00 | 26.16 | 6  |
| ATOM | 653 | O   | THR | 367 | 16.935 | 31.841 | 47.372 | 1.00 | 25.50 | 8  |
| ATOM | 654 | N   | PRO | 368 | 17.434 | 30.189 | 48.799 | 1.00 | 23.54 | 7  |
| ATOM | 655 | CD  | PRO | 368 | 17.966 | 29.604 | 50.036 | 1.00 | 24.08 | 6  |
| ATOM | 656 | CA  | PRO | 368 | 17.342 | 29.195 | 47.733 | 1.00 | 20.99 | 6  |
| ATOM | 657 | CB  | PRO | 368 | 17.791 | 27.884 | 48.421 | 1.00 | 23.25 | 6  |
| ATOM | 658 | CG  | PRO | 368 | 18.717 | 28.387 | 49.540 | 1.00 | 25.50 | 6  |
| ATOM | 659 | C   | PRO | 368 | 15.867 | 29.144 | 47.309 | 1.00 | 18.85 | 6  |
| ATOM | 660 | O   | PRO | 368 | 15.577 | 28.973 | 46.130 | 1.00 | 18.28 | 8  |
| ATOM | 661 | N   | MET | 369 | 14.951 | 29.252 | 48.271 | 1.00 | 16.87 | 7  |
| ATOM | 662 | CA  | MET | 369 | 13.519 | 29.254 | 47.932 | 1.00 | 18.73 | 6  |
| ATOM | 663 | CB  | MET | 369 | 12.668 | 29.686 | 49.110 | 1.00 | 17.86 | 6  |
| ATOM | 664 | CG  | MET | 369 | 11.198 | 29.784 | 48.779 | 1.00 | 17.41 | 6  |
| ATOM | 665 | SD  | MET | 369 | 10.297 | 30.313 | 50.291 | 1.00 | 22.80 | 16 |
| ATOM | 666 | CE  | MET | 369 | 9.850  | 28.817 | 50.943 | 1.00 | 18.91 | 6  |
| ATOM | 667 | C   | MET | 369 | 13.210 | 30.249 | 46.795 | 1.00 | 20.73 | 6  |
| ATOM | 668 | O   | MET | 369 | 12.695 | 29.871 | 45.734 | 1.00 | 21.58 | 8  |
| ATOM | 669 | N   | PHE | 370 | 13.500 | 31.534 | 47.040 | 1.00 | 22.10 | 7  |
| ATOM | 670 | CA  | PHE | 370 | 13.169 | 32.537 | 46.019 | 1.00 | 23.21 | 6  |
| ATOM | 671 | CB  | PHE | 370 | 13.182 | 33.971 | 46.582 | 1.00 | 22.60 | 6  |
| ATOM | 672 | CG  | PHE | 370 | 11.994 | 34.278 | 47.453 | 1.00 | 23.31 | 6  |
| ATOM | 673 | CD1 | PHE | 370 | 11.971 | 33.925 | 48.823 | 1.00 | 25.56 | 6  |
| ATOM | 674 | CD2 | PHE | 370 | 10.893 | 34.875 | 46.921 | 1.00 | 24.85 | 6  |
| ATOM | 675 | CE1 | PHE | 370 | 10.828 | 34.196 | 49.605 | 1.00 | 24.07 | 6  |
| ATOM | 676 | CE2 | PHE | 370 | 9.777  | 35.145 | 47.666 | 1.00 | 25.17 | 6  |
| ATOM | 677 | CZ  | PHE | 370 | 9.730  | 34.811 | 49.021 | 1.00 | 27.62 | 6  |
| ATOM | 678 | C   | PHE | 370 | 14.026 | 32.439 | 44.783 | 1.00 | 23.76 | 6  |
| ATOM | 679 | O   | PHE | 370 | 13.597 | 32.803 | 43.690 | 1.00 | 24.18 | 8  |
| ATOM | 680 | N   | SER | 371 | 15.251 | 31.979 | 44.945 | 1.00 | 23.62 | 7  |
| ATOM | 681 | CA  | SER | 371 | 16.091 | 31.825 | 43.784 | 1.00 | 23.74 | 6  |
| ATOM | 682 | CB  | SER | 371 | 17.455 | 31.340 | 44.250 | 1.00 | 25.68 | 6  |
| ATOM | 683 | OG  | SER | 371 | 18.336 | 31.438 | 43.153 | 1.00 | 29.39 | 8  |
| ATOM | 684 | C   | SER | 371 | 15.387 | 30.771 | 42.868 | 1.00 | 21.96 | 6  |
| ATOM | 685 | O   | SER | 371 | 15.272 | 30.944 | 41.613 | 1.00 | 19.76 | 8  |
| ATOM | 686 | N   | PHE | 372 | 14.928 | 29.676 | 43.480 | 1.00 | 18.27 | 7  |
| ATOM | 687 | CA  | PHE | 372 | 14.240 | 28.664 | 42.690 | 1.00 | 18.05 | 6  |
| ATOM | 688 | CB  | PHE | 372 | 13.861 | 27.453 | 43.557 | 1.00 | 17.30 | 6  |
| ATOM | 689 | CG  | PHE | 372 | 12.999 | 26.482 | 42.852 | 1.00 | 18.83 | 6  |
| ATOM | 690 | CD1 | PHE | 372 | 13.564 | 25.676 | 41.885 | 1.00 | 18.36 | 6  |
| ATOM | 691 | CD2 | PHE | 372 | 11.659 | 26.326 | 43.194 | 1.00 | 18.44 | 6  |
| ATOM | 692 | CE1 | PHE | 372 | 12.839 | 24.709 | 41.262 | 1.00 | 22.71 | 6  |
| ATOM | 693 | CE2 | PHE | 372 | 10.910 | 25.340 | 42.571 | 1.00 | 20.16 | 6  |
| ATOM | 694 | CZ  | PHE | 372 | 11.506 | 24.527 | 41.603 | 1.00 | 19.39 | 6  |
| ATOM | 695 | C   | PHE | 372 | 12.957 | 29.232 | 41.991 | 1.00 | 19.15 | 6  |
| ATOM | 696 | O   | PHE | 372 | 12.736 | 28.949 | 40.788 | 1.00 | 18.15 | 8  |
| ATOM | 697 | N   | TYR | 373 | 12.125 | 30.010 | 42.707 | 1.00 | 18.39 | 7  |
| ATOM | 698 | CA  | TYR | 373 | 10.894 | 30.569 | 42.119 | 1.00 | 19.57 | 6  |
| ATOM | 699 | CB  | TYR | 373 | 10.156 | 31.477 | 43.107 | 1.00 | 18.29 | 6  |
| ATOM | 700 | CG  | TYR | 373 | 9.584  | 30.790 | 44.316 | 1.00 | 19.02 | 6  |
| ATOM | 701 | CD1 | TYR | 373 | 9.342  | 29.421 | 44.318 | 1.00 | 19.27 | 6  |

APPENDIX 1-continued

STRUCTURE COORDINATES FOR FXR LBD COMPLEXED WITH FEXARAMINE

| ATOM | 702 | CE1 | TYR | 373 | 8.755 | 28.821 | 45.402 | 1.00 | 19.82 | 6 |
|---|---|---|---|---|---|---|---|---|---|---|
| ATOM | 703 | CD2 | TYR | 373 | 9.226 | 31.532 | 45.467 | 1.00 | 18.64 | 6 |
| ATOM | 704 | CE2 | TYR | 373 | 8.651 | 30.918 | 46.589 | 1.00 | 19.78 | 6 |
| ATOM | 705 | CZ | TYR | 373 | 8.417 | 29.563 | 46.544 | 1.00 | 19.87 | 6 |
| ATOM | 706 | OH | TYR | 373 | 7.908 | 28.880 | 47.640 | 1.00 | 18.83 | 8 |
| ATOM | 707 | C | TYR | 373 | 11.238 | 31.384 | 40.854 | 1.00 | 21.91 | 6 |
| ATOM | 708 | O | TYR | 373 | 10.561 | 31.281 | 39.818 | 1.00 | 20.54 | 8 |
| ATOM | 709 | N | LYS | 374 | 12.327 | 32.145 | 40.934 | 1.00 | 23.61 | 7 |
| ATOM | 710 | CA | LYS | 374 | 12.775 | 32.948 | 39.790 | 1.00 | 26.50 | 6 |
| ATOM | 711 | CB | LYS | 374 | 13.960 | 33.868 | 40.173 | 1.00 | 29.49 | 6 |
| ATOM | 712 | CG | LYS | 374 | 13.629 | 34.909 | 41.229 | 1.00 | 35.57 | 6 |
| ATOM | 713 | CD | LYS | 374 | 12.595 | 35.878 | 40.618 | 1.00 | 40.48 | 6 |
| ATOM | 714 | CE | LYS | 374 | 12.285 | 35.575 | 39.126 | 1.00 | 43.83 | 6 |
| ATOM | 715 | NZ | LYS | 374 | 10.831 | 35.197 | 38.902 | 1.00 | 44.66 | 7 |
| ATOM | 716 | C | LYS | 374 | 13.266 | 32.020 | 38.727 | 1.00 | 25.35 | 6 |
| ATOM | 717 | O | LYS | 374 | 12.903 | 32.144 | 37.548 | 1.00 | 26.16 | 8 |
| ATOM | 718 | N | SER | 375 | 14.097 | 31.070 | 39.132 | 1.00 | 25.05 | 7 |
| ATOM | 719 | CA | SER | 375 | 14.687 | 30.172 | 38.181 | 1.00 | 24.04 | 6 |
| ATOM | 720 | CB | SER | 375 | 15.594 | 29.188 | 38.901 | 1.00 | 24.76 | 6 |
| ATOM | 721 | OG | SER | 375 | 16.090 | 28.224 | 37.984 | 1.00 | 24.17 | 8 |
| ATOM | 722 | C | SER | 375 | 13.700 | 29.422 | 37.313 | 1.00 | 25.83 | 6 |
| ATOM | 723 | O | SER | 375 | 13.840 | 29.370 | 36.080 | 1.00 | 26.22 | 8 |
| ATOM | 724 | N | ILE | 376 | 12.686 | 28.835 | 37.939 | 1.00 | 25.43 | 7 |
| ATOM | 725 | CA | ILE | 376 | 11.720 | 28.073 | 37.169 | 1.00 | 25.67 | 6 |
| ATOM | 726 | CB | ILE | 376 | 10.976 | 27.026 | 38.017 | 1.00 | 27.81 | 6 |
| ATOM | 727 | CG2 | ILE | 376 | 10.050 | 27.704 | 39.019 | 1.00 | 26.42 | 6 |
| ATOM | 728 | CG1 | ILE | 376 | 10.193 | 26.099 | 37.086 | 1.00 | 30.85 | 6 |
| ATOM | 729 | CD1 | ILE | 376 | 9.769 | 24.773 | 37.754 | 1.00 | 32.32 | 6 |
| ATOM | 730 | C | ILE | 376 | 10.769 | 29.056 | 36.487 | 1.00 | 23.70 | 6 |
| ATOM | 731 | O | ILE | 376 | 10.244 | 28.765 | 35.428 | 1.00 | 23.13 | 8 |
| ATOM | 732 | N | GLY | 377 | 10.605 | 30.244 | 37.051 | 1.00 | 22.29 | 7 |
| ATOM | 733 | CA | GLY | 377 | 9.765 | 31.233 | 36.391 | 1.00 | 21.42 | 6 |
| ATOM | 734 | C | GLY | 377 | 10.311 | 31.632 | 35.008 | 1.00 | 21.64 | 6 |
| ATOM | 735 | O | GLY | 377 | 9.567 | 32.070 | 34.096 | 1.00 | 20.06 | 8 |
| ATOM | 736 | N | GLU | 378 | 11.638 | 31.510 | 34.847 | 1.00 | 23.21 | 7 |
| ATOM | 737 | CA | GLU | 378 | 12.284 | 31.790 | 33.536 | 1.00 | 24.44 | 6 |
| ATOM | 738 | CB | GLU | 378 | 13.812 | 31.687 | 33.624 | 1.00 | 24.68 | 6 |
| ATOM | 739 | CG | GLU | 378 | 14.433 | 32.792 | 34.397 | 1.00 | 29.72 | 6 |
| ATOM | 740 | CD | GLU | 378 | 15.949 | 32.580 | 34.571 | 1.00 | 34.23 | 6 |
| ATOM | 741 | OE1 | GLU | 378 | 16.582 | 32.004 | 33.647 | 1.00 | 33.28 | 8 |
| ATOM | 742 | OE2 | GLU | 378 | 16.497 | 33.008 | 35.625 | 1.00 | 36.12 | 8 |
| ATOM | 743 | C | GLU | 378 | 11.828 | 30.790 | 32.471 | 1.00 | 24.16 | 6 |
| ATOM | 744 | O | GLU | 378 | 11.945 | 31.051 | 31.284 | 1.00 | 23.87 | 8 |
| ATOM | 745 | N | LEU | 379 | 11.351 | 29.627 | 32.856 | 1.00 | 23.79 | 7 |
| ATOM | 746 | CA | LEU | 379 | 10.916 | 28.690 | 31.810 | 1.00 | 25.23 | 6 |
| ATOM | 747 | CB | LEU | 379 | 11.001 | 27.278 | 32.392 | 1.00 | 24.01 | 6 |
| ATOM | 748 | CG | LEU | 379 | 12.448 | 26.867 | 32.758 | 1.00 | 27.85 | 6 |
| ATOM | 749 | CD1 | LEU | 379 | 12.496 | 25.459 | 33.132 | 1.00 | 26.09 | 6 |
| ATOM | 750 | CD2 | LEU | 379 | 13.415 | 27.024 | 31.537 | 1.00 | 26.52 | 6 |
| ATOM | 751 | C | LEU | 379 | 9.466 | 29.007 | 31.260 | 1.00 | 23.19 | 6 |
| ATOM | 752 | O | LEU | 379 | 8.988 | 28.400 | 30.296 | 1.00 | 23.76 | 8 |
| ATOM | 753 | N | LYS | 380 | 8.775 | 29.929 | 31.901 | 1.00 | 22.23 | 7 |
| ATOM | 754 | CA | LYS | 380 | 7.420 | 30.287 | 31.482 | 1.00 | 25.06 | 6 |
| ATOM | 755 | CB | LYS | 380 | 7.496 | 31.160 | 30.231 | 1.00 | 26.20 | 6 |
| ATOM | 756 | CG | LYS | 380 | 8.485 | 32.294 | 30.380 | 1.00 | 30.84 | 6 |
| ATOM | 757 | CD | LYS | 380 | 8.321 | 33.260 | 29.190 | 1.00 | 35.79 | 6 |
| ATOM | 758 | CE | LYS | 380 | 9.401 | 34.374 | 29.158 | 1.00 | 39.66 | 6 |
| ATOM | 759 | NZ | LYS | 380 | 10.649 | 34.032 | 28.365 | 1.00 | 40.21 | 7 |
| ATOM | 760 | C | LYS | 380 | 6.550 | 29.036 | 31.194 | 1.00 | 23.61 | 6 |
| ATOM | 761 | O | LYS | 380 | 5.897 | 28.935 | 30.164 | 1.00 | 22.42 | 8 |
| ATOM | 762 | N | MET | 381 | 6.551 | 28.078 | 32.113 | 1.00 | 21.57 | 7 |
| ATOM | 763 | CA | MET | 381 | 5.760 | 26.880 | 31.855 | 1.00 | 21.39 | 6 |
| ATOM | 764 | CB | MET | 381 | 6.153 | 25.794 | 32.861 | 1.00 | 21.45 | 6 |
| ATOM | 765 | CG | MET | 381 | 7.626 | 25.398 | 32.836 | 1.00 | 25.21 | 6 |
| ATOM | 766 | SD | MET | 381 | 8.005 | 24.440 | 34.325 | 1.00 | 27.43 | 16 |
| ATOM | 767 | CE | MET | 381 | 6.658 | 23.493 | 34.392 | 1.00 | 27.50 | 6 |
| ATOM | 768 | C | MET | 381 | 4.241 | 27.093 | 31.873 | 1.00 | 19.99 | 6 |
| ATOM | 769 | O | MET | 381 | 3.749 | 27.935 | 32.608 | 1.00 | 20.28 | 8 |
| ATOM | 770 | N | THR | 382 | 3.502 | 26.368 | 31.030 | 1.00 | 20.88 | 7 |
| ATOM | 771 | CA | THR | 382 | 2.042 | 26.463 | 31.049 | 1.00 | 19.14 | 6 |
| ATOM | 772 | CB | THR | 382 | 1.396 | 25.889 | 29.766 | 1.00 | 19.39 | 6 |
| ATOM | 773 | OG1 | THR | 382 | 1.688 | 24.482 | 29.676 | 1.00 | 18.31 | 8 |
| ATOM | 774 | CG2 | THR | 382 | 1.939 | 26.614 | 28.521 | 1.00 | 18.66 | 6 |
| ATOM | 775 | C | THR | 382 | 1.555 | 25.594 | 32.228 | 1.00 | 19.36 | 6 |
| ATOM | 776 | O | THR | 382 | 2.344 | 24.816 | 32.841 | 1.00 | 17.49 | 8 |
| ATOM | 777 | N | GLN | 383 | 0.276 | 25.751 | 32.567 | 1.00 | 17.92 | 7 |
| ATOM | 778 | CA | GLN | 383 | −0.334 | 24.948 | 33.641 | 1.00 | 19.83 | 6 |

APPENDIX 1-continued

STRUCTURE COORDINATES FOR FXR LBD COMPLEXED WITH FEXARAMINE

| ATOM | 779 | CB  | GLN | 383 | −1.828 | 25.320 | 33.813 | 1.00 | 21.28 | 6 |
| ---- | --- | --- | --- | --- | ------ | ------ | ------ | ---- | ----- | - |
| ATOM | 780 | CG  | GLN | 383 | −2.494 | 24.698 | 35.094 | 1.00 | 28.08 | 6 |
| ATOM | 781 | CD  | GLN | 383 | −4.076 | 24.726 | 35.091 | 1.00 | 32.74 | 6 |
| ATOM | 782 | OE1 | GLN | 383 | −4.735 | 24.870 | 36.153 | 1.00 | 35.35 | 8 |
| ATOM | 783 | NE2 | GLN | 383 | −4.674 | 24.565 | 33.897 | 1.00 | 31.92 | 7 |
| ATOM | 784 | C   | GLN | 383 | −0.204 | 23.437 | 33.252 | 1.00 | 18.37 | 6 |
| ATOM | 785 | O   | GLN | 383 | 0.004  | 22.589 | 34.121 | 1.00 | 18.49 | 8 |
| ATOM | 786 | N   | GLU | 384 | −0.334 | 23.113 | 31.960 | 1.00 | 18.33 | 7 |
| ATOM | 787 | CA  | GLU | 384 | −0.190 | 21.710 | 31.563 | 1.00 | 19.34 | 6 |
| ATOM | 788 | CB  | GLU | 384 | −0.505 | 21.513 | 30.049 | 1.00 | 20.07 | 6 |
| ATOM | 789 | CG  | GLU | 384 | −2.000 | 21.770 | 29.745 | 1.00 | 22.34 | 6 |
| ATOM | 790 | CD  | GLU | 384 | −2.319 | 21.706 | 28.236 | 1.00 | 25.69 | 6 |
| ATOM | 791 | OE1 | GLU | 384 | −1.413 | 21.884 | 27.427 | 1.00 | 26.17 | 8 |
| ATOM | 792 | OE2 | GLU | 384 | −3.483 | 21.458 | 27.837 | 1.00 | 26.85 | 8 |
| ATOM | 793 | C   | GLU | 384 | 1.220  | 21.216 | 31.895 | 1.00 | 19.98 | 6 |
| ATOM | 794 | O   | GLU | 384 | 1.373  | 20.114 | 32.432 | 1.00 | 17.01 | 8 |
| ATOM | 795 | N   | GLU | 385 | 2.243  | 22.028 | 31.587 | 1.00 | 17.80 | 7 |
| ATOM | 796 | CA  | GLU | 385 | 3.611  | 21.631 | 31.918 | 1.00 | 17.45 | 6 |
| ATOM | 797 | CB  | GLU | 385 | 4.608  | 22.649 | 31.378 | 1.00 | 16.42 | 6 |
| ATOM | 798 | CG  | GLU | 385 | 4.738  | 22.522 | 29.860 | 1.00 | 18.03 | 6 |
| ATOM | 799 | CD  | GLU | 385 | 5.280  | 23.818 | 29.336 | 1.00 | 19.59 | 6 |
| ATOM | 800 | OE1 | GLU | 385 | 4.486  | 24.766 | 29.074 | 1.00 | 20.92 | 8 |
| ATOM | 801 | OE2 | GLU | 385 | 6.518  | 23.916 | 29.271 | 1.00 | 19.49 | 8 |
| ATOM | 802 | C   | GLU | 385 | 3.815  | 21.454 | 33.435 | 1.00 | 17.61 | 6 |
| ATOM | 803 | O   | GLU | 385 | 4.403  | 20.437 | 33.863 | 1.00 | 17.28 | 8 |
| ATOM | 804 | N   | TYR | 386 | 3.307  | 22.379 | 34.244 | 1.00 | 15.40 | 7 |
| ATOM | 805 | CA  | TYR | 386 | 3.476  | 22.193 | 35.696 | 1.00 | 16.28 | 6 |
| ATOM | 806 | CB  | TYR | 386 | 2.891  | 23.349 | 36.504 | 1.00 | 17.10 | 6 |
| ATOM | 807 | CG  | TYR | 386 | 3.846  | 24.483 | 36.745 | 1.00 | 18.99 | 6 |
| ATOM | 808 | CD1 | TYR | 386 | 4.756  | 24.427 | 37.766 | 1.00 | 20.84 | 6 |
| ATOM | 809 | CE1 | TYR | 386 | 5.563  | 25.515 | 38.051 | 1.00 | 23.05 | 6 |
| ATOM | 810 | CD2 | TYR | 386 | 3.766  | 25.643 | 35.998 | 1.00 | 20.35 | 6 |
| ATOM | 811 | CE2 | TYR | 386 | 4.574  | 26.752 | 36.268 | 1.00 | 22.60 | 6 |
| ATOM | 812 | CZ  | TYR | 386 | 5.471  | 26.669 | 37.288 | 1.00 | 24.26 | 6 |
| ATOM | 813 | OH  | TYR | 386 | 6.346  | 27.711 | 37.535 | 1.00 | 27.07 | 8 |
| ATOM | 814 | C   | TYR | 386 | 2.779  | 20.928 | 36.170 | 1.00 | 16.40 | 6 |
| ATOM | 815 | O   | TYR | 386 | 3.287  | 20.239 | 37.044 | 1.00 | 17.66 | 8 |
| ATOM | 816 | N   | ALA | 387 | 1.566  | 20.674 | 35.671 | 1.00 | 14.81 | 7 |
| ATOM | 817 | CA  | ALA | 387 | 0.813  | 19.485 | 36.115 | 1.00 | 14.98 | 6 |
| ATOM | 818 | CB  | ALA | 387 | −0.628 | 19.413 | 35.429 | 1.00 | 15.82 | 6 |
| ATOM | 819 | C   | ALA | 387 | 1.604  | 18.189 | 35.794 | 1.00 | 15.05 | 6 |
| ATOM | 820 | O   | ALA | 387 | 1.722  | 17.313 | 36.676 | 1.00 | 14.49 | 8 |
| ATOM | 821 | N   | LEU | 388 | 2.095  | 18.066 | 34.560 | 1.00 | 14.72 | 7 |
| ATOM | 822 | CA  | LEU | 388 | 2.863  | 16.875 | 34.167 | 1.00 | 16.46 | 6 |
| ATOM | 823 | CB  | LEU | 388 | 3.152  | 16.869 | 32.657 | 1.00 | 15.66 | 6 |
| ATOM | 824 | CG  | LEU | 388 | 2.117  | 16.161 | 31.748 | 1.00 | 18.69 | 6 |
| ATOM | 825 | CD1 | LEU | 388 | 2.223  | 14.619 | 31.987 | 1.00 | 20.30 | 6 |
| ATOM | 826 | CD2 | LEU | 388 | 0.720  | 16.613 | 32.125 | 1.00 | 21.34 | 6 |
| ATOM | 827 | C   | LEU | 388 | 4.198  | 16.797 | 34.959 | 1.00 | 15.98 | 6 |
| ATOM | 828 | O   | LEU | 388 | 4.602  | 15.689 | 35.404 | 1.00 | 13.29 | 8 |
| ATOM | 829 | N   | LEU | 389 | 4.871  | 17.940 | 35.144 | 1.00 | 15.33 | 7 |
| ATOM | 830 | CA  | LEU | 389 | 6.137  | 17.834 | 35.890 | 1.00 | 14.94 | 6 |
| ATOM | 831 | CB  | LEU | 389 | 6.889  | 19.144 | 35.896 | 1.00 | 15.79 | 6 |
| ATOM | 832 | CG  | LEU | 389 | 8.331  | 19.047 | 36.364 | 1.00 | 17.32 | 6 |
| ATOM | 833 | CD1 | LEU | 389 | 9.131  | 18.227 | 35.343 | 1.00 | 16.03 | 6 |
| ATOM | 834 | CD2 | LEU | 389 | 8.907  | 20.478 | 36.485 | 1.00 | 18.51 | 6 |
| ATOM | 835 | C   | LEU | 389 | 5.883  | 17.357 | 37.334 | 1.00 | 14.12 | 6 |
| ATOM | 836 | O   | LEU | 389 | 6.661  | 16.572 | 37.903 | 1.00 | 13.80 | 8 |
| ATOM | 837 | N   | THR | 390 | 4.762  | 17.795 | 37.898 | 1.00 | 15.10 | 7 |
| ATOM | 838 | CA  | THR | 390 | 4.366  | 17.410 | 39.272 | 1.00 | 13.91 | 6 |
| ATOM | 839 | CB  | THR | 390 | 3.134  | 18.231 | 39.748 | 1.00 | 14.30 | 6 |
| ATOM | 840 | OG1 | THR | 390 | 3.494  | 19.637 | 39.696 | 1.00 | 18.36 | 8 |
| ATOM | 841 | CG2 | THR | 390 | 2.743  | 17.859 | 41.249 | 1.00 | 13.78 | 6 |
| ATOM | 842 | C   | THR | 390 | 4.053  | 15.893 | 39.327 | 1.00 | 14.21 | 6 |
| ATOM | 843 | O   | THR | 390 | 4.470  | 15.213 | 40.234 | 1.00 | 15.26 | 8 |
| ATOM | 844 | N   | ALA | 391 | 3.308  | 15.378 | 38.355 | 1.00 | 14.62 | 7 |
| ATOM | 845 | CA  | ALA | 391 | 3.014  | 13.968 | 38.293 | 1.00 | 13.24 | 6 |
| ATOM | 846 | CB  | ALA | 391 | 2.107  | 13.713 | 37.113 | 1.00 | 15.33 | 6 |
| ATOM | 847 | C   | ALA | 391 | 4.345  | 13.187 | 38.118 | 1.00 | 14.72 | 6 |
| ATOM | 848 | O   | ALA | 391 | 4.548  | 12.133 | 38.751 | 1.00 | 13.37 | 8 |
| ATOM | 849 | N   | ILE | 392 | 5.247  | 13.684 | 37.287 | 1.00 | 13.13 | 7 |
| ATOM | 850 | CA  | ILE | 392 | 6.575  | 12.963 | 37.092 | 1.00 | 16.12 | 6 |
| ATOM | 851 | CB  | ILE | 392 | 7.328  | 13.614 | 35.949 | 1.00 | 14.45 | 6 |
| ATOM | 852 | CG2 | ILE | 392 | 8.827  | 13.191 | 35.901 | 1.00 | 16.87 | 6 |
| ATOM | 853 | CG1 | ILE | 392 | 6.602  | 13.233 | 34.678 | 1.00 | 16.27 | 6 |
| ATOM | 854 | CD1 | ILE | 392 | 7.091  | 14.136 | 33.490 | 1.00 | 18.18 | 6 |
| ATOM | 855 | C   | ILE | 392 | 7.436  | 12.934 | 38.355 | 1.00 | 16.58 | 6 |

APPENDIX 1-continued

STRUCTURE COORDINATES FOR FXR LBD COMPLEXED WITH FEXARAMINE

| ATOM | 856 | O | ILE | 392 | 8.092 | 11.928 | 38.676 | 1.00 | 16.99 | 8 |
|------|-----|-----|-----|-----|-------|--------|--------|------|-------|---|
| ATOM | 857 | N | VAL | 393 | 7.400 | 14.044 | 39.082 | 1.00 | 16.17 | 7 |
| ATOM | 858 | CA | VAL | 393 | 8.091 | 14.125 | 40.352 | 1.00 | 17.56 | 6 |
| ATOM | 859 | CB | VAL | 393 | 7.958 | 15.503 | 40.998 | 1.00 | 18.35 | 6 |
| ATOM | 860 | CG1 | VAL | 393 | 8.519 | 15.440 | 42.409 | 1.00 | 21.30 | 6 |
| ATOM | 861 | CG2 | VAL | 393 | 8.731 | 16.591 | 40.195 | 1.00 | 20.45 | 6 |
| ATOM | 862 | C | VAL | 393 | 7.469 | 13.106 | 41.345 | 1.00 | 17.21 | 6 |
| ATOM | 863 | O | VAL | 393 | 8.206 | 12.442 | 42.077 | 1.00 | 14.47 | 8 |
| ATOM | 864 | N | ILE | 394 | 6.129 | 12.993 | 41.410 | 1.00 | 15.70 | 7 |
| ATOM | 865 | CA | ILE | 394 | 5.516 | 12.068 | 42.391 | 1.00 | 15.27 | 6 |
| ATOM | 866 | CB | ILE | 394 | 3.964 | 12.310 | 42.490 | 1.00 | 15.62 | 6 |
| ATOM | 867 | CG2 | ILE | 394 | 3.302 | 11.247 | 43.332 | 1.00 | 12.98 | 6 |
| ATOM | 868 | CG1 | ILE | 394 | 3.681 | 13.714 | 43.071 | 1.00 | 17.17 | 6 |
| ATOM | 869 | CD1 | ILE | 394 | 2.279 | 14.186 | 42.757 | 1.00 | 14.90 | 6 |
| ATOM | 870 | C | ILE | 394 | 5.820 | 10.592 | 42.007 | 1.00 | 16.06 | 6 |
| ATOM | 871 | O | ILE | 394 | 6.180 | 9.737 | 42.863 | 1.00 | 14.53 | 8 |
| ATOM | 872 | N | LEU | 395 | 5.652 | 10.292 | 40.738 | 1.00 | 14.10 | 7 |
| ATOM | 873 | CA | LEU | 395 | 5.976 | 8.961 | 40.244 | 1.00 | 15.38 | 6 |
| ATOM | 874 | CB | LEU | 395 | 5.072 | 8.678 | 39.080 | 1.00 | 14.05 | 6 |
| ATOM | 875 | CG | LEU | 395 | 3.571 | 8.648 | 39.384 | 1.00 | 16.30 | 6 |
| ATOM | 876 | CD1 | LEU | 395 | 2.856 | 8.626 | 37.994 | 1.00 | 16.58 | 6 |
| ATOM | 877 | CD2 | LEU | 395 | 3.193 | 7.350 | 40.234 | 1.00 | 18.82 | 6 |
| ATOM | 878 | C | LEU | 395 | 7.493 | 8.747 | 39.897 | 1.00 | 16.08 | 6 |
| ATOM | 879 | O | LEU | 395 | 7.856 | 8.285 | 38.774 | 1.00 | 14.33 | 8 |
| ATOM | 880 | N | SER | 396 | 8.359 | 9.006 | 40.897 | 1.00 | 16.14 | 7 |
| ATOM | 881 | CA | SER | 396 | 9.819 | 8.857 | 40.770 | 1.00 | 18.25 | 6 |
| ATOM | 882 | CB | SER | 396 | 10.591 | 9.879 | 41.642 | 1.00 | 18.93 | 6 |
| ATOM | 883 | OG | SER | 396 | 10.309 | 11.194 | 41.187 | 1.00 | 22.70 | 8 |
| ATOM | 884 | C | SER | 396 | 10.229 | 7.446 | 41.175 | 1.00 | 17.49 | 6 |
| ATOM | 885 | O | SER | 396 | 10.095 | 7.050 | 42.329 | 1.00 | 17.49 | 8 |
| ATOM | 886 | N | PRO | 397 | 10.777 | 6.682 | 40.236 | 1.00 | 20.06 | 7 |
| ATOM | 887 | CD | PRO | 397 | 11.042 | 6.990 | 38.829 | 1.00 | 19.90 | 6 |
| ATOM | 888 | CA | PRO | 397 | 11.166 | 5.309 | 40.578 | 1.00 | 21.55 | 6 |
| ATOM | 889 | CB | PRO | 397 | 11.424 | 4.652 | 39.217 | 1.00 | 23.55 | 6 |
| ATOM | 890 | CG | PRO | 397 | 11.842 | 5.775 | 38.372 | 1.00 | 24.21 | 6 |
| ATOM | 891 | C | PRO | 397 | 12.347 | 5.169 | 41.470 | 1.00 | 24.51 | 6 |
| ATOM | 892 | O | PRO | 397 | 12.550 | 4.095 | 42.008 | 1.00 | 26.01 | 8 |
| ATOM | 893 | N | ASP | 398 | 13.084 | 6.256 | 41.659 | 1.00 | 26.15 | 7 |
| ATOM | 894 | CA | ASP | 398 | 14.284 | 6.238 | 42.482 | 1.00 | 30.10 | 6 |
| ATOM | 895 | CB | ASP | 398 | 15.325 | 7.140 | 41.810 | 1.00 | 34.11 | 6 |
| ATOM | 896 | CG | ASP | 398 | 14.840 | 8.598 | 41.658 | 1.00 | 40.89 | 6 |
| ATOM | 897 | OD1 | ASP | 398 | 15.380 | 9.452 | 42.392 | 1.00 | 45.30 | 8 |
| ATOM | 898 | OD2 | ASP | 398 | 13.930 | 8.917 | 40.828 | 1.00 | 44.89 | 8 |
| ATOM | 899 | C | ASP | 398 | 14.054 | 6.620 | 43.958 | 1.00 | 28.78 | 6 |
| ATOM | 900 | O | ASP | 398 | 15.020 | 6.840 | 44.693 | 1.00 | 28.70 | 8 |
| ATOM | 901 | N | ARG | 399 | 12.797 | 6.683 | 44.399 | 1.00 | 26.20 | 7 |
| ATOM | 902 | CA | ARG | 399 | 12.540 | 7.026 | 45.788 | 1.00 | 27.04 | 6 |
| ATOM | 903 | CB | ARG | 399 | 11.029 | 7.259 | 46.052 | 1.00 | 26.80 | 6 |
| ATOM | 904 | CG | ARG | 399 | 10.362 | 8.314 | 45.160 | 1.00 | 25.69 | 6 |
| ATOM | 905 | CD | ARG | 399 | 11.016 | 9.589 | 45.506 | 1.00 | 26.81 | 6 |
| ATOM | 906 | NE | ARG | 399 | 10.400 | 10.788 | 45.016 | 1.00 | 26.65 | 7 |
| ATOM | 907 | CZ | ARG | 399 | 10.916 | 11.971 | 45.103 | 1.00 | 28.44 | 6 |
| ATOM | 908 | NH1 | ARG | 399 | 12.075 | 12.047 | 45.724 | 1.00 | 34.16 | 7 |
| ATOM | 909 | NH2 | ARG | 399 | 10.372 | 13.036 | 44.484 | 1.00 | 21.40 | 7 |
| ATOM | 910 | C | ARG | 399 | 13.065 | 5.975 | 46.764 | 1.00 | 29.93 | 6 |
| ATOM | 911 | O | ARG | 399 | 13.075 | 4.762 | 46.502 | 1.00 | 30.14 | 8 |
| ATOM | 912 | N | GLN | 400 | 13.483 | 6.453 | 47.921 | 1.00 | 30.34 | 7 |
| ATOM | 913 | CA | GLN | 400 | 13.987 | 5.555 | 48.924 | 1.00 | 32.89 | 6 |
| ATOM | 914 | CB | GLN | 400 | 14.485 | 6.364 | 50.121 | 1.00 | 36.60 | 6 |
| ATOM | 915 | CG | GLN | 400 | 15.498 | 5.625 | 50.996 | 1.00 | 43.09 | 6 |
| ATOM | 916 | CD | GLN | 400 | 16.776 | 6.462 | 51.193 | 1.00 | 46.68 | 6 |
| ATOM | 917 | OE1 | GLN | 400 | 16.701 | 7.607 | 51.691 | 1.00 | 48.33 | 8 |
| ATOM | 918 | NE2 | GLN | 400 | 17.954 | 5.907 | 50.783 | 1.00 | 48.29 | 7 |
| ATOM | 919 | C | GLN | 400 | 12.834 | 4.646 | 49.332 | 1.00 | 31.46 | 6 |
| ATOM | 920 | O | GLN | 400 | 11.666 | 5.050 | 49.256 | 1.00 | 31.23 | 8 |
| ATOM | 921 | N | TYR | 401 | 13.164 | 3.413 | 49.689 | 1.00 | 29.84 | 7 |
| ATOM | 922 | CA | TYR | 401 | 12.181 | 2.432 | 50.150 | 1.00 | 30.47 | 6 |
| ATOM | 923 | CB | TYR | 401 | 11.353 | 2.993 | 51.323 | 1.00 | 33.56 | 6 |
| ATOM | 924 | CG | TYR | 401 | 12.201 | 3.584 | 52.426 | 1.00 | 37.77 | 6 |
| ATOM | 925 | CD1 | TYR | 401 | 13.073 | 2.786 | 53.193 | 1.00 | 40.82 | 6 |
| ATOM | 926 | CE1 | TYR | 401 | 13.944 | 3.378 | 54.186 | 1.00 | 42.16 | 6 |
| ATOM | 927 | CD2 | TYR | 401 | 12.192 | 4.956 | 52.654 | 1.00 | 40.80 | 6 |
| ATOM | 928 | CE2 | TYR | 401 | 13.037 | 5.560 | 53.620 | 1.00 | 42.75 | 6 |
| ATOM | 929 | CZ | TYR | 401 | 13.910 | 4.779 | 54.386 | 1.00 | 42.98 | 6 |
| ATOM | 930 | OH | TYR | 401 | 14.686 | 5.467 | 55.325 | 1.00 | 43.71 | 8 |
| ATOM | 931 | C | TYR | 401 | 11.238 | 1.864 | 49.100 | 1.00 | 27.69 | 6 |
| ATOM | 932 | O | TYR | 401 | 10.370 | 1.092 | 49.459 | 1.00 | 30.16 | 8 |

APPENDIX 1-continued

STRUCTURE COORDINATES FOR FXR LBD COMPLEXED WITH FEXARAMINE

| ATOM | 933 | N | ILE | 402 | 11.404 | 2.203 | 47.816 | 1.00 | 25.78 | 7 |
|---|---|---|---|---|---|---|---|---|---|---|
| ATOM | 934 | CA | ILE | 402 | 10.553 | 1.613 | 46.774 | 1.00 | 22.84 | 6 |
| ATOM | 935 | CB | ILE | 402 | 10.657 | 2.402 | 45.434 | 1.00 | 23.00 | 6 |
| ATOM | 936 | CG2 | ILE | 402 | 9.958 | 1.650 | 44.282 | 1.00 | 20.56 | 6 |
| ATOM | 937 | CG1 | ILE | 402 | 10.121 | 3.850 | 45.653 | 1.00 | 22.46 | 6 |
| ATOM | 938 | CD1 | ILE | 402 | 8.640 | 3.961 | 46.085 | 1.00 | 19.57 | 6 |
| ATOM | 939 | C | ILE | 402 | 10.952 | 0.141 | 46.543 | 1.00 | 23.39 | 6 |
| ATOM | 940 | O | ILE | 402 | 12.110 | −0.159 | 46.267 | 1.00 | 24.51 | 8 |
| ATOM | 941 | N | LYS | 403 | 10.012 | −0.776 | 46.672 | 1.00 | 21.45 | 7 |
| ATOM | 942 | CA | LYS | 403 | 10.322 | −2.199 | 46.454 | 1.00 | 22.37 | 6 |
| ATOM | 943 | CB | LYS | 403 | 9.377 | −3.054 | 47.297 | 1.00 | 23.85 | 6 |
| ATOM | 944 | CG | LYS | 403 | 9.285 | −2.666 | 48.755 | 1.00 | 24.84 | 6 |
| ATOM | 945 | CD | LYS | 403 | 8.266 | −3.523 | 49.543 | 1.00 | 27.54 | 6 |
| ATOM | 946 | CE | LYS | 403 | 6.847 | −3.362 | 48.990 | 1.00 | 29.42 | 6 |
| ATOM | 947 | NZ | LYS | 403 | 5.777 | −4.144 | 49.737 | 1.00 | 26.53 | 7 |
| ATOM | 948 | C | LYS | 403 | 10.212 | −2.600 | 44.958 | 1.00 | 21.56 | 6 |
| ATOM | 949 | O | LYS | 403 | 10.998 | −3.437 | 44.464 | 1.00 | 23.77 | 8 |
| ATOM | 950 | N | ASP | 404 | 9.264 | −2.031 | 44.218 | 1.00 | 19.81 | 7 |
| ATOM | 951 | CA | ASP | 404 | 9.109 | −2.402 | 42.834 | 1.00 | 19.54 | 6 |
| ATOM | 952 | CB | ASP | 404 | 7.707 | −2.981 | 42.650 | 1.00 | 20.40 | 6 |
| ATOM | 953 | CG | ASP | 404 | 7.491 | −3.598 | 41.294 | 1.00 | 21.64 | 6 |
| ATOM | 954 | OD1 | ASP | 404 | 8.262 | −3.275 | 40.332 | 1.00 | 22.02 | 8 |
| ATOM | 955 | OD2 | ASP | 404 | 6.537 | −4.396 | 41.166 | 1.00 | 22.85 | 8 |
| ATOM | 956 | C | ASP | 404 | 9.316 | −1.123 | 41.999 | 1.00 | 21.83 | 6 |
| ATOM | 957 | O | ASP | 404 | 8.330 | −0.405 | 41.698 | 1.00 | 20.39 | 8 |
| ATOM | 958 | N | ARG | 405 | 10.620 | −0.763 | 41.740 | 1.00 | 19.67 | 7 |
| ATOM | 959 | CA | ARG | 405 | 10.922 | 0.446 | 40.934 | 1.00 | 21.72 | 6 |
| ATOM | 960 | CB | ARG | 405 | 12.422 | 0.802 | 40.947 | 1.00 | 22.49 | 6 |
| ATOM | 961 | CG | ARG | 405 | 12.991 | 1.041 | 42.311 | 1.00 | 26.87 | 6 |
| ATOM | 962 | CD | ARG | 405 | 14.505 | 1.034 | 42.248 | 1.00 | 28.56 | 6 |
| ATOM | 963 | NE | ARG | 405 | 15.045 | 1.021 | 43.580 | 1.00 | 33.84 | 7 |
| ATOM | 964 | CZ | ARG | 405 | 14.837 | 1.983 | 44.449 | 1.00 | 35.85 | 6 |
| ATOM | 965 | NH1 | ARG | 405 | 14.045 | 2.999 | 44.068 | 1.00 | 39.18 | 7 |
| ATOM | 966 | NH2 | ARG | 405 | 15.510 | 1.994 | 45.616 | 1.00 | 33.69 | 7 |
| ATOM | 967 | C | ARG | 405 | 10.479 | 0.333 | 39.464 | 1.00 | 20.83 | 6 |
| ATOM | 968 | O | ARG | 405 | 10.122 | 1.370 | 38.840 | 1.00 | 20.11 | 8 |
| ATOM | 969 | N | GLU | 406 | 10.452 | −0.902 | 38.830 | 1.00 | 18.43 | 7 |
| ATOM | 970 | CA | GLU | 406 | 10.075 | −0.883 | 37.436 | 1.00 | 21.37 | 6 |
| ATOM | 971 | CB | GLU | 406 | 10.438 | −2.201 | 36.709 | 1.00 | 27.61 | 6 |
| ATOM | 972 | CG | GLU | 406 | 9.622 | −3.386 | 37.197 | 1.00 | 35.26 | 6 |
| ATOM | 973 | CD | GLU | 406 | 8.356 | −3.661 | 36.318 | 1.00 | 43.68 | 6 |
| ATOM | 974 | OE1 | GLU | 406 | 8.048 | −2.857 | 35.350 | 1.00 | 46.60 | 8 |
| ATOM | 975 | OE2 | GLU | 406 | 7.660 | −4.693 | 36.586 | 1.00 | 47.06 | 8 |
| ATOM | 976 | C | GLU | 406 | 8.586 | −0.573 | 37.256 | 1.00 | 20.47 | 6 |
| ATOM | 977 | O | GLU | 406 | 8.189 | 0.016 | 36.234 | 1.00 | 18.47 | 8 |
| ATOM | 978 | N | ALA | 407 | 7.755 | −1.010 | 38.215 | 1.00 | 18.83 | 7 |
| ATOM | 979 | CA | ALA | 407 | 6.306 | −0.704 | 38.153 | 1.00 | 18.20 | 6 |
| ATOM | 980 | CB | ALA | 407 | 5.581 | −1.288 | 39.387 | 1.00 | 18.50 | 6 |
| ATOM | 981 | C | ALA | 407 | 6.170 | 0.845 | 38.153 | 1.00 | 17.66 | 6 |
| ATOM | 982 | O | ALA | 407 | 5.344 | 1.397 | 37.405 | 1.00 | 18.48 | 8 |
| ATOM | 983 | N | VAL | 408 | 6.968 | 1.577 | 38.954 | 1.00 | 17.76 | 7 |
| ATOM | 984 | CA | VAL | 408 | 6.823 | 3.087 | 38.926 | 1.00 | 18.35 | 6 |
| ATOM | 985 | CB | VAL | 408 | 7.570 | 3.805 | 40.157 | 1.00 | 18.47 | 6 |
| ATOM | 986 | CG1 | VAL | 408 | 7.318 | 5.370 | 40.146 | 1.00 | 14.56 | 6 |
| ATOM | 987 | CG2 | VAL | 408 | 7.098 | 3.190 | 41.478 | 1.00 | 15.70 | 6 |
| ATOM | 988 | C | VAL | 408 | 7.337 | 3.652 | 37.617 | 1.00 | 19.56 | 6 |
| ATOM | 989 | O | VAL | 408 | 6.735 | 4.546 | 36.974 | 1.00 | 19.62 | 8 |
| ATOM | 990 | N | GLU | 409 | 8.476 | 3.117 | 37.201 | 1.00 | 19.33 | 7 |
| ATOM | 991 | CA | GLU | 409 | 9.068 | 3.554 | 35.922 | 1.00 | 21.81 | 6 |
| ATOM | 992 | CB | GLU | 409 | 10.298 | 2.680 | 35.676 | 1.00 | 20.80 | 6 |
| ATOM | 993 | CG | GLU | 409 | 10.995 | 2.934 | 34.387 | 1.00 | 30.47 | 6 |
| ATOM | 994 | CD | GLU | 409 | 12.256 | 2.050 | 34.269 | 1.00 | 34.12 | 6 |
| ATOM | 995 | OE1 | GLU | 409 | 12.110 | 0.809 | 34.458 | 1.00 | 35.74 | 8 |
| ATOM | 996 | OE2 | GLU | 409 | 13.358 | 2.621 | 34.007 | 1.00 | 37.61 | 8 |
| ATOM | 997 | C | GLU | 409 | 8.039 | 3.425 | 34.774 | 1.00 | 19.31 | 6 |
| ATOM | 998 | O | GLU | 409 | 7.899 | 4.303 | 33.897 | 1.00 | 20.15 | 8 |
| ATOM | 999 | N | LYS | 410 | 7.301 | 2.324 | 34.775 | 1.00 | 20.62 | 7 |
| ATOM | 1000 | CA | LYS | 410 | 6.308 | 2.109 | 33.710 | 1.00 | 21.57 | 6 |
| ATOM | 1001 | CB | LYS | 410 | 5.782 | 0.684 | 33.794 | 1.00 | 22.00 | 6 |
| ATOM | 1002 | CG | LYS | 410 | 6.881 | −0.318 | 33.434 | 1.00 | 24.82 | 6 |
| ATOM | 1003 | CD | LYS | 410 | 6.439 | −1.772 | 33.607 | 1.00 | 29.47 | 6 |
| ATOM | 1004 | CE | LYS | 410 | 7.583 | −2.728 | 33.207 | 1.00 | 31.74 | 6 |
| ATOM | 1005 | NZ | LYS | 410 | 7.101 | −4.120 | 33.517 | 1.00 | 35.37 | 7 |
| ATOM | 1006 | C | LYS | 410 | 5.162 | 3.129 | 33.721 | 1.00 | 20.15 | 6 |
| ATOM | 1007 | O | LYS | 410 | 4.450 | 3.348 | 32.704 | 1.00 | 18.16 | 8 |
| ATOM | 1008 | N | LEU | 411 | 4.966 | 3.733 | 34.888 | 1.00 | 18.65 | 7 |
| ATOM | 1009 | CA | LEU | 411 | 3.936 | 4.742 | 35.048 | 1.00 | 17.75 | 6 |

APPENDIX 1-continued

STRUCTURE COORDINATES FOR FXR LBD COMPLEXED WITH FEXARAMINE

| ATOM | 1010 | CB  | LEU | 411 | 3.420  | 4.748  | 36.533 | 1.00 | 18.67 | 6 |
| ATOM | 1011 | CG  | LEU | 411 | 2.598  | 3.520  | 36.922 | 1.00 | 20.48 | 6 |
| ATOM | 1012 | CD1 | LEU | 411 | 1.931  | 3.757  | 38.334 | 1.00 | 20.57 | 6 |
| ATOM | 1013 | CD2 | LEU | 411 | 1.473  | 3.352  | 35.836 | 1.00 | 20.41 | 6 |
| ATOM | 1014 | C   | LEU | 411 | 4.522  | 6.088  | 34.705 | 1.00 | 16.78 | 6 |
| ATOM | 1015 | O   | LEU | 411 | 3.864  | 6.948  | 34.158 | 1.00 | 18.66 | 8 |
| ATOM | 1016 | N   | GLN | 412 | 5.798  | 6.282  | 35.015 | 1.00 | 16.32 | 7 |
| ATOM | 1017 | CA  | GLN | 412 | 6.392  | 7.587  | 34.783 | 1.00 | 14.92 | 6 |
| ATOM | 1018 | CB  | GLN | 412 | 7.670  | 7.742  | 35.625 | 1.00 | 15.65 | 6 |
| ATOM | 1019 | CG  | GLN | 412 | 8.145  | 9.185  | 35.732 | 1.00 | 15.44 | 6 |
| ATOM | 1020 | CD  | GLN | 412 | 9.539  | 9.267  | 36.263 | 1.00 | 16.45 | 6 |
| ATOM | 1021 | OE1 | GLN | 412 | 10.436 | 8.556  | 35.781 | 1.00 | 15.48 | 8 |
| ATOM | 1022 | NE2 | GLN | 412 | 9.759  | 10.128 | 37.256 | 1.00 | 12.68 | 7 |
| ATOM | 1023 | C   | GLN | 412 | 6.764  | 7.849  | 33.312 | 1.00 | 17.36 | 6 |
| ATOM | 1024 | O   | GLN | 412 | 6.637  | 8.940  | 32.821 | 1.00 | 15.53 | 8 |
| ATOM | 1025 | N   | GLU | 413 | 7.096  | 6.939  | 32.586 | 1.00 | 18.73 | 7 |
| ATOM | 1026 | CA  | GLU | 413 | 7.755  | 6.989  | 31.266 | 1.00 | 21.78 | 6 |
| ATOM | 1027 | CB  | GLU | 413 | 8.276  | 5.588  | 30.880 | 1.00 | 24.70 | 6 |
| ATOM | 1028 | CG  | GLU | 413 | 9.704  | 5.651  | 30.307 | 1.00 | 33.12 | 6 |
| ATOM | 1029 | CD  | GLU | 413 | 10.727 | 6.545  | 31.138 | 1.00 | 37.10 | 6 |
| ATOM | 1030 | OE1 | GLU | 413 | 11.030 | 6.266  | 32.325 | 1.00 | 37.65 | 8 |
| ATOM | 1031 | OE2 | GLU | 413 | 11.247 | 7.547  | 30.575 | 1.00 | 39.21 | 8 |
| ATOM | 1032 | C   | GLU | 413 | 6.855  | 7.573  | 30.142 | 1.00 | 19.47 | 6 |
| ATOM | 1033 | O   | GLU | 413 | 7.291  | 8.385  | 29.351 | 1.00 | 18.65 | 8 |
| ATOM | 1034 | N   | PRO | 414 | 5.459  | 7.146  | 30.378 | 1.00 | 20.07 | 7 |
| ATOM | 1035 | CD  | PRO | 414 | 5.067  | 5.893  | 31.055 | 1.00 | 19.68 | 6 |
| ATOM | 1036 | CA  | PRO | 414 | 4.401  | 7.717  | 29.518 | 1.00 | 19.49 | 6 |
| ATOM | 1037 | CB  | PRO | 414 | 3.137  | 6.902  | 29.854 | 1.00 | 19.44 | 6 |
| ATOM | 1038 | CG  | PRO | 414 | 3.677  | 5.575  | 30.456 | 1.00 | 23.13 | 6 |
| ATOM | 1039 | C   | PRO | 414 | 4.172  | 9.222  | 29.800 | 1.00 | 19.10 | 6 |
| ATOM | 1040 | O   | PRO | 414 | 3.825  | 9.991  | 28.910 | 1.00 | 16.88 | 8 |
| ATOM | 1041 | N   | LEU | 415 | 4.340  | 9.636  | 31.050 | 1.00 | 17.87 | 7 |
| ATOM | 1042 | CA  | LEU | 415 | 4.102  | 11.070 | 31.395 | 1.00 | 17.08 | 6 |
| ATOM | 1043 | CB  | LEU | 415 | 3.944  | 11.215 | 32.935 | 1.00 | 18.37 | 6 |
| ATOM | 1044 | CG  | LEU | 415 | 2.775  | 10.339 | 33.494 | 1.00 | 18.91 | 6 |
| ATOM | 1045 | CD1 | LEU | 415 | 2.575  | 10.455 | 34.992 | 1.00 | 18.35 | 6 |
| ATOM | 1046 | CD2 | LEU | 415 | 1.472  | 10.791 | 32.774 | 1.00 | 21.95 | 6 |
| ATOM | 1047 | C   | LEU | 415 | 5.256  | 11.903 | 30.877 | 1.00 | 16.87 | 6 |
| ATOM | 1048 | O   | LEU | 415 | 5.088  | 13.033 | 30.418 | 1.00 | 15.92 | 8 |
| ATOM | 1049 | N   | LEU | 416 | 6.455  | 11.346 | 30.994 | 1.00 | 16.05 | 7 |
| ATOM | 1050 | CA  | LEU | 416 | 7.605  | 12.040 | 30.455 | 1.00 | 16.12 | 6 |
| ATOM | 1051 | CB  | LEU | 416 | 8.857  | 11.237 | 30.725 | 1.00 | 14.67 | 6 |
| ATOM | 1052 | CG  | LEU | 416 | 9.381  | 11.348 | 32.170 | 1.00 | 15.86 | 6 |
| ATOM | 1053 | CD1 | LEU | 416 | 10.281 | 10.101 | 32.507 | 1.00 | 17.06 | 6 |
| ATOM | 1054 | CD2 | LEU | 416 | 10.129 | 12.651 | 32.292 | 1.00 | 17.58 | 6 |
| ATOM | 1055 | C   | LEU | 416 | 7.410  | 12.210 | 28.921 | 1.00 | 15.67 | 6 |
| ATOM | 1056 | O   | LEU | 416 | 7.773  | 13.255 | 28.359 | 1.00 | 16.65 | 8 |
| ATOM | 1057 | N   | ASP | 417 | 6.901  | 11.178 | 28.245 | 1.00 | 17.40 | 7 |
| ATOM | 1058 | CA  | ASP | 417 | 6.636  | 11.302 | 26.808 | 1.00 | 18.62 | 6 |
| ATOM | 1059 | CB  | ASP | 417 | 6.176  | 9.941  | 26.211 | 1.00 | 20.86 | 6 |
| ATOM | 1060 | CG  | ASP | 417 | 7.320  | 8.885  | 26.214 | 1.00 | 23.35 | 6 |
| ATOM | 1061 | OD1 | ASP | 417 | 8.466  | 9.315  | 26.294 | 1.00 | 24.26 | 8 |
| ATOM | 1062 | OD2 | ASP | 417 | 7.096  | 7.651  | 26.102 | 1.00 | 24.28 | 8 |
| ATOM | 1063 | C   | ASP | 417 | 5.591  | 12.425 | 26.532 | 1.00 | 18.79 | 6 |
| ATOM | 1064 | O   | ASP | 417 | 5.782  | 13.213 | 25.589 | 1.00 | 20.06 | 8 |
| ATOM | 1065 | N   | VAL | 418 | 4.483  | 12.473 | 27.289 | 1.00 | 16.50 | 7 |
| ATOM | 1066 | CA  | VAL | 418 | 3.523  | 13.552 | 27.119 | 1.00 | 16.29 | 6 |
| ATOM | 1067 | CB  | VAL | 418 | 2.276  | 13.369 | 28.019 | 1.00 | 18.28 | 6 |
| ATOM | 1068 | CG1 | VAL | 418 | 1.410  | 14.652 | 27.991 | 1.00 | 16.09 | 6 |
| ATOM | 1069 | CG2 | VAL | 418 | 1.462  | 12.108 | 27.519 | 1.00 | 17.51 | 6 |
| ATOM | 1070 | C   | VAL | 418 | 4.154  | 14.935 | 27.402 | 1.00 | 18.27 | 6 |
| ATOM | 1071 | O   | VAL | 418 | 3.923  | 15.901 | 26.637 | 1.00 | 18.89 | 8 |
| ATOM | 1072 | N   | LEU | 419 | 5.006  | 15.032 | 28.427 | 1.00 | 16.19 | 7 |
| ATOM | 1073 | CA  | LEU | 419 | 5.625  | 16.328 | 28.730 | 1.00 | 16.99 | 6 |
| ATOM | 1074 | CB  | LEU | 419 | 6.393  | 16.262 | 30.058 | 1.00 | 14.52 | 6 |
| ATOM | 1075 | CG  | LEU | 419 | 7.078  | 17.571 | 30.398 | 1.00 | 17.89 | 6 |
| ATOM | 1076 | CD1 | LEU | 419 | 5.986  | 18.713 | 30.571 | 1.00 | 16.23 | 6 |
| ATOM | 1077 | CD2 | LEU | 419 | 7.931  | 17.304 | 31.746 | 1.00 | 16.46 | 6 |
| ATOM | 1078 | C   | LEU | 419 | 6.547  | 16.760 | 27.607 | 1.00 | 17.42 | 6 |
| ATOM | 1079 | O   | LEU | 419 | 6.566  | 17.949 | 27.191 | 1.00 | 14.69 | 8 |
| ATOM | 1080 | N   | GLN | 420 | 7.321  | 15.824 | 27.102 | 1.00 | 19.78 | 7 |
| ATOM | 1081 | CA  | GLN | 420 | 8.196  | 16.194 | 25.978 | 1.00 | 22.39 | 6 |
| ATOM | 1082 | CB  | GLN | 420 | 9.019  | 14.996 | 25.554 | 1.00 | 26.26 | 6 |
| ATOM | 1083 | CG  | GLN | 420 | 9.848  | 15.238 | 24.317 | 1.00 | 31.05 | 6 |
| ATOM | 1084 | CD  | GLN | 420 | 10.542 | 13.952 | 23.893 | 1.00 | 36.40 | 6 |
| ATOM | 1085 | OE1 | GLN | 420 | 11.542 | 13.563 | 24.497 | 1.00 | 37.49 | 8 |
| ATOM | 1086 | NE2 | GLN | 420 | 9.993  | 13.271 | 22.859 | 1.00 | 38.17 | 7 |

APPENDIX 1-continued

STRUCTURE COORDINATES FOR FXR LBD COMPLEXED WITH FEXARAMINE

| ATOM | 1087 | C   | GLN | 420 | 7.325  | 16.719 | 24.799 | 1.00 | 23.07 | 6  |
| ---- | ---- | --- | --- | --- | ------ | ------ | ------ | ---- | ----- | -- |
| ATOM | 1088 | O   | GLN | 420 | 7.654  | 17.739 | 24.141 | 1.00 | 24.67 | 8  |
| ATOM | 1089 | N   | LYS | 421 | 6.238  | 16.044 | 24.465 | 1.00 | 21.61 | 7  |
| ATOM | 1090 | CA  | LYS | 421 | 5.366  | 16.635 | 23.452 | 1.00 | 22.20 | 6  |
| ATOM | 1091 | CB  | LYS | 421 | 4.127  | 15.767 | 23.208 | 1.00 | 23.43 | 6  |
| ATOM | 1092 | CG  | LYS | 421 | 4.413  | 14.373 | 22.783 | 1.00 | 29.40 | 6  |
| ATOM | 1093 | CD  | LYS | 421 | 5.095  | 14.348 | 21.485 | 1.00 | 32.52 | 6  |
| ATOM | 1094 | CE  | LYS | 421 | 5.072  | 12.897 | 20.824 | 1.00 | 36.37 | 6  |
| ATOM | 1095 | NZ  | LYS | 421 | 3.653  | 12.299 | 20.674 | 1.00 | 37.16 | 7  |
| ATOM | 1096 | C   | LYS | 421 | 4.805  | 18.045 | 23.841 | 1.00 | 20.49 | 6  |
| ATOM | 1097 | O   | LYS | 421 | 4.708  | 18.927 | 22.985 | 1.00 | 20.84 | 8  |
| ATOM | 1098 | N   | LEU | 422 | 4.389  | 18.247 | 25.098 | 1.00 | 19.58 | 7  |
| ATOM | 1099 | CA  | LEU | 422 | 3.824  | 19.540 | 25.517 | 1.00 | 18.69 | 6  |
| ATOM | 1100 | CB  | LEU | 422 | 3.382  | 19.511 | 26.966 | 1.00 | 17.35 | 6  |
| ATOM | 1101 | CG  | LEU | 422 | 2.127  | 18.675 | 27.223 | 1.00 | 19.81 | 6  |
| ATOM | 1102 | CD1 | LEU | 422 | 1.821  | 18.558 | 28.701 | 1.00 | 21.65 | 6  |
| ATOM | 1103 | CD2 | LEU | 422 | 0.995  | 19.354 | 26.437 | 1.00 | 22.49 | 6  |
| ATOM | 1104 | C   | LEU | 422 | 4.843  | 20.640 | 25.328 | 1.00 | 20.29 | 6  |
| ATOM | 1105 | O   | LEU | 422 | 4.479  | 21.751 | 24.894 | 1.00 | 19.74 | 8  |
| ATOM | 1106 | N   | CYS | 423 | 6.106  | 20.331 | 25.643 | 1.00 | 18.79 | 7  |
| ATOM | 1107 | CA  | CYS | 423 | 7.190  | 21.322 | 25.464 | 1.00 | 20.73 | 6  |
| ATOM | 1108 | CB  | CYS | 423 | 8.541  | 20.707 | 25.915 | 1.00 | 18.78 | 6  |
| ATOM | 1109 | SG  | CYS | 423 | 8.497  | 20.555 | 27.781 | 1.00 | 19.20 | 16 |
| ATOM | 1110 | C   | CYS | 423 | 7.278  | 21.751 | 23.982 | 1.00 | 22.59 | 6  |
| ATOM | 1111 | O   | CYS | 423 | 7.554  | 22.908 | 23.683 | 1.00 | 22.67 | 8  |
| ATOM | 1112 | N   | LYS | 424 | 7.068  | 20.837 | 23.075 | 1.00 | 23.92 | 7  |
| ATOM | 1113 | CA  | LYS | 424 | 7.221  | 21.223 | 21.673 | 1.00 | 26.49 | 6  |
| ATOM | 1114 | CB  | LYS | 424 | 7.472  | 19.955 | 20.851 | 1.00 | 30.34 | 6  |
| ATOM | 1115 | CG  | LYS | 424 | 7.305  | 20.100 | 19.372 | 1.00 | 37.67 | 6  |
| ATOM | 1116 | CD  | LYS | 424 | 8.387  | 19.326 | 18.699 | 1.00 | 42.21 | 6  |
| ATOM | 1117 | CE  | LYS | 424 | 8.253  | 19.450 | 17.190 | 1.00 | 44.24 | 6  |
| ATOM | 1118 | NZ  | LYS | 424 | 6.786  | 19.345 | 16.808 | 1.00 | 47.45 | 7  |
| ATOM | 1119 | C   | LYS | 424 | 5.930  | 21.935 | 21.184 | 1.00 | 27.23 | 6  |
| ATOM | 1120 | O   | LYS | 424 | 6.006  | 22.934 | 20.480 | 1.00 | 28.14 | 8  |
| ATOM | 1121 | N   | ILE | 425 | 4.703  | 21.559 | 21.818 | 1.00 | 26.63 | 7  |
| ATOM | 1122 | CA  | ILE | 425 | 3.442  | 22.266 | 21.508 | 1.00 | 27.00 | 6  |
| ATOM | 1123 | CB  | ILE | 425 | 2.169  | 21.530 | 22.153 | 1.00 | 27.35 | 6  |
| ATOM | 1124 | CG2 | ILE | 425 | 0.868  | 22.531 | 22.190 | 1.00 | 27.37 | 6  |
| ATOM | 1125 | CG1 | ILE | 425 | 1.902  | 20.214 | 21.397 | 1.00 | 28.64 | 6  |
| ATOM | 1126 | CD1 | ILE | 425 | 0.812  | 19.385 | 22.076 | 1.00 | 31.67 | 6  |
| ATOM | 1127 | C   | ILE | 425 | 3.446  | 23.735 | 22.008 | 1.00 | 26.48 | 6  |
| ATOM | 1128 | O   | ILE | 425 | 3.099  | 24.670 | 21.279 | 1.00 | 26.48 | 8  |
| ATOM | 1129 | N   | HIS | 426 | 3.854  | 23.939 | 23.249 | 1.00 | 24.95 | 7  |
| ATOM | 1130 | CA  | HIS | 426 | 3.835  | 25.271 | 23.794 | 1.00 | 24.86 | 6  |
| ATOM | 1131 | CB  | HIS | 426 | 3.556  | 25.183 | 25.313 | 1.00 | 24.69 | 6  |
| ATOM | 1132 | CG  | HIS | 426 | 2.162  | 24.729 | 25.641 | 1.00 | 24.71 | 6  |
| ATOM | 1133 | CD2 | HIS | 426 | 0.954  | 25.213 | 25.250 | 1.00 | 23.92 | 6  |
| ATOM | 1134 | ND1 | HIS | 426 | 1.900  | 23.613 | 26.415 | 1.00 | 22.78 | 7  |
| ATOM | 1135 | CE1 | HIS | 426 | 0.588  | 23.422 | 26.479 | 1.00 | 22.53 | 6  |
| ATOM | 1136 | NE2 | HIS | 426 | −0.006 | 24.379 | 25.772 | 1.00 | 25.71 | 7  |
| ATOM | 1137 | C   | HIS | 426 | 5.067  | 26.181 | 23.514 | 1.00 | 24.55 | 6  |
| ATOM | 1138 | O   | HIS | 426 | 4.975  | 27.391 | 23.632 | 1.00 | 22.28 | 8  |
| ATOM | 1139 | N   | GLN | 427 | 6.204  | 25.609 | 23.167 | 1.00 | 24.11 | 7  |
| ATOM | 1140 | CA  | GLN | 427 | 7.384  | 26.419 | 22.917 | 1.00 | 25.32 | 6  |
| ATOM | 1141 | CB  | GLN | 427 | 8.242  | 26.553 | 24.192 | 1.00 | 26.75 | 6  |
| ATOM | 1142 | CG  | GLN | 427 | 7.637  | 27.413 | 25.340 | 1.00 | 26.51 | 6  |
| ATOM | 1143 | CD  | GLN | 427 | 8.673  | 27.750 | 26.439 | 1.00 | 31.10 | 6  |
| ATOM | 1144 | OE1 | GLN | 427 | 8.298  | 28.044 | 27.603 | 1.00 | 31.48 | 8  |
| ATOM | 1145 | NE2 | GLN | 427 | 9.983  | 27.723 | 26.074 | 1.00 | 29.86 | 7  |
| ATOM | 1146 | C   | GLN | 427 | 8.176  | 25.801 | 21.774 | 1.00 | 27.56 | 6  |
| ATOM | 1147 | O   | GLN | 427 | 9.351  | 25.445 | 21.898 | 1.00 | 27.06 | 8  |
| ATOM | 1148 | N   | PRO | 428 | 7.526  | 25.701 | 20.611 | 1.00 | 28.74 | 7  |
| ATOM | 1149 | CD  | PRO | 428 | 6.245  | 26.324 | 20.249 | 1.00 | 28.48 | 6  |
| ATOM | 1150 | CA  | PRO | 428 | 8.180  | 25.117 | 19.442 | 1.00 | 30.35 | 6  |
| ATOM | 1151 | CB  | PRO | 428 | 7.117  | 25.238 | 18.356 | 1.00 | 31.91 | 6  |
| ATOM | 1152 | CG  | PRO | 428 | 6.382  | 26.508 | 18.729 | 1.00 | 30.42 | 6  |
| ATOM | 1153 | C   | PRO | 428 | 9.479  | 25.810 | 19.038 | 1.00 | 31.95 | 6  |
| ATOM | 1154 | O   | PRO | 428 | 10.299 | 25.186 | 18.399 | 1.00 | 32.66 | 8  |
| ATOM | 1155 | N   | GLU | 429 | 9.667  | 27.069 | 19.425 | 1.00 | 33.51 | 7  |
| ATOM | 1156 | CA  | GLU | 429 | 10.859 | 27.813 | 19.022 | 1.00 | 36.19 | 6  |
| ATOM | 1157 | CB  | GLU | 429 | 10.551 | 29.310 | 18.872 | 1.00 | 36.14 | 6  |
| ATOM | 1158 | CG  | GLU | 429 | 10.297 | 30.096 | 20.176 | 1.00 | 39.46 | 6  |
| ATOM | 1159 | CD  | GLU | 429 | 9.103  | 29.596 | 21.022 | 1.00 | 41.32 | 6  |
| ATOM | 1160 | OE1 | GLU | 429 | 7.989  | 29.298 | 20.502 | 1.00 | 41.17 | 8  |
| ATOM | 1161 | OE2 | GLU | 429 | 9.300  | 29.540 | 22.247 | 1.00 | 43.92 | 8  |
| ATOM | 1162 | C   | GLU | 429 | 12.013 | 27.634 | 19.977 | 1.00 | 37.32 | 6  |
| ATOM | 1163 | O   | GLU | 429 | 13.050 | 28.270 | 19.799 | 1.00 | 39.02 | 8  |

APPENDIX 1-continued

STRUCTURE COORDINATES FOR FXR LBD COMPLEXED WITH FEXARAMINE

| ATOM | 1164 | N | ASN | 430 | 11.836 | 26.761 | 20.970 | 1.00 | 36.99 | 7 |
|---|---|---|---|---|---|---|---|---|---|---|
| ATOM | 1165 | CA | ASN | 430 | 12.834 | 26.506 | 21.996 | 1.00 | 37.06 | 6 |
| ATOM | 1166 | CB | ASN | 430 | 12.363 | 27.170 | 23.307 | 1.00 | 41.16 | 6 |
| ATOM | 1167 | CG | ASN | 430 | 13.477 | 27.336 | 24.337 | 1.00 | 44.13 | 6 |
| ATOM | 1168 | OD1 | ASN | 430 | 13.537 | 28.359 | 25.036 | 1.00 | 47.94 | 8 |
| ATOM | 1169 | ND2 | ASN | 430 | 14.361 | 26.343 | 24.441 | 1.00 | 46.05 | 7 |
| ATOM | 1170 | C | ASN | 430 | 12.987 | 24.993 | 22.160 | 1.00 | 36.64 | 6 |
| ATOM | 1171 | O | ASN | 430 | 12.451 | 24.396 | 23.099 | 1.00 | 33.95 | 8 |
| ATOM | 1172 | N | PRO | 431 | 13.740 | 24.352 | 21.243 | 1.00 | 35.67 | 7 |
| ATOM | 1173 | CD | PRO | 431 | 14.370 | 24.993 | 20.073 | 1.00 | 35.91 | 6 |
| ATOM | 1174 | CA | PRO | 431 | 13.986 | 22.904 | 21.234 | 1.00 | 35.65 | 6 |
| ATOM | 1175 | CB | PRO | 431 | 14.861 | 22.705 | 20.011 | 1.00 | 36.93 | 6 |
| ATOM | 1176 | CG | PRO | 431 | 14.439 | 23.852 | 19.098 | 1.00 | 36.97 | 6 |
| ATOM | 1177 | C | PRO | 431 | 14.618 | 22.263 | 22.475 | 1.00 | 35.36 | 6 |
| ATOM | 1178 | O | PRO | 431 | 14.462 | 21.068 | 22.708 | 1.00 | 35.99 | 8 |
| ATOM | 1179 | N | GLN | 432 | 15.339 | 23.055 | 23.260 | 1.00 | 33.39 | 7 |
| ATOM | 1180 | CA | GLN | 432 | 15.956 | 22.543 | 24.458 | 1.00 | 31.54 | 6 |
| ATOM | 1181 | CB | GLN | 432 | 17.223 | 23.354 | 24.773 | 1.00 | 35.01 | 6 |
| ATOM | 1182 | CG | GLN | 432 | 16.953 | 24.594 | 25.632 | 1.00 | 40.15 | 6 |
| ATOM | 1183 | CD | GLN | 432 | 17.928 | 25.747 | 25.322 | 1.00 | 43.73 | 6 |
| ATOM | 1184 | OE1 | GLN | 432 | 18.073 | 26.139 | 24.153 | 1.00 | 46.27 | 8 |
| ATOM | 1185 | NE2 | GLN | 432 | 18.607 | 26.284 | 26.365 | 1.00 | 44.57 | 7 |
| ATOM | 1186 | C | GLN | 432 | 15.002 | 22.700 | 25.643 | 1.00 | 28.52 | 6 |
| ATOM | 1187 | O | GLN | 432 | 15.365 | 22.363 | 26.758 | 1.00 | 26.75 | 8 |
| ATOM | 1188 | N | HIS | 433 | 13.804 | 23.229 | 25.412 | 1.00 | 24.03 | 7 |
| ATOM | 1189 | CA | HIS | 433 | 12.917 | 23.476 | 26.549 | 1.00 | 22.84 | 6 |
| ATOM | 1190 | CB | HIS | 433 | 11.577 | 24.050 | 26.043 | 1.00 | 22.27 | 6 |
| ATOM | 1191 | CG | HIS | 433 | 10.614 | 24.385 | 27.140 | 1.00 | 23.73 | 6 |
| ATOM | 1192 | CD2 | HIS | 433 | 9.322 | 24.023 | 27.333 | 1.00 | 22.94 | 6 |
| ATOM | 1193 | ND1 | HIS | 433 | 10.904 | 25.303 | 28.125 | 1.00 | 22.94 | 7 |
| ATOM | 1194 | CE1 | HIS | 433 | 9.827 | 25.517 | 28.861 | 1.00 | 23.55 | 6 |
| ATOM | 1195 | NE2 | HIS | 433 | 8.852 | 24.748 | 28.402 | 1.00 | 24.36 | 7 |
| ATOM | 1196 | C | HIS | 433 | 12.693 | 22.270 | 27.479 | 1.00 | 21.51 | 6 |
| ATOM | 1197 | O | HIS | 433 | 12.811 | 22.383 | 28.725 | 1.00 | 22.71 | 8 |
| ATOM | 1198 | N | PHE | 434 | 12.465 | 21.103 | 26.886 | 1.00 | 20.30 | 7 |
| ATOM | 1199 | CA | PHE | 434 | 12.183 | 19.915 | 27.679 | 1.00 | 24.11 | 6 |
| ATOM | 1200 | CB | PHE | 434 | 11.810 | 18.725 | 26.813 | 1.00 | 24.68 | 6 |
| ATOM | 1201 | CG | PHE | 434 | 11.644 | 17.432 | 27.598 | 1.00 | 26.29 | 6 |
| ATOM | 1202 | CD1 | PHE | 434 | 10.509 | 17.272 | 28.404 | 1.00 | 26.38 | 6 |
| ATOM | 1203 | CD2 | PHE | 434 | 12.534 | 16.334 | 27.433 | 1.00 | 26.46 | 6 |
| ATOM | 1204 | CE1 | PHE | 434 | 10.231 | 16.066 | 29.010 | 1.00 | 26.26 | 6 |
| ATOM | 1205 | CE2 | PHE | 434 | 12.274 | 15.081 | 28.049 | 1.00 | 26.51 | 6 |
| ATOM | 1206 | CZ | PHE | 434 | 11.100 | 14.954 | 28.841 | 1.00 | 26.11 | 6 |
| ATOM | 1207 | C | PHE | 434 | 13.366 | 19.581 | 28.564 | 1.00 | 25.13 | 6 |
| ATOM | 1208 | O | PHE | 434 | 13.191 | 19.238 | 29.768 | 1.00 | 23.78 | 8 |
| ATOM | 1209 | N | ALA | 435 | 14.564 | 19.681 | 27.979 | 1.00 | 24.03 | 7 |
| ATOM | 1210 | CA | ALA | 435 | 15.801 | 19.471 | 28.753 | 1.00 | 25.07 | 6 |
| ATOM | 1211 | CB | ALA | 435 | 17.042 | 19.659 | 27.860 | 1.00 | 24.83 | 6 |
| ATOM | 1212 | C | ALA | 435 | 15.899 | 20.469 | 29.905 | 1.00 | 24.15 | 6 |
| ATOM | 1213 | O | ALA | 435 | 16.343 | 20.095 | 30.995 | 1.00 | 25.10 | 8 |
| ATOM | 1214 | N | CYS | 436 | 15.497 | 21.731 | 29.681 | 1.00 | 24.44 | 7 |
| ATOM | 1215 | CA | CYS | 436 | 15.579 | 22.766 | 30.729 | 1.00 | 26.19 | 6 |
| ATOM | 1216 | CB | CYS | 436 | 15.221 | 24.170 | 30.226 | 1.00 | 27.98 | 6 |
| ATOM | 1217 | SG | CYS | 436 | 16.405 | 24.731 | 28.990 | 1.00 | 36.71 | 16 |
| ATOM | 1218 | C | CYS | 436 | 14.688 | 22.425 | 31.889 | 1.00 | 25.04 | 6 |
| ATOM | 1219 | O | CYS | 436 | 15.084 | 22.641 | 33.029 | 1.00 | 25.74 | 8 |
| ATOM | 1220 | N | LEU | 437 | 13.515 | 21.857 | 31.603 | 1.00 | 23.61 | 7 |
| ATOM | 1221 | CA | LEU | 437 | 12.588 | 21.446 | 32.653 | 1.00 | 21.74 | 6 |
| ATOM | 1222 | CB | LEU | 437 | 11.277 | 20.892 | 32.094 | 1.00 | 23.21 | 6 |
| ATOM | 1223 | CG | LEU | 437 | 10.184 | 21.913 | 31.743 | 1.00 | 25.15 | 6 |
| ATOM | 1224 | CD1 | LEU | 437 | 9.887 | 22.604 | 32.990 | 1.00 | 25.88 | 6 |
| ATOM | 1225 | CD2 | LEU | 437 | 10.581 | 22.995 | 30.737 | 1.00 | 26.62 | 6 |
| ATOM | 1226 | C | LEU | 437 | 13.249 | 20.354 | 33.487 | 1.00 | 22.31 | 6 |
| ATOM | 1227 | O | LEU | 437 | 13.266 | 20.454 | 34.724 | 1.00 | 21.51 | 8 |
| ATOM | 1228 | N | LEU | 438 | 13.771 | 19.317 | 32.831 | 1.00 | 21.09 | 7 |
| ATOM | 1229 | CA | LEU | 438 | 14.422 | 18.247 | 33.572 | 1.00 | 25.04 | 6 |
| ATOM | 1230 | CB | LEU | 438 | 14.989 | 17.158 | 32.633 | 1.00 | 27.63 | 6 |
| ATOM | 1231 | CG | LEU | 438 | 13.897 | 16.509 | 31.808 | 1.00 | 28.85 | 6 |
| ATOM | 1232 | CD1 | LEU | 438 | 14.464 | 15.409 | 30.940 | 1.00 | 29.12 | 6 |
| ATOM | 1233 | CD2 | LEU | 438 | 12.828 | 15.983 | 32.761 | 1.00 | 28.90 | 6 |
| ATOM | 1234 | C | LEU | 438 | 15.551 | 18.814 | 34.428 | 1.00 | 25.06 | 6 |
| ATOM | 1235 | O | LEU | 438 | 15.723 | 18.420 | 35.583 | 1.00 | 24.77 | 8 |
| ATOM | 1236 | N | GLY | 439 | 16.281 | 19.773 | 33.860 | 1.00 | 27.05 | 7 |
| ATOM | 1237 | CA | GLY | 439 | 17.394 | 20.406 | 34.550 | 1.00 | 28.73 | 6 |
| ATOM | 1238 | C | GLY | 439 | 16.938 | 20.998 | 35.871 | 1.00 | 29.15 | 6 |
| ATOM | 1239 | O | GLY | 439 | 17.542 | 20.768 | 36.947 | 1.00 | 31.44 | 8 |
| ATOM | 1240 | N | ARG | 440 | 15.833 | 21.715 | 35.819 | 1.00 | 28.15 | 7 |

APPENDIX 1-continued

STRUCTURE COORDINATES FOR FXR LBD COMPLEXED WITH FEXARAMINE

| ATOM | 1241 | CA  | ARG | 440 | 15.292 | 22.355 | 37.016 | 1.00 | 28.50 | 6 |
| ATOM | 1242 | CB  | ARG | 440 | 14.109 | 23.270 | 36.712 | 1.00 | 28.90 | 6 |
| ATOM | 1243 | CG  | ARG | 440 | 14.430 | 24.413 | 35.749 | 1.00 | 32.17 | 6 |
| ATOM | 1244 | CD  | ARG | 440 | 15.666 | 25.248 | 36.114 | 1.00 | 31.21 | 6 |
| ATOM | 1245 | NE  | ARG | 440 | 15.609 | 26.637 | 35.634 | 1.00 | 32.35 | 7 |
| ATOM | 1246 | CZ  | ARG | 440 | 16.008 | 27.102 | 34.438 | 1.00 | 32.55 | 6 |
| ATOM | 1247 | NH1 | ARG | 440 | 16.534 | 26.276 | 33.522 | 1.00 | 28.84 | 7 |
| ATOM | 1248 | NH2 | ARG | 440 | 15.872 | 28.411 | 34.158 | 1.00 | 30.85 | 7 |
| ATOM | 1249 | C   | ARG | 440 | 14.911 | 21.367 | 38.093 | 1.00 | 29.85 | 6 |
| ATOM | 1250 | O   | ARG | 440 | 14.803 | 21.758 | 39.267 | 1.00 | 26.84 | 8 |
| ATOM | 1251 | N   | LEU | 441 | 14.699 | 20.097 | 37.711 | 1.00 | 29.24 | 7 |
| ATOM | 1252 | CA  | LEU | 441 | 14.375 | 19.045 | 38.679 | 1.00 | 31.53 | 6 |
| ATOM | 1253 | CB  | LEU | 441 | 14.062 | 17.743 | 37.945 | 1.00 | 32.72 | 6 |
| ATOM | 1254 | CG  | LEU | 441 | 12.623 | 17.286 | 38.032 | 1.00 | 34.18 | 6 |
| ATOM | 1255 | CD1 | LEU | 441 | 11.642 | 18.400 | 37.664 | 1.00 | 35.57 | 6 |
| ATOM | 1256 | CD2 | LEU | 441 | 12.460 | 16.117 | 37.106 | 1.00 | 35.32 | 6 |
| ATOM | 1257 | C   | LEU | 441 | 15.511 | 18.838 | 39.689 | 1.00 | 30.69 | 6 |
| ATOM | 1258 | O   | LEU | 441 | 15.269 | 18.523 | 40.877 | 1.00 | 31.86 | 8 |
| ATOM | 1259 | N   | THR | 442 | 16.749 | 19.015 | 39.231 | 1.00 | 30.05 | 7 |
| ATOM | 1260 | CA  | THR | 442 | 17.906 | 18.910 | 40.105 | 1.00 | 29.81 | 6 |
| ATOM | 1261 | CB  | THR | 442 | 19.273 | 19.045 | 39.309 | 1.00 | 31.61 | 6 |
| ATOM | 1262 | OG1 | THR | 442 | 19.473 | 17.870 | 38.508 | 1.00 | 35.27 | 8 |
| ATOM | 1263 | CG2 | THR | 442 | 20.396 | 19.124 | 40.217 | 1.00 | 30.46 | 6 |
| ATOM | 1264 | C   | THR | 442 | 17.857 | 19.999 | 41.193 | 1.00 | 28.42 | 6 |
| ATOM | 1265 | O   | THR | 442 | 18.097 | 19.713 | 42.385 | 1.00 | 26.82 | 8 |
| ATOM | 1266 | N   | GLU | 443 | 17.545 | 21.232 | 40.786 | 1.00 | 24.22 | 7 |
| ATOM | 1267 | CA  | GLU | 443 | 17.446 | 22.325 | 41.724 | 1.00 | 22.79 | 6 |
| ATOM | 1268 | CB  | GLU | 443 | 17.148 | 23.638 | 40.973 | 1.00 | 24.26 | 6 |
| ATOM | 1269 | CG  | GLU | 443 | 17.134 | 24.841 | 41.903 | 1.00 | 27.14 | 6 |
| ATOM | 1270 | CD  | GLU | 443 | 16.927 | 26.171 | 41.174 | 1.00 | 31.11 | 6 |
| ATOM | 1271 | OE1 | GLU | 443 | 16.882 | 27.217 | 41.855 | 1.00 | 31.94 | 8 |
| ATOM | 1272 | OE2 | GLU | 443 | 16.798 | 26.174 | 39.915 | 1.00 | 32.42 | 8 |
| ATOM | 1273 | C   | GLU | 443 | 16.313 | 22.011 | 42.705 | 1.00 | 21.04 | 6 |
| ATOM | 1274 | O   | GLU | 443 | 16.373 | 22.277 | 43.913 | 1.00 | 20.94 | 8 |
| ATOM | 1275 | N   | LEU | 444 | 15.253 | 21.438 | 42.187 | 1.00 | 19.67 | 7 |
| ATOM | 1276 | CA  | LEU | 444 | 14.107 | 21.143 | 43.057 | 1.00 | 19.40 | 6 |
| ATOM | 1277 | CB  | LEU | 444 | 12.935 | 20.613 | 42.237 | 1.00 | 19.41 | 6 |
| ATOM | 1278 | CG  | LEU | 444 | 11.636 | 20.330 | 42.996 | 1.00 | 19.58 | 6 |
| ATOM | 1279 | CD1 | LEU | 444 | 11.066 | 21.637 | 43.571 | 1.00 | 16.04 | 6 |
| ATOM | 1280 | CD2 | LEU | 444 | 10.714 | 19.622 | 42.043 | 1.00 | 21.69 | 6 |
| ATOM | 1281 | C   | LEU | 444 | 14.451 | 20.131 | 44.166 | 1.00 | 19.39 | 6 |
| ATOM | 1282 | O   | LEU | 444 | 13.982 | 20.243 | 45.313 | 1.00 | 15.57 | 8 |
| ATOM | 1283 | N   | ARG | 445 | 15.298 | 19.165 | 43.837 | 1.00 | 18.73 | 7 |
| ATOM | 1284 | CA  | ARG | 445 | 15.602 | 18.165 | 44.832 | 1.00 | 18.88 | 6 |
| ATOM | 1285 | CB  | ARG | 445 | 16.237 | 16.927 | 44.221 | 1.00 | 23.88 | 6 |
| ATOM | 1286 | CG  | ARG | 445 | 15.353 | 16.194 | 43.227 | 1.00 | 28.79 | 6 |
| ATOM | 1287 | CD  | ARG | 445 | 16.028 | 14.912 | 42.748 | 1.00 | 34.64 | 6 |
| ATOM | 1288 | NE  | ARG | 445 | 15.352 | 14.341 | 41.565 | 1.00 | 38.63 | 7 |
| ATOM | 1289 | CZ  | ARG | 445 | 15.643 | 14.622 | 40.286 | 1.00 | 40.01 | 6 |
| ATOM | 1290 | NH1 | ARG | 445 | 16.616 | 15.464 | 39.978 | 1.00 | 41.00 | 7 |
| ATOM | 1291 | NH2 | ARG | 445 | 14.935 | 14.074 | 39.297 | 1.00 | 41.02 | 7 |
| ATOM | 1292 | C   | ARG | 445 | 16.462 | 18.675 | 45.950 | 1.00 | 18.83 | 6 |
| ATOM | 1293 | O   | ARG | 445 | 16.517 | 18.039 | 47.006 | 1.00 | 18.30 | 8 |
| ATOM | 1294 | N   | THR | 446 | 17.155 | 19.787 | 45.744 | 1.00 | 18.21 | 7 |
| ATOM | 1295 | CA  | THR | 446 | 17.960 | 20.307 | 46.858 | 1.00 | 20.13 | 6 |
| ATOM | 1296 | CB  | THR | 446 | 18.844 | 21.558 | 46.456 | 1.00 | 18.59 | 6 |
| ATOM | 1297 | OG1 | THR | 446 | 18.003 | 22.682 | 46.254 | 1.00 | 19.19 | 8 |
| ATOM | 1298 | CG2 | THR | 446 | 19.700 | 21.300 | 45.145 | 1.00 | 19.27 | 6 |
| ATOM | 1299 | C   | THR | 446 | 17.050 | 20.707 | 48.039 | 1.00 | 20.34 | 6 |
| ATOM | 1300 | O   | THR | 446 | 17.500 | 20.751 | 49.212 | 1.00 | 21.59 | 8 |
| ATOM | 1301 | N   | PHE | 447 | 15.777 | 21.045 | 47.767 | 1.00 | 18.53 | 7 |
| ATOM | 1302 | CA  | PHE | 447 | 14.915 | 21.416 | 48.882 | 1.00 | 16.86 | 6 |
| ATOM | 1303 | CB  | PHE | 447 | 13.594 | 22.017 | 48.402 | 1.00 | 18.21 | 6 |
| ATOM | 1304 | CG  | PHE | 447 | 13.800 | 23.366 | 47.776 | 1.00 | 19.49 | 6 |
| ATOM | 1305 | CD1 | PHE | 447 | 14.001 | 23.484 | 46.399 | 1.00 | 17.01 | 6 |
| ATOM | 1306 | CD2 | PHE | 447 | 13.979 | 24.498 | 48.590 | 1.00 | 18.47 | 6 |
| ATOM | 1307 | CE1 | PHE | 447 | 14.391 | 24.734 | 45.824 | 1.00 | 18.27 | 6 |
| ATOM | 1308 | CE2 | PHE | 447 | 14.368 | 25.727 | 48.019 | 1.00 | 17.72 | 6 |
| ATOM | 1309 | CZ  | PHE | 447 | 14.569 | 25.824 | 46.636 | 1.00 | 16.62 | 6 |
| ATOM | 1310 | C   | PHE | 447 | 14.680 | 20.288 | 49.840 | 1.00 | 15.58 | 6 |
| ATOM | 1311 | O   | PHE | 447 | 14.257 | 20.551 | 50.968 | 1.00 | 15.13 | 8 |
| ATOM | 1312 | N   | ASN | 448 | 14.953 | 19.048 | 49.443 | 1.00 | 14.96 | 7 |
| ATOM | 1313 | CA  | ASN | 448 | 14.792 | 17.956 | 50.442 | 1.00 | 15.50 | 6 |
| ATOM | 1314 | CB  | ASN | 448 | 15.042 | 16.598 | 49.822 | 1.00 | 15.33 | 6 |
| ATOM | 1315 | CG  | ASN | 448 | 13.972 | 16.209 | 48.904 | 1.00 | 18.64 | 6 |
| ATOM | 1316 | OD1 | ASN | 448 | 12.776 | 16.155 | 49.265 | 1.00 | 19.32 | 8 |
| ATOM | 1317 | ND2 | ASN | 448 | 14.371 | 15.940 | 47.675 | 1.00 | 15.83 | 7 |

APPENDIX 1-continued

STRUCTURE COORDINATES FOR FXR LBD COMPLEXED WITH FEXARAMINE

| ATOM | 1318 | C | ASN | 448 | 15.789 | 18.185 | 51.633 | 1.00 | 16.62 | 6 |
|---|---|---|---|---|---|---|---|---|---|---|
| ATOM | 1319 | O | ASN | 448 | 15.496 | 17.928 | 52.821 | 1.00 | 15.09 | 8 |
| ATOM | 1320 | N | HIS | 449 | 16.965 | 18.719 | 51.294 | 1.00 | 17.00 | 7 |
| ATOM | 1321 | CA | HIS | 449 | 17.957 | 19.036 | 52.311 | 1.00 | 17.97 | 6 |
| ATOM | 1322 | CB | HIS | 449 | 19.346 | 19.023 | 51.676 | 1.00 | 21.40 | 6 |
| ATOM | 1323 | CG | HIS | 449 | 19.663 | 17.689 | 51.135 | 1.00 | 23.56 | 6 |
| ATOM | 1324 | CD2 | HIS | 449 | 19.720 | 17.225 | 49.863 | 1.00 | 26.68 | 6 |
| ATOM | 1325 | ND1 | HIS | 449 | 19.859 | 16.603 | 51.959 | 1.00 | 25.22 | 7 |
| ATOM | 1326 | CE1 | HIS | 449 | 20.023 | 15.516 | 51.217 | 1.00 | 27.79 | 6 |
| ATOM | 1327 | NE2 | HIS | 449 | 19.940 | 15.862 | 49.938 | 1.00 | 26.22 | 7 |
| ATOM | 1328 | C | HIS | 449 | 17.658 | 20.339 | 52.986 | 1.00 | 18.56 | 6 |
| ATOM | 1329 | O | HIS | 449 | 17.682 | 20.383 | 54.229 | 1.00 | 16.38 | 8 |
| ATOM | 1330 | N | HIS | 450 | 17.310 | 21.388 | 52.221 | 1.00 | 16.59 | 7 |
| ATOM | 1331 | CA | HIS | 450 | 17.028 | 22.660 | 52.870 | 1.00 | 17.63 | 6 |
| ATOM | 1332 | CB | HIS | 450 | 16.665 | 23.780 | 51.882 | 1.00 | 21.71 | 6 |
| ATOM | 1333 | CG | HIS | 450 | 17.696 | 24.036 | 50.837 | 1.00 | 25.68 | 6 |
| ATOM | 1334 | CD2 | HIS | 450 | 17.596 | 24.064 | 49.477 | 1.00 | 26.30 | 6 |
| ATOM | 1335 | ND1 | HIS | 450 | 19.017 | 24.310 | 51.142 | 1.00 | 26.33 | 7 |
| ATOM | 1336 | CE1 | HIS | 450 | 19.684 | 24.503 | 50.007 | 1.00 | 29.65 | 6 |
| ATOM | 1337 | NE2 | HIS | 450 | 18.848 | 24.361 | 48.984 | 1.00 | 27.96 | 7 |
| ATOM | 1338 | C | HIS | 450 | 15.873 | 22.515 | 53.867 | 1.00 | 16.73 | 6 |
| ATOM | 1339 | O | HIS | 450 | 15.905 | 23.121 | 54.957 | 1.00 | 15.77 | 8 |
| ATOM | 1340 | N | HIS | 451 | 14.880 | 21.712 | 53.515 | 1.00 | 14.42 | 7 |
| ATOM | 1341 | CA | HIS | 451 | 13.727 | 21.563 | 54.401 | 1.00 | 16.33 | 6 |
| ATOM | 1342 | CB | HIS | 451 | 12.643 | 20.849 | 53.647 | 1.00 | 17.84 | 6 |
| ATOM | 1343 | CG | HIS | 451 | 11.285 | 21.019 | 54.240 | 1.00 | 20.31 | 6 |
| ATOM | 1344 | CD2 | HIS | 451 | 10.551 | 20.179 | 55.006 | 1.00 | 20.24 | 6 |
| ATOM | 1345 | ND1 | HIS | 451 | 10.548 | 22.183 | 54.113 | 1.00 | 20.16 | 7 |
| ATOM | 1346 | CE1 | HIS | 451 | 9.414 | 22.041 | 54.783 | 1.00 | 21.85 | 6 |
| ATOM | 1347 | NE2 | HIS | 451 | 9.393 | 20.836 | 55.337 | 1.00 | 20.59 | 7 |
| ATOM | 1348 | C | HIS | 451 | 14.075 | 20.789 | 55.715 | 1.00 | 16.77 | 6 |
| ATOM | 1349 | O | HIS | 451 | 13.641 | 21.167 | 56.795 | 1.00 | 16.58 | 8 |
| ATOM | 1350 | N | ALA | 452 | 14.827 | 19.687 | 55.597 | 1.00 | 17.79 | 7 |
| ATOM | 1351 | CA | ALA | 452 | 15.230 | 18.880 | 56.784 | 1.00 | 20.08 | 6 |
| ATOM | 1352 | CB | ALA | 452 | 16.147 | 17.677 | 56.353 | 1.00 | 18.72 | 6 |
| ATOM | 1353 | C | ALA | 452 | 16.008 | 19.803 | 57.744 | 1.00 | 19.33 | 6 |
| ATOM | 1354 | O | ALA | 452 | 15.834 | 19.703 | 58.957 | 1.00 | 20.31 | 8 |
| ATOM | 1355 | N | GLU | 453 | 16.894 | 20.649 | 57.185 | 1.00 | 19.86 | 7 |
| ATOM | 1356 | CA | GLU | 453 | 17.723 | 21.603 | 57.977 | 1.00 | 19.53 | 6 |
| ATOM | 1357 | CB | GLU | 453 | 18.696 | 22.401 | 57.070 | 1.00 | 19.40 | 6 |
| ATOM | 1358 | CG | GLU | 453 | 19.665 | 23.329 | 57.876 | 1.00 | 24.14 | 6 |
| ATOM | 1359 | CD | GLU | 453 | 20.651 | 24.041 | 56.958 | 1.00 | 28.20 | 6 |
| ATOM | 1360 | OE1 | GLU | 453 | 21.298 | 25.016 | 57.376 | 1.00 | 31.33 | 8 |
| ATOM | 1361 | OE2 | GLU | 453 | 20.782 | 23.645 | 55.786 | 1.00 | 31.30 | 8 |
| ATOM | 1362 | C | GLU | 453 | 16.814 | 22.609 | 58.719 | 1.00 | 19.65 | 6 |
| ATOM | 1363 | O | GLU | 453 | 16.887 | 22.805 | 59.945 | 1.00 | 17.80 | 8 |
| ATOM | 1364 | N | MET | 454 | 15.953 | 23.228 | 57.928 | 1.00 | 17.19 | 7 |
| ATOM | 1365 | CA | MET | 454 | 15.022 | 24.199 | 58.417 | 1.00 | 18.01 | 6 |
| ATOM | 1366 | CB | MET | 454 | 14.175 | 24.689 | 57.230 | 1.00 | 18.26 | 6 |
| ATOM | 1367 | CG | MET | 454 | 13.148 | 25.715 | 57.594 | 1.00 | 18.57 | 6 |
| ATOM | 1368 | SD | MET | 454 | 11.605 | 25.022 | 58.285 | 1.00 | 19.34 | 16 |
| ATOM | 1369 | CE | MET | 454 | 10.805 | 24.045 | 56.759 | 1.00 | 17.75 | 6 |
| ATOM | 1370 | C | MET | 454 | 14.111 | 23.661 | 59.524 | 1.00 | 16.12 | 6 |
| ATOM | 1371 | O | MET | 454 | 13.902 | 24.335 | 60.530 | 1.00 | 16.56 | 8 |
| ATOM | 1372 | N | LEU | 455 | 13.573 | 22.468 | 59.350 | 1.00 | 15.99 | 7 |
| ATOM | 1373 | CA | LEU | 455 | 12.697 | 21.907 | 60.356 | 1.00 | 17.79 | 6 |
| ATOM | 1374 | CB | LEU | 455 | 12.143 | 20.592 | 59.832 | 1.00 | 19.10 | 6 |
| ATOM | 1375 | CG | LEU | 455 | 10.666 | 20.430 | 59.407 | 1.00 | 23.57 | 6 |
| ATOM | 1376 | CD1 | LEU | 455 | 10.063 | 21.690 | 59.023 | 1.00 | 23.89 | 6 |
| ATOM | 1377 | CD2 | LEU | 455 | 10.511 | 19.333 | 58.364 | 1.00 | 22.65 | 6 |
| ATOM | 1378 | C | LEU | 455 | 13.339 | 21.647 | 61.724 | 1.00 | 20.79 | 6 |
| ATOM | 1379 | O | LEU | 455 | 12.653 | 21.708 | 62.774 | 1.00 | 17.76 | 8 |
| ATOM | 1380 | N | MET | 456 | 14.648 | 21.353 | 61.693 | 1.00 | 18.90 | 7 |
| ATOM | 1381 | CA | MET | 456 | 15.344 | 20.946 | 62.892 | 1.00 | 21.58 | 6 |
| ATOM | 1382 | CB | MET | 456 | 16.840 | 20.677 | 62.600 | 1.00 | 23.24 | 6 |
| ATOM | 1383 | CG | MET | 456 | 17.436 | 19.752 | 63.648 | 1.00 | 31.39 | 6 |
| ATOM | 1384 | SD | MET | 456 | 16.527 | 18.145 | 63.770 | 1.00 | 37.13 | 16 |
| ATOM | 1385 | CE | MET | 456 | 16.639 | 17.762 | 61.998 | 1.00 | 30.52 | 6 |
| ATOM | 1386 | C | MET | 456 | 15.149 | 21.868 | 64.076 | 1.00 | 19.80 | 6 |
| ATOM | 1387 | O | MET | 456 | 14.804 | 21.383 | 65.151 | 1.00 | 21.15 | 8 |
| ATOM | 1388 | N | SER | 457 | 15.285 | 23.173 | 63.865 | 1.00 | 18.39 | 7 |
| ATOM | 1389 | CA | SER | 457 | 15.111 | 24.150 | 64.944 | 1.00 | 19.75 | 6 |
| ATOM | 1390 | CB | SER | 457 | 15.454 | 25.558 | 64.421 | 1.00 | 22.04 | 6 |
| ATOM | 1391 | OG | SER | 457 | 14.885 | 26.503 | 65.289 | 1.00 | 25.45 | 8 |
| ATOM | 1392 | C | SER | 457 | 13.692 | 24.124 | 65.569 | 1.00 | 18.21 | 6 |
| ATOM | 1393 | O | SER | 457 | 13.534 | 24.171 | 66.797 | 1.00 | 16.38 | 8 |
| ATOM | 1394 | N | TRP | 458 | 12.668 | 24.041 | 64.710 | 1.00 | 18.00 | 7 |

APPENDIX 1-continued

STRUCTURE COORDINATES FOR FXR LBD COMPLEXED WITH FEXARAMINE

| ATOM | 1395 | CA | TRP | 458 | 11.287 | 23.922 | 65.146 | 1.00 | 18.11 | 6 |
| --- | --- | --- | --- | --- | --- | --- | --- | --- | --- | --- |
| ATOM | 1396 | CB | TRP | 458 | 10.338 | 23.874 | 63.914 | 1.00 | 17.42 | 6 |
| ATOM | 1397 | CG | TRP | 458 | 10.376 | 25.142 | 63.132 | 1.00 | 19.25 | 6 |
| ATOM | 1398 | CD2 | TRP | 458 | 9.632 | 26.364 | 63.422 | 1.00 | 20.22 | 6 |
| ATOM | 1399 | CE2 | TRP | 458 | 9.987 | 27.318 | 62.403 | 1.00 | 20.22 | 6 |
| ATOM | 1400 | CE3 | TRP | 458 | 8.715 | 26.740 | 64.422 | 1.00 | 21.29 | 6 |
| ATOM | 1401 | CD1 | TRP | 458 | 11.138 | 25.408 | 62.010 | 1.00 | 23.66 | 6 |
| ATOM | 1402 | NE1 | TRP | 458 | 10.897 | 26.726 | 61.573 | 1.00 | 22.29 | 7 |
| ATOM | 1403 | CZ2 | TRP | 458 | 9.438 | 28.657 | 62.398 | 1.00 | 20.39 | 6 |
| ATOM | 1404 | CZ3 | TRP | 458 | 8.172 | 28.067 | 64.412 | 1.00 | 20.96 | 6 |
| ATOM | 1405 | CH2 | TRP | 458 | 8.536 | 29.000 | 63.406 | 1.00 | 19.89 | 6 |
| ATOM | 1406 | C | TRP | 458 | 11.142 | 22.593 | 65.923 | 1.00 | 17.70 | 6 |
| ATOM | 1407 | O | TRP | 458 | 10.426 | 22.540 | 66.885 | 1.00 | 17.69 | 8 |
| ATOM | 1408 | N | ARG | 459 | 11.814 | 21.522 | 65.505 | 1.00 | 15.90 | 7 |
| ATOM | 1409 | CA | ARG | 459 | 11.660 | 20.252 | 66.226 | 1.00 | 19.67 | 6 |
| ATOM | 1410 | CB | ARG | 459 | 12.283 | 19.058 | 65.471 | 1.00 | 17.13 | 6 |
| ATOM | 1411 | CG | ARG | 459 | 11.674 | 18.795 | 64.064 | 1.00 | 22.30 | 6 |
| ATOM | 1412 | CD | ARG | 459 | 12.080 | 17.424 | 63.441 | 1.00 | 27.44 | 6 |
| ATOM | 1413 | NE | ARG | 459 | 11.747 | 16.467 | 64.475 | 1.00 | 33.39 | 7 |
| ATOM | 1414 | CZ | ARG | 459 | 12.149 | 15.205 | 64.525 | 1.00 | 35.52 | 6 |
| ATOM | 1415 | NH1 | ARG | 459 | 12.892 | 14.798 | 63.541 | 1.00 | 34.15 | 7 |
| ATOM | 1416 | NH2 | ARG | 459 | 11.814 | 14.392 | 65.571 | 1.00 | 36.79 | 7 |
| ATOM | 1417 | C | ARG | 459 | 12.313 | 20.323 | 67.626 | 1.00 | 20.39 | 6 |
| ATOM | 1418 | O | ARG | 459 | 11.716 | 19.861 | 68.644 | 1.00 | 20.44 | 8 |
| ATOM | 1419 | N | VAL | 460 | 13.512 | 20.885 | 67.700 | 1.00 | 20.75 | 7 |
| ATOM | 1420 | CA | VAL | 460 | 14.082 | 20.862 | 69.026 | 1.00 | 22.58 | 6 |
| ATOM | 1421 | CB | VAL | 460 | 15.614 | 20.966 | 69.027 | 1.00 | 22.95 | 6 |
| ATOM | 1422 | CG1 | VAL | 460 | 16.200 | 19.838 | 68.255 | 1.00 | 21.12 | 6 |
| ATOM | 1423 | CG2 | VAL | 460 | 16.049 | 22.158 | 68.343 | 1.00 | 21.39 | 6 |
| ATOM | 1424 | C | VAL | 460 | 13.455 | 21.992 | 69.895 | 1.00 | 24.38 | 6 |
| ATOM | 1425 | O | VAL | 460 | 13.690 | 22.023 | 71.101 | 1.00 | 23.93 | 8 |
| ATOM | 1426 | N | ASN | 461 | 12.607 | 22.886 | 69.400 | 1.00 | 26.17 | 7 |
| ATOM | 1427 | CA | ASN | 461 | 12.179 | 23.921 | 70.338 | 1.00 | 30.11 | 6 |
| ATOM | 1428 | CB | ASN | 461 | 12.261 | 25.218 | 69.609 | 1.00 | 30.28 | 6 |
| ATOM | 1429 | CG | ASN | 461 | 13.524 | 25.827 | 69.822 | 1.00 | 32.22 | 6 |
| ATOM | 1430 | OD1 | ASN | 461 | 13.852 | 26.115 | 70.970 | 1.00 | 36.22 | 8 |
| ATOM | 1431 | ND2 | ASN | 461 | 14.323 | 25.957 | 68.790 | 1.00 | 31.57 | 7 |
| ATOM | 1432 | C | ASN | 461 | 10.807 | 23.602 | 70.759 | 1.00 | 32.15 | 6 |
| ATOM | 1433 | O | ASN | 461 | 10.001 | 24.451 | 71.252 | 1.00 | 32.31 | 8 |
| ATOM | 1434 | N | ASP | 462 | 10.332 | 22.748 | 70.981 | 1.00 | 34.41 | 7 |
| ATOM | 1435 | CA | ASP | 462 | 9.301 | 22.093 | 70.393 | 1.00 | 38.60 | 6 |
| ATOM | 1436 | CB | ASP | 462 | 9.831 | 20.690 | 70.133 | 1.00 | 43.46 | 6 |
| ATOM | 1437 | CG | ASP | 462 | 9.147 | 20.102 | 69.040 | 1.00 | 45.47 | 6 |
| ATOM | 1438 | OD1 | ASP | 462 | 7.947 | 20.088 | 69.338 | 1.00 | 48.07 | 8 |
| ATOM | 1439 | OD2 | ASP | 462 | 9.774 | 19.693 | 68.023 | 1.00 | 48.78 | 8 |
| ATOM | 1440 | C | ASP | 462 | 7.935 | 22.301 | 70.933 | 1.00 | 39.22 | 6 |
| ATOM | 1441 | O | ASP | 462 | 7.725 | 23.401 | 71.185 | 1.00 | 45.00 | 8 |
| ATOM | 1442 | N | HIS | 463 | 7.675 | 23.122 | 69.621 | 1.00 | 36.56 | 7 |
| ATOM | 1443 | CA | HIS | 463 | 6.541 | 23.070 | 68.712 | 1.00 | 33.62 | 6 |
| ATOM | 1444 | CB | HIS | 463 | 6.991 | 23.751 | 67.401 | 1.00 | 31.81 | 6 |
| ATOM | 1445 | CG | HIS | 463 | 7.354 | 25.182 | 67.597 | 1.00 | 31.93 | 6 |
| ATOM | 1446 | CD2 | HIS | 463 | 6.554 | 26.267 | 67.716 | 1.00 | 28.93 | 6 |
| ATOM | 1447 | ND1 | HIS | 463 | 8.640 | 25.610 | 67.888 | 1.00 | 31.28 | 7 |
| ATOM | 1448 | CE1 | HIS | 463 | 8.600 | 26.901 | 68.194 | 1.00 | 30.44 | 6 |
| ATOM | 1449 | NE2 | HIS | 463 | 7.347 | 27.314 | 68.100 | 1.00 | 32.05 | 7 |
| ATOM | 1450 | C | HIS | 463 | 5.867 | 21.710 | 68.406 | 1.00 | 31.10 | 6 |
| ATOM | 1451 | O | HIS | 463 | 6.502 | 20.681 | 68.088 | 1.00 | 30.85 | 8 |
| ATOM | 1452 | N | LYS | 464 | 4.556 | 21.802 | 68.345 | 1.00 | 30.56 | 7 |
| ATOM | 1453 | CA | LYS | 464 | 3.763 | 20.625 | 68.138 | 1.00 | 30.42 | 6 |
| ATOM | 1454 | CB | LYS | 464 | 2.625 | 20.762 | 69.095 | 1.00 | 34.48 | 6 |
| ATOM | 1455 | CG | LYS | 464 | 2.211 | 19.488 | 69.691 | 1.00 | 40.34 | 6 |
| ATOM | 1456 | CD | LYS | 464 | 1.104 | 19.723 | 70.752 | 1.00 | 45.18 | 6 |
| ATOM | 1457 | CE | LYS | 464 | 0.564 | 18.435 | 71.405 | 1.00 | 48.59 | 6 |
| ATOM | 1458 | NZ | LYS | 464 | −0.666 | 18.796 | 72.297 | 1.00 | 50.10 | 7 |
| ATOM | 1459 | C | LYS | 464 | 3.270 | 20.485 | 66.705 | 1.00 | 26.40 | 6 |
| ATOM | 1460 | O | LYS | 464 | 2.397 | 21.272 | 66.251 | 1.00 | 26.68 | 8 |
| ATOM | 1461 | N | PHE | 465 | 3.799 | 19.499 | 66.018 | 1.00 | 23.27 | 7 |
| ATOM | 1462 | CA | PHE | 465 | 3.432 | 19.256 | 64.648 | 1.00 | 22.87 | 6 |
| ATOM | 1463 | CB | PHE | 465 | 4.560 | 18.496 | 63.972 | 1.00 | 19.62 | 6 |
| ATOM | 1464 | CG | PHE | 465 | 5.710 | 19.379 | 63.556 | 1.00 | 21.10 | 6 |
| ATOM | 1465 | CD1 | PHE | 465 | 6.750 | 19.693 | 64.444 | 1.00 | 20.42 | 6 |
| ATOM | 1466 | CD2 | PHE | 465 | 5.752 | 19.908 | 62.275 | 1.00 | 21.47 | 6 |
| ATOM | 1467 | CE1 | PHE | 465 | 7.842 | 20.545 | 64.073 | 1.00 | 19.62 | 6 |
| ATOM | 1468 | CE2 | PHE | 465 | 6.856 | 20.782 | 61.864 | 1.00 | 21.27 | 6 |
| ATOM | 1469 | CZ | PHE | 465 | 7.888 | 21.101 | 62.759 | 1.00 | 19.15 | 6 |
| ATOM | 1470 | C | PHE | 465 | 2.167 | 18.413 | 64.641 | 1.00 | 21.65 | 6 |
| ATOM | 1471 | O | PHE | 465 | 2.035 | 17.490 | 65.436 | 1.00 | 22.93 | 8 |

APPENDIX 1-continued

STRUCTURE COORDINATES FOR FXR LBD COMPLEXED WITH FEXARAMINE

| ATOM | 1472 | N   | THR | 466 | 1.242  | 18.736 | 63.760 | 1.00 | 21.55 | 7 |
|------|------|-----|-----|-----|--------|--------|--------|------|-------|---|
| ATOM | 1473 | CA  | THR | 466 | 0.009  | 18.002 | 63.671 | 1.00 | 21.21 | 6 |
| ATOM | 1474 | CB  | THR | 466 | -0.954 | 18.598 | 62.568 | 1.00 | 21.65 | 6 |
| ATOM | 1475 | OG1 | THR | 466 | -0.362 | 18.494 | 61.255 | 1.00 | 21.89 | 8 |
| ATOM | 1476 | CG2 | THR | 466 | -1.301 | 20.024 | 62.874 | 1.00 | 19.86 | 6 |
| ATOM | 1477 | C   | THR | 466 | 0.308  | 16.553 | 63.278 | 1.00 | 21.47 | 6 |
| ATOM | 1478 | O   | THR | 466 | 1.374  | 16.236 | 62.712 | 1.00 | 19.80 | 8 |
| ATOM | 1479 | N   | PRO | 467 | -0.660 | 15.661 | 63.538 | 1.00 | 22.08 | 7 |
| ATOM | 1480 | CD  | PRO | 467 | -1.768 | 15.767 | 64.521 | 1.00 | 24.47 | 6 |
| ATOM | 1481 | CA  | PRO | 467 | -0.390 | 14.268 | 63.156 | 1.00 | 21.12 | 6 |
| ATOM | 1482 | CB  | PRO | 467 | -1.624 | 13.475 | 63.644 | 1.00 | 20.85 | 6 |
| ATOM | 1483 | CG  | PRO | 467 | -2.536 | 14.481 | 64.343 | 1.00 | 24.34 | 6 |
| ATOM | 1484 | C   | PRO | 467 | -0.199 | 14.076 | 61.643 | 1.00 | 19.51 | 6 |
| ATOM | 1485 | O   | PRO | 467 | 0.559  | 13.223 | 61.229 | 1.00 | 18.67 | 8 |
| ATOM | 1486 | N   | LEU | 468 | -0.885 | 14.876 | 60.826 | 1.00 | 19.19 | 7 |
| ATOM | 1487 | CA  | LEU | 468 | -0.676 | 14.754 | 59.387 | 1.00 | 18.12 | 6 |
| ATOM | 1488 | CB  | LEU | 468 | -1.684 | 15.618 | 58.619 | 1.00 | 21.41 | 6 |
| ATOM | 1489 | CG  | LEU | 468 | -1.440 | 15.809 | 57.120 | 1.00 | 22.59 | 6 |
| ATOM | 1490 | CD1 | LEU | 468 | -1.470 | 14.473 | 56.412 | 1.00 | 21.97 | 6 |
| ATOM | 1491 | CD2 | LEU | 468 | -2.617 | 16.705 | 56.545 | 1.00 | 24.15 | 6 |
| ATOM | 1492 | C   | LEU | 468 | 0.781  | 15.179 | 59.027 | 1.00 | 17.01 | 6 |
| ATOM | 1493 | O   | LEU | 468 | 1.440  | 14.484 | 58.250 | 1.00 | 15.29 | 8 |
| ATOM | 1494 | N   | LEU | 469 | 1.292  | 16.274 | 59.602 | 1.00 | 14.97 | 7 |
| ATOM | 1495 | CA  | LEU | 469 | 2.653  | 16.674 | 59.299 | 1.00 | 15.66 | 6 |
| ATOM | 1496 | CB  | LEU | 469 | 2.934  | 18.106 | 59.744 | 1.00 | 15.55 | 6 |
| ATOM | 1497 | CG  | LEU | 469 | 1.990  | 19.137 | 59.024 | 1.00 | 18.80 | 6 |
| ATOM | 1498 | CD1 | LEU | 469 | 2.351  | 20.653 | 59.470 | 1.00 | 19.65 | 6 |
| ATOM | 1499 | CD2 | LEU | 469 | 2.096  | 18.929 | 57.446 | 1.00 | 18.44 | 6 |
| ATOM | 1500 | C   | LEU | 469 | 3.663  | 15.671 | 59.881 | 1.00 | 16.29 | 6 |
| ATOM | 1501 | O   | LEU | 469 | 4.659  | 15.393 | 59.204 | 1.00 | 14.93 | 8 |
| ATOM | 1502 | N   | CYS | 470 | 3.415  | 15.102 | 61.077 | 1.00 | 16.63 | 7 |
| ATOM | 1503 | CA  | CYS | 470 | 4.372  | 14.101 | 61.630 | 1.00 | 17.51 | 6 |
| ATOM | 1504 | CB  | CYS | 470 | 3.951  | 13.520 | 62.988 | 1.00 | 18.34 | 6 |
| ATOM | 1505 | SG  | CYS | 470 | 4.008  | 14.791 | 64.298 | 1.00 | 25.58 | 16 |
| ATOM | 1506 | C   | CYS | 470 | 4.515  | 12.931 | 60.667 | 1.00 | 20.22 | 6 |
| ATOM | 1507 | O   | CYS | 470 | 5.623  | 12.422 | 60.466 | 1.00 | 18.40 | 8 |
| ATOM | 1508 | N   | GLU | 471 | 3.428  | 12.571 | 59.892 | 1.00 | 19.96 | 7 |
| ATOM | 1509 | CA  | GLU | 471 | 3.363  | 11.355 | 59.099 | 1.00 | 21.93 | 6 |
| ATOM | 1510 | CB  | GLU | 471 | 1.911  | 11.018 | 58.720 | 1.00 | 24.55 | 6 |
| ATOM | 1511 | CG  | GLU | 471 | 1.518  | 9.609  | 58.942 | 1.00 | 31.98 | 6 |
| ATOM | 1512 | CD  | GLU | 471 | 2.618  | 8.598  | 58.646 | 1.00 | 30.87 | 6 |
| ATOM | 1513 | OE1 | GLU | 471 | 2.695  | 8.036  | 57.520 | 1.00 | 32.35 | 8 |
| ATOM | 1514 | OE2 | GLU | 471 | 3.396  | 8.354  | 59.578 | 1.00 | 34.47 | 8 |
| ATOM | 1515 | C   | GLU | 471 | 4.137  | 11.489 | 57.763 | 1.00 | 20.36 | 6 |
| ATOM | 1516 | O   | GLU | 471 | 4.884  | 10.588 | 57.364 | 1.00 | 20.19 | 8 |
| ATOM | 1517 | N   | ILE | 472 | 3.733  | 12.796 | 57.307 | 1.00 | 19.78 | 7 |
| ATOM | 1518 | CA  | ILE | 472 | 4.257  | 13.088 | 55.948 | 1.00 | 19.28 | 6 |
| ATOM | 1519 | CB  | ILE | 472 | 3.380  | 14.106 | 55.185 | 1.00 | 21.54 | 6 |
| ATOM | 1520 | CG2 | ILE | 472 | 4.025  | 14.453 | 53.749 | 1.00 | 20.47 | 6 |
| ATOM | 1521 | CG1 | ILE | 472 | 2.062  | 13.436 | 54.771 | 1.00 | 25.47 | 6 |
| ATOM | 1522 | CD1 | ILE | 472 | 1.330  | 12.803 | 55.835 | 1.00 | 31.00 | 6 |
| ATOM | 1523 | C   | ILE | 472 | 5.683  | 13.534 | 55.929 | 1.00 | 18.52 | 6 |
| ATOM | 1524 | O   | ILE | 472 | 6.438  | 13.142 | 55.016 | 1.00 | 17.85 | 8 |
| ATOM | 1525 | N   | TRP | 473 | 6.065  | 14.282 | 56.951 | 1.00 | 17.41 | 7 |
| ATOM | 1526 | CA  | TRP | 473 | 7.448  | 14.839 | 57.067 | 1.00 | 19.38 | 6 |
| ATOM | 1527 | CB  | TRP | 473 | 7.380  | 16.275 | 57.566 | 1.00 | 19.90 | 6 |
| ATOM | 1528 | CG  | TRP | 473 | 6.842  | 17.241 | 56.553 | 1.00 | 18.49 | 6 |
| ATOM | 1529 | CD2 | TRP | 473 | 6.636  | 18.648 | 56.720 | 1.00 | 19.11 | 6 |
| ATOM | 1530 | CE2 | TRP | 473 | 6.185  | 19.149 | 55.452 | 1.00 | 19.28 | 6 |
| ATOM | 1531 | CE3 | TRP | 473 | 6.755  | 19.545 | 57.799 | 1.00 | 18.57 | 6 |
| ATOM | 1532 | CD1 | TRP | 473 | 6.535  | 16.949 | 55.240 | 1.00 | 18.91 | 6 |
| ATOM | 1533 | NE1 | TRP | 473 | 6.144  | 18.093 | 54.580 | 1.00 | 20.26 | 7 |
| ATOM | 1534 | CZ2 | TRP | 473 | 5.911  | 20.506 | 55.243 | 1.00 | 18.78 | 6 |
| ATOM | 1535 | CZ3 | TRP | 473 | 6.465  | 20.887 | 57.591 | 1.00 | 21.04 | 6 |
| ATOM | 1536 | CH2 | TRP | 473 | 6.029  | 21.361 | 56.324 | 1.00 | 20.67 | 6 |
| ATOM | 1537 | C   | TRP | 473 | 8.358  | 14.045 | 57.999 | 1.00 | 21.96 | 6 |
| ATOM | 1538 | O   | TRP | 473 | 9.519  | 14.361 | 58.189 | 1.00 | 20.89 | 8 |
| ATOM | 1539 | N   | ASP | 474 | 7.794  | 12.999 | 58.579 | 1.00 | 23.33 | 7 |
| ATOM | 1540 | CA  | ASP | 474 | 8.488  | 12.138 | 59.483 | 1.00 | 26.65 | 6 |
| ATOM | 1541 | CB  | ASP | 474 | 9.499  | 11.278 | 58.714 | 1.00 | 33.08 | 6 |
| ATOM | 1542 | CG  | ASP | 474 | 8.865  | 9.992  | 58.227 | 1.00 | 37.35 | 6 |
| ATOM | 1543 | OD1 | ASP | 474 | 9.302  | 8.900  | 58.653 | 1.00 | 44.86 | 8 |
| ATOM | 1544 | OD2 | ASP | 474 | 7.877  | 10.049 | 57.468 | 1.00 | 42.64 | 8 |
| ATOM | 1545 | C   | ASP | 474 | 9.107  | 12.853 | 60.659 | 1.00 | 26.85 | 6 |
| ATOM | 1546 | O   | ASP | 474 | 10.290 | 12.712 | 60.916 | 1.00 | 26.66 | 8 |
| ATOM | 1547 | N   | VAL | 475 | 8.285  | 13.622 | 61.373 | 1.00 | 26.36 | 7 |
| ATOM | 1548 | CA  | VAL | 475 | 8.719  | 14.324 | 62.544 | 1.00 | 26.65 | 6 |

APPENDIX 1-continued

STRUCTURE COORDINATES FOR FXR LBD COMPLEXED WITH FEXARAMINE

| ATOM | 1549 | CB | VAL | 475 | 8.665 | 15.867 | 62.355 | 1.00 | 27.22 | 6 |
|---|---|---|---|---|---|---|---|---|---|---|
| ATOM | 1550 | CG1 | VAL | 475 | 9.530 | 16.315 | 61.145 | 1.00 | 26.80 | 6 |
| ATOM | 1551 | CG2 | VAL | 475 | 7.193 | 16.320 | 62.177 | 1.00 | 24.70 | 6 |
| ATOM | 1552 | C | VAL | 475 | 7.710 | 13.915 | 63.642 | 1.00 | 29.66 | 6 |
| ATOM | 1553 | O | VAL | 475 | 6.773 | 13.094 | 63.410 | 1.00 | 27.46 | 8 |
| ATOM | 1554 | OXT | VAL | 475 | 7.809 | 14.473 | 64.750 | 1.00 | 33.53 | 8 |
| ATOM | 1 | C1 | FEX | 1 | 6.578 | 24.730 | 58.626 | 1.00 | 22.38 | 6 |
| ATOM | 2 | N1 | FEX | 1 | 6.458 | 24.174 | 60.065 | 1.00 | 20.26 | 7 |
| ATOM | 3 | C2 | FEX | 1 | 5.227 | 23.546 | 60.618 | 1.00 | 20.19 | 6 |
| ATOM | 4 | C3 | FEX | 1 | 7.894 | 24.485 | 60.743 | 1.00 | 20.55 | 6 |
| ATOM | 5 | C4 | FEX | 1 | 7.783 | 25.403 | 57.967 | 1.00 | 24.19 | 6 |
| ATOM | 6 | C5 | FEX | 1 | 7.734 | 25.896 | 56.610 | 1.00 | 22.43 | 6 |
| ATOM | 7 | C6 | FEX | 1 | 6.502 | 25.781 | 55.813 | 1.00 | 24.06 | 6 |
| ATOM | 8 | C7 | FEX | 1 | 5.306 | 25.108 | 56.466 | 1.00 | 23.96 | 6 |
| ATOM | 9 | C8 | FEX | 1 | 5.354 | 24.611 | 57.822 | 1.00 | 22.08 | 6 |
| ATOM | 10 | C9 | FEX | 1 | 6.522 | 26.238 | 54.715 | 1.00 | 25.61 | 6 |
| ATOM | 11 | C10 | FEX | 1 | 5.223 | 26.851 | 54.327 | 1.00 | 26.67 | 6 |
| ATOM | 12 | C11 | FEX | 1 | 5.011 | 27.479 | 53.086 | 1.00 | 27.33 | 6 |
| ATOM | 13 | C12 | FEX | 1 | 6.093 | 27.546 | 52.148 | 1.00 | 27.57 | 6 |
| ATOM | 14 | C13 | FEX | 1 | 7.326 | 26.980 | 52.489 | 1.00 | 28.27 | 6 |
| ATOM | 15 | C14 | FEX | 1 | 7.553 | 26.343 | 53.721 | 1.00 | 26.97 | 6 |
| ATOM | 16 | C15 | FEX | 1 | 5.993 | 28.218 | 50.808 | 1.00 | 29.22 | 6 |
| ATOM | 17 | N2 | FEX | 1 | 5.061 | 29.111 | 50.445 | 1.00 | 30.16 | 7 |
| ATOM | 18 | C16 | FEX | 1 | 3.889 | 28.787 | 49.996 | 1.00 | 33.64 | 6 |
| ATOM | 19 | O1 | FEX | 1 | 3.450 | 27.529 | 49.815 | 1.00 | 33.87 | 8 |
| ATOM | 20 | C17 | FEX | 1 | 5.733 | 30.473 | 50.853 | 1.00 | 28.79 | 6 |
| ATOM | 21 | C18 | FEX | 1 | 6.736 | 31.223 | 50.098 | 1.00 | 26.38 | 6 |
| ATOM | 22 | C19 | FEX | 1 | 7.260 | 32.491 | 50.540 | 1.00 | 25.49 | 6 |
| ATOM | 23 | C20 | FEX | 1 | 6.796 | 33.078 | 51.764 | 1.00 | 26.55 | 6 |
| ATOM | 24 | C21 | FEX | 1 | 5.822 | 32.406 | 52.583 | 1.00 | 27.70 | 6 |
| ATOM | 25 | C22 | FEX | 1 | 5.295 | 31.098 | 52.109 | 1.00 | 27.63 | 6 |
| ATOM | 26 | C23 | FEX | 1 | 5.226 | 32.596 | 53.733 | 1.00 | 29.18 | 6 |
| ATOM | 27 | C24 | FEX | 1 | 4.905 | 32.093 | 54.942 | 1.00 | 30.89 | 6 |
| ATOM | 28 | C25 | FEX | 1 | 5.121 | 32.873 | 56.142 | 1.00 | 30.54 | 6 |
| ATOM | 29 | O2 | FEX | 1 | 4.366 | 32.387 | 57.318 | 1.00 | 29.43 | 8 |
| ATOM | 30 | O3 | FEX | 1 | 5.940 | 34.001 | 56.319 | 1.00 | 31.02 | 8 |
| ATOM | 31 | C26 | FEX | 1 | 4.574 | 33.117 | 58.506 | 1.00 | 30.57 | 6 |
| ATOM | 32 | C27 | FEX | 1 | 3.118 | 29.861 | 49.757 | 1.00 | 34.18 | 6 |
| ATOM | 33 | C28 | FEX | 1 | 1.681 | 29.914 | 50.605 | 1.00 | 36.36 | 6 |
| ATOM | 34 | C29 | FEX | 1 | 0.795 | 31.179 | 50.327 | 1.00 | 36.77 | 6 |
| ATOM | 35 | C30 | FEX | 1 | 0.325 | 31.610 | 48.701 | 1.00 | 36.95 | 6 |
| ATOM | 36 | C31 | FEX | 1 | 1.715 | 31.463 | 47.837 | 1.00 | 35.29 | 6 |
| ATOM | 37 | C32 | FEX | 1 | 2.796 | 30.288 | 48.187 | 1.00 | 36.97 | 6 |
| END | | | | | | | | | | |

APPENDIX 2

Up Regulated Genes with Treatment Fex:

| Accession Number | Fold Change (Fex/DMSO) | Gene Description |
|---|---|---|
| NM_004617 | 11.90 | "HOMO SAPIENS TRANSMEMBRANE 4 SUPERFAMILY MEMBER 4 (TM4SF4), MRNA." |
| NM_003195 | 10.29 | "HOMO SAPIENS TRANSCRIPTION ELONGATION FACTOR A (SII), 2 (TCEA2), MRNA." |
| NM_000893 | 9.17 | "HOMO SAPIENS KININOGEN (KNG), MRNA." |
| NM_138961 | 6.12 | "HOMO SAPIENS SIMILAR TO ENDOTHELIAL CELL-SELECTIVE ADHESION MOLECULE (ESAM), MRNA" |
| NM_139284 | 4.53 | "HOMO SAPIENS LEUCINE-RICH REPEAT LGI FAMILY, MEMBER 4 (LGI4), MRNA" |
| AP000501 | 4.12 | "HOMO SAPIENS GENOMIC DNA, CHROMOSOME 8P11.2, CLONE: 91H23 TO 9-41" |
| NM_000394 | 3.96 | "HOMO SAPIENS CRYSTALLIN, ALPHA A (CRYAA), MRNA." |
| BM701748 | 3.78 | UI-E-CQ1-AEW-L-18-0-UI.R1 HOMO SAPIENS CDNA 5' END |
| NM_006209 | 3.64 | "HOMO SAPIENS ECTONUCLEOTIDE PYROPHOSPHATASE/PHOSPHODIESTERASE 2 (AUTOTAXIN) (ENPP2), MRNA." |
| NM_018602 | 3.39 | "HOMO SAPIENS DNAJ (HSP40) HOMOLOG, SUBFAMILY A, MEMBER 4 (DNAJA4), MRNA" |
| AA442232 | 3.32 | "ZV60H08.R1 SOARES_TESTIS_NHT HOMO SAPIENS CDNA CLONE IMAGE: 758079 5', MRNA SEQUENCE" |
| NM_031916 | 3.28 | "HOMO SAPIENS AKAP-ASSOCIATED SPERM PROTEIN (ASP), MRNA." |
| NM_022148 | 3.15 | "HOMO SAPIENS CYTOKINE RECEPTOR-LIKE FACTOR 2 (CRLF2), MRNA" |

APPENDIX 2-continued

Up Regulated Genes with Treatment Fex:

| Accession Number | Fold Change (Fex/DMSO) | Gene Description |
|---|---|---|
| NM_024935 | 3.14 | "HOMO SAPIENS HYPOTHETICAL PROTEIN FLJ13687 (FLJ13687), MRNA." |
| NM_032866 | 3.11 | "HOMO SAPIENS HYPOTHETICAL PROTEIN FLJ14957 (FLJ14957), MRNA." |
| NM_032471 | 3.02 | "HOMO SAPIENS PROTEIN KINASE (CAMP-DEPENDENT, CATALYTIC) INHIBITOR BETA (PKIB), MRNA." |
| NM_013370 | 3.00 | "HOMO SAPIENS PREGNANCY-INDUCED GROWTH INHIBITOR (OKL38), MRNA." |
| AL163259 | 2.99 | NULL |
| NM_000151 | 2.83 | "HOMO SAPIENS GLUCOSE-6-PHOSPHATASE, CATALYTIC (GLYCOGEN STORAGE DISEASE TYPE I, VON GIERKE DISEASE) (G6PC), MRNA." |
| NM_020689 | 2.78 | "HOMO SAPIENS SODIUM CALCIUM EXCHANGER (NCKX3), MRNA." |
| NM_021098 | 2.71 | "HOMO SAPIENS CALCIUM CHANNEL, VOLTAGE-DEPENDENT, ALPHA 1H SUBUNIT (CACNA1H), MRNA" |
| NM_024984 | 2.67 | "HOMO SAPIENS HYPOTHETICAL PROTEIN FLJ12193 (FLJ12193), MRNA" |
| NM_021778 | 2.65 | "HOMO SAPIENS A DISINTEGRIN AND METALLOPROTEINASE DOMAIN 28 (ADAM28), TRANSCRIPT VARIANT 2, MRNA." |
| AF123462 | 2.59 | "HOMO SAPIENS BAC526N18 NEUREXIN III GENE, PARTIAL CDS" |
| 129456.1 | 2.59 | NULL |
| AB020858 | 2.56 | "HOMO SAPIENS GENOMIC DNA OF 8P21.3–P22 ANTI-ONCOGENE OF HEPATOCELLULAR COLORECTAL AND NON-SMALL CELL LUNG CANCER, SEGMENT 1/11" |
| NM_016445 | 2.56 | "HOMO SAPIENS PLECKSTRIN 2 (MOUSE) HOMOLOG (PLEK2), MRNA." |
| NM_003614 | 2.53 | "HOMO SAPIENS GALANIN RECEPTOR 3 (GALR3), MRNA." |
| NM_145047 | 2.49 | "HOMO SAPIENS OXIDORED-NITRO DOMAIN-CONTAINING PROTEIN (NOR1), MRNA" |
| NM_001552 | 2.45 | "HOMO SAPIENS INSULIN-LIKE GROWTH FACTOR BINDING PROTEIN 4 (IGFBP4), MRNA" |
| AB002366 | 2.42 | "HUMAN MRNA FOR KIAA0368 GENE, PARTIAL CDS" |
| NM_031957 | 2.41 | "HOMO SAPIENS KERATIN ASSOCIATED PROTEIN 1.5 (KRTAP1.5), MRNA" |
| NM_020659 | 2.38 | "HOMO SAPIENS TWEETY HOMOLOG 1 (DROSOPHILA) (TTYH1), MRNA." |
| AB028998 | 2.37 | "HOMO SAPIENS MRNA FOR KIAA1075 PROTEIN, PARTIAL CDS" |
| NM_001678 | 2.36 | "HOMO SAPIENS ATPASE, NA+/K+ TRANSPORTING, BETA 2 POLYPEPTIDE (ATP1B2), MRNA." |
| NM_014375 | 2.35 | "HOMO SAPIENS FETUIN B (FETUB), MRNA." |
| NM_000361 | 2.33 | "HOMO SAPIENS THROMBOMODULIN (THBD), MRNA." |
| NM_004259 | 2.33 | "HOMO SAPIENS RECQ PROTEIN-LIKE 5 (RECQL5), MRNA." |
| NM_000106 | 2.33 | "HOMO SAPIENS CYTOCHROME P450, SUBFAMILY IID (DEBRISOQUINE, SPARTEINE, ETC., -METABOLIZING), POLYPEPTIDE 6 (CYP2D6), MRNA." |
| NM_003742 | 2.31 | "HOMO SAPIENS ATP-BINDING CASSETTE, SUB-FAMILY B (MDR/TAP), MEMBER 11 (ABCB11), MRNA." |
| NM_003044 | 2.28 | "HOMO SAPIENS SOLUTE CARRIER FAMILY 6 (NEUROTRANSMITTER TRANSPORTER, BETAINE/GABA), MEMBER 12 (SLC6A12), MRNA." |
| NM_001546 | 2.27 | "HOMO SAPIENS INHIBITOR OF DNA BINDING 4, DOMINANT NEGATIVE HELIX-LOOP-HELIX PROTEIN (ID4), MRNA" |
| AF069061 | 2.25 | "HOMO SAPIENS GLCNAC-1-P TRANSFERASE GENE, EXONS 1 THROUGH 4" |
| NM_012444 | 2.25 | "HOMO SAPIENS SPO11 MEIOTIC PROTEIN COVALENTLY BOUND TO DSB-LIKE (S. CEREVISIAE) (SPO11), MRNA" |
| NM_000901 | 2.24 | "HOMO SAPIENS NUCLEAR RECEPTOR SUBFAMILY 3, GROUP C, MEMBER 2 (NR3C2), MRNA." |
| AK027705 | 2.22 | "HOMO SAPIENS CDNA FLJ14799 FIS, CLONE NT2RP4001351, WEAKLY SIMILAR TO HUMAN OVARIAN CANCER DOWNREGULATED MYOSIN HEAVY CHAIN HOMOLOG (DOC1) MRNA" |
| NM_052890 | 2.20 | "HOMO SAPIENS PEPTIDOGLYCAN RECOGNITION PROTEIN L PRECURSOR (PGLYRP), MRNA" |
| NM_018379 | 2.19 | "HOMO SAPIENS HYPOTHETICAL PROTEIN FLJ11280 (FLJ11280), MRNA" |
| NM_005434 | 2.19 | "HOMO SAPIENS BENE PROTEIN (BENE), MRNA" |
| NM_004183 | 2.18 | "HOMO SAPIENS VITELLIFORM MACULAR DYSTROPHY (BEST DISEASE, BESTROPHIN) (VMD2), MRNA" |
| NM_005141 | 2.18 | "HOMO SAPIENS FIBRINOGEN, B BETA POLYPEPTIDE (FGB), MRNA." |
| NM_001496 | 2.16 | "HOMO SAPIENS GDNF FAMILY RECEPTOR ALPHA 3 (GFRA3), MRNA." |
| NM_003240 | 2.15 | "HOMO SAPIENS ENDOMETRIAL BLEEDING ASSOCIATED FACTOR (LEFT-RIGHT DETERMINATION, FACTOR A; TRANSFORMING GROWTH FACTOR BETA SUPERFAMILY) (EBAF), MRNA." |
| NM_032413 | 2.14 | "HOMO SAPIENS NORMAL MUCOSA OF ESOPHAGUS SPECIFIC 1 (NMES1), MRNA" |
| BC035779 | 2.14 | "HOMO SAPIENS, SIMILAR TO SOLUTE CARRIER FAMILY 9 (SODIUM/HYDROGEN EXCHANGER), ISOFORM 7, CLONE MGC: 46316 IMAGE: 5590356, MRNA, COMPLETE CDS" |
| NM_021949 | 2.13 | "HOMO SAPIENS ATPASE, CA++ TRANSPORTING, PLASMA MEMBRANE 3 (ATP2B3), MRNA." |
| BE348404 | 2.12 | "HW17D06.X1 HOMO SAPIENS CDNA, 3' END" |
| NM_021233 | 2.12 | "HOMO SAPIENS DNASE II-LIKE ACID DNASE (DLAD), TRANSCRIPT VARIANT 1, MRNA" |

APPENDIX 2-continued

Up Regulated Genes with Treatment Fex:

| Accession Number | Fold Change (Fex/DMSO) | Gene Description |
|---|---|---|
| NM_004669 | 2.12 | "HOMO SAPIENS CHLORIDE INTRACELLULAR CHANNEL 3 (CLIC3), MRNA." |
| NM_015685 | 2.12 | "HOMO SAPIENS SYNDECAN BINDING PROTEIN (SYNTENIN) 2 (SDCBP2), MRNA." |
| NM_014945 | 2.11 | "HOMO SAPIENS KIAA0843 PROTEIN (KIAA0843), MRNA." |
| X98507 | 2.11 | H. SAPIENS MRNA FOR MYOSIN-I BETA |
| AK056268 | 2.11 | "HOMO SAPIENS CDNA FLJ31706 FIS, CLONE NT2RI2006210, MODERATELY SIMILAR TO MUS MUSCULUS SHD MRNA" |
| AL137400 | 2.10 | HOMO SAPIENS MRNA; CDNA DKFZP434L162 (FROM CLONE DKFZP434L162) |
| NM_000808 | 2.09 | "HOMO SAPIENS GAMMA-AMINOBUTYRIC ACID (GABA) A RECEPTOR, ALPHA 3 (GABRA3), MRNA." |
| 1387891.1 | 2.09 | NULL |
| AF260225 | 2.08 | "HOMO SAPIENS TESTIN 2 AND TESTIN 3 GENES, COMPLETE CDS, ALTERNATIVELY SPLICED" |
| NM_007163 | 2.08 | "HOMO SAPIENS SOLUTE CARRIER FAMILY 14 (UREA TRANSPORTER), MEMBER 2 (SLC14A2), MRNA." |
| AB046859 | 2.08 | "HOMO SAPIENS MRNA FOR KIAA1639 PROTEIN, PARTIAL CDS" |
| NM_002022 | 2.07 | "HOMO SAPIENS FLAVIN CONTAINING MONOOXYGENASE 4 (FMO4), MRNA." |
| NM_000366 | 2.06 | "HOMO SAPIENS TROPOMYOSIN 1 (ALPHA) (TPM1), MRNA" |
| NM_021146 | 2.06 | "HOMO SAPIENS ANGIOPOIETIN-LIKE FACTOR (CTD6), MRNA." |
| NM_031961 | 2.06 | "HOMO SAPIENS KERATIN ASSOCIATED PROTEIN 9.2 (KRTAP9.2), MRNA" |
| NM_005971 | 2.06 | "HOMO SAPIENS FXYD DOMAIN-CONTAINING ION TRANSPORT REGULATOR 3 (FXYD3), TRANSCRIPT VARIANT 1, MRNA" |
| AK026600 | 2.05 | "HOMO SAPIENS CDNA: FLJ22947 FIS, CLONE KAT09234" |
| NM_012277 | 2.05 | "HOMO SAPIENS PANCREATIC BETA CELL GROWTH FACTOR (INGAP), MRNA." |
| S71547 | 2.04 | "{ECCDNA 24, EXTRACHROMOSOMAL CIRCULAR DNA} [HUMAN, HELA S3 CELLS, GENOMIC, 806 NT]" |
| NM_002625 | 2.04 | "HOMO SAPIENS 6-PHOSPHOFRUCTO-2-KINASE/FRUCTOSE-2,6-BIPHOSPHATASE 1 (PFKFB1), MRNA." |
| U71218 | 2.04 | "HUMAN CLONE C74F4, 24KB PROXIMAL CMT1A-REP SEQUENCE" |
| AA427982 | 2.03 | "HUMAN KRUPPEL RELATED ZINC FINGER PROTEIN (HTF10) MRNA, COMPLETE CDS." |
| NM_014242 | 2.02 | "HOMO SAPIENS ZINC FINGER PROTEIN 237 (ZNF237), MRNA." |
| AF070586 | 2.02 | HOMO SAPIENS CLONE 24528 MRNA SEQUENCE |
| NM_000482 | 2.01 | "HOMO SAPIENS APOLIPOPROTEIN A-IV (APOA4), MRNA" |
| M30894 | 2.00 | "GNL\|UG\|HS#S3370 HUMAN T-CELL RECEPTOR TI REARRANGED GAMMA CHAIN MRNA V-J-C REGION, COMPLETE CDS/CDS = (140,1156)/ GB = M30894/GI = 339406/UG = HS.112259/LEN = 1586" |
| BC016979 | 2.00 | "HOMO SAPIENS, CLONE MGC: 21802 IMAGE: 4181575, MRNA, COMPLETE CDS" |
| NM_002666 | 1.99 | "HOMO SAPIENS PERILIPIN (PLIN), MRNA." |
| NM_144659 | 1.98 | "HOMO SAPIENS T-COMPLEX 10A-2 (LOC140290), MRNA" |
| NM_006160 | 1.97 | "HOMO SAPIENS NEUROGENIC DIFFERENTIATION 2 (NEUROD2), MRNA." |
| AL137581 | 1.97 | HOMO SAPIENS MRNA; CDNA DKFZP434B0610 (FROM CLONE DKFZP434B0610); PARTIAL CDS |
| BC024316 | 1.97 | "HOMO SAPIENS, CLONE IMAGE: 3912859, MRNA" |
| AL049328 | 1.97 | HOMO SAPIENS MRNA; CDNA DKFZP564E026 (FROM CLONE DKFZP564E026) |
| NM_017734 | 1.96 | "HOMO SAPIENS PALMDELPHIN (PALMD), MRNA." |
| AK022620 | 1.96 | "HOMO SAPIENS CDNA FLJ12558 FIS, CLONE NT2RM4000787" |
| NM_000873 | 1.95 | "HOMO SAPIENS INTERCELLULAR ADHESION MOLECULE 2 (ICAM2), MRNA" |
| U84003 | 1.95 | "HOMO SAPIENS BRIDGING INTEGRATOR PROTEIN-1 (BIN1) GENE, EXONS 7–12" |
| NM_052962 | 1.95 | "HOMO SAPIENS CLASS II CYTOKINE RECEPTOR (IL22RA2), MRNA" |
| NM_015577 | 1.95 | "HOMO SAPIENS RETINOIC ACID INDUCED 14 (RAI14), MRNA." |
| NM_144626 | 1.93 | "HOMO SAPIENS HYPOTHETICAL PROTEIN MGC17299 (MGC17299), MRNA" |
| AF217965 | 1.93 | HOMO SAPIENS CLONE PP102 UNKNOWN MRNA |
| NM_002701 | 1.93 | "HOMO SAPIENS POU DOMAIN, CLASS 5, TRANSCRIPTION FACTOR 1 (POU5F1), MRNA." |
| NM_031418 | 1.93 | "HOMO SAPIENS CHROMOSOME 11 OPEN READING FRAME 25 (C11ORF25), MRNA." |
| NM_013391 | 1.93 | "HOMO SAPIENS DIMETHYLGLYCINE DEHYDROGENASE PRECURSOR (DMGDH), MRNA." |
| U82670 | 1.93 | "HOMO SAPIENS XQ28 OF HIGH-MOBILITY GROUP PROTEIN 17 RETROPSEUDOGENE (PSHMG17), COMPLETE SEQUENCE; AND MELANOMA ANTIGEN FAMILY A1 (MAGEA1) AND ZINC FINGER PROTEIN 275 (ZNF275) GENES, COMPLETE CDS" |
| NM_000964 | 1.93 | "HOMO SAPIENS RETINOIC ACID RECEPTOR, ALPHA (RARA), MRNA" |

APPENDIX 2-continued

Up Regulated Genes with Treatment Fex:

| Accession Number | Fold Change (Fex/DMSO) | Gene Description |
|---|---|---|
| S70612 | 1.92 | "GLYCINE TRANSPORTER TYPE 1C {ALTERNATIVELY SPLICED} [HUMAN, SUBSTANTIA NIGRA, MRNA, 2202 NT]" |
| AK021786 | 1.92 | "*HOMO SAPIENS* CDNA FLJ11724 FIS, CLONE HEMBA1005331" |
| Y15067 | 1.91 | *HOMO SAPIENS* MRNA FOR ZN-FINGER PROTEIN ZNF232 |
| AL110262 | 1.91 | *HOMO SAPIENS* MRNA; CDNA DKFZP586F0221 (FROM CLONE DKFZP586F0221) |
| Z64378 | 1.91 | "*H. SAPIENS* CPG ISLAND DNA GENOMIC MSE1 FRAGMENT, CLONE 114F7, REVERSE READ CPG114F7.RT1A" |
| AW963947 | 1.91 | EST376020 *HOMO SAPIENS* CDNA |
| NM_001767 | 1.91 | "*HOMO SAPIENS* CD2 ANTIGEN (P50), SHEEP RED BLOOD CELL RECEPTOR (CD2), MRNA" |
| U41384 | 1.91 | "HUMAN SMALL NUCLEAR RIBONUCLEAR PROTEIN ASSOCIATED POLYPEPTIDE N (SNRPN) GENE AND PRADER-WILLI SYNDROME GENE, COMPLETE SEQUENCE." |
| NM_012320 | 1.90 | "*HOMO SAPIENS* LYSOPHOSPHOLIPASE 3 (LYSOSOMAL PHOSPHOLIPASE A2) (LYPLA3), MRNA" |
| AB011116 | 1.90 | "*HOMO SAPIENS* MRNA FOR KIAA0544 PROTEIN, PARTIAL CDS" |
| NM_018915 | 1.89 | "*HOMO SAPIENS* PROTOCADHERIN GAMMA SUBFAMILY A, 2 (PCDHGA2), TRANSCRIPT VARIANT 1, MRNA" |
| NM_003157 | 1.89 | "*HOMO SAPIENS* SERINE/THREONINE KINASE 2 (STK2), MRNA." |
| NM_004072 | 1.89 | "*HOMO SAPIENS* CHEMOKINE-LIKE RECEPTOR 1 (CMKLR1), MRNA." |
| AK001546 | 1.89 | "*HOMO SAPIENS* CDNA FLJ10684 FIS, CLONE NT2RP3000220" |
| NM_014151 | 1.88 | "*HOMO SAPIENS* HSPC053 PROTEIN (HSPC053), MRNA" |
| 449023.1 | 1.88 | NULL |
| NM_032259 | 1.88 | "*HOMO SAPIENS* HYPOTHETICAL PROTEIN DKFZP434F054 (DKFZP434F054), MRNA" |
| NM_001169 | 1.88 | "*HOMO SAPIENS* AQUAPORIN 8 (AQP8), MRNA." |
| X79535 | 1.88 | "HUMAN MRNA FOR BETA TUBULIN, CLONE NUK_278." |
| U10689 | 1.87 | "HUMAN MAGE-5A ANTIGEN (MAGE5A) GENE, COMPLETE CDS" |
| AF324499 | 1.87 | "*HOMO SAPIENS* OLFACTORY-LIKE RECEPTOR MRNA, COMPLETE CDS" |
| AL133659 | 1.87 | *HOMO SAPIENS* MRNA; CDNA DKFZP434K0227 (FROM CLONE DKFZP434K0227); PARTIAL CDS |
| NM_032962 | 1.86 | "*HOMO SAPIENS* SMALL INDUCIBLE CYTOKINE SUBFAMILY A (CYS-CYS), MEMBER 14 (SCYA14), TRANSCRIPT VARIANT 2, MRNA." |
| BC013181 | 1.86 | "*HOMO SAPIENS*, CLONE MGC: 21682 IMAGE: 4385873, MRNA, COMPLETE CDS" |
| NM_019038 | 1.86 | "*HOMO SAPIENS* HYPOTHETICAL PROTEIN (FLJ11045), MRNA." |
| W89128 | 1.86 | "ZH69C04.S1 *HOMO SAPIENS* CDNA, 3' END" |
| 1327919.2 | 1.85 | NULL |
| NM_005165 | 1.85 | "*HOMO SAPIENS* ALDOLASE C, FRUCTOSE-BISPHOSPHATE (ALDOC), MRNA." |
| NM_014037 | 1.85 | "*HOMO SAPIENS* NTT5 PROTEIN (NTT5), MRNA." |
| H10529 | 1.85 | "YM04A08.R1 *HOMO SAPIENS* CDNA, 5' END" |
| NM_032687 | 1.85 | PROTEIN OF UNKNOWN FUNCTION |
| AJ292466 | 1.84 | "*HOMO SAPIENS* MRNA FOR WDR9 PROTEIN (WDR9 GENE), FORM B" |
| NM_002190 | 1.84 | "*HOMO SAPIENS* INTERLEUKIN 17 (CYTOTOXIC T-LYMPHOCYTE-ASSOCIATED SERINE ESTERASE 8) (IL17), MRNA." |
| AF191622 | 1.84 | "*HOMO SAPIENS* FILAMIN (FLNB) GENE, EXON 35" |
| NM_052863 | 1.84 | "*HOMO SAPIENS* SECRETOGLOBIN, FAMILY 3A, MEMBER 1 (SCGB3A1), MRNA" |
| 201531.1 | 1.84 | NULL |
| NM_001727 | 1.83 | "*HOMO SAPIENS* BOMBESIN-LIKE RECEPTOR 3 (BRS3), MRNA" |
| X63578 | 1.83 | *H. SAPIENS* GENE FOR PARVALBUMIN |
| NM_014897 | 1.83 | "*HOMO SAPIENS* KIAA0924 PROTEIN (KIAA0924), MRNA." |
| NM_031200 | 1.83 | "*HOMO SAPIENS* CHEMOKINE (C—C MOTIF) RECEPTOR 9 (CCR9), TRANSCRIPT VARIANT A, MRNA." |
| AL157504 | 1.83 | *HOMO SAPIENS* MRNA; CDNA DKFZP586O0724 (FROM CLONE DKFZP586O0724) |
| BC031087 | 1.83 | "*HOMO SAPIENS*, SIMILAR TO GAMMA-AMINOBUTYRIC-ACID RECEPTOR GAMMA-1 SUBUNIT PRECURSOR (GABA(A) RECEPTOR), CLONE MGC: 33838 IMAGE: 5289008, MRNA, COMPLETE CDS" |
| NM_014461 | 1.81 | "*HOMO SAPIENS* CONTACTIN 6 (CNTN6), MRNA." |
| AB047819 | 1.81 | "*HOMO SAPIENS* GCMA/GCM1 GENE FOR CHORION-SPECIFIC TRANSCRIPTION FACTOR GCMA, COMPLETE CDS" |
| NM_003264 | 1.81 | "*HOMO SAPIENS* TOLL-LIKE RECEPTOR 2 (TLR2), MRNA." |
| NM_000508 | 1.81 | "*HOMO SAPIENS* FIBRINOGEN, A ALPHA POLYPEPTIDE (FGA), TRANSCRIPT VARIANT ALPHA-E, MRNA." |
| AK021635 | 1.81 | "*HOMO SAPIENS* CDNA FLJ11573 FIS, CLONE HEMBA1003376" |
| NM_032211 | 1.80 | "*HOMO SAPIENS* LYSYL OXIDASE-LIKE 4 (LOXL4), MRNA" |
| NM_033014 | 1.80 | "*HOMO SAPIENS* OSTEOGLYCIN (OSTEOINDUCTIVE FACTOR, MIMECAN) (OGN), TRANSCRIPT VARIANT 1, MRNA." |
| AB020636 | 1.80 | "*HOMO SAPIENS* MRNA FOR KIAA0829 PROTEIN, PARTIAL CDS" |
| AJ242910 | 1.80 | *HOMO SAPIENS* MRNA FOR N-ACETYLGLUCOSAMINE KINASE |

APPENDIX 2-continued

Up Regulated Genes with Treatment Fex:

| Accession Number | Fold Change (Fex/DMSO) | Gene Description |
| --- | --- | --- |
| X52852 | 1.80 | HUMAN CYCLOPHILIN-RELATED PROCESSED PSEUDOGENE |
| NM_014069 | 1.80 | "HOMO SAPIENS SPR1 PROTEIN (SPR1), MRNA." |
| NM_032607 | 1.80 | "HOMO SAPIENS CREB/ATF FAMILY TRANSCRIPTION FACTOR (CREB-H), MRNA" |
| 1462881.1 | 1.79 | "MEMBER OF THE RHODOPSIN FAMILY OF G PROTEIN-COUPLED RECEPTORS (GPCR), HAS MODERATE SIMILARITY TO OLFACTORY RECEPTOR 41 (MOUSE OLFR41), WHICH MAY HAVE A ROLE IN OLFACTORY RESPONSE AND INTERACTS PREFERENTIALLY WITH HEPTANAL" |
| AF300796 | 1.79 | "HOMO SAPIENS SIALIC ACID-SPECIFIC 9-O-ACETYLESTERASE I MRNA, COMPLETE CDS" |
| NM_006204 | 1.79 | "HOMO SAPIENS PHOSPHODIESTERASE 6C, CGMP-SPECIFIC, CONE, ALPHA PRIME (PDE6C), MRNA." |
| NM_033066 | 1.79 | "HOMO SAPIENS MEMBRANE PROTEIN, PALMITOYLATED 4 (MAGUK P55 SUBFAMILY MEMBER 4) (MPP4), MRNA" |
| NM_000341 | 1.79 | "HOMO SAPIENS SOLUTE CARRIER FAMILY 3 (CYSTINE, DIBASIC AND NEUTRAL AMINO ACID TRANSPORTERS, ACTIVATOR OF CYSTINE, DIBASIC AND NEUTRAL AMINO ACID TRANSPORT), MEMBER 1 (SLC3A1), MRNA." |
| 1452359.3 | 1.78 | NULL |
| AL080103 | 1.78 | HOMO SAPIENS MRNA; CDNA DKFZP564N2216 (FROM CLONE DKFZP564N2216) |
| D86992 | 1.78 | "HOMO SAPIENS IMMUNOGLOBULIN LAMBDA GENE LOCUS DNA, CLONE: 123E1 UPSTREAM CONTIG" |
| NM_021038 | 1.78 | "HOMO SAPIENS MUSCLEBLIND-LIKE (DROSOPHILA) (MBNL), MRNA." |
| 958731.1 | 1.78 | "MEMBER OF THE SHORT-CHAIN DEHYDROGENASE-REDUCTASE FAMILY, HAS A REGION OF LOW SIMILARITY TO 11 BETA-HYDROXYSTEROID DEHYDROGENASE (MOUSE HSD11B1), WHICH IS A MICROSOMAL CARBONYL REDUCTASE THAT HAS 11 BETA-DEHYDROGENASE AND 11-OXO REDUCTASE ACTIVITY" |
| NM_021135 | 1.77 | "HOMO SAPIENS RIBOSOMAL PROTEIN S6 KINASE, 90 KD, POLYPEPTIDE 2 (RPS6KA2), MRNA" |
| NM_000773 | 1.77 | "HOMO SAPIENS CYTOCHROME P450, SUBFAMILY IIE (ETHANOL-INDUCIBLE) (CYP2E), MRNA." |
| NM_000487 | 1.77 | "HOMO SAPIENS ARYLSULFATASE A (ARSA), MRNA." |
| AL049431 | 1.77 | HOMO SAPIENS MRNA; CDNA DKFZP586J211 (FROM CLONE DKFZP586J211) |
| AW406117 | 1.76 | "HUMAN LAMBDA CLONE 247 FRA3B REGION DNA, CYCLOPHILIN PSEUDOGENE, PARTIAL SEQUENCE, AND HPV16 VIRAL INTEGRATION SITE." |
| NM_002934 | 1.76 | "HOMO SAPIENS RIBONUCLEASE, RNASE A FAMILY, 2 (LIVER, EOSINOPHIL-DERIVED NEUROTOXIN) (RNASE2), MRNA" |
| NM_001347 | 1.76 | "HOMO SAPIENS DIACYLGLYCEROL KINASE, THETA (110 KD) (DGKQ), MRNA" |
| AB023173 | 1.76 | "HOMO SAPIENS MRNA FOR KIAA0956 PROTEIN, PARTIAL CDS" |
| BC025726 | 1.76 | "HOMO SAPIENS, POTASSIUM CHANNEL, SUBFAMILY K, MEMBER 17 (TASK-4), CLONE MGC: 34117 IMAGE: 5201326, MRNA, COMPLETE CDS" |
| AB001517 | 1.76 | "HOMO SAPIENS DNA FOR TMEM1 PROTEIN, PWP2 PROTEIN, KNP-I ALPHA PROTEIN AND KNP-I BETA PROTEIN, PARTIAL AND COMPLETE CDS" |
| U28480 | 1.76 | "HUMAN UNCOUPLING PROTEIN (UCP) MRNA, COMPLETE CDS" |
| NM_002881 | 1.75 | "HOMO SAPIENS V-RAL SIMIAN LEUKEMIA VIRAL ONCOGENE HOMOLOG B (RAS RELATED; GTP BINDING PROTEIN) (RALB), MRNA." |
| NM_021871 | 1.75 | "HOMO SAPIENS FIBRINOGEN, A ALPHA POLYPEPTIDE (FGA), TRANSCRIPT VARIANT ALPHA, MRNA" |
| NM_032989 | 1.75 | "HOMO SAPIENS BCL2-ANTAGONIST OF CELL DEATH (BAD), TRANSCRIPT VARIANT 2, MRNA." |
| NM_003960 | 1.75 | "HOMO SAPIENS KIDNEY-AND LIVER-SPECIFIC GENE (CML1), MRNA." |
| NM_014693 | 1.75 | "HOMO SAPIENS ENDOTHELIN CONVERTING ENZYME 2 (ECE2), MRNA." |
| NM_001323 | 1.74 | "HOMO SAPIENS CYSTATIN E/M (CST6), MRNA." |
| AL832363 | 1.74 | HOMO SAPIENS MRNA; CDNA DKFZP451N156 (FROM CLONE DKFZP451N156) |
| NM_003272 | 1.74 | "HOMO SAPIENS TRANSMEMBRANE 7 SUPERFAMILY MEMBER 1 (UPREGULATED IN KIDNEY) (TM7SF1), MRNA." |
| NM_005018 | 1.74 | "HOMO SAPIENS PROGRAMMED CELL DEATH 1 (PDCD1), MRNA." |
| AK057674 | 1.74 | "HOMO SAPIENS CDNA FLJ33112 FIS, CLONE TRACH2001109" |
| AI797481 | 1.74 | WE88E01.X1 HOMO SAPIENS CDNA 3' END |
| NM_014965 | 1.74 | "HOMO SAPIENS KIAA1042 PROTEIN (KIAA1042), MRNA." |
| NM_004570 | 1.73 | "HOMO SAPIENS PHOSPHOINOSITIDE-3-KINASE, CLASS 2, GAMMA POLYPEPTIDE (PIK3C2G), MRNA." |
| AK025583 | 1.73 | "HOMO SAPIENS CDNA: FLJ21930 FIS, CLONE HEP04301, HIGHLY SIMILAR TO HSU90916 HUMAN CLONE 23815 MRNA SEQUENCE" |
| 1397221.43 | 1.73 | NULL |

APPENDIX 2-continued

Up Regulated Genes with Treatment Fex:

| Accession Number | Fold Change (Fex/DMSO) | Gene Description |
|---|---|---|
| AF345906 | 1.73 | "*HOMO SAPIENS* LIM MINERALIZATION PROTEIN 3 MRNA, COMPLETE CDS" |
| NM_032642 | 1.73 | "*HOMO SAPIENS* WINGLESS-TYPE MMTV INTEGRATION SITE FAMILY, MEMBER 5B (WNT5B), TRANSCRIPT VARIANT 1, MRNA." |
| 1329470.331 | 1.73 | NULL |
| M61170 | 1.73 | "HUMAN POLYMORPHIC EPITHELIAL MUCIN (PEM) GENE, COMPLETE CDS" |
| NM_000627 | 1.73 | "*HOMO SAPIENS* LATENT TRANSFORMING GROWTH FACTOR BETA BINDING PROTEIN 1 (LTBP1), MRNA." |
| NM_145276 | 1.72 | "*HOMO SAPIENS* SIMILAR TO KRUPPEL-TYPE ZINC FINGER (C2H2) (LOC147837), MRNA" |
| 1353408.4 | 1.72 | NULL |
| AF052160 | 1.72 | *HOMO SAPIENS* CLONE 24629 MRNA SEQUENCE |
| NM_002600 | 1.72 | "*HOMO SAPIENS* PHOSPHODIESTERASE 4B, CAMP-SPECIFIC (PHOSPHODIESTERASE E4 DUNCE HOMOLOG, *DROSOPHILA*) (PDE4B), MRNA." |
| D28877 | 1.72 | "*HOMO SAPIENS* HNRPA2B1 GENE FOR HNRNP PROTEIN A2 AND B1, COMPLETE CDS" |
| AK022354 | 1.71 | "*HOMO SAPIENS* CDNA FLJ12292 FIS, CLONE MAMMA1001812" |
| NM_003734 | 1.71 | "*HOMO SAPIENS* AMINE OXIDASE, COPPER CONTAINING 3 (VASCULAR ADHESION PROTEIN 1) (AOC3), MRNA." |
| NM_004921 | 1.71 | "*HOMO SAPIENS* CHLORIDE CHANNEL, CALCIUM ACTIVATED, FAMILY MEMBER 3 (CLCA3), MRNA" |
| BC034709 | 1.71 | "*HOMO SAPIENS*, SIMILAR TO GAP JUNCTION BETA-4 PROTEIN (CONNEXIN 30.3) (CX30.3), CLONE MGC: 21116 IMAGE: 4755173, MRNA, COMPLETE CDS" |
| NM_014912 | 1.71 | "*HOMO SAPIENS* KIAA0940 PROTEIN (KIAA0940), MRNA." |
| NM_018639 | 1.70 | "*HOMO SAPIENS* CS BOX-CONTAINING WD PROTEIN (LOC55884), MRNA." |
| 979318.3 | 1.70 | "PROTEIN CONTAINING 11 LEUCINE RICH REPEATS, WHICH MEDIATE PROTEIN-PROTEIN INTERACTIONS, HAS A REGION OF LOW SIMILARITY TO HUMAN IGFALS, WHICH IS ACID-LABILE SUBUNIT OF THE INSULIN-LIKE GROWTH FACTOR (IGF) BINDING PROTEIN THAT MAY MODULATE IGF ACTIVITY" |
| AK024603 | 1.70 | "*HOMO SAPIENS* CDNA: FLJ20950 FIS, CLONE ADSE01927" |
| NM_022370 | 1.70 | "*HOMO SAPIENS* HYPOTHETICAL PROTEIN FLJ21044 SIMILAR TO RBIG1 (FLJ21044), MRNA" |
| NM_014954 | 1.70 | "*HOMO SAPIENS* KIAA0985 PROTEIN (KIAA0985), MRNA." |
| M64497 | 1.70 | "HUMAN APOLIPOPROTEIN AI REGULATORY PROTEIN (ARP-1) MRNA, COMPLETE CDS" |
| AB032986 | 1.70 | "*HOMO SAPIENS* MRNA FOR KIAA1160 PROTEIN, PARTIAL CDS" |
| AK094585 | 1.70 | "*HOMO SAPIENS* CDNA FLJ37266 FIS, CLONE BRAMY2011280" |
| NM_018592 | 1.69 | "*HOMO SAPIENS* HYPOTHETICAL PROTEIN PRO0800 (PRO0800), MRNA" |
| AF222345 | 1.69 | "*HOMO SAPIENS* SUPPRESSOR OF FUSED VARIANT 3 MRNA, ALTERNATIVELY SPLICED, COMPLETE CDS" |
| AJ420504 | 1.69 | *HOMO SAPIENS* MRNA FULL LENGTH INSERT CDNA CLONE EUROIMAGE 2069692 |
| NM_001656 | 1.69 | "*HOMO SAPIENS* ADP-RIBOSYLATION FACTOR DOMAIN PROTEIN 1, 64 KD (ARFD1), TRANSCRIPT VARIANT ALPHA, MRNA." |
| AA868513 | 1.69 | "AK43C02.S1 *HOMO SAPIENS* CDNA, 3' END" |
| NM_012400 | 1.69 | "*HOMO SAPIENS* PHOSPHOLIPASE A2, GROUP IID (PLA2G2D), MRNA." |
| NM_003662 | 1.69 | "*HOMO SAPIENS* PIRIN (PIR), MRNA." |
| U41302 | 1.69 | "HUMAN CHROMOSOME 16 CREATINE TRANSPORTER (SLC6A8) AND (CDM) PARALOGOUS GENES, COMPLETE CDS" |
| AU133056 | 1.69 | "AU133056 *HOMO SAPIENS* CDNA, 5' END" |
| AB040903 | 1.69 | "*HOMO SAPIENS* MRNA FOR KIAA1470 PROTEIN, PARTIAL CDS" |
| U17081 | 1.69 | "HUMAN FATTY ACID BINDING PROTEIN (FABP3) GENE, COMPLETE CDS." |
| AB029001 | 1.68 | "*HOMO SAPIENS* MRNA FOR KIAA1078 PROTEIN, PARTIAL CDS" |
| J03040 | 1.68 | "HUMAN SPARC/OSTEONECTIN MRNA, COMPLETE CDS" |
| AK024251 | 1.68 | "*HOMO SAPIENS* CDNA FLJ14189 FIS, CLONE NT2RP2006184, HIGHLY SIMILAR TO *HOMO SAPIENS* MRNA FOR KIAA0918 PROTEIN" |
| NM_004286 | 1.68 | "*HOMO SAPIENS* GTP BINDING PROTEIN 1 (GTPBP1), MRNA" |
| NM_005980 | 1.68 | "*HOMO SAPIENS* S100 CALCIUM BINDING PROTEIN P (S100P), MRNA." |
| NM_005953 | 1.68 | "METALLOTHIONEIN 2A, FUNCTIONS IN METAL HOMEOSTASIS AND PROTECTS AGAINST HEAVY-METAL TOXICITY, MAY HAVE ROLES IN THE REGULATION OF CELLULAR PROLIFERATION, APOPTOSIS, AND MALIGNANT PROGRESSION" |
| AF195513 | 1.68 | "*HOMO SAPIENS* PUR-GAMMA A-FORM (PURG) MRNA, COMPLETE CDS" |
| NM_003546 | 1.68 | "*HOMO SAPIENS* H4 HISTONE FAMILY, MEMBER K (H4FK), MRNA" |
| NM_000869 | 1.67 | "*HOMO SAPIENS* 5-HYDROXYTRYPTAMINE (SEROTONIN) RECEPTOR 3A (HTR3A), MRNA." |
| 218630.6 | 1.67 | PROTEIN OF UNKNOWN FUNCTION |

APPENDIX 2-continued

Up Regulated Genes with Treatment Fex:

| Accession Number | Fold Change (Fex/DMSO) | Gene Description |
|---|---|---|
| NM_000217 | 1.67 | "*HOMO SAPIENS* POTASSIUM VOLTAGE-GATED CHANNEL, SHAKER-RELATED SUBFAMILY, MEMBER 1 (EPISODIC ATAXIA WITH MYOKYMIA) (KCNA1), MRNA." |
| AB033030 | 1.67 | "*HOMO SAPIENS* MRNA FOR KIAA1204 PROTEIN, PARTIAL CDS" |
| BC012362 | 1.67 | "*HOMO SAPIENS*, CLONE MGC: 20484 IMAGE: 4650072, MRNA, COMPLETE CDS" |
| AA001334 | 1.67 | "ZH83C02.R1 *HOMO SAPIENS* CDNA, 5' END" |
| NM_001114 | 1.67 | "*HOMO SAPIENS* ADENYLATE CYCLASE 7 (ADCY7), MRNA." |
| NM_006759 | 1.67 | "*HOMO SAPIENS* UDP-GLUCOSE PYROPHOSPHORYLASE 2 (UGP2), MRNA." |
| NM_152270 | 1.67 | "*HOMO SAPIENS* HYPOTHETICAL PROTEIN FLJ34922 (FLJ34922), MRNA" |
| NM_025206 | 1.67 | "*HOMO SAPIENS* FER-1-LIKE 4 (*C. ELEGANS*) (FER1L4), MRNA" |
| NM_031305 | 1.66 | "*HOMO SAPIENS* HYPOTHETICAL PROTEIN DKFZP564B1162 (DKFZP564B1162), MRNA" |
| H09245 | 1.66 | "YL98A12.S1 *HOMO SAPIENS* CDNA, 3' END" |
| 1042260.1 | 1.66 | NULL |
| NM_004950 | 1.66 | "*HOMO SAPIENS* DERMATAN SULFATE PROTEOGLYCAN 3 (DSPG3), MRNA." |
| AB007969 | 1.66 | "*HOMO SAPIENS* MRNA, CHROMOSOME 1 SPECIFIC TRANSCRIPT KIAA0500" |
| NM_000705 | 1.66 | "*HOMO SAPIENS* ATPASE, H+/K+ EXCHANGING, BETA POLYPEPTIDE (ATP4B), MRNA." |
| NM_002965 | 1.66 | "*HOMO SAPIENS* S100 CALCIUM BINDING PROTEIN A9 (CALGRANULIN B) (S100A9), MRNA" |
| NM_006149 | 1.66 | "*HOMO SAPIENS* LECTIN, GALACTOSIDE-BINDING, SOLUBLE, 4 (GALECTIN 4) (LGALS4), MRNA" |
| AL163248 | 1.66 | *HOMO SAPIENS* CHROMOSOME 21 SEGMENT HS21C048 |
| AF009640 | 1.66 | "*HOMO SAPIENS* CLONE 33 IMMUNOGLOBULIN-LIKE TRANSCRIPT 5 PROTEIN MRNA, COMPLETE CDS" |
| NM_017786 | 1.66 | "*HOMO SAPIENS* HYPOTHETICAL PROTEIN FLJ20366 (FLJ20366), MRNA." |
| AF217796 | 1.66 | "*HOMO SAPIENS* SCG10 LIKE-PROTEIN, HELICASE-LIKE PROTEIN NHL, M68, AND ADP-RIBOSYLATION FACTOR RELATED PROTEIN 1 (ARFRP1) GENES, COMPLETE CDS" |
| NM_015230 | 1.66 | "*HOMO SAPIENS* CENTAURIN, DELTA 1 (CENTD1), MRNA." |
| NM_000802 | 1.66 | "*HOMO SAPIENS* FOLATE RECEPTOR 1 (ADULT) (FOLR1), TRANSCRIPT VARIANT 1, MRNA" |
| BC014851 | 1.66 | "*HOMO SAPIENS*, SIMILAR TO LUNATIC FRINGE GENE HOMOLOG (*DROSOPHILA*), CLONE MGC: 22145 IMAGE: 4453156, MRNA, COMPLETE CDS" |
| AK000789 | 1.66 | "*HOMO SAPIENS* CDNA FLJ20782 FIS, CLONE COL03841" |
| NM_006810 | 1.66 | "*HOMO SAPIENS* FOR PROTEIN DISULFIDE ISOMERASE-RELATED (PDIR), MRNA." |
| NM_030984 | 1.65 | "*HOMO SAPIENS* THROMBOXANE A SYNTHASE 1 (PLATELET, CYTOCHROME P450, SUBFAMILY V) (TBXAS1), TRANSCRIPT VARIANT TXS-II, MRNA." |
| NM_145016 | 1.65 | "*HOMO SAPIENS* HYPOTHETICAL PROTEIN MGC24009 (MGC24009), MRNA" |
| AK002122 | 1.65 | "*HOMO SAPIENS* CDNA FLJ11260 FIS, CLONE PLACE1009060, WEAKLY SIMILAR TO BRO1 PROTEIN" |
| AB006627 | 1.65 | "*HOMO SAPIENS* MRNA FOR KIAA0289 GENE, PARTIAL CDS" |
| AK022892 | 1.65 | "*HOMO SAPIENS* CDNA FLJ12830 FIS, CLONE NT2RP2003073" |
| AF088219 | 1.65 | "HUMAN CC CHEMOKINE GENE CLUSTER, COMPLETE SEQUENCE." |
| BC035035 | 1.65 | "*HOMO SAPIENS*, SIMILAR TO ECTONUCLEOTIDE PYROPHOSPHATASE/PHOSPHODIESTERASE 5, CLONE MGC: 33971 IMAGE: 5259487, MRNA, COMPLETE CDS" |
| AF147791 | 1.65 | "*HOMO SAPIENS* MUCIN 11 (MUC11) MRNA, PARTIAL CDS" |
| AU127911 | 1.65 | AU127911 *HOMO SAPIENS* CDNA 5' END |
| L13738 | 1.65 | "*HOMO SAPIENS* ACTIVATED P21CDC42HS KINASE (ACK1) MRNA, COMPLETE CDS" |
| U78027 | 1.65 | "*HOMO SAPIENS* BRUTON'S TYROSINE KINASE (BTK), ALPHA-D-GALACTOSIDASE A (GLA), L44-LIKE RIBOSOMAL PROTEIN (L44L) AND FTP3 (FTP3) GENES, COMPLETE CDS" |
| AB037770 | 1.65 | "*HOMO SAPIENS* MRNA FOR KIAA1349 PROTEIN, PARTIAL CDS" |
| AK025586 | 1.65 | "*HOMO SAPIENS* CDNA: FLJ21933 FIS, CLONE HEP04337" |
| NM_138569 | 1.65 | "*HOMO SAPIENS* HYPOTHETICAL PROTEIN MGC18257 (MGC18257), MRNA" |
| AB011542 | 1.65 | "*HOMO SAPIENS* MRNA FOR MEGF9, PARTIAL CDS" |
| NM_015644 | 1.64 | "*HOMO SAPIENS* DKFZP434B103 PROTEIN (DKFZP434B103), MRNA." |
| NM_012472 | 1.64 | "*HOMO SAPIENS* TESTIS SPECIFIC LEUCINE RICH REPEAT PROTEIN (TSLRP), MRNA." |
| NM_031371 | 1.64 | "*HOMO SAPIENS* RBP1-LIKE PROTEIN (BCAA), TRANSCRIPT VARIANT 2, MRNA." |
| AI766221 | 1.64 | "WH68B09.X1 *HOMO SAPIENS* CDNA, 3' END" |

APPENDIX 2-continued

Up Regulated Genes with Treatment Fex:

| Accession Number | Fold Change (Fex/DMSO) | Gene Description |
|---|---|---|
| NM_003878 | 1.64 | "HOMO SAPIENS GAMMA-GLUTAMYL HYDROLASE (CONJUGASE, FOLYLPOLYGAMMAGLUTAMYL HYDROLASE) (GGH), MRNA." |
| NM_000761 | 1.64 | "HOMO SAPIENS CYTOCHROME P450, SUBFAMILY I (AROMATIC COMPOUND-INDUCIBLE), POLYPEPTIDE 2 (CYP1A2), MRNA." |
| AL137595 | 1.64 | HOMO SAPIENS MRNA; CDNA DKFZP434P0810 (FROM CLONE DKFZP434P0810) |
| AL543586 | 1.64 | AL543586 HOMO SAPIENS CDNA |
| AW276618 | 1.64 | "XR17C08.X1 HOMO SAPIENS CDNA, 3' END" |
| AK023156 | 1.64 | "HOMO SAPIENS CDNA FLJ13094 FIS, CLONE NT2RP3002163" |
| NM_022768 | 1.64 | "HOMO SAPIENS RNA BINDING MOTIF PROTEIN 15 (RBM15), MRNA" |
| NM_007150 | 1.64 | "HOMO SAPIENS ZINC FINGER PROTEIN 185 (LIM DOMAIN) (ZNF185), MRNA." |
| AK024371 | 1.64 | "HOMO SAPIENS CDNA FLJ14309 FIS, CLONE PLACE3000221" |
| AP003115 | 1.63 | "HOMO SAPIENS GENOMIC DNA, CHROMOSOME 8Q23, CLONE: KB1000E4" |
| 1401244.3 | 1.63 | NULL |
| NM_000033 | 1.63 | "HOMO SAPIENS ATP-BINDING CASSETTE, SUB-FAMILY D (ALD), MEMBER 1 (ABCD1), MRNA." |
| NM_005542 | 1.63 | "HOMO SAPIENS INSULIN INDUCED GENE 1 (INSIG1), MRNA." |
| NM_004374 | 1.63 | "HOMO SAPIENS CYTOCHROME C OXIDASE SUBUNIT VIC (COX6C), NUCLEAR GENE ENCODING MITOCHONDRIAL PROTEIN, MRNA" |
| NM_017878 | 1.63 | "HOMO SAPIENS HYPOTHETICAL PROTEIN FLJ20556 (FLJ20556), MRNA." |
| NM_006214 | 1.63 | "HOMO SAPIENS PHYTANOYL-COA HYDROXYLASE (REFSUM DISEASE) (PHYH), MRNA." |
| NM_006918 | 1.63 | "HOMO SAPIENS STEROL-C5-DESATURASE (ERG3 DELTA-5-DESATURASE HOMOLOG, FUNGAL)-LIKE (SC5DL), MRNA" |
| NM_014629 | 1.63 | "HOMO SAPIENS RHO GUANINE NUCLEOTIDE EXCHANGE FACTOR (GEF) 10 (ARHGEF10), MRNA." |
| U63721 | 1.63 | "HUMAN ELASTIN (ELN) GENE, PARTIAL CDS, AND LIM-KINASE (LIMK1) GENE, COMPLETE CDS." |
| AU129688 | 1.63 | AU129688 HOMO SAPIENS CDNA 5' END |
| AL122040 | 1.63 | HOMO SAPIENS MRNA; CDNA DKFZP434G1972 (FROM CLONE DKFZP434G1972) |
| AL163263 | 1.63 | NULL |
| NM_014029 | 1.63 | "HOMO SAPIENS HSPC022 PROTEIN (HSPC022), MRNA" |
| NM_003554 | 1.62 | "HOMO SAPIENS OLFACTORY RECEPTOR, FAMILY 1, SUBFAMILY E, MEMBER 2 (OR1E2), MRNA" |
| NM_015074 | 1.62 | "HOMO SAPIENS KINESIN FAMILY MEMBER 1B (KIF1B), MRNA." |
| BC002575 | 1.62 | "HOMO SAPIENS, CLONE IMAGE: 3161568, MRNA, PARTIAL CDS" |
| NM_014131 | 1.62 | "HOMO SAPIENS PRO0514 PROTEIN (PRO0514), MRNA" |
| AL163277 | 1.62 | NULL |
| 1455058.1 | 1.62 | NULL |
| NM_022792 | 1.62 | "HOMO SAPIENS MATRIX METALLOPROTEINASE 19 (MMP19), TRANSCRIPT VARIANT RASI-9, MRNA." |
| NM_020344 | 1.62 | "HOMO SAPIENS SOLUTE CARRIER FAMILY 24 (SODIUM/POTASSIUM/CALCIUM EXCHANGER), MEMBER 2 (SLC24A2), MRNA" |
| NM_003980 | 1.62 | "HOMO SAPIENS MICROTUBULE-ASSOCIATED PROTEIN 7 (MAP7), MRNA." |
| S57283 | 1.62 | "HOMO SAPIENS ENDOTHELIN ET-B RECEPTOR MRNA, COMPLETE CDS" |
| NM_006564 | 1.62 | "HOMO SAPIENS G PROTEIN-COUPLED RECEPTOR (TYMSTR), MRNA." |
| BC011693 | 1.62 | "HOMO SAPIENS, CLONE IMAGE: 3140802, MRNA" |
| AF117615 | 1.62 | "HOMO SAPIENS HEME-BINDING PROTEIN (HBP) MRNA, COMPLETE CDS" |
| NM_002196 | 1.62 | "HOMO SAPIENS INSULINOMA-ASSOCIATED 1 (INSM1), MRNA." |
| 1044035.1 | 1.61 | NULL |
| NM_000438 | 1.61 | "HOMO SAPIENS PAIRED BOX GENE 3 (WAARDENBURG SYNDROME 1) (PAX3), TRANSCRIPT VARIANT PAX3A, MRNA" |
| NM_002405 | 1.61 | "HOMO SAPIENS MANIC FRINGE HOMOLOG (DROSOPHILA) (MFNG), MRNA." |
| NM_006113 | 1.61 | "HOMO SAPIENS VAV 3 ONCOGENE (VAV3), MRNA." |
| AL080148 | 1.61 | HOMO SAPIENS MRNA; CDNA DKFZP434B204 (FROM CLONE DKFZP434B204); PARTIAL CDS |
| AK056569 | 1.61 | "HOMO SAPIENS CDNA FLJ32007 FIS, CLONE NT2RP7009481, WEAKLY SIMILAR TO DROSOPHILA MELANOGASTER DISPATCHED MRNA" |
| NM_018104 | 1.61 | "HOMO SAPIENS HYPOTHETICAL PROTEIN FLJ10474 (FLJ10474), MRNA." |
| NM_012339 | 1.61 | "HOMO SAPIENS TRANSMEMBRANE 4 SUPERFAMILY MEMBER (TETRASPAN NET-7) (NET-7), MRNA." |
| NM_001684 | 1.61 | "HOMO SAPIENS ATPASE, CA++ TRANSPORTING, PLASMA MEMBRANE 4 (ATP2B4), MRNA" |
| NM_016098 | 1.61 | "HOMO SAPIENS HSPC040 PROTEIN (LOC51660), MRNA." |
| NM_002997 | 1.61 | "HOMO SAPIENS SYNDECAN 1 (SDC1), MRNA." |
| AF098485 | 1.61 | "HOMO SAPIENS NAPSIN 2 PRECURSOR, MRNA, PARTIAL SEQUENCE" |

APPENDIX 2-continued

Up Regulated Genes with Treatment Fex:

| Accession Number | Fold Change (Fex/DMSO) | Gene Description |
|---|---|---|
| NM_006672 | 1.61 | "HOMO SAPIENS SOLUTE CARRIER FAMILY 22 (ORGANIC ANION TRANSPORTER), MEMBER 7 (SLC22A7), MRNA." |
| BG476978 | 1.61 | "HUMAN GENE FOR RYUDOCAN CORE PROTEIN, EXON1–5, COMPLETE CDS." |
| AL133568 | 1.61 | HOMO SAPIENS MRNA; CDNA DKFZP434N197 (FROM CLONE DKFZP434N197) |
| NM_005588 | 1.60 | "HOMO SAPIENS MEPRIN A, ALPHA (PABA PEPTIDE HYDROLASE) (MEP1A), MRNA." |
| NM_003943 | 1.60 | "HOMO SAPIENS GENETHONIN 1 (GENX-3414), MRNA." |
| AC006017 | 1.60 | "HUMAN ALR-LIKE PROTEIN MRNA, COMPLETE CDS." |
| AL080186 | 1.60 | HOMO SAPIENS MRNA; CDNA DKFZP564B0769 (FROM CLONE DKFZP564B0769); PARTIAL CDS |
| BC003417 | 1.60 | "HOMO SAPIENS, NADH DEHYDROGENASE (UBIQUINONE) 1 ALPHA SUBCOMPLEX, 10 (42 KD), CLONE MGC: 5103 IMAGE: 3451514, MRNA, COMPLETE CDS" |
| NM_006601 | 1.60 | "HOMO SAPIENS UNACTIVE PROGESTERONE RECEPTOR, 23 KD (P23), MRNA" |
| AF218941 | 1.60 | "HOMO SAPIENS CLONE W39395 FORMIN 2-LIKE PROTEIN MRNA, PARTIAL CDS" |
| AA702323 | 1.60 | "ZI83E03.S1 HOMO SAPIENS CDNA, 3' END" |
| NM_001082 | 1.60 | "HOMO SAPIENS CYTOCHROME P450, SUBFAMILY IVF, POLYPEPTIDE 2 (CYP4F2), MRNA" |
| NM_017726 | 1.60 | "HOMO SAPIENS PROTEIN PHOSPHATASE 1, REGULATORY (INHIBITOR) SUBUNIT 14D (PPP1R14D), MRNA" |
| AA263106 | 1.60 | "HUMAN NUCLEIC ACID BINDING PROTEIN GENE, COMPLETE CDS." |
| NM_003038 | 1.59 | "HOMO SAPIENS SOLUTE CARRIER FAMILY 1 (GLUTAMATE/NEUTRAL AMINO ACID TRANSPORTER), MEMBER 4 (SLC1A4), MRNA." |
| NM_030788 | 1.59 | "HOMO SAPIENS DC-SPECIFIC TRANSMEMBRANE PROTEIN (LOC81501), MRNA" |
| AP000506 | 1.59 | "HOMO SAPIENS GENOMIC DNA, CHROMOSOME 6P21.3, HLA CLASS I REGION, SECTION 5/20" |
| NM_025012 | 1.59 | "HOMO SAPIENS HYPOTHETICAL PROTEIN FLJ13769 (FLJ13769), MRNA" |
| NM_000659 | 1.59 | "HOMO SAPIENS AUTOIMMUNE REGULATOR (AUTOIMMUNE POLYENDOCRINOPATHY CANDIDIASIS ECTODERMAL DYSTROPHY) (AIRE), TRANSCRIPT VARIANT 3, MRNA." |
| NM_004046 | 1.59 | "HOMO SAPIENS ATP SYNTHASE, H+ TRANSPORTING, MITOCHONDRIAL F1 COMPLEX, ALPHA SUBUNIT, ISOFORM 1, CARDIAC MUSCLE (ATP5A1), MRNA" |
| NM_021905 | 1.59 | "HOMO SAPIENS GAMMA-AMINOBUTYRIC ACID (GABA) B RECEPTOR, 1 (GABBR1), TRANSCRIPT VARIANT 4, MRNA." |
| NM_000054 | 1.59 | "HOMO SAPIENS ARGININE VASOPRESSIN RECEPTOR 2 (NEPHROGENIC DIABETES INSIPIDUS) (AVPR2), MRNA." |
| NM_020997 | 1.59 | "HOMO SAPIENS LEFT-RIGHT DETERMINATION, FACTOR B (LEFTB), MRNA" |
| NM_005044 | 1.59 | "HOMO SAPIENS PROTEIN KINASE, X-LINKED (PRKX), MRNA." |
| AI807896 | 1.59 | "HUMAN MYOSIN-IXB MRNA, COMPLETE CDS." |
| NM_001897 | 1.59 | "HOMO SAPIENS CHONDROITIN SULFATE PROTEOGLYCAN 4 (MELANOMA-ASSOCIATED) (CSPG4), MRNA." |
| NM_013937 | 1.59 | "HOMO SAPIENS OLFACTORY RECEPTOR, FAMILY 11, SUBFAMILY A, MEMBER 1 (OR11A1), MRNA." |
| NM_003830 | 1.59 | "HOMO SAPIENS SIALIC ACID BINDING IG-LIKE LECTIN 5 (SIGLEC5), MRNA." |
| NM_006274 | 1.59 | "HOMO SAPIENS SMALL INDUCIBLE CYTOKINE SUBFAMILY A (CYS-CYS), MEMBER 19 (SCYA19), MRNA." |
| AL049365 | 1.59 | HOMO SAPIENS MRNA; CDNA DKFZP586A0618 (FROM CLONE DKFZP586A0618) |
| NM_002980 | 1.59 | "HOMO SAPIENS SECRETIN RECEPTOR (SCTR), MRNA." |
| Y11710 | 1.59 | "H. SAPIENS MRNA FOR EXTRACELLULAR MATRIX PROTEIN COLLAGEN TYPE XIV, C-TERMINUS" |
| AB040928 | 1.59 | "HOMO SAPIENS MRNA FOR KIAA1495 PROTEIN, PARTIAL CDS" |
| BC022416 | 1.59 | "HOMO SAPIENS, CLONE IMAGE: 4243767, MRNA" |
| NM_001103 | 1.58 | "HOMO SAPIENS ACTININ, ALPHA 2 (ACTN2), MRNA." |
| S79669 | 1.58 | "STEROIDOGENIC ACUTE REGULATOY PROTEIN [HUMAN, FOLLICLE CELLS, MRNA, 1641 NT]" |
| 1001739.3 | 1.58 | NULL |
| Z62748 | 1.58 | "H. SAPIENS CPG ISLAND DNA GENOMIC MSE1 FRAGMENT, CLONE 72E12, REVERSE READ CPG72E12.RT1A" |
| NM_001313 | 1.58 | "HOMO SAPIENS COLLAPSIN RESPONSE MEDIATOR PROTEIN 1 (CRMP1), MRNA." |
| NM_000428 | 1.58 | "HOMO SAPIENS LATENT TRANSFORMING GROWTH FACTOR BETA BINDING PROTEIN 2 (LTBP2), MRNA." |
| NM_020653 | 1.58 | "HOMO SAPIENS ZINC FINGER PROTEIN 287 (ZNF287), MRNA" |
| NM_024301 | 1.58 | "HOMO SAPIENS FUKUTIN-RELATED PROTEIN (FKRP), MRNA" |
| AK023517 | 1.58 | "HOMO SAPIENS CDNA FLJ13455 FIS, CLONE PLACE1003256" |

APPENDIX 2-continued

Up Regulated Genes with Treatment Fex:

| Accession Number | Fold Change (Fex/DMSO) | Gene Description |
|---|---|---|
| NM_006188 | 1.58 | "*HOMO SAPIENS* ONCOMODULIN (OCM), MRNA" |
| BC011682 | 1.58 | "*HOMO SAPIENS*, SIMILAR TO CATHEPSIN F, CLONE MGC: 19716 IMAGE: 3535532, MRNA, COMPLETE CDS" |
| AB017915 | 1.58 | "*HOMO SAPIENS* MRNA FOR CHONDROITIN 6-SULFOTRANSFERASE, COMPLETE CDS" |
| NM_002461 | 1.58 | "*HOMO SAPIENS* MEVALONATE (DIPHOSPHO) DECARBOXYLASE (MVD), MRNA." |
| 1503660.5 | 1.58 | NULL |
| BC023566 | 1.57 | "*HOMO SAPIENS*, SIMILAR TO HYPOTHETICAL PROTEIN FLJ31614, CLONE MGC: 20726 IMAGE: 4138119, MRNA, COMPLETE CDS" |
| NM_016615 | 1.57 | "*HOMO SAPIENS* SOLUTE CARRIER FAMILY 6 (NEUROTRANSMITTER TRANSPORTER, GABA), MEMBER 13 (SLC6A13), MRNA." |
| NM_006540 | 1.57 | "*HOMO SAPIENS* NUCLEAR RECEPTOR COACTIVATOR 2 (NCOA2), MRNA." |
| U45432 | 1.57 | "HUMAN ETV6 GENE, PROMOTER REGION AND PARTIAL CDS" |
| NM_014056 | 1.57 | "*HOMO SAPIENS* DKFZP564K247 PROTEIN (DKFZP564K247), MRNA." |
| NM_014191 | 1.57 | "*HOMO SAPIENS* SODIUM CHANNEL, VOLTAGE GATED, TYPE VIII, ALPHA POLYPEPTIDE (SCN8A), MRNA" |
| 240937.12 | 1.57 | "PROTEIN OF UNKNOWN FUNCTION, HAS HIGH SIMILARITY TO UNCHARACTERIZED MOUSE 4931408A02RIK" |
| X07855 | 1.57 | "HUMAN GENE FOR ALPHA-SUBUNIT OF GI2 EXON 9, A GTP-BINDING SIGNAL TRANSDUCTION PROTEIN" |
| NM_001748 | 1.57 | "*HOMO SAPIENS* CALPAIN 2, (M/II) LARGE SUBUNIT (CAPN2), MRNA." |
| NM_024492 | 1.57 | "*HOMO SAPIENS* APOLIPOPROTEIN (A) RELATED GENE C (APOARGC), TRANSCRIPT VARIANT 1, MRNA" |
| AB023185 | 1.57 | "*HOMO SAPIENS* MRNA FOR KIAA0968 PROTEIN, PARTIAL CDS" |
| NM_007036 | 1.57 | "*HOMO SAPIENS* ENDOTHELIAL CELL-SPECIFIC MOLECULE 1 (ESM1), MRNA." |
| D11086 | 1.57 | HUMAN MRNA FOR INTERLEUKIN 2 RECEPTOR GAMMA CHAIN |
| AB014581 | 1.57 | "*HOMO SAPIENS* MRNA FOR KIAA0681 PROTEIN, PARTIAL CDS" |
| NM_001994 | 1.57 | "*HOMO SAPIENS* COAGULATION FACTOR XIII, B POLYPEPTIDE (F13B), MRNA" |
| NM_018162 | 1.57 | "*HOMO SAPIENS* HYPOTHETICAL PROTEIN FLJ10633 (FLJ10633), MRNA." |
| BC000429 | 1.57 | "*HOMO SAPIENS*, CHROMOSOME 14 OPEN READING FRAME 2, CLONE MGC: 8356 IMAGE: 2819801, MRNA, COMPLETE CDS" |
| AF060568 | 1.57 | "HUMAN PROMYELOCYTIC LEUKEMIA ZINC FINGER PROTEIN (PLZF) GENE, COMPLETE CDS." |
| NM_020980 | 1.57 | "*HOMO SAPIENS* AQUAPORIN 9 (AQP9), MRNA." |
| S72487 | 1.56 | "ORF1 5' TO PD-ECGF/TP...ORF2 5' TO PD-ECGF/TP [HUMAN, EPIDERMOID CARCINOMA CELL LINE A431, MRNA, 3 GENES, 1718 NT]" |
| NM_006934 | 1.56 | "*HOMO SAPIENS* SOLUTE CARRIER FAMILY 6 (NEUROTRANSMITTER TRANSPORTER, GLYCINE), MEMBER 9 (SLC6A9), MRNA." |
| NM_006006 | 1.56 | "*HOMO SAPIENS* ZINC FINGER PROTEIN 145 (KRUPPEL-LIKE, EXPRESSED IN PROMYELOCYTIC LEUKEMIA) (ZNF145), MRNA." |
| NM_002652 | 1.56 | "*HOMO SAPIENS* PROLACTIN-INDUCED PROTEIN (PIP), MRNA." |
| NM_000707 | 1.56 | "*HOMO SAPIENS* ARGININE VASOPRESSIN RECEPTOR 1B (AVPR1B), MRNA" |
| NM_000908 | 1.56 | "*HOMO SAPIENS* NATRIURETIC PEPTIDE RECEPTOR C/GUANYLATE CYCLASE C (ATRIONATRIURETIC PEPTIDE RECEPTOR C) (NPR3), MRNA." |
| AB033096 | 1.56 | "*HOMO SAPIENS* MRNA FOR KIAA1270 PROTEIN, PARTIAL CDS" |
| AL137558 | 1.56 | *HOMO SAPIENS* MRNA; CDNA DKFZP434L1020 (FROM CLONE DKFZP434L1020) |
| BI759599 | 1.56 | "603047034F1 *HOMO SAPIENS* CDNA, 5' END" |
| AK023849 | 1.56 | "*HOMO SAPIENS* CDNA FLJ13787 FIS, CLONE PLACE4000670" |
| 1116941.1 | 1.56 | NULL |
| NM_019003 | 1.56 | "*HOMO SAPIENS* SPINDLIN-LIKE (LOC54466), MRNA" |
| NM_031488 | 1.56 | "*HOMO SAPIENS* HYPOTHETICAL PROTEIN DKFZP761I141 (DKFZP761I141), MRNA" |
| AB032947 | 1.56 | "*HOMO SAPIENS* MRNA FOR KIAA1121 PROTEIN, PARTIAL CDS" |
| AF057177 | 1.56 | *HOMO SAPIENS* T-CELL RECEPTOR GAMMA V1 GENE REGION |
| NM_007072 | 1.56 | "*HOMO SAPIENS* HERV-H LTR-ASSOCIATING 2 (HHLA2), MRNA" |
| NM_001145 | 1.56 | "*HOMO SAPIENS* ANGIOGENIN, RIBONUCLEASE, RNASE A FAMILY, 5 (ANG), MRNA." |
| AF287967 | 1.55 | "*HOMO SAPIENS* HOMEOBOX B7 (HOXB7) GENE, PARTIAL CDS; AND HOMEOBOX B6 (HOXB6), HOMEOBOX B5 (HOXB5), HOMEOBOX B4 (HOXB4), AND HOMEOBOX B3 (HOXB3) GENES, COMPLETE CDS" |
| AF251237 | 1.55 | "*HOMO SAPIENS* XAGE-1 MRNA, COMPLETE CDS" |
| 1105672.1 | 1.55 | NULL |
| NM_004312 | 1.55 | "*HOMO SAPIENS* ARRESTIN 3, RETINAL (X-ARRESTIN) (ARR3), MRNA" |
| AK056198 | 1.55 | "*HOMO SAPIENS* CDNA FLJ31636 FIS, CLONE NT2RI2003481" |
| NM_004049 | 1.55 | "*HOMO SAPIENS* BCL2-RELATED PROTEIN A1 (BCL2A1), MRNA." |
| NM_003049 | 1.55 | "*HOMO SAPIENS* SOLUTE CARRIER FAMILY 10 (SODIUM/BILE ACID COTRANSPORTER FAMILY), MEMBER 1 (SLC10A1), MRNA." |

APPENDIX 2-continued

Up Regulated Genes with Treatment Fex:

| Accession Number | Fold Change (Fex/DMSO) | Gene Description |
| --- | --- | --- |
| NM_005122 | 1.55 | "*HOMO SAPIENS* NUCLEAR RECEPTOR SUBFAMILY 1, GROUP I, MEMBER 3 (NR1I3), MRNA" |
| NM_014698 | 1.55 | "*HOMO SAPIENS* KIAA0792 GENE PRODUCT (KIAA0792), MRNA." |
| AF168787 | 1.55 | "*HOMO SAPIENS* VANILLOID RECEPTOR GENE, PARTIAL SEQUENCE; CARKL AND CTNS GENES, COMPLETE CDS; TIP1 GENE, PARTIAL CDS; P2X5B AND P2X5A GENES, COMPLETE CDS; AND HUMINAE GENE, PARTIAL CDS" |
| AP000517 | 1.55 | "*HOMO SAPIENS* GENOMIC DNA, CHROMOSOME 6P21.3, HLA CLASS I REGION, SECTION 16/20" |
| NM_014509 | 1.55 | "*HOMO SAPIENS* SERINE HYDROLASE-LIKE (SERHL), MRNA" |
| M96843 | 1.55 | "HUMAN STRIATED MUSCLE CONTRACTION REGULATORY PROTEIN (ID2B) MRNA, COMPLETE CDS" |
| NM_003854 | 1.55 | "*HOMO SAPIENS* INTERLEUKIN 1 RECEPTOR-LIKE 2 (IL1RL2), MRNA." |
| NM_003787 | 1.55 | "*HOMO SAPIENS* NUCLEOLAR PROTEIN 4 (NOL4), MRNA." |
| NM_005364 | 1.55 | "*HOMO SAPIENS* MELANOMA ANTIGEN, FAMILY A, 8 (MAGEA8), MRNA" |
| NM_021969 | 1.55 | "*HOMO SAPIENS* NUCLEAR RECEPTOR SUBFAMILY 0, GROUP B, MEMBER 2 (NR0B2), MRNA." |
| Z83075 | 1.55 | "*H. SAPIENS* FANCONI ANAEMIA GROUP A GENE, EXONS 12, 13 AND 14" |
| NM_000733 | 1.55 | "*HOMO SAPIENS* CD3E ANTIGEN, EPSILON POLYPEPTIDE (TIT3 COMPLEX) (CD3E), MRNA." |
| NM_002985 | 1.55 | "*HOMO SAPIENS* SMALL INDUCIBLE CYTOKINE A5 (RANTES) (SCYA5), MRNA" |
| NM_012306 | 1.55 | "*HOMO SAPIENS* LIFEGUARD (KIAA0950), MRNA" |
| AF195821 | 1.55 | "*HOMO SAPIENS* TNG2 (TNG2) MRNA, COMPLETE CDS" |
| NM_001231 | 1.55 | "*HOMO SAPIENS* CALSEQUESTRIN 1 (FAST-TWITCH, SKELETAL MUSCLE) (CASQ1), NUCLEAR GENE ENCODING MITOCHONDRIAL PROTEIN, MRNA." |
| AJ414563 | 1.55 | *HOMO SAPIENS* CX25 GENE FOR CONNEXIN25 |
| AK074985 | 1.55 | "*HOMO SAPIENS* CDNA FLJ90504 FIS, CLONE NT2RP3004090, WEAKLY SIMILAR TO GOLIATH PROTEIN" |
| NM_001056 | 1.54 | "*HOMO SAPIENS* SULFOTRANSFERASE FAMILY, CYTOSOLIC, 1C, MEMBER 1 (SULT1C1), MRNA" |
| NM_001186 | 1.54 | "*HOMO SAPIENS* BTB AND CNC HOMOLOGY 1, BASIC LEUCINE ZIPPER TRANSCRIPTION FACTOR 1 (BACH1), MRNA." |
| NM_000207 | 1.54 | "*HOMO SAPIENS* INSULIN (INS), MRNA." |
| NM_006760 | 1.54 | "*HOMO SAPIENS* UROPLAKIN 2 (UPK2), MRNA." |
| T54189 | 1.54 | "YA92C11.R1 *HOMO SAPIENS* CDNA, 5' END" |
| AK022712 | 1.54 | "*HOMO SAPIENS* CDNA FLJ12650 FIS, CLONE NT2RM4002054" |
| NM_018249 | 1.54 | "*HOMO SAPIENS* CDK5 REGULATORY SUBUNIT ASSOCIATED PROTEIN 2 (CDK5RAP2), MRNA" |
| NM_015366 | 1.54 | "*HOMO SAPIENS* RHO GTPASE ACTIVATING PROTEIN 8 (ARHGAP8), MRNA." |
| 1452330.5 | 1.54 | NULL |
| L25940 | 1.54 | "*HOMO SAPIENS* INTEGRAL NUCLEAR ENVELOPE INNER MEMBRANE PROTEIN (LBR) GENE, EXON 11" |
| AA318707 | 1.54 | "HUMAN CYSTIC FIBROSIS ANTIGEN MRNA, COMPLETE CDS." |
| AL137407 | 1.54 | *HOMO SAPIENS* MRNA; CDNA DKFZP434M232 (FROM CLONE DKFZP434M232) |
| NM_002248 | 1.54 | "*HOMO SAPIENS* POTASSIUM INTERMEDIATE/SMALL CONDUCTANCE CALCIUM-ACTIVATED CHANNEL, SUBFAMILY N, MEMBER 1 (KCNN1), MRNA." |
| NM_005544 | 1.54 | "*HOMO SAPIENS* INSULIN RECEPTOR SUBSTRATE 1 (IRS1), MRNA." |
| AF281074 | 1.54 | "*HOMO SAPIENS* NEUROPILIN 2 (NRP2) GENE, COMPLETE CDS, ALTERNATIVELY SPLICED" |
| AL359946 | 1.54 | *HOMO SAPIENS* MRNA; CDNA DKFZP762G026 (FROM CLONE DKFZP762G026) |
| AL137296 | 1.54 | *HOMO SAPIENS* MRNA; CDNA DKFZP434M0416 (FROM CLONE DKFZP434M0416) |
| NM_001068 | 1.54 | "*HOMO SAPIENS* TOPOISOMERASE (DNA) II BETA (180 KD) (TOP2B), MRNA." |
| NM_014213 | 1.54 | "*HOMO SAPIENS* HOMEO BOX D9 (HOXD9), MRNA." |
| NM_003392 | 1.54 | "*HOMO SAPIENS* WINGLESS-TYPE MMTV INTEGRATION SITE FAMILY, MEMBER 5A (WNT5A), MRNA." |
| AA463818 | 1.54 | ZX67D04.R1 *HOMO SAPIENS* CDNA 5' END |
| NM_032578 | 1.54 | "*HOMO SAPIENS* MYOPALLADIN (FLJ14437), MRNA" |
| AL512713 | 1.54 | *HOMO SAPIENS* MRNA; CDNA DKFZP547D086 (FROM CLONE DKFZP547D086) |
| NM_017707 | 1.54 | "*HOMO SAPIENS* HYPOTHETICAL PROTEIN FLJ20199 (FLJ20199), MRNA." |
| NM_014217 | 1.54 | "*HOMO SAPIENS* POTASSIUM CHANNEL, SUBFAMILY K, MEMBER 2 (KCNK2), MRNA" |
| AK025814 | 1.54 | "*HOMO SAPIENS* CDNA: FLJ22161 FIS, CLONE HRC00290" |
| X69908 | 1.54 | HUMAN GENE FOR MITOCHONDRIAL ATP SYNTHASE C SUBUNIT (P2 FORM). |
| AL163300 | 1.54 | *HOMO SAPIENS* CHROMOSOME 21 SEGMENT HS21C100 |

APPENDIX 2-continued

Up Regulated Genes with Treatment Fex:

| Accession Number | Fold Change (Fex/DMSO) | Gene Description |
|---|---|---|
| NM_024895 | 1.53 | "HOMO SAPIENS HYPOTHETICAL PROTEIN FLJ23209 (FLJ23209), MRNA" |
| NM_058164 | 1.53 | "HOMO SAPIENS OLFACTOMEDIN 2 (OLFM2), MRNA." |
| AK074293 | 1.53 | "HOMO SAPIENS CDNA FLJ23713 FIS, CLONE HEP12771, HIGHLY SIMILAR TO GRPE PROTEIN HOMOLOG 2 PRECURSOR" |
| D50375 | 1.53 | "HOMO SAPIENS MRNA FOR SILENCER ELEMENT, COMPLETE CDS" |
| NM_003350 | 1.53 | "HOMO SAPIENS UBIQUITIN-CONJUGATING ENZYME E2 VARIANT 2 (UBE2V2), MRNA." |
| NM_024320 | 1.53 | "HOMO SAPIENS HYPOTHETICAL PROTEIN MGC11242 (MGC11242), MRNA" |
| AA873020 | 1.53 | "OA17H03.S1 HOMO SAPIENS CDNA, 3' END" |
| NM_004385 | 1.53 | "HOMO SAPIENS CHONDROITIN SULFATE PROTEOGLYCAN 2 (VERSICAN) (CSPG2), MRNA." |
| NM_022127 | 1.53 | "HOMO SAPIENS SOLUTE CARRIER FAMILY 28 (SODIUM-COUPLED NUCLEOSIDE TRANSPORTER), MEMBER 3 (SLC28A3), MRNA" |
| NM_000359 | 1.53 | "HOMO SAPIENS TRANSGLUTAMINASE 1 (K POLYPEPTIDE EPIDERMAL TYPE I, PROTEIN-GLUTAMINE-GAMMA-GLUTAMYLTRANSFERASE) (TGM1), MRNA." |
| AL137616 | 1.53 | HOMO SAPIENS MRNA; CDNA DKFZP434O1311 (FROM CLONE DKFZP434O1311) |
| AA297451 | 1.53 | EST112980 HOMO SAPIENS CDNA 5' END/CLONE_END = 5' |
| 1503632.3 | 1.53 | NULL |
| NM_000387 | 1.53 | "HOMO SAPIENS SOLUTE CARRIER FAMILY 25 (CARNITINE/ACYLCARNITINE TRANSLOCASE), MEMBER 20 (SLC25A20), MITOCHONDRIAL PROTEIN ENCODED BY NUCLEAR GENE, MRNA" |
| AF139131 | 1.53 | "HOMO SAPIENS BECLIN 1 (BECN1) MRNA, COMPLETE CDS" |
| NM_080792 | 1.53 | "HOMO SAPIENS BRAIN-IMMUNOGLOBULIN-LIKE MOLECULE WITH TYROSINE-BASED ACTIVATION MOTIFS (BIT), MRNA" |
| M63391 | 1.53 | "HUMAN DESMIN GENE, COMPLETE CDS." |
| D86980 | 1.52 | "HUMAN MRNA FOR KIAA0227 GENE, PARTIAL CDS" |
| NM_138379 | 1.52 | "HOMO SAPIENS HYPOTHETICAL PROTEIN BC008988 (LOC91937), MRNA" |
| AF217490 | 1.52 | "HOMO SAPIENS FRAGILE 16D OXIDO REDUCTASE (FOR) GENE, EXONS 8, 9, AND PARTIAL CDS" |
| NM_003629 | 1.52 | "HOMO SAPIENS PHOSPHOINOSITIDE-3-KINASE, REGULATORY SUBUNIT, POLYPEPTIDE 3 (P55, GAMMA) (PIK3R3), MRNA." |
| NM_052884 | 1.52 | "HOMO SAPIENS SIALIC ACID BINDING IG-LIKE LECTIN 11 (SIGLEC11), MRNA" |
| AK024406 | 1.52 | "HOMO SAPIENS CDNA FLJ14344 FIS, CLONE THYRO1001142" |
| AL162066 | 1.52 | HOMO SAPIENS MRNA; CDNA DKFZP762D096 (FROM CLONE DKFZP762D096); PARTIAL CDS |
| AK055539 | 1.52 | "HOMO SAPIENS CDNA FLJ30977 FIS, CLONE HHDPC2000095, HIGHLY SIMILAR TO CRICETULUS GRISEUS LAYILIN MRNA" |
| NM_015425 | 1.52 | "HOMO SAPIENS DKFZP586M0122 PROTEIN (DKFZP586M0122), MRNA." |
| NM_032108 | 1.52 | "HOMO SAPIENS SEMA DOMAIN, TRANSMEMBRANE DOMAIN (TM), AND CYTOPLASMIC DOMAIN, (SEMAPHORIN) 6B (SEMA6B), MRNA." |
| NM_000811 | 1.52 | "HOMO SAPIENS GAMMA-AMINOBUTYRIC ACID (GABA) A RECEPTOR, ALPHA 6 (GABRA6), MRNA" |
| AI718785 | 1.52 | AS58H10.X1 HOMO SAPIENS CDNA 3' END |
| NM_000748 | 1.52 | "HOMO SAPIENS CHOLINERGIC RECEPTOR, NICOTINIC, BETA POLYPEPTIDE 2 (NEURONAL) (CHRNB2), MRNA" |
| NM_006850 | 1.52 | "HOMO SAPIENS INTERLEUKIN 24 (IL24), MRNA." |
| J05312 | 1.52 | "HUMAN LIPOPROTEIN ASSOCIATED COAGULATION INHIBITOR (LACI) GENE, EXON 9." |
| NM_002588 | 1.52 | "HOMO SAPIENS PROTOCADHERIN GAMMA SUBFAMILY C, 3 (PCDHGC3), TRANSCRIPT VARIANT 1, MRNA" |
| NM_031929 | 1.52 | "HOMO SAPIENS TESTIS-SPECIFIC TRANSCRIPT, Y-LINKED 11 (TTTY11), MRNA" |
| AI038940 | 1.52 | "OY86E05.X1 HOMO SAPIENS CDNA, 3' END" |
| NM_003482 | 1.52 | "HOMO SAPIENS MYELOID/LYMPHOID OR MIXED-LINEAGE LEUKEMIA 2 (MLL2), MRNA" |
| U66047 | 1.52 | HOMO SAPIENS CLONE Z'3-1 PLACENTA EXPRESSED MRNA FROM CHROMOSOME X |
| NM_014909 | 1.52 | "HOMO SAPIENS KIAA1036 PROTEIN (KIAA1036), MRNA." |
| AA873769 | 1.52 | "OI06F02.S1 NCI_CGAP_GC4 HOMO SAPIENS CDNA CLONE IMAGE: 1475739 3', MRNA SEQUENCE" |
| AA037140 | 1.52 | "ZC53F10.R1 HOMO SAPIENS CDNA, 5' END" |
| NM_006365 | 1.52 | "HOMO SAPIENS TRANSCRIPTIONAL ACTIVATOR OF THE C-FOS PROMOTER (CROC4), MRNA" |
| NM_003803 | 1.52 | "HOMO SAPIENS MYOMESIN 1 (SKELEMIN) (185 KD) (MYOM1), MRNA." |
| AB023151 | 1.52 | "HOMO SAPIENS MRNA FOR KIAA0934 PROTEIN, PARTIAL CDS" |
| NM_006662 | 1.52 | "HOMO SAPIENS SNF2-RELATED CBP ACTIVATOR PROTEIN (SRCAP), MRNA." |
| NM_032369 | 1.52 | "HOMO SAPIENS HYPOTHETICAL PROTEIN MGC15619 (MGC15619), MRNA" |

APPENDIX 2-continued

Up Regulated Genes with Treatment Fex:

| Accession Number | Fold Change (Fex/DMSO) | Gene Description |
|---|---|---|
| AL163259 | 1.52 | NULL |
| NM_000836 | 1.52 | "HOMO SAPIENS GLUTAMATE RECEPTOR, IONOTROPIC, N-METHYL D-ASPARTATE 2D (GRIN2D), MRNA" |
| M10014 | 1.51 | HUMAN FIBRINOGEN GENE (FGG). |
| NM_017618 | 1.51 | "HOMO SAPIENS HYPOTHETICAL PROTEIN FLJ20006 (FLJ20006), MRNA" |
| AB009076 | 1.51 | "HOMO SAPIENS GENE FOR COMPLEMENT C1S, PARTIAL CDS" |
| AF118081 | 1.51 | "HOMO SAPIENS PRO1900 MRNA, COMPLETE CDS" |
| NM_004694 | 1.51 | "HOMO SAPIENS SOLUTE CARRIER FAMILY 16 (MONOCARBOXYLIC ACID TRANSPORTERS), MEMBER 6 (SLC16A6), MRNA." |
| AI052482 | 1.51 | "OZ19F08.X1 HOMO SAPIENS CDNA, 3' END" |
| 887776.1 | 1.51 | "PROTEIN WITH VERY STRONG SIMILARITY TO ALBUMIN (RAT ALB), WHICH IS A BLOOD PLASMA PROTEIN, HUMAN ALB IS ASSOCIATED WITH FAMILIAL DYSALBUMINEMIC HYPERTHYROXINEMIA AND ANALBUMINEMIA, MEMBER OF THE SERUM ALBUMIN FAMILY" |
| AF313465 | 1.51 | "HOMO SAPIENS SODIUM BICARBONATE COTRANSPORTER (SLC4A9) MRNA, PARTIAL CDS" |
| M17285 | 1.51 | HUMAN INSULIN-LIKE GROWTH FACTOR (IGF-II) GENE |
| M87708 | 1.51 | HUMAN SIMPLE REPEAT POLYMORPHISM |
| NM_080739 | 1.51 | "HOMO SAPIENS CHROMOSOME 20 OPEN READING FRAME 141 (C20ORF141), MRNA." |
| NM_032621 | 1.51 | "HOMO SAPIENS X-LINKED PROTEIN (DJ79P11.1), MRNA." |
| NM_005425 | 1.51 | "HOMO SAPIENS TRANSITION PROTEIN 2 (DURING HISTONE TO PROTAMINE REPLACEMENT) (TNP2), MRNA." |
| NM_007017 | 1.51 | "HOMO SAPIENS SRY (SEX DETERMINING REGION Y)-BOX 30 (SOX30), MRNA." |
| NM_000340 | 1.51 | "HOMO SAPIENS SOLUTE CARRIER FAMILY 2 (FACILITATED GLUCOSE TRANSPORTER), MEMBER 2 (SLC2A2), MRNA." |
| NM_018652 | 1.51 | "HOMO SAPIENS GOLGIN-LIKE PROTEIN (GLP), MRNA" |
| NM_031275 | 1.51 | "HOMO SAPIENS TESTIS EXPRESSED SEQUENCE 12 (TEX12), MRNA" |
| NM_002650 | 1.51 | "HOMO SAPIENS PHOSPHATIDYLINOSITOL 4-KINASE, CATALYTIC, ALPHA POLYPEPTIDE (PIK4CA), TRANSCRIPT VARIANT 1, MRNA." |
| NM_006258 | 1.51 | "HOMO SAPIENS PROTEIN KINASE, CGMP-DEPENDENT, TYPE I (PRKG1), MRNA." |
| AB020671 | 1.51 | "HOMO SAPIENS MRNA FOR KIAA0864 PROTEIN, PARTIAL CDS" |
| NM_024787 | 1.51 | "HOMO SAPIENS HYPOTHETICAL PROTEIN FLJ12526 (FLJ12526), MRNA" |
| AF055378 | 1.51 | "HOMO SAPIENS LONG FORM TRANSCRIPTION FACTOR C-MAF (C-MAF) GENE, EXON 2 AND PARTIAL CDS" |
| BC001427 | 1.51 | "HOMO SAPIENS, HYPOTHETICAL PROTEIN FLJ11320, CLONE MGC: 894 IMAGE: 3139599, MRNA, COMPLETE CDS" |
| NM_022803 | 1.51 | "HOMO SAPIENS UNCOUPLING PROTEIN 3 (MITOCHONDRIAL, PROTON CARRIER) (UCP3), TRANSCRIPT VARIANT SHORT, NUCLEAR GENE ENCODING MITOCHONDRIAL PROTEIN, MRNA." |
| NM_016944 | 1.51 | "HOMO SAPIENS TASTE RECEPTOR, TYPE 2, MEMBER 4 (TAS2R4), MRNA" |
| L44140 | 1.51 | "HUMAN CHROMOSOME X REGION FROM FILAMIN (FLN) GENE TO GLUCOSE-6-PHOSPHATE DEHYDROGENASE (G6PD) GENE, COMPLETE CDS'S." |
| AB046814 | 1.51 | "HOMO SAPIENS MRNA FOR KIAA1594 PROTEIN, PARTIAL CDS" |
| AK000694 | 1.50 | "HOMO SAPIENS CDNA FLJ20687 FIS, CLONE KAIA302, HIGHLY SIMILAR TO AF039702 HOMO SAPIENS ANTIGEN NY-CO-43 MRNA" |
| AK024999 | 1.50 | "HOMO SAPIENS CDNA: FLJ21346 FIS, CLONE COL02705" |
| NM_003212 | 1.50 | "HOMO SAPIENS TERATOCARCINOMA-DERIVED GROWTH FACTOR 1 (TDGF1), MRNA" |
| NM_014634 | 1.50 | "HOMO SAPIENS KIAA0015 GENE PRODUCT (KIAA0015), MRNA." |
| AP000497 | 1.50 | "HOMO SAPIENS GENOMIC DNA, CHROMOSOME 3P21.3, CLONE: 301 TO 308, ANTI-ONCOGENE REGION, SECTION 5/5" |
| NM_020482 | 1.50 | "HOMO SAPIENS ACTIVATOR OF CAMP-RESPONSIVE ELEMENT MODULATOR (CREM) IN TESTIS (ACT), MRNA" |
| NM_001330 | 1.50 | "HOMO SAPIENS CARDIOTROPHIN 1 (CTF1), MRNA." |
| NM_005275 | 1.50 | "HOMO SAPIENS GUANINE NUCLEOTIDE BINDING PROTEIN-LIKE 1 (GNL1), MRNA" |

APPENDIX 3

Down Regulated Genes with Treatment Fex:

| Accession Number | Fold Change (Fex/DMSO) | Gene Description |
|---|---|---|
| NM_006984 | 0.13 | "HOMO SAPIENS CLAUDIN 10 (CLDN10), MRNA" |
| NM_000710 | 0.17 | "HOMO SAPIENS BRADYKININ RECEPTOR B1 (BDKRB1), MRNA" |

APPENDIX 3-continued

Down Regulated Genes with Treatment Fex:

| Accession Number | Fold Change (Fex/DMSO) | Gene Description |
|---|---|---|
| NM_031958 | 0.20 | "*HOMO SAPIENS* KERATIN ASSOCIATED PROTEIN 3.1 (KRTAP3.1), MRNA" |
| 475365.6 | 0.21 | "MEMBER OF THE CARBOXYPEPTIDASE A METALLOPROTEASE (M14) FAMILY OF ZINC CARBOXYPEPTIDASES, HAS MODERATE SIMILARITY TO CARBOXYPEPTIDASE B2 (MOUSE CPB2), WHICH IS A PLASMA PRO-FORM METALLOPROTEASE THAT IS AN ACUTE PHASE PROTEIN UPREGULATED IN INFLAMMATION" |
| AK026959 | 0.23 | "*HOMO SAPIENS* CDNA: FLJ23306 FIS, CLONE HEP11541" |
| NM_030572 | 0.23 | "*HOMO SAPIENS* HYPOTHETICAL PROTEIN MGC10946 (MGC10946), MRNA" |
| NM_004407 | 0.24 | "*HOMO SAPIENS* DENTIN MATRIX ACIDIC PHOSPHOPROTEIN (DMP1), MRNA" |
| NM_018436 | 0.25 | "*HOMO SAPIENS* ALLANTOICASE (ALLC), MRNA" |
| NM_003102 | 0.26 | "*HOMO SAPIENS* SUPEROXIDE DISMUTASE 3, EXTRACELLULAR (SOD3), MRNA" |
| NM_004575 | 0.26 | "*HOMO SAPIENS* POU DOMAIN, CLASS 4, TRANSCRIPTION FACTOR 2 (POU4F2), MRNA" |
| D28113 | 0.26 | "HUMAN MRNA FOR MOBP (MYELIN-ASSOCIATED OLIGODENDROCYTIC BASIC PROTEIN), COMPLETE CDS, CLONE HOPRP1" |
| NM_144658 | 0.28 | "*HOMO SAPIENS* HYPOTHETICAL PROTEIN FLJ32122 (FLJ32122), MRNA" |
| NM_000584 | 0.29 | "*HOMO SAPIENS* INTERLEUKIN 8 (IL8), MRNA." |
| NM_024687 | 0.30 | "*HOMO SAPIENS* HYPOTHETICAL PROTEIN FLJ23049 (FLJ23049), MRNA" |
| NM_014391 | 0.31 | "*HOMO SAPIENS* CARDIAC ANKYRIN REPEAT PROTEIN (CARP), MRNA" |
| Z60717 | 0.31 | "*H. SAPIENS* CPG ISLAND DNA GENOMIC MSE1 FRAGMENT, CLONE 33A10, FORWARD READ CPG33A10.FT1|" |
| NM_024340 | 0.32 | "*HOMO SAPIENS* HYPOTHETICAL PROTEIN MGC4179 (MGC4179), MRNA" |
| D86425 | 0.32 | "*HOMO SAPIENS* MRNA FOR OSTEONIDOGEN, COMPLETE CDS" |
| AL122109 | 0.33 | *HOMO SAPIENS* MRNA; CDNA DKFZP434M1827 (FROM CLONE DKFZP434M1827) |
| NM_024306 | 0.33 | "*HOMO SAPIENS* FATTY ACID HYDROXYLASE (FAAH), MRNA" |
| AF043195 | 0.34 | "*HOMO SAPIENS* TIGHT JUNCTION PROTEIN ZO-2 (TJP2) GENE, ALTERNATIVE PROMOTER PA AND EXON A" |
| NM_002089 | 0.35 | "*HOMO SAPIENS* GRO2 ONCOGENE (GRO2), MRNA." |
| NM_018679 | 0.35 | "*HOMO SAPIENS* T-COMPLEX 11 (MOUSE) (TCP11), MRNA" |
| NM_003311 | 0.35 | "*HOMO SAPIENS* TUMOR SUPPRESSING SUBTRANSFERABLE CANDIDATE 3 (TSSC3), MRNA." |
| NM_014890 | 0.36 | "*HOMO SAPIENS* DOWNREGULATED IN OVARIAN CANCER 1 (DOC1), MRNA." |
| NM_032883 | 0.36 | "*HOMO SAPIENS* CHROMOSOME 20 OPEN READING FRAME 100 (C20ORF100), MRNA" |
| NM_005925 | 0.36 | "*HOMO SAPIENS* MEPRIN A, BETA (MEP1B), MRNA" |
| BC000623 | 0.37 | "*HOMO SAPIENS*, SIMILAR TO HYPOTHETICAL PROTEIN FLJ20211, CLONE MGC: 1068 IMAGE: 3346325, MRNA, COMPLETE CDS" |
| 180648.1 | 0.37 | PROTEIN CONTAINING FIVE MORN (MEMBRANE OCCUPATION AND RECOGNITION NEXUS) REPEATS |
| NM_032263 | 0.38 | "*HOMO SAPIENS* HYPOTHETICAL PROTEIN DKFZP434B227 (DKFZP434B227), MRNA" |
| AK023937 | 0.38 | "*HOMO SAPIENS* CDNA FLJ13875 FIS, CLONE THYRO1001374, WEAKLY SIMILAR TO CYTOSOLIC ACYL COENZYME A THIOESTER HYDROLASE (EC 3.1.2.2)" |
| AK026071 | 0.38 | "*HOMO SAPIENS* CDNA: FLJ22418 FIS, CLONE HRC08590" |
| D55641 | 0.39 | "HUMAN SKIN FIBROBLAST PABL (PSEUDOAUTOSOMAL BOUNDARY-LIKE SEQUENCE) MRNA, CLONE SK13" |
| BF692587 | 0.39 | 602248939F1 *HOMO SAPIENS* CDNA 5' END |
| AF168681 | 0.39 | "*HOMO SAPIENS* CRIM1 PROTEIN GENE, PARTIAL CDS; AND FEZ2 GENE, PARTIAL SEQUENCE" |
| AL046937 | 0.40 | DKFZP586I2417_R1 *HOMO SAPIENS* CDNA 5' END |
| NM_014331 | 0.40 | "*HOMO SAPIENS* SOLUTE CARRIER FAMILY 7, (CATIONIC AMINO ACID TRANSPORTER, Y+ SYSTEM) MEMBER 11 (SLC7A11), MRNA" |
| NM_012275 | 0.41 | "*HOMO SAPIENS* INTERLEUKIN 1 FAMILY, MEMBERS 5 (DELTA) (IL1F5), MRNA" |
| NM_015003 | 0.42 | "*HOMO SAPIENS* GOLGIN-67 (KIAA0855), MRNA" |
| U09197 | 0.42 | HUMAN 5.5 KB MRNA UPREGULATED IN RETINOIC ACID TREATED HL-60 NEUTROPHILIC CELLS |
| AL137477 | 0.42 | *HOMO SAPIENS* MRNA; CDNA DKFZP434K2323 (FROM CLONE DKFZP434K2323); PARTIAL CDS |
| NM_006516 | 0.42 | "*HOMO SAPIENS* SOLUTE CARRIER FAMILY 2 (FACILITATED GLUCOSE TRANSPORTER), MEMBER 1 (SLC2A1), MRNA." |
| AI435998 | 0.42 | "TH80E05.X1 *HOMO SAPIENS* CDNA, 3' END" |
| AL050169 | 0.42 | *HOMO SAPIENS* MRNA; CDNA DKFZP586D0922 (FROM CLONE DKFZP586D0922) |
| NM_006279 | 0.42 | "*HOMO SAPIENS* SIALYLTRANSFERASE 6 (N-ACETYLLACOSAMINIDE ALPHA 2,3-SIALYLTRANSFERASE) (SIAT6), MRNA." |
| NM_006163 | 0.42 | "*HOMO SAPIENS* NUCLEAR FACTOR (ERYTHROID-DERIVED 2), 45 KD (NFE2), MRNA." |
| BC035810 | 0.43 | "*HOMO SAPIENS*, CLONE IMAGE: 5754421, MRNA, PARTIAL CDS" |
| AK026485 | 0.43 | "*HOMO SAPIENS* CDNA: FLJ22832 FIS, CLONE KAIA4195" |
| NM_017911 | 0.43 | "*HOMO SAPIENS* HYPOTHETICAL PROTEIN FLJ20635 (FLJ20635), MRNA" |
| L40326 | 0.43 | "*HOMO SAPIENS* HEPATITIS B VIRUS X-ASSOCIATED PROTEIN 1 MRNA, COMPLETE CDS" |
| AK000819 | 0.44 | "*HOMO SAPIENS* CDNA FLJ20812 FIS, CLONE ADSE01316" |
| NM_002423 | 0.44 | "*HOMO SAPIENS* MATRIX METALLOPROTEINASE 7 (MATRILYSIN, UTERINE) (MMP7), MRNA." |

APPENDIX 3-continued

Down Regulated Genes with Treatment Fex:

| Accession Number | Fold Change (Fex/DMSO) | Gene Description |
|---|---|---|
| AK097430 | 0.44 | "HOMO SAPIENS CDNA FLJ40111 FIS, CLONE TESTI2008320, MODERATELY SIMILAR TO HOMO SAPIENS MITOGEN-ACTIVATED PROTEIN KINASE PHOSPHATASE X (MKPX) MRNA" |
| NM_015515 | 0.45 | "HOMO SAPIENS TYPE I INTERMEDIATE FILAMENT CYTOKERATIN (HAIK1), MRNA." |
| NM_139215 | 0.45 | "HOMO SAPIENS TAF15 RNA POLYMERASE II, TATA BOX BINDING PROTEIN (TBP)-ASSOCIATED FACTOR, 68 KD (TAF15), TRANSCRIPT VARIANT 1, MRNA" |
| NM_003025 | 0.45 | "HOMO SAPIENS SH3-DOMAIN GRB2-LIKE 1 (SH3GL1), MRNA." |
| BC007008 | 0.45 | "HOMO SAPIENS, CRYSTALLIN, ALPHA B, CLONE MGC: 12326 IMAGE: 3933748, MRNA, COMPLETE CDS" |
| NM_005195 | 0.46 | "HOMO SAPIENS CCAAT/ENHANCER BINDING PROTEIN (C/EBP), DELTA (CEBPD), MRNA." |
| NM_004591 | 0.46 | "HOMO SAPIENS SMALL INDUCIBLE CYTOKINE SUBFAMILY A (CYS-CYS), MEMBER 20 (SCYA20), MRNA" |
| AK024998 | 0.46 | "HOMO SAPIENS CDNA: FLJ21345 FIS, CLONE COL02694" |
| NM_017773 | 0.47 | "HUMAN DEFENSIN 6 MRNA, COMPLETE CDS." |
| AP000505 | 0.47 | "HOMO SAPIENS GENOMIC DNA, CHROMOSOME 6P21.3, HLA CLASS I REGION, SECTION 4/20" |
| NM_012206 | 0.47 | "HOMO SAPIENS HEPATITIS A VIRUS CELLULAR RECEPTOR 1 (HAVCR-1), MRNA." |
| NM_016218 | 0.47 | "HOMO SAPIENS POLYMERASE (DNA-DIRECTED) KAPPA (POLK), MRNA" |
| NM_021634 | 0.47 | "HOMO SAPIENS LEUCINE-RICH REPEAT-CONTAINING G PROTEIN-COUPLED RECEPTOR 7 (LGR7), MRNA" |
| AB032969 | 0.47 | "HOMO SAPIENS MRNA FOR KIAA1143 PROTEIN, PARTIAL CDS" |
| NM_005354 | 0.47 | "HOMO SAPIENS JUN D PROTO-ONCOGENE (JUND), MRNA." |
| NM_001554 | 0.48 | "HOMO SAPIENS CYSTEINE-RICH, ANGIOGENIC INDUCER, 61 (CYR61), MRNA" |
| NM_000928 | 0.48 | "HOMO SAPIENS PHOSPHOLIPASE A2, GROUP IB (PANCREAS) (PLA2G1B), NUCLEAR GENE ENCODING MITOCHONDRIAL PROTEIN, MRNA" |
| NM_017736 | 0.48 | "HOMO SAPIENS HYPOTHETICAL PROTEIN FLJ20274 (FLJ20274), MRNA" |
| M37457 | 0.48 | "HUMAN NA+, K+-ATPASE CATALYTIC SUBUNIT ALPHA-III ISOFORM GENE, EXON 23, CLONE LAMBDA-NK-ALPHA-R3-2" |
| NM_000530 | 0.49 | "HOMO SAPIENS MYELIN PROTEIN ZERO (CHARCOT-MARIE-TOOTH NEUROPATHY 1B) (MPZ), MRNA" |
| D43639 | 0.49 | "HUMAN GENE FOR PREPROADRENOMEDULLIN, COMPLETE CDS (EXON 1–4)" |
| NM_005420 | 0.49 | "HOMO SAPIENS SULFOTRANSFERASE, ESTROGEN-PREFERRING (STE), MRNA." |
| NM_032837 | 0.49 | "HOMO SAPIENS HYPOTHETICAL PROTEIN FLJ14775 (FLJ14775), MRNA" |
| 203751.1 | 0.49 | PROTEIN OF UNKNOWN FUNCTION |
| NM_021101 | 0.49 | "HOMO SAPIENS CLAUDIN 1 (CLDN1), MRNA." |
| NM_024889 | 0.49 | "HOMO SAPIENS HYPOTHETICAL PROTEIN FLJ23537 (FLJ23537), MRNA" |
| NM_022133 | 0.49 | "HOMO SAPIENS SORTING NEXIN 16 (SNX16), MRNA" |
| AB011128 | 0.49 | "HOMO SAPIENS MRNA FOR KIAA0556 PROTEIN, PARTIAL CDS" |
| AK090409 | 0.49 | HOMO SAPIENS MRNA FOR FLJ00300 PROTEIN |
| NM_022122 | 0.49 | "HOMO SAPIENS MATRIX METALLOPROTEINASE 27 (MMP27), MRNA" |
| NM_001300 | 0.50 | "HOMO SAPIENS CORE PROMOTER ELEMENT BINDING PROTEIN (COPEB), MRNA" |
| NM_003557 | 0.50 | "HOMO SAPIENS PHOSPHATIDYLINOSITOL-4-PHOSPHATE 5-KINASE, TYPE I, ALPHA (PIP5K1A), MRNA." |
| AB037779 | 0.50 | "HOMO SAPIENS MRNA FOR KIAA1358 PROTEIN, PARTIAL CDS" |
| NM_004420 | 0.50 | "HOMO SAPIENS DUAL SPECIFICITY PHOSPHATASE 8 (DUSP8), MRNA." |
| NM_005627 | 0.50 | "HOMO SAPIENS SERUM/GLUCOCORTICOID REGULATED KINASE (SGK), MRNA." |
| 1168293.1 | 0.50 | NULL |
| AB007892 | 0.50 | "HOMO SAPIENS KIAA0432 MRNA, COMPLETE CDS" |
| NM_016140 | 0.50 | "HOMO SAPIENS BRAIN SPECIFIC PROTEIN (LOC51673), MRNA." |
| NM_012342 | 0.50 | "HOMO SAPIENS PUTATIVE TRANSMEMBRANE PROTEIN (NMA), MRNA." |
| NM_001086 | 0.50 | "HOMO SAPIENS ARYLACETAMIDE DEACETYLASE (ESTERASE) (AADAC), MRNA." |
| 1345454.1 | 0.50 | NULL |
| NM_033344 | 0.50 | "HOMO SAPIENS EGL NINE HOMOLOG 3 (C. ELEGANS) (EGLN3), MRNA." |
| NM_003113 | 0.51 | "HOMO SAPIENS NUCLEAR ANTIGEN SP100 (SP100), MRNA" |
| BC015134 | 0.51 | "HOMO SAPIENS, CLONE IMAGE: 3934391, MRNA" |
| NM_002260 | 0.51 | "HOMO SAPIENS KILLER CELL LECTIN-LIKE RECEPTOR SUBFAMILY C, MEMBER 2 (KLRC2), MRNA." |
| AK097698 | 0.51 | "HOMO SAPIENS CDNA FLJ40379 FIS, CLONE TESTI2035262, WEAKLY SIMILAR TO PROACTIVATOR POLYPEPTIDE PRECURSOR" |
| BC004982 | 0.51 | "HOMO SAPIENS, GLUCOSE PHOSPHATE ISOMERASE, CLONE MGC: 3935 IMAGE: 2906270, MRNA, COMPLETE CDS" |
| NM_001629 | 0.51 | "HOMO SAPIENS ARACHIDONATE 5-LIPOXYGENASE-ACTIVATING PROTEIN (ALOX5AP), MRNA." |
| NM_023068 | 0.51 | "HOMO SAPIENS SIALOADHESIN (SN), MRNA" |
| NM_005978 | 0.52 | "HOMO SAPIENS S100 CALCIUM BINDING PROTEIN A2 (S100A2), MRNA." |
| Z72499 | 0.52 | H. SAPIENS MRNA FOR HERPESVIRUS ASSOCIATED UBIQUITIN-SPECIFIC PROTEASE (HAUSP) |

APPENDIX 3-continued

Down Regulated Genes with Treatment Fex:

| Accession Number | Fold Change (Fex/DMSO) | Gene Description |
|---|---|---|
| AP003355 | 0.52 | "HOMO SAPIENS GENOMIC DNA, CHROMOSOME 8Q23, CLONE: KB1517D11" |
| NM_033260 | 0.52 | "HOMO SAPIENS WINGED HELIX/FORKHEAD TRANSCRIPTION FACTOR (HFH1), MRNA" |
| NM_001901 | 0.52 | "HOMO SAPIENS CONNECTIVE TISSUE GROWTH FACTOR (CTGF), MRNA." |
| NM_001562 | 0.52 | "HOMO SAPIENS INTERLEUKIN 18 (INTERFERON-GAMMA-INDUCING FACTOR) (IL18), MRNA." |
| 1401176.1 | 0.52 | NULL |
| AJ420585 | 0.52 | HOMO SAPIENS MRNA FULL LENGTH INSERT CDNA CLONE EUROIMAGE 1964662 |
| BG752423 | 0.52 | "602730910F1 NIH_MGC_43 HOMO SAPIENS CDNA CLONE IMAGE: 4874427 5', MRNA SEQUENCE" |
| BC008810 | 0.52 | "HOMO SAPIENS, CLONE IMAGE: 3948909, MRNA, PARTIAL CDS" |
| NM_020299 | 0.52 | "HOMO SAPIENS ALDO-KETO REDUCTASE FAMILY 1, MEMBER B10 (ALDOSE REDUCTASE) (AKR1B10), MRNA." |
| NM_003358 | 0.52 | "HOMO SAPIENS UDP-GLUCOSE CERAMIDE GLUCOSYLTRANSFERASE (UGCG), MRNA." |
| M80478 | 0.52 | "HUMAN PLATELET GLYCOPROTEIN IX PRECURSOR (GPIX) GENE, COMPLETE CDS" |
| NM_001657 | 0.53 | "HOMO SAPIENS AMPHIREGULIN (SCHWANNOMA-DERIVED GROWTH FACTOR) (AREG), MRNA." |
| NM_003212 | 0.53 | "HOMO SAPIENS TERATOCARCINOMA-DERIVED GROWTH FACTOR 1 (TDGF1), MRNA." |
| NM_024325 | 0.53 | "HOMO SAPIENS HYPOTHETICAL PROTEIN MGC10715 (MGC10715), MRNA" |
| NM_005242 | 0.53 | "HOMO SAPIENS COAGULATION FACTOR II (THROMBIN) RECEPTOR-LIKE 1 (F2RL1), MRNA" |
| NM_005797 | 0.53 | "HOMO SAPIENS EPITHELIAL V-LIKE ANTIGEN 1 (EVA1), MRNA." |
| NM_001348 | 0.53 | "HOMO SAPIENS DEATH-ASSOCIATED PROTEIN KINASE 3 (DAPK3), MRNA." |
| NM_024501 | 0.53 | "HOMO SAPIENS HOMEO BOX D1 (HOXD1), MRNA" |
| NM_004864 | 0.53 | "HOMO SAPIENS PROSTATE DIFFERENTIATION FACTOR (PLAB), MRNA" |
| AF016903 | 0.53 | "HOMO SAPIENS AGRIN PRECURSOR MRNA, PARTIAL CDS" |
| NM_152908 | 0.53 | "HOMO SAPIENS HYPOTHETICAL PROTEIN FLJ31196 (FLJ31196), MRNA" |
| NM_006753 | 0.54 | "HOMO SAPIENS SURFEIT 6 (SURF6), MRNA" |
| NM_017654 | 0.54 | "HOMO SAPIENS HYPOTHETICAL PROTEIN FLJ20073 (FLJ20073), MRNA" |
| NM_001165 | 0.54 | "HOMO SAPIENS BACULOVIRAL IAP REPEAT-CONTAINING 3 (BIRC3), MRNA." |
| NM_016639 | 0.54 | "HOMO SAPIENS TYPE I TRANSMEMBRANE PROTEIN FN14 (FN14), MRNA." |
| AL162045 | 0.54 | HOMO SAPIENS MRNA; CDNA DKFZP761P0212 (FROM CLONE DKFZP761P0212); PARTIAL CDS |
| AK026784 | 0.54 | "HOMO SAPIENS CDNA: FLJ23131 FIS, CLONE LNG08502" |
| NM_145298 | 0.54 | "HOMO SAPIENS SIMILAR TO PHORBOLIN 3 (APOBEC1-LIKE) (LOC200316), MRNA" |
| BG546997 | 0.54 | 602573989F1 HOMO SAPIENS CDNA 5' END |
| NM_017651 | 0.54 | "HOMO SAPIENS HYPOTHETICAL PROTEIN FLJ20069 (FLJ20069), MRNA" |
| NM_001346 | 0.54 | "HOMO SAPIENS DIACYLGLYCEROL KINASE, GAMMA (90 KD) (DGKG), MRNA." |
| NM_030587 | 0.54 | "HOMO SAPIENS UDP-GAL: BETAGLCNAC BETA 1,4-GALACTOSYLTRANSFERASE, POLYPEPTIDE 2 (B4GALT2), TRANSCRIPT VARIANT 1, MRNA." |
| NM_024796 | 0.54 | "HOMO SAPIENS HYPOTHETICAL PROTEIN FLJ22639 (FLJ22639), MRNA" |
| NM_015720 | 0.54 | "HOMO SAPIENS ENDOGLYCAN (PODLX2), MRNA." |
| AK023317 | 0.54 | "HOMO SAPIENS CDNA FLJ13255 FIS, CLONE OVARC1000800, MODERATELY SIMILAR TO MITOCHONDRIAL STRESS-70 PROTEIN PRECURSOR" |
| NM_006901 | 0.54 | "HOMO SAPIENS MYOSIN IXA (MYO9A), MRNA." |
| NM_001553 | 0.55 | "HOMO SAPIENS INSULIN-LIKE GROWTH FACTOR BINDING PROTEIN 7 (IGFBP7), MRNA" |
| M80899 | 0.55 | "HUMAN NOVEL PROTEIN AHNAK MRNA, PARTIAL SEQUENCE" |
| NM_002658 | 0.55 | "HOMO SAPIENS PLASMINOGEN ACTIVATOR, UROKINASE (PLAU), MRNA." |
| NM_012227 | 0.55 | "HOMO SAPIENS PSEUDOAUTOSOMAL GTP-BINDING PROTEIN-LIKE (PGPL), MRNA." |
| NM_022783 | 0.55 | "HOMO SAPIENS HYPOTHETICAL PROTEIN FLJ12428 (FLJ12428), MRNA." |
| AK024489 | 0.55 | "HOMO SAPIENS MRNA FOR FLJ00089 PROTEIN, PARTIAL CDS" |
| NM_002228 | 0.55 | "HOMO SAPIENS V-JUN SARCOMA VIRUS 17 ONCOGENE HOMOLOG (AVIAN) (JUN), MRNA." |
| NM_000683 | 0.55 | "HOMO SAPIENS ADRENERGIC, ALPHA-2C-, RECEPTOR (ADRA2C), MRNA." |
| AL136680 | 0.55 | HOMO SAPIENS MRNA; CDNA DKFZP564C2478 (FROM CLONE DKFZP564C2478); COMPLETE CDS |
| NM_006931 | 0.55 | "HOMO SAPIENS SOLUTE CARRIER FAMILY 2 (FACILITATED GLUCOSE TRANSPORTER), MEMBER 3 (SLC2A3), MRNA." |
| NM_019096 | 0.55 | "HOMO SAPIENS GTP BINDING PROTEIN 2 (GTPBP2), MRNA." |
| AF218032 | 0.55 | HOMO SAPIENS CLONE PP902 UNKNOWN MRNA |
| NM_002648 | 0.55 | "HOMO SAPIENS PIM-1 ONCOGENE (PIM1), MRNA." |
| NM_002892 | 0.55 | "HOMO SAPIENS RETINOBLASTOMA BINDING PROTEIN 1 (RBBP1), TRANSCRIPT VARIANT 1, MRNA" |
| NM_032119 | 0.55 | "HOMO SAPIENS VERY LARGE G PROTEIN-COUPLED RECEPTOR 1 (VLGR1), MRNA" |
| NM_024606 | 0.55 | "HOMO SAPIENS HYPOTHETICAL PROTEIN FLJ11756 (FLJ11756), MRNA." |

APPENDIX 3-continued

Down Regulated Genes with Treatment Fex:

| Accession Number | Fold Change (Fex/DMSO) | Gene Description |
|---|---|---|
| NM_003082 | 0.56 | "HOMO SAPIENS SMALL NUCLEAR RNA ACTIVATING COMPLEX, POLYPEPTIDE 1, 43 KD (SNAPC1), MRNA." |
| NM_022837 | 0.56 | "HOMO SAPIENS HYPOTHETICAL PROTEIN FLJ22833 (FLJ22833), MRNA" |
| NM_025043 | 0.56 | "HOMO SAPIENS HYPOTHETICAL PROTEIN FLJ22404 (FLJ22404), MRNA" |
| NM_004468 | 0.56 | "HOMO SAPIENS FOUR AND A HALF LIM DOMAINS 3 (FHL3), MRNA." |
| L19314 | 0.56 | "HUMAN HRY GENE, COMPLETE CDS" |
| AL119114 | 0.56 | "DKFZP761H1212_S1 HOMO SAPIENS CDNA, 3' END" |
| NM_001453 | 0.56 | "HOMO SAPIENS FORKHEAD BOX C1 (FOXC1), MRNA" |
| NM_000354 | 0.56 | "HOMO SAPIENS SERINE (OR CYSTEINE) PROTEINASE INHIBITOR, CLADE A (ALPHA-1 ANTIPROTEINASE, ANTITRYPSIN), MEMBER 7 (SERPINA7), MRNA" |
| X03069 | 0.56 | HUMAN MRNA FOR HLA-D CLASS II ANTIGEN DR1 BETA CHAIN |
| NM_152901 | 0.56 | "HOMO SAPIENS PYRIN-DOMAIN CONTAINING PROTEIN 1 (PYC1), MRNA" |
| NM_012242 | 0.56 | "HOMO SAPIENS DICKKOPF HOMOLOG 1 (XENOPUS LAEVIS) (DKK1), MRNA." |
| NM_033445 | 0.56 | "HOMO SAPIENS SIMILAR TO H2A HISTONE FAMILY, MEMBER A (H. SAPIENS) (MGC3165), MRNA" |
| X70287 | 0.56 | "H. SAPIENS GENE FOR THIOREDOXIN, EXONS 2 AND 3" |
| NM_018177 | 0.56 | "HOMO SAPIENS NEDD4 BINDING PROTEIN 2 (N4BP2), MRNA" |
| AL390142 | 0.56 | HOMO SAPIENS MRNA; CDNA DKFZP547N024 (FROM CLONE DKFZP547N024) |
| AB038689 | 0.56 | "HOMO SAPIENS AHSG GENE FOR ALPHA2-HS GLYCOPROTEIN, COMPLETE CDS" |
| NM_017876 | 0.56 | "HOMO SAPIENS HYPOTHETICAL PROTEIN FLJ20552 (FLJ20552), MRNA." |
| AL834442 | 0.56 | HOMO SAPIENS MRNA; CDNA DKFZP761B2210 (FROM CLONE DKFZP761B2210) |
| NG_001068 | 0.56 | "HOMO SAPIENS ACTIN, GAMMA PSEUDOGENE 1 (ACTGP1) ON CHROMOSOME 3" |
| NM_012267 | 0.56 | "HOMO SAPIENS HSP70-INTERACTING PROTEIN (HSPBP1), MRNA." |
| NM_024114 | 0.57 | "HOMO SAPIENS HYPOTHETICAL PROTEIN MGC4827 (MGC4827), MRNA" |
| NM_000337 | 0.57 | "HOMO SAPIENS SARCOGLYCAN, DELTA (35 KD DYSTROPHIN-ASSOCIATED GLYCOPROTEIN) (SGCD), MRNA" |
| NM_018929 | 0.57 | "HOMO SAPIENS PROTOCADHERIN GAMMA SUBFAMILY C, 5 (PCDHGC5), TRANSCRIPT VARIANT 1, MRNA" |
| NM_015363 | 0.57 | "HOMO SAPIENS ZINC FINGER, IMPRINTED 2 (ZIM2), MRNA" |
| NM_004064 | 0.57 | "HOMO SAPIENS CYCLIN-DEPENDENT KINASE INHIBITOR 1B (P27, KIP1) (CDKN1B), MRNA" |
| NM_015894 | 0.57 | "HOMO SAPIENS STATHMIN-LIKE 3 (STMN3), MRNA." |
| NM_014810 | 0.57 | "HOMO SAPIENS KIAA0480 GENE PRODUCT (KIAA0480), MRNA." |
| NM_005035 | 0.57 | "HOMO SAPIENS POLYMERASE (RNA) MITOCHONDRIAL (DNA DIRECTED) (POLRMT), NUCLEAR GENE ENCODING MITOCHONDRIAL PROTEIN, MRNA" |
| 475198.1 | 0.57 | "PROTEIN WITH HIGH SIMILARITY TO RAT RINZF, WHICH BINDS A RAT GAS REGULATORY ELEMENT IMPORTANT FOR PANCREAS INSULINOMA-SPECIFIC EXPRESSION, CONTAINS TWO C2H2 TYPE ZINC FINGER DOMAINS AND A BTB (BR-C, TTK AND BABOR) OR POZ (POX VIRUS AND ZINC FINGER) DOMAI |
| NM_017958 | 0.57 | "HOMO SAPIENS HYPOTHETICAL PROTEIN FLJ20783 (FLJ20783), MRNA." |
| AB051492 | 0.57 | "HOMO SAPIENS MRNA FOR KIAA1705 PROTEIN, PARTIAL CDS" |
| NM_032624 | 0.57 | "HOMO SAPIENS HYPOTHETICAL BRAIN PROTEIN MY050 (MY050), MRNA" |
| NM_002307 | 0.57 | "HOMO SAPIENS LECTIN, GALACTOSIDE-BINDING, SOLUBLE, 7 (GALECTIN 7) (LGALS7), MRNA." |
| NM_002333 | 0.57 | "HOMO SAPIENS LOW DENSITY LIPOPROTEIN RECEPTOR-RELATED PROTEIN 3 (LRP3), MRNA." |
| AK027843 | 0.57 | "HOMO SAPIENS CDNA FLJ14937 FIS, CLONE PLACE1010231, WEAKLY SIMILAR TO CELL SURFACE GLYCOPROTEIN EMR1 PRECURSOR" |
| NM_006623 | 0.57 | "HOMO SAPIENS PHOSPHOGLYCERATE DEHYDROGENASE (PHGDH), MRNA" |
| NM_024765 | 0.57 | "HOMO SAPIENS HYPOTHETICAL PROTEIN FLJ12401 (FLJ12401), MRNA" |
| AF181897 | 0.58 | "HOMO SAPIENS WRN (WRN) GENE, COMPLETE CDS" |
| 1330303.1 | 0.58 | NULL |
| NM_139314 | 0.58 | "HOMO SAPIENS ANGIOPOIETIN-LIKE 4 (ANGPTL4), TRANSCRIPT VARIANT 1, MRNA" |
| M25295 | 0.58 | "HUMAN KERATINOCYTE GROWTH FACTOR MRNA, COMPLETE CDS" |
| NM_001550 | 0.58 | "HOMO SAPIENS INTERFERON-RELATED DEVELOPMENTAL REGULATOR 1 (IFRD1), MRNA" |
| NM_014059 | 0.58 | "HOMO SAPIENS RGC32 PROTEIN (RGC32), MRNA" |
| NM_018017 | 0.58 | "HOMO SAPIENS HYPOTHETICAL PROTEIN FLJ10188 (FLJ10188), MRNA." |
| NM_020130 | 0.58 | "HOMO SAPIENS CHROMOSOME 8 OPEN READING FRAME 4 (C8ORF4), MRNA" |
| NM_002856 | 0.58 | "HOMO SAPIENS POLIOVIRUS RECEPTOR-RELATED 2 (HERPESVIRUS ENTRY MEDIATOR B) (PVRL2), MRNA." |
| J02853 | 0.58 | "HOMO SAPIENS CASEIN KINASE II ALPHA SUBUNIT MRNA, COMPLETE CDS" |
| NM_018364 | 0.58 | "HOMO SAPIENS HYPOTHETICAL PROTEIN FLJ11220 (FLJ11220), MRNA" |
| NM_000670 | 0.58 | "HOMO SAPIENS ALCOHOL DEHYDROGENASE 4 (CLASS II), PI POLYPEPTIDE (ADH4), MRNA." |
| AK095284 | 0.58 | "HOMO SAPIENS CDNA FLJ37965 FIS, CLONE CTONG2009844" |
| U65404 | 0.58 | "HUMAN ERYTHROID-SPECIFIC TRANSCRIPTION FACTOR EKLF MRNA, COMPLETE CDS" |
| NM_004269 | 0.58 | "HOMO SAPIENS COFACTOR REQUIRED FOR SP1 TRANSCRIPTIONAL ACTIVATION, SUBUNIT 8 (34 KD) (CRSP8), MRNA." |
| NM_018231 | 0.58 | "HOMO SAPIENS HYPOTHETICAL PROTEIN FLJ10815 (FLJ10815), MRNA." |

APPENDIX 3-continued

Down Regulated Genes with Treatment Fex:

| Accession Number | Fold Change (Fex/DMSO) | Gene Description |
| --- | --- | --- |
| AF070443 | 0.58 | "*HOMO SAPIENS* GLCNAC-1-P TRANSFERASE GENE, EXONS 5 THROUGH 9 AND COMPLETE CDS" |
| NM_024679 | 0.58 | "*HOMO SAPIENS* HYPOTHETICAL PROTEIN FLJ11939 (FLJ11939), MRNA" |
| NM_000422 | 0.58 | "*HOMO SAPIENS* KERATIN 17 (KRT17), MRNA" |
| AF274889 | 0.58 | "*HOMO SAPIENS* GLUCOSE TRANSPORTER 3 GENE, EXONS 1 TO 6" |
| NM_052830 | 0.58 | "*HOMO SAPIENS* GAMMA-GLUTAMYLTRANSFERASE-LIKE 3 (GGTL3), MRNA" |
| 1330160.23 | 0.58 | PROTEIN OF UNKNOWN FUNCTION |
| 403813.2 | 0.58 | PROTEIN OF UNKNOWN FUNCTION |
| NM_020921 | 0.58 | "*HOMO SAPIENS* NINEIN (GSK3B INTERACTING PROTEIN) (NIN), MRNA" |
| NM_024067 | 0.58 | "*HOMO SAPIENS* HYPOTHETICAL PROTEIN MGC2718 (MGC2718), MRNA" |
| NM_016210 | 0.59 | "*HOMO SAPIENS* G20 PROTEIN (LOC51161), MRNA." |
| BC008357 | 0.59 | "*HOMO SAPIENS*, CLONE IMAGE: 3605655, MRNA" |
| NM_006086 | 0.59 | "*HOMO SAPIENS* TUBULIN, BETA, 4 (TUBB4), MRNA." |
| NM_014502 | 0.59 | "*HOMO SAPIENS* NUCLEAR MATRIX PROTEIN NMP200 RELATED TO SPLICING FACTOR PRP19 (NMP200), MRNA." |
| NM_001614 | 0.59 | "*HOMO SAPIENS* ACTIN, GAMMA 1 (ACTG1), MRNA" |
| NM_030753 | 0.59 | "*HOMO SAPIENS* WINGLESS-TYPE MMTV INTEGRATION SITE FAMILY, MEMBER 3 (WNT3), MRNA" |
| NM_001345 | 0.59 | "*HOMO SAPIENS* DIACYLGLYCEROL KINASE, ALPHA (80 KD) (DGKA), MRNA." |
| NM_014824 | 0.59 | "*HOMO SAPIENS* KIAA0769 GENE PRODUCT (KIAA0769), MRNA." |
| AF288992 | 0.59 | "*HOMO SAPIENS* 15 KDA SELENOPROTEIN (SEP15) GENE, COMPLETE CDS" |
| AK025134 | 0.59 | "*HOMO SAPIENS* CDNA: FLJ21481 FIS, CLONE COL05066" |
| NM_001387 | 0.59 | "*HOMO SAPIENS* DIHYDROPYRIMIDINASE-LIKE 3 (DPYSL3), MRNA." |
| AY074491 | 0.59 | "*HOMO SAPIENS* EEG1S (EEG1) MRNA, COMPLETE CDS; ALTERNATIVELY SPLICED" |
| 1138110.2 | 0.59 | NULL |
| NM_018647 | 0.59 | "*HOMO SAPIENS* TUMOR NECROSIS FACTOR RECEPTOR SUPERFAMILY, MEMBER 19 (TNFRSF19), MRNA" |
| NM_012124 | 0.59 | "*HOMO SAPIENS* CYSTEINE AND HISTIDINE-RICH DOMAIN (CHORD)-CONTAINING, ZINC BINDING PROTEIN 1 (CHORDC1), MRNA." |
| NM_005139 | 0.59 | "*HOMO SAPIENS* ANNEXIN A3 (ANXA3), MRNA." |
| NM_004964 | 0.59 | "*HOMO SAPIENS* HISTONE DEACETYLASE 1 (HDAC1), MRNA." |
| Y00815 | 0.59 | HUMAN MRNA FOR LCA-HOMOLOG. LAR PROTEIN (LEUKOCYTE ANTIGEN RELATED) |
| NM_006336 | 0.59 | "*HOMO SAPIENS* ZYG HOMOLOG (ZYG), MRNA." |
| X15804 | 0.59 | HUMAN MRNA FOR ALPHA-ACTININ |
| AK021570 | 0.59 | "*HOMO SAPIENS* CDNA FLJ11508 FIS, CLONE HEMBA1002162" |
| X69654 | 0.59 | *H. SAPIENS* MRNA FOR RIBOSOMAL PROTEIN S26 |
| NM_025085 | 0.59 | "*HOMO SAPIENS* HYPOTHETICAL PROTEIN FLJ13340 (FLJ13340), TRANSCRIPT VARIANT 2, MRNA" |
| AJ251973 | 0.59 | *HOMO SAPIENS* PARTIAL STEERIN-1 GENE |
| NM_005936 | 0.59 | "*HOMO SAPIENS* MYELOID/LYMPHOID OR MIXED-LINEAGE LEUKEMIA (TRITHORAX HOMOLOG, *DROSOPHILA*); TRANSLOCATED TO, 4 (MLLT4), MRNA" |
| NM_001216 | 0.59 | "*HOMO SAPIENS* CARBONIC ANHYDRASE IX (CA9), MRNA." |
| NM_005560 | 0.60 | "*HOMO SAPIENS* LAMININ, ALPHA 5 (LAMA5), MRNA" |
| NM_018227 | 0.60 | "*HOMO SAPIENS* HYPOTHETICAL PROTEIN FLJ10808 (FLJ10808), MRNA." |
| NM_007355 | 0.60 | "*HOMO SAPIENS* HEAT SHOCK 90 KD PROTEIN 1, BETA (HSPCB), MRNA." |
| NM_003657 | 0.60 | "*HOMO SAPIENS* BREAST CARCINOMA AMPLIFIED SEQUENCE 1 (BCAS1), MRNA." |
| NM_003107 | 0.60 | "*HOMO SAPIENS* SRY (SEX DETERMINING REGION Y)-BOX 4 (SOX4), MRNA." |
| NM_020665 | 0.60 | "*HOMO SAPIENS* KIDNEY-SPECIFIC MEMBRANE PROTEIN (NX-17), MRNA." |
| AB033025 | 0.60 | "*HOMO SAPIENS* MRNA FOR KIAA1199 PROTEIN, PARTIAL CDS" |
| NM_014330 | 0.60 | "*HOMO SAPIENS* PROTEIN PHOSPHATASE 1, REGULATORY (INHIBITOR) SUBUNIT 15A (PPP1R15A), MRNA" |
| NM_001946 | 0.60 | "*HOMO SAPIENS* DUAL SPECIFICITY PHOSPHATASE 6 (DUSP6), TRANSCRIPT VARIANT 1, MRNA" |
| NM_031449 | 0.60 | "*HOMO SAPIENS* KIAA1886 PROTEIN (DKFZP761I2123), MRNA." |
| AK023110 | 0.60 | "*HOMO SAPIENS* CDNA FLJ13048 FIS, CLONE NT2RP3001399, WEAKLY SIMILAR TO SSU72 PROTEIN" |
| NM_018669 | 0.60 | "*HOMO SAPIENS* WD REPEAT DOMAIN 4 (WDR4), TRANSCRIPT VARIANT 1, MRNA" |
| NM_032649 | 0.60 | "*HOMO SAPIENS* GLUTAMATE CARBOXYPEPTIDASE-LIKE PROTEIN 2 (CPGL2), MRNA" |
| AL122071 | 0.60 | *HOMO SAPIENS* MRNA; CDNA DKFZP434H1235 (FROM CLONE DKFZP434H1235); PARTIAL CDS |
| NM_004672 | 0.60 | "*HOMO SAPIENS* MITOGEN-ACTIVATED PROTEIN KINASE KINASE KINASE 6 (MAP3K6), MRNA" |
| AF085987 | 0.60 | *HOMO SAPIENS* FULL LENGTH INSERT CDNA CLONE YU05C01 |
| NM_030970 | 0.60 | "*HOMO SAPIENS* HYPOTHETICAL PROTEIN MGC3771 (MGC3771), MRNA" |
| AL137721 | 0.60 | *HOMO SAPIENS* MRNA; CDNA DKFZP761H221 (FROM CLONE DKFZP761H221) |
| NM_006282 | 0.60 | "*HOMO SAPIENS* SERINE/THREONINE KINASE 4 (STK4), MRNA" |
| AK023905 | 0.60 | "*HOMO SAPIENS* CDNA FLJ13843 FIS, CLONE THYRO1000796" |
| BC021898 | 0.60 | "*HOMO SAPIENS*, CLONE MGC: 17284 IMAGE: 4340257, MRNA, COMPLETE CDS" |

APPENDIX 3-continued

Down Regulated Genes with Treatment Fex:

| Accession Number | Fold Change (Fex/DMSO) | Gene Description |
|---|---|---|
| M92843 | 0.60 | "*H. SAPIENS* ZINC FINGER TRANSCRIPTIONAL REGULATOR MRNA, COMPLETE CDS" |
| NM_002276 | 0.60 | "*HOMO SAPIENS* KERATIN 19 (KRT19), MRNA" |
| NM_004363 | 0.60 | "*HOMO SAPIENS* CARCINOEMBRYONIC ANTIGEN-RELATED CELL ADHESION MOLECULE 5 (CEACAM5), MRNA" |
| NM_002273 | 0.61 | "*HOMO SAPIENS* KERATIN 8 (KRT8), MRNA" |
| BF663771 | 0.61 | 602145203F1 *HOMO SAPIENS* CDNA 5' END |
| M14333 | 0.61 | "GNL|UG|HS#S341910 *HOMO SAPIENS* C-SYN PROTOONCOGENE MRNA, COMPLETE CDS /CDS = (579, 2192) /GB = M14333 /GI = 181171 /UG = HS.169370 /LEN = 2647" |
| NM_033292 | 0.61 | "*HOMO SAPIENS* CASPASE 1, APOPTOSIS-RELATED CYSTEINE PROTEASE (INTERLEUKIN 1, BETA, CONVERTASE) (CASP1), TRANSCRIPT VARIANT ALPHA, MRNA." |
| BC003641 | 0.61 | "*HOMO SAPIENS*, CLONE MGC: 4645 IMAGE: 3529568, MRNA, COMPLETE CDS" |
| NM_030760 | 0.61 | "*HOMO SAPIENS* ENDOTHELIAL DIFFERENTIATION, SPHINGOLIPID G-PROTEIN-COUPLED RECEPTOR, 8 (EDG8), MRNA" |
| BC003693 | 0.61 | "*HOMO SAPIENS*, SIMILAR TO RIKEN CDNA 3930401K13 GENE, CLONE IMAGE: 3454556, MRNA, PARTIAL CDS" |
| NM_000930 | 0.61 | "*HOMO SAPIENS* PLASMINOGEN ACTIVATOR, TISSUE (PLAT), TRANSCRIPT VARIANT 1, MRNA" |
| NM_018096 | 0.61 | "*HOMO SAPIENS* HYPOTHETICAL PROTEIN SIMILAR TO BETA-TRANSDUCIN FAMILY (FLJ10458), MRNA." |
| NM_001240 | 0.61 | "*HOMO SAPIENS* CYCLIN T1 (CCNT1), MRNA." |
| NM_001299 | 0.61 | "*HOMO SAPIENS* CALPONIN 1, BASIC, SMOOTH MUSCLE (CNN1), MRNA" |
| NM_001621 | 0.61 | "*HOMO SAPIENS* ARYL HYDROCARBON RECEPTOR (AHR), MRNA." |
| NM_005082 | 0.61 | "*HOMO SAPIENS* ZINC FINGER PROTEIN 147 (ESTROGEN-RESPONSIVE FINGER PROTEIN) (ZNF147), MRNA." |
| NM_004845 | 0.61 | "*HOMO SAPIENS* PHOSPHATE CYTIDYLYLTRANSFERASE 1, CHOLINE, BETA ISOFORM (PCYT1B), MRNA." |
| NM_003286 | 0.61 | "*HOMO SAPIENS* TOPOISOMERASE (DNA) I (TOP1), MRNA." |
| NM_144660 | 0.61 | "*HOMO SAPIENS* HYPOTHETICAL PROTEIN FLJ25082 (FLJ25082), MRNA" |
| NM_004904 | 0.61 | "*HOMO SAPIENS* CAMP RESPONSE ELEMENT-BINDING PROTEIN CRE-BPA (H_GS165L15.1), MRNA" |
| AB033075 | 0.61 | "*HOMO SAPIENS* MRNA FOR KIAA1249 PROTEIN, PARTIAL CDS" |
| NM_020239 | 0.61 | "*HOMO SAPIENS* SMALL PROTEIN EFFECTOR 1 OF CDC42 (SPEC1), MRNA" |
| NM_005902 | 0.61 | "*HOMO SAPIENS* MAD, MOTHERS AGAINST DECAPENTAPLEGIC HOMOLOG 3 (*DROSOPHILA*) (MADH3), MRNA" |
| NM_014296 | 0.61 | "*HOMO SAPIENS* CALPAIN 7 (CAPN7), MRNA." |
| NM_025049 | 0.61 | "*HOMO SAPIENS* HYPOTHETICAL PROTEIN FLJ22692 (FLJ22692), MRNA" |
| NM_001674 | 0.61 | "*HOMO SAPIENS* ACTIVATING TRANSCRIPTION FACTOR 3 (ATF3), MRNA" |
| NM_021960 | 0.61 | "*HOMO SAPIENS* MYELOID CELL LEUKEMIA SEQUENCE 1 (BCL2-RELATED) (MCL1), MRNA" |
| NM_024498 | 0.61 | "*HOMO SAPIENS* ZINC FINGER PROTEIN 117 (HPF9) (ZNF117), MRNA" |
| NM_018006 | 0.61 | "*HOMO SAPIENS* HYPOTHETICAL PROTEIN FLJ10140 (FLJ10140), MRNA" |
| NM_001124 | 0.61 | "*HOMO SAPIENS* ADRENOMEDULLIN (ADM), MRNA." |
| NM_016377 | 0.61 | "*HOMO SAPIENS* A KINASE (PRKA) ANCHOR PROTEIN 7 (AKAP7), MRNA." |
| AK026965 | 0.61 | "*HOMO SAPIENS* CDNA: FLJ23312 FIS, CLONE HEP11874" |
| NM_031944 | 0.61 | "*HOMO SAPIENS* MIX-LIKE HOMEOBOX PROTEIN 1 (MILD1), MRNA" |
| AK023426 | 0.61 | "*HOMO SAPIENS* CDNA FLJ13364 FIS, CLONE PLACE1000292" |
| NM_058189 | 0.61 | "*HOMO SAPIENS* CHROMOSOME 21 OPEN READING FRAME 69 (C21ORF69), MRNA" |
| 1502211.1 | 0.61 | NULL |
| NM_023008 | 0.62 | "*HOMO SAPIENS* HYPOTHETICAL PROTEIN FLJ12949 (FLJ12949), MRNA" |
| NM_004706 | 0.62 | "*HOMO SAPIENS* RHO GUANINE NUCLEOTIDE EXCHANGE FACTOR (GEF) 1 (ARHGEF1), MRNA." |
| NM_001619 | 0.62 | "*HOMO SAPIENS* ADRENERGIC, BETA, RECEPTOR KINASE 1 (ADRBK1), MRNA" |
| NM_003952 | 0.62 | "*HOMO SAPIENS* RIBOSOMAL PROTEIN S6 KINASE, 70 KD, POLYPEPTIDE 2 (RPS6KB2), MRNA." |
| NM_003407 | 0.62 | "*HOMO SAPIENS* ZINC FINGER PROTEIN 36, C3H TYPE, HOMOLOG (MOUSE) (ZFP36), MRNA." |
| 1400651.5 | 0.62 | NULL |
| NM_013275 | 0.62 | "*HOMO SAPIENS* NASOPHARYNGEAL CARCINOMA SUSCEPTIBILITY PROTEIN (LZ16), MRNA." |
| X62006 | 0.62 | *H. SAPIENS* PTB-1 GENE FOR POLYPIRIMIDINE TRACT BINDING PROTEIN |
| NM_001949 | 0.62 | "*HOMO SAPIENS* E2F TRANSCRIPTION FACTOR 3 (E2F3) MRNA, COMPLETE CDS." |
| NM_145006 | 0.62 | "*HOMO SAPIENS* HYPOTHETICAL PROTEIN MGC26847 (MGC26847), MRNA" |
| NM_145252 | 0.62 | "*HOMO SAPIENS* SIMILAR TO COMMON SALIVARY PROTEIN 1 (LOC124220), MRNA" |
| NM_003414 | 0.62 | "*HOMO SAPIENS* ZINC FINGER PROTEIN 267 (ZNF267), TRANSCRIPT VARIANT 498723, MRNA." |
| NM_017818 | 0.62 | "*HOMO SAPIENS* WD REPEAT DOMAIN 8 (WDR8), MRNA." |
| NM_022343 | 0.62 | "*HOMO SAPIENS* CHROMOSOME 9 OPEN READING FRAME 19 (C9ORF19), MRNA" |

APPENDIX 3-continued

Down Regulated Genes with Treatment Fex:

| Accession Number | Fold Change (Fex/DMSO) | Gene Description |
|---|---|---|
| AL163305 | 0.62 | NULL |
| NM_016014 | 0.62 | "HOMO SAPIENS CGI-67 PROTEIN (LOC51104), MRNA." |
| NM_005969 | 0.62 | "HOMO SAPIENS NUCLEOSOME ASSEMBLY PROTEIN 1-LIKE 4 (NAP1L4), MRNA." |
| NM_002939 | 0.62 | "HOMO SAPIENS RIBONUCLEASE/ANGIOGENIN INHIBITOR (RNH), MRNA." |
| 101314.1 | 0.62 | NULL |
| NM_016123 | 0.62 | "HOMO SAPIENS PUTATIVE PROTEIN KINASE NY-REN-64 ANTIGEN (LOC51135), MRNA." |
| NM_016265 | 0.62 | "HOMO SAPIENS GIOT-3 FOR GONADOTROPIN INDUCIBLE TRANSCRIPTION REPRESSOR-3 (GIOT-3), MRNA." |
| NM_032873 | 0.62 | "HOMO SAPIENS NM23-PHOSPHORYLATED UNKNOWN SUBSTRATE (MGC15437), MRNA" |
| NM_030575 | 0.62 | "HOMO SAPIENS HYPOTHETICAL PROTEIN MGC10334 (MGC10334), MRNA." |
| NM_032678 | 0.62 | "HOMO SAPIENS HYPOTHETICAL PROTEIN MGC3413 (MGC3413), MRNA" |
| AF025772 | 0.62 | "HOMO SAPIENS C2H2 ZINC FINGER PROTEIN (ZNF189) GENE, ALTERNATIVE SPLICE PRODUCTS, COMPLETE CDS" |
| AK025461 | 0.62 | "HOMO SAPIENS CDNA: FLJ21808 FIS, CLONE HEP00851, HIGHLY SIMILAR TO AF151843 HOMO SAPIENS CGI-85 PROTEIN MRNA" |
| NM_001461 | 0.62 | "HOMO SAPIENS FLAVIN CONTAINING MONOOXYGENASE 5 (FMO5), MRNA." |
| AK027136 | 0.62 | "HOMO SAPIENS CDNA: FLJ23483 FIS, CLONE KAIA04052" |
| NM_003683 | 0.62 | "HOMO SAPIENS DNA SEGMENT ON CHROMOSOME 21 (UNIQUE) 2056 EXPRESSED SEQUENCE (D21S2056E), MRNA." |
| NM_004218 | 0.62 | "HOMO SAPIENS RAB11B, MEMBER RAS ONCOGENE FAMILY (RAB11B), MRNA" |
| NM_004207 | 0.62 | "HOMO SAPIENS SOLUTE CARRIER FAMILY 16 (MONOCARBOXYLIC ACID TRANSPORTERS), MEMBER 3 (SLC16A3), MRNA." |
| NM_006781 | 0.62 | "HOMO SAPIENS CHROMOSOME 6 OPEN READING FRAME 10 (C6ORF10), MRNA." |
| AF075019 | 0.62 | HOMO SAPIENS FULL LENGTH INSERT CDNA YI29A01 |
| NM_012319 | 0.62 | "HOMO SAPIENS LIV-1 PROTEIN, ESTROGEN REGULATED (LIV-1), MRNA." |
| NM_004447 | 0.62 | "HOMO SAPIENS EPIDERMAL GROWTH FACTOR RECEPTOR PATHWAY SUBSTRATE 8 (EPS8), MRNA." |
| NM_024616 | 0.62 | "HOMO SAPIENS HYPOTHETICAL PROTEIN FLJ23186 (FLJ23186), MRNA" |
| NM_004766 | 0.62 | "HOMO SAPIENS COATOMER PROTEIN COMPLEX, SUBUNIT BETA 2 (BETA PRIME) (COPB2), MRNA." |
| NM_005735 | 0.62 | "HOMO SAPIENS ARP1 ACTIN-RELATED PROTEIN 1 HOMOLOG B, CENTRACTIN BETA (YEAST) (ACTR1B), MRNA." |
| BC007722 | 0.62 | "HOMO SAPIENS, GLYCYL-TRNA SYNTHETASE, CLONE MGC: 12625 IMAGE: 4299853, MRNA, COMPLETE CDS" |
| NM_016076 | 0.62 | "HOMO SAPIENS CGI-146 PROTEIN (LOC51029), MRNA." |
| NM_018226 | 0.62 | "HOMO SAPIENS ARGINYL AMINOPEPTIDASE (AMINOPEPTIDASE B)-LIKE 1 (RNPEPL1), MRNA." |
| NM_015995 | 0.63 | "HOMO SAPIENS KRUPPEL-LIKE FACTOR 13 (KLF13), MRNA." |
| NM_001647 | 0.63 | "HOMO SAPIENS APOLIPOPROTEIN D (APOD), MRNA" |
| BQ720870 | 0.63 | AGENCOURT_8296718 HOMO SAPIENS CDNA 5' END |
| NM_002850 | 0.63 | "HOMO SAPIENS PROTEIN TYROSINE PHOSPHATASE, RECEPTOR TYPE, S (PTPRS), MRNA." |
| AK024447 | 0.63 | "HOMO SAPIENS MRNA FOR FLJ00037 PROTEIN, PARTIAL CDS" |
| NM_019058 | 0.63 | "HOMO SAPIENS HIF-1 RESPONSIVE RTP801 (RTP801), MRNA" |
| BC016029 | 0.63 | "HOMO SAPIENS, CLONE MGC: 16974 IMAGE: 3921313, MRNA, COMPLETE CDS" |
| BI906953 | 0.63 | "HUMAN ERK5 MRNA, COMPLETE CDS." |
| NM_030578 | 0.63 | "HOMO SAPIENS HYPOTHETICAL PROTEIN MGC4093 (MGC4093), MRNA" |
| AB011539 | 0.63 | "HOMO SAPIENS MRNA FOR MEGF6 PROTEIN (KIAA0815), PARTIAL CDS" |
| NM_003995 | 0.63 | "HOMO SAPIENS NATRIURETIC PEPTIDE RECEPTOR B/GUANYLATE CYCLASE B (ATRIONATRIURETIC PEPTIDE RECEPTOR B) (NPR2), MRNA." |
| U24152 | 0.63 | "P21 ACTIVATED KINASE 1, A SERINE-THREONINE KINASE THAT IS ACTIVATED BY THE RHO-RELATED GTPASES CDC42 AND RAC1, INVOLVED IN REGULATION OF MAP KINASE CASCADES, CYTOSKELETAL CHANGES ASSOCIATED WITH CELL POLARITY AND MIGRATION, AND INHIBITION OF APOPTOSIS" |
| 331232.27 | 0.63 | "ERYTHROCYTE MEMBRANE PROTEIN BAND 4.9 (DEMATIN), A MEMBER OF THE VILLIN SUPERFAMILY, BINDS AND BUNDLES ACTIN, MAY CONTROL CELL SHAPE AND SIZE, MAY BE INVOLVED IN PROSTATE TUMORIGENESIS" |
| 1502800.17 | 0.63 | "PROTEIN OF UNKNOWN FUNCTION, HAS LOW SIMILARITY TO UNCHARACTERIZED C. ELEGANS F08G12.1" |
| NM_019063 | 0.63 | "HOMO SAPIENS CHROMOSOME 2 OPEN READING FRAME 2 (C2ORF2), MRNA." |
| NM_006391 | 0.63 | "HOMO SAPIENS RAN BINDING PROTEIN 7 (RANBP7), MRNA" |
| NM_005572 | 0.63 | "HOMO SAPIENS LAMIN A/C (LMNA), MRNA" |
| NM_004403 | 0.63 | "HOMO SAPIENS DEAFNESS, AUTOSOMAL DOMINANT 5 (DFNA5), MRNA." |
| AK025703 | 0.63 | "HOMO SAPIENS CDNA: FLJ22050 FIS, CLONE HEP09454" |
| BC022091 | 0.63 | "HOMO SAPIENS, SIMILAR TO SIDEROFLEXIN 2, CLONE MGC: 4567 IMAGE: 3029622, MRNA, COMPLETE CDS" |
| NM_018294 | 0.63 | "HOMO SAPIENS HYPOTHETICAL PROTEIN FLJ10998 (FLJ10998), MRNA." |
| NM_032179 | 0.63 | "HOMO SAPIENS HYPOTHETICAL PROTEIN FLJ20542 (FLJ20542), MRNA." |
| NM_002670 | 0.63 | "HOMO SAPIENS PLASTIN 1 (I ISOFORM) (PLS1), MRNA." |

APPENDIX 3-continued

Down Regulated Genes with Treatment Fex:

| Accession Number | Fold Change (Fex/DMSO) | Gene Description |
|---|---|---|
| NM_025019 | 0.63 | "HOMO SAPIENS LIKELY ORTHOLOG OF MOUSE TUBULIN ALPHA 4 (FLJ13940), MRNA" |
| NM_005962 | 0.63 | "HOMO SAPIENS MAX INTERACTING PROTEIN 1 (MXI1), MRNA." |
| AF079099 | 0.63 | "HOMO SAPIENS ARGININE-TRNA-PROTEIN TRANSFERASE 1-2P (ATE1) MRNA, ALTERNATIVELY SPLICED PRODUCT, PARTIAL CDS" |
| NM_152905 | 0.63 | "HOMO SAPIENS NEURAL PRECURSOR CELL EXPRESSED, DEVELOPMENTALLY DOWN-REGULATED 1 (NEDD1), MRNA" |
| NM_012329 | 0.63 | "HOMO SAPIENS MONOCYTE TO MACROPHAGE DIFFERENTIATION-ASSOCIATED (MMD), MRNA." |
| NM_016428 | 0.63 | "HOMO SAPIENS NESH PROTEIN (NESH), MRNA." |
| NM_033490 | 0.63 | "HOMO SAPIENS CELL DIVISION CYCLE 2-LIKE 1 (PITSLRE PROTEINS) (CDC2L1), TRANSCRIPT VARIANT 6, MRNA" |
| AK021583 | 0.63 | "HOMO SAPIENS CDNA FLJ11521 FIS, CLONE HEMBA1002486" |
| NM_031991 | 0.63 | "HOMO SAPIENS POLYPYRIMIDINE TRACT BINDING PROTEIN (HETEROGENEOUS NUCLEAR RIBONUCLEOPROTEIN I) (PTB), TRANSCRIPT VARIANT 3, MRNA." |
| AL137663 | 0.63 | HOMO SAPIENS MRNA; CDNA DKFZP434G227 (FROM CLONE DKFZP434G227) |
| AK056644 | 0.63 | "HOMO SAPIENS CDNA FLJ32082 FIS, CLONE OCBBF2000231, WEAKLY SIMILAR TO PHOSPHOLIPASE A2 INHIBITOR SUBUNIT B PRECURSOR" |
| NM_032587 | 0.63 | "HOMO SAPIENS CASPASE RECRUITMENT DOMAIN FAMILY, MEMBER 6 (CARD6), MRNA" |
| NM_002115 | 0.63 | "HOMO SAPIENS HEXOKINASE 3 (WHITE CELL) (HK3), NUCLEAR GENE ENCODING MITOCHONDRIAL PROTEIN, MRNA." |
| NM_024677 | 0.64 | "HOMO SAPIENS HYPOTHETICAL PROTEIN FLJ14001 (FLJ14001), MRNA" |
| NM_016262 | 0.64 | "HOMO SAPIENS EPSILON-TUBULIN (LOC51175), MRNA." |
| NM_024595 | 0.64 | "HOMO SAPIENS HYPOTHETICAL PROTEIN FLJ12666 (FLJ12666), MRNA" |
| AB023211 | 0.64 | "HOMO SAPIENS MRNA FOR KIAA0994 PROTEIN, PARTIAL CDS" |
| NM_001902 | 0.64 | "HOMO SAPIENS CYSTATHIONASE (CYSTATHIONINE GAMMA-LYASE) (CTH), MRNA." |
| NM_004593 | 0.64 | "HOMO SAPIENS SPLICING FACTOR, ARGININE/SERINE-RICH 10 (TRANSFORMER 2 HOMOLOG, DROSOPHILA) (SFRS10), MRNA." |
| NM_007114 | 0.64 | "HOMO SAPIENS TATA ELEMENT MODULATORY FACTOR 1 (TMF1), MRNA." |
| AK057059 | 0.64 | "HOMO SAPIENS CDNA FLJ32497 FIS, CLONE SKNSH2000250, HIGHLY SIMILAR TO R. NORVEGICUS MRNA FOR K+ CHANNEL PROTEIN, BETA SUBUNIT" |
| NM_016120 | 0.64 | "HOMO SAPIENS PUTATIVE RING ZINC FINGER PROTEIN NY-REN-43 ANTIGEN (LOC51132), MRNA." |
| AL122046 | 0.64 | HOMO SAPIENS MRNA; CDNA DKFZP434O0515 (FROM CLONE DKFZP434O0515) |
| BQ430788 | 0.64 | AGENCOURT_7776027 HOMO SAPIENS CDNA 5' END |
| NM_000641 | 0.64 | "HOMO SAPIENS INTERLEUKIN 11 (IL11), MRNA" |
| NM_145241 | 0.64 | "HOMO SAPIENS SIMILAR TO SPERMATID WD-REPEAT PROTEIN (LOC114987), MRNA" |
| NM_000287 | 0.64 | "HOMO SAPIENS PEROXISOMAL BIOGENESIS FACTOR 6 (PEX6), MRNA." |
| L47234 | 0.64 | "HOMO SAPIENS ERCC2 (ERCC2) AND KINESIN LIGHT CHAIN (KLC2) GENES, COMPLETE CDS, COMPLETE SEQUENCE" |
| X65178 | 0.64 | H. SAPIENS GENE FOR SUBSTANCE P RECEPTOR (EXON 2) |
| BC012155 | 0.64 | "HOMO SAPIENS, CLONE IMAGE: 4561787, MRNA" |
| AE006466 | 0.64 | HOMO SAPIENS 16P13.3 SEQUENCE SECTION 5 OF 8 |
| NM_024096 | 0.64 | "HOMO SAPIENS HYPOTHETICAL PROTEIN MGC5627 (MGC5627), MRNA" |
| NM_012484 | 0.64 | "HOMO SAPIENS HYALURONAN-MEDIATED MOTILITY RECEPTOR (RHAMM) (HMMR), TRANSCRIPT VARIANT 1, MRNA" |
| AK026064 | 0.64 | "HOMO SAPIENS CDNA: FLJ22411 FIS, CLONE HRC08456" |
| NM_003713 | 0.64 | "HOMO SAPIENS PHOSPHATIDIC ACID PHOSPHATASE TYPE 2B (PPAP2B), MRNA." |
| NM_015437 | 0.64 | "HOMO SAPIENS DKFZP586N0819 PROTEIN (DKFZP586N0819), MRNA" |
| AW328201 | 0.64 | "DR04H10.X1 NIH_MGC_3 HOMO SAPIENS CDNA CLONE IMAGE: 2847235 5', MRNA SEQUENCE" |
| NM_006247 | 0.64 | "HOMO SAPIENS PROTEIN PHOSPHATASE 5, CATALYTIC SUBUNIT (PPP5C), MRNA." |
| AF051160 | 0.64 | "HOMO SAPIENS TYROSINE PHOSPHATASE (PRL-1) GENE, COMPLETE CDS" |
| NM_002184 | 0.64 | "HOMO SAPIENS INTERLEUKIN 6 SIGNAL TRANSDUCER (GP130, ONCOSTATIN M RECEPTOR) (IL6ST), MRNA." |
| AF047690 | 0.64 | "HUMAN ATP-BINDING CASSETTE PROTEIN M-ABC1 MRNA, NUCLEAR GENE ENCODING MITOCHONDRIAL PROTEIN, COMPLETE CDS." |
| BG564693 | 0.64 | "602589902F1 HOMO SAPIENS CDNA, 5' END" |
| NM_005239 | 0.64 | "HOMO SAPIENS V-ETS ERYTHROBLASTOSIS VIRUS E26 ONCOGENE HOMOLOG 2 (AVIAN) (ETS2), MRNA" |
| NM_021131 | 0.64 | "HOMO SAPIENS PROTEIN PHOSPHATASE 2A, REGULATORY SUBUNIT B' (PR53) (PPP2R4), MRNA." |
| NM_003243 | 0.64 | "HOMO SAPIENS TRANSFORMING GROWTH FACTOR, BETA RECEPTOR III (BETAGLYCAN, 300 KD) (TGFBR3), MRNA." |
| BG535739 | 0.64 | 602563859F1 HOMO SAPIENS CDNA 5' END |
| NM_001087 | 0.64 | "HOMO SAPIENS ANGIO-ASSOCIATED, MIGRATORY CELL PROTEIN (AAMP), MRNA." |
| NM_019011 | 0.64 | "HOMO SAPIENS TRIAD3 PROTEIN (TRIAD3), MRNA." |

APPENDIX 3-continued

Down Regulated Genes with Treatment Fex:

| Accession Number | Fold Change (Fex/DMSO) | Gene Description |
|---|---|---|
| NM_005660 | 0.64 | "HOMO SAPIENS SOLUTE CARRIER FAMILY 35 (UDP-GALACTOSE TRANSPORTER), MEMBER 2 (SLC35A2), MRNA" |
| AK024739 | 0.64 | "HOMO SAPIENS CDNA: FLJ21086 FIS, CLONE CAS03272" |
| AK055853 | 0.64 | "HOMO SAPIENS CDNA FLJ31291 FIS, CLONE KIDNE2007356" |
| AB010443 | 0.64 | "HOMO SAPIENS DNA, DLEC1 TO ORCTL4 GENE REGION, SECTION 1/2 (DLEC1, ORCTL3, ORCTL4 GENES, COMPLETE CDS)." |
| NM_002695 | 0.64 | "HOMO SAPIENS POLYMERASE (RNA) II (DNA DIRECTED) POLYPEPTIDE E (25 KD) (POLR2E), MRNA." |
| NM_018304 | 0.64 | "HOMO SAPIENS HYPOTHETICAL PROTEIN FLJ11029 (FLJ11029), MRNA" |
| NM_032484 | 0.64 | "HOMO SAPIENS D11LGP1E-LIKE (LGP1), MRNA" |
| AL832781 | 0.64 | HOMO SAPIENS MRNA; CDNA DKFZP686L057 (FROM CLONE DKFZP686L057) |
| NM_021027 | 0.64 | "HOMO SAPIENS UDP GLYCOSYLTRANSFERASE 1 FAMILY, POLYPEPTIDE A9 (UGT1A9), MRNA." |
| NM_021993 | 0.64 | "HOMO SAPIENS FUS INTERACTING PROTEIN (SERINE-ARGININE RICH) 2 (FUSIP2), MRNA." |
| NM_014420 | 0.64 | "HOMO SAPIENS DICKKOPF HOMOLOG 4 (XENOPUS LAEVIS) (DKK4), MRNA" |
| BC015931 | 0.64 | "HOMO SAPIENS, RAB35, MEMBER RAS ONCOGENE FAMILY, CLONE MGC: 8924 IMAGE: 3907209, MRNA, COMPLETE CDS" |
| NM_006706 | 0.64 | "HOMO SAPIENS TRANSCRIPTION ELONGATION REGULATOR 1 (CA150) (TCERG1), MRNA" |
| AF155117 | 0.64 | "HOMO SAPIENS NY-REN-62 ANTIGEN MRNA, PARTIAL CDS" |
| AB033086 | 0.65 | "HOMO SAPIENS MRNA FOR KIAA1260 PROTEIN, PARTIAL CDS" |
| NM_000666 | 0.65 | "HOMO SAPIENS AMINOACYLASE 1 (ACY1), MRNA." |
| NM_052932 | 0.65 | "HOMO SAPIENS PRO-ONCOSIS RECEPTOR INDUCING MEMBRANE INJURY GENE (PORIMIN), MRNA" |
| NM_005605 | 0.65 | "HOMO SAPIENS PROTEIN PHOSPHATASE 3 (FORMERLY 2B), CATALYTIC SUBUNIT, GAMMA ISOFORM (CALCINEURIN A GAMMA) (PPP3CC), MRNA." |
| BC036771 | 0.65 | "HOMO SAPIENS, CLONE MGC: 46680 IMAGE: 5576828, MRNA, COMPLETE CDS" |
| NM_000433 | 0.65 | "HOMO SAPIENS NEUTROPHIL CYTOSOLIC FACTOR 2 (65 KD, CHRONIC GRANULOMATOUS DISEASE, AUTOSOMAL 2) (NCF2), MRNA." |
| NM_007198 | 0.65 | "HOMO SAPIENS PROLINE SYNTHETASE CO-TRANSCRIBED HOMOLOG (BACTERIAL) (PROSC), MRNA" |
| AB028645 | 0.65 | "HOMO SAPIENS MRNA FOR CBL-C, COMPLETE CDS" |
| NM_004040 | 0.65 | "HOMO SAPIENS RAS HOMOLOG GENE FAMILY, MEMBER B (ARHB), MRNA" |
| AK096820 | 0.65 | "HOMO SAPIENS CDNA FLJ39501 FIS, CLONE PROST2016980, MODERATELY SIMILAR TO CYTOCHROME P450 4F2 (EC 1.14.13.30)" |
| NM_007054 | 0.65 | "HOMO SAPIENS KINESIN FAMILY MEMBER 3A (KIF3A), MRNA." |
| NM_002227 | 0.65 | "HOMO SAPIENS JANUS KINASE 1 (A PROTEIN TYROSINE KINASE) (JAK1), MRNA." |
| NM_030674 | 0.65 | "HOMO SAPIENS AMINO ACID TRANSPORTER SYSTEM A1 (ATA1), MRNA." |
| AB025432 | 0.65 | "HOMO SAPIENS MRNA FOR GILZ, COMPLETE CDS" |
| NM_015945 | 0.65 | "HOMO SAPIENS OVARIAN CANCER OVEREXPRESSED 1 (OVCOV1), MRNA" |
| BC012362 | 0.65 | "HOMO SAPIENS, CLONE MGC: 20484 IMAGE: 4650072, MRNA, COMPLETE CDS" |
| NM_020993 | 0.65 | "HOMO SAPIENS B-CELL CLL/LYMPHOMA 7A (BCL7A), MRNA" |
| NM_032219 | 0.65 | "HOMO SAPIENS HYPOTHETICAL PROTEIN FLJ22269 (FLJ22269), MRNA." |
| NM_024604 | 0.65 | "HOMO SAPIENS HYPOTHETICAL PROTEIN FLJ21908 (FLJ21908), MRNA." |
| NM_004203 | 0.65 | "HOMO SAPIENS MEMBRANE-ASSOCIATED TYROSINE- AND THREONINE-SPECIFIC CDC2-INHIBITORY KINASE (PKMYT1), MRNA" |
| NM_005979 | 0.65 | "HOMO SAPIENS S100 CALCIUM BINDING PROTEIN A13 (S100A13), MRNA." |
| 1075733.1 | 0.65 | NULL |
| BG678787 | 0.65 | 602624339F1 HOMO SAPIENS CDNA 5' END |
| AK021872 | 0.65 | "HOMO SAPIENS CDNA FLJ11810 FIS, CLONE HEMBA1006347, MODERATELY SIMILAR TO MALES-ABSENT ON THE FIRST PROTEIN (EC 2.3.1.—)" |
| NM_022114 | 0.65 | "HOMO SAPIENS PR DOMAIN CONTAINING 16 (PRDM16), MRNA" |
| NM_002834 | 0.65 | "HOMO SAPIENS PROTEIN TYROSINE PHOSPHATASE, NON-RECEPTOR TYPE 11 (PTPN11), TRANSCRIPT VARIANT 1, MRNA" |
| NM_003468 | 0.65 | "HOMO SAPIENS FRIZZLED HOMOLOG 5 (DROSOPHILA) (FZD5), MRNA" |
| NM_016022 | 0.65 | "HOMO SAPIENS CGI-78 PROTEIN (LOC51107), MRNA." |
| BC001096 | 0.65 | "HOMO SAPIENS, CLONE IMAGE: 3507281, MRNA, PARTIAL CDS" |
| NM_032769 | 0.65 | "HOMO SAPIENS HYPOTHETICAL PROTEIN MGC16212 (MGC16212), MRNA" |
| AF118108 | 0.65 | "HOMO SAPIENS LYMPHATIC ENDOTHELIUM-SPECIFIC HYALURONAN RECEPTOR LYVE-1 MRNA, COMPLETE CDS" |
| NM_005276 | 0.65 | "HOMO SAPIENS GLYCEROL-3-PHOSPHATE DEHYDROGENASE 1 (SOLUBLE) (GPD1), MRNA" |
| NM_015621 | 0.65 | "HOMO SAPIENS DKFZP434C171 PROTEIN (DKFZP434C171), MRNA." |
| NM_004749 | 0.65 | "HOMO SAPIENS CELL CYCLE PROGRESSION 2 PROTEIN (CPR2), MRNA." |
| AF088062 | 0.65 | HOMO SAPIENS FULL LENGTH INSERT CDNA CLONE ZD74E10 |
| 1082602.1 | 0.65 | "PROTEIN WITH HIGH SIMILARITY TO ZINC-FINGER PROTEIN (HUMAN ZNF10), WHICH INHIBITS SOME COMPONENTS OF RNA POLYMERASE II AND III TRANSCRIPTION, CONTAINS FIFTEEN C2H2 TYPE ZINC FINGER DOMAINS, WHICH BIND NUCLEIC ACIDS" |
| AF037448 | 0.65 | "HOMO SAPIENS RRM RNA BINDING PROTEIN GRY-RBP (GRY-RBP) MRNA, COMPLETE CDS" |
| NM_030792 | 0.65 | "HOMO SAPIENS HYPOTHETICAL PROTEIN PP1665 (PP1665), MRNA" |

APPENDIX 3-continued

Down Regulated Genes with Treatment Fex:

| Accession Number | Fold Change (Fex/DMSO) | Gene Description |
|---|---|---|
| AF113511 | 0.65 | "*HOMO SAPIENS* INTEGRIN SUBUNIT ALPHA-2 (ITGA2) GENE, ITGA2-2 ALLELE, 3'UTR" |
| NM_005433 | 0.65 | "*HOMO SAPIENS* V-YES-1 YAMAGUCHI SARCOMA VIRAL ONCOGENE HOMOLOG 1 (YES1), MRNA." |
| NM_020123 | 0.65 | "*HOMO SAPIENS* ENDOMEMBRANE PROTEIN EMP70 PRECURSOR ISOLOG (LOC56889), MRNA." |
| AP000500 | 0.65 | "*HOMO SAPIENS* GENOMIC DNA, CHROMOSOME 3P21.3, CLONE: 603 TO 320, ANTI-ONCOGENE REGION, SECTION 3/3" |
| BC012170 | 0.65 | "*HOMO SAPIENS*, SIMILAR TO RIKEN CDNA 6230427J02 GENE, CLONE MGC: 20416 IMAGE: 4642270, MRNA, COMPLETE CDS" |
| D50683 | 0.65 | "*HOMO SAPIENS* MRNA FOR TGF-BETAIIR ALPHA, COMPLETE CDS" |
| NM_003236 | 0.65 | "*HOMO SAPIENS* TRANSFORMING GROWTH FACTOR, ALPHA (TGFA), MRNA." |
| AB058760 | 0.65 | "*HOMO SAPIENS* MRNA FOR KIAA1857 PROTEIN, PARTIAL CDS" |
| BM724842 | 0.65 | "UI-E-EJ0-AIS-H-20-0-UI.R1 *HOMO SAPIENS* CDNA, 5' END" |
| NM_003244 | 0.65 | "*HOMO SAPIENS* TGFB-INDUCED FACTOR (TALE FAMILY HOMEOBOX) (TGIF), MRNA." |
| NM_018986 | 0.65 | "*HOMO SAPIENS* HYPOTHETICAL PROTEIN (FLJ20356), MRNA." |
| NM_016629 | 0.65 | "*HOMO SAPIENS* HYPOTHETICAL PROTEIN (LOC51323), MRNA." |
| NM_005787 | 0.65 | "*HOMO SAPIENS* NOT56 (*D. MELANOGASTER*)-LIKE PROTEIN (NOT56L), MRNA." |
| NM_004357 | 0.65 | "*HOMO SAPIENS* CD151 ANTIGEN (CD151), TRANSCRIPT VARIANT 1, MRNA" |
| NM_144643 | 0.65 | "*HOMO SAPIENS* HYPOTHETICAL PROTEIN FLJ30655 (FLJ30655), MRNA" |
| BC018130 | 0.65 | "*HOMO SAPIENS*, COAGULATION FACTOR II (THROMBIN) RECEPTOR-LIKE 1, CLONE MGC: 9298 IMAGE: 3895653, MRNA, COMPLETE CDS" |
| NM_000426 | 0.65 | "*HOMO SAPIENS* LAMININ, ALPHA 2 (MEROSIN, CONGENITAL MUSCULAR DYSTROPHY) (LAMA2), MRNA." |
| AK024835 | 0.65 | "*HOMO SAPIENS* CDNA: FLJ21182 FIS, CLONE CAS11560, HIGHLY SIMILAR TO D83735 *HOMO SAPIENS* MRNA FOR NEUTRAL CALPONIN" |
| NM_007034 | 0.65 | "*HOMO SAPIENS* DNAJ (HSP40) HOMOLOG, SUBFAMILY B, MEMBER 4 (DNAJB4), MRNA." |
| BQ430527 | 0.66 | AGENCOURT_7723632 *HOMO SAPIENS* CDNA 5' END |
| NM_015533 | 0.66 | "*HOMO SAPIENS* DKFZP586B1621 PROTEIN (DKFZP586B1621), MRNA" |
| NM_006386 | 0.66 | "*HOMO SAPIENS* DEAD/H (ASP-GLU-ALA-ASP/HIS) BOX POLYPEPTIDE 17 (72 KD) (DDX17), TRANSCRIPT VARIANT 1, MRNA." |
| NM_004417 | 0.66 | "*HOMO SAPIENS* DUAL SPECIFICITY PHOSPHATASE 1 (DUSP1), MRNA." |
| NM_002350 | 0.66 | "*HOMO SAPIENS* V-YES-1 YAMAGUCHI SARCOMA VIRAL RELATED ONCOGENE HOMOLOG (LYN), MRNA." |
| AK024950 | 0.66 | "*HOMO SAPIENS* CDNA: FLJ21297 FIS, CLONE COL02035" |
| NM_001283 | 0.66 | "*HOMO SAPIENS* ADAPTOR-RELATED PROTEIN COMPLEX 1, SIGMA 1 SUBUNIT (AP1S1), TRANSCRIPT VARIANT 1, MRNA." |
| NM_004387 | 0.66 | "*HOMO SAPIENS* CARDIAC-SPECIFIC HOMEO BOX (CSX), MRNA." |
| NM_013311 | 0.66 | "*HOMO SAPIENS* INSULIN PROMOTER FACTOR 1, HOMEODOMAIN TRANSCRIPTION FACTOR (IPF1), MRNA" |
| NM_014604 | 0.66 | "*HOMO SAPIENS* TAX INTERACTION PROTEIN 1 (TIP-1), MRNA" |
| AJ229040 | 0.66 | *HOMO SAPIENS* 959 KB CONTIG BETWEEN AML1 AND CBR1 ON CHROMOSOME 21Q22 |
| AL117595 | 0.66 | *HOMO SAPIENS* MRNA; CDNA DKFZP564C2063 (FROM CLONE DKFZP564C2063) |
| NM_005384 | 0.66 | "*HOMO SAPIENS* NUCLEAR FACTOR, INTERLEUKIN 3 REGULATED (NFIL3), MRNA." |
| AK024490 | 0.66 | "*HOMO SAPIENS* MRNA FOR FLJ00092 PROTEIN, PARTIAL CDS" |
| NM_016084 | 0.66 | "*HOMO SAPIENS* RAS, DEXAMETHASONE-INDUCED 1 (RASD1), MRNA." |
| NM_004999 | 0.66 | "*HOMO SAPIENS* MYOSIN VI (MYO6), MRNA." |
| NM_006844 | 0.66 | "*HOMO SAPIENS* ILVB (BACTERIAL ACETOLACTATE SYNTHASE)-LIKE (ILVBL), MRNA." |
| NM_018015 | 0.66 | "*HOMO SAPIENS* HYPOTHETICAL PROTEIN FLJ10178 (FLJ10178), MRNA" |
| NM_032287 | 0.66 | "*HOMO SAPIENS* HYPOTHETICAL PROTEIN DKFZP761O17121 (DKFZP761O17121), MRNA." |
| U32642 | 0.66 | "HUMAN H4 GENE, INTRON 1, PARTIAL SEQUENCE" |
| NM_080385 | 0.66 | "*HOMO SAPIENS* CARBOXYPEPTIDASE A5 (CPA5), MRNA" |
| AF132811 | 0.66 | "*HOMO SAPIENS* NECTIN-LIKE PROTEIN 2 (NECL2) MRNA, COMPLETE CDS" |
| U09847 | 0.66 | "HUMAN ZINC FINGER PROTEIN (ZNF138) MRNA, PARTIAL CDS" |
| NM_014770 | 0.66 | "*HOMO SAPIENS* CENTAURIN, GAMMA 1 (CENTG1), MRNA" |
| NM_016016 | 0.66 | "*HOMO SAPIENS* CGI-69 PROTEIN (LOC51629), MRNA" |
| NM_004099 | 0.66 | "*HOMO SAPIENS* ERYTHROCYTE MEMBRANE PROTEIN BAND 7.2 (STOMATIN) (EPB72), MRNA" |
| NM_018347 | 0.66 | "*HOMO SAPIENS* CHROMOSOME 20 OPEN READING FRAME 29 (C20ORF29), MRNA." |
| NM_002895 | 0.66 | "*HOMO SAPIENS* RETINOBLASTOMA-LIKE 1 (P107) (RBL1), MRNA" |
| AB033093 | 0.66 | "*HOMO SAPIENS* MRNA FOR KIAA1267 PROTEIN, PARTIAL CDS" |
| BC000712 | 0.66 | "*HOMO SAPIENS*, SIMILAR TO KINESIN FAMILY MEMBER C1, CLONE MGC: 1202 IMAGE: 3506669, MRNA, COMPLETE CDS" |
| NM_003897 | 0.66 | "*HOMO SAPIENS* IMMEDIATE EARLY RESPONSE 3 (IER3), TRANSCRIPT VARIANT SHORT, MRNA." |
| NM_018725 | 0.66 | "*HOMO SAPIENS* INTERLEUKIN 17B RECEPTOR (IL17BR), MRNA" |
| NM_032307 | 0.66 | "*HOMO SAPIENS* HYPOTHETICAL PROTEIN MGC10999 (MGC10999), MRNA" |

APPENDIX 3-continued

Down Regulated Genes with Treatment Fex:

| Accession Number | Fold Change (Fex/DMSO) | Gene Description |
|---|---|---|
| NM_025008 | 0.66 | "*HOMO SAPIENS* HYPOTHETICAL PROTEIN FLJ13544 (FLJ13544), MRNA" |
| Y14321 | 0.66 | "*HOMO SAPIENS* PMP69 GENE, EXONS 8, 9, 10 & 11" |
| NM_024048 | 0.66 | "*HOMO SAPIENS* HYPOTHETICAL PROTEIN MGC3020 (MGC3020), MRNA" |
| NM_025106 | 0.66 | "*HOMO SAPIENS* SPRY DOMAIN-CONTAINING SOCS BOX PROTEIN SSB-1 (FLJ22393), MRNA." |
| NM_002906 | 0.66 | "*HOMO SAPIENS* RADIXIN (RDX), MRNA" |
| NM_152338 | 0.66 | "*HOMO SAPIENS* ZYMOGEN GRANULE PROTEIN 16 (ZG16), MRNA" |
| BC019623 | 0.66 | "*HOMO SAPIENS*, CLONE IMAGE: 4539469, MRNA, PARTIAL CDS" |
| AF218848 | 0.66 | "*HOMO SAPIENS* BETA II SPECTRIN-SHORT ISOFORM MRNA, PARTIAL CDS" |
| NM_006313 | 0.66 | "*HOMO SAPIENS* UBIQUITIN SPECIFIC PROTEASE 15 (USP15), MRNA." |
| M92300 | 0.66 | "HUMAN HUMAN VOLTAGE-DEPENDENT CALCIUM CHANNEL BETA-1 SUBUNIT, EXONS 1–4" |
| AL163263 | 0.66 | NULL |
| NM_030974 | 0.66 | "*HOMO SAPIENS* HYPOTHETICAL PROTEIN DKFZP434N1923 (DKFZP434N1923), MRNA" |
| NM_022139 | 0.66 | "*HOMO SAPIENS* GDNF FAMILY RECEPTOR ALPHA 4 (GFRA4), TRANSCRIPT VARIANT 1, MRNA" |
| L44140 | 0.66 | "*HOMO SAPIENS* CHROMOSOME X REGION FROM FILAMIN (FLN) GENE TO GLUCOSE-6-PHOSPHATE DEHYDROGENASE (G6PD) GENE, COMPLETE CDS'S" |
| M87507 | 0.66 | "HOMO SAPIEN INTERLEUKIN-1 BETA CONVERTASE (IL1BCE) MRNA, COMPLETE CDS" |
| NM_004095 | 0.66 | "*HOMO SAPIENS* EUKARYOTIC TRANSLATION INITIATION FACTOR 4E BINDING PROTEIN 1 (EIF4EBP1), MRNA" |
| NM_080678 | 0.66 | "*HOMO SAPIENS* NEDD8-CONJUGATING ENZYME (NCE2), MRNA" |
| NM_007097 | 0.66 | "*HOMO SAPIENS* CLATHRIN, LIGHT POLYPEPTIDE (LCB) (CLTB), MRNA." |
| NM_020142 | 0.66 | "*HOMO SAPIENS* NADH: UBIQUINONE OXIDOREDUCTASE MLRQ SUBUNIT HOMOLOG (LOC56901), MRNA" |
| NM_012141 | 0.66 | "*HOMO SAPIENS* DEAD/H (ASP-GLU-ALA-ASP/HIS) BOX POLYPEPTIDE 26 (DDX26), MRNA." |
| NM_005257 | 0.66 | "*HOMO SAPIENS* GATA BINDING PROTEIN 6 (GATA6), MRNA." |
| BC002766 | 0.66 | "*HOMO SAPIENS*, SIMILAR TO KIAA0998 PROTEIN, CLONE MGC: 4173 IMAGE: 3632160, MRNA, COMPLETE CDS" |
| NM_002084 | 0.66 | "*HOMO SAPIENS* GLUTATHIONE PEROXIDASE 3 (PLASMA) (GPX3), MRNA" |
| NM_017855 | 0.66 | "*HOMO SAPIENS* HYPOTHETICAL PROTEIN FLJ20513 (FLJ20513), MRNA" |
| AB018353 | 0.66 | "*HOMO SAPIENS* MRNA FOR KIAA0810 PROTEIN, PARTIAL CDS" |
| NM_018475 | 0.66 | "*HOMO SAPIENS* TPA REGULATED LOCUS (TPARL), MRNA" |
| NM_018078 | 0.66 | "*HOMO SAPIENS* HYPOTHETICAL PROTEIN FLJ10378 (FLJ10378), MRNA" |
| NM_017838 | 0.66 | "*HOMO SAPIENS* NUCLEOLAR PROTEIN FAMILY A, MEMBER 2 (H/ACA SMALL NUCLEOLAR RNPS) (NOLA2), MRNA." |
| NM_005475 | 0.66 | "*HOMO SAPIENS* LYMPHOCYTE ADAPTOR PROTEIN (LNK), MRNA." |
| NM_002961 | 0.66 | "*HOMO SAPIENS* S100 CALCIUM BINDING PROTEIN A4 (CALCIUM PROTEIN, CALVASCULIN, METASTASIN, MURINE PLACENTAL HOMOLOG) (S100A4), TRANSCRIPT VARIANT 1, MRNA" |
| AL133626 | 0.67 | *HOMO SAPIENS* MRNA; CDNA DKFZP434K0522 (FROM CLONE DKFZP434K0522) |
| X65644 | 0.67 | *H. SAPIENS* MRNA MBP-2 FOR MHC BINDING PROTEIN 2 |
| NM_006270 | 0.67 | "*HOMO SAPIENS* RELATED RAS VIRAL (R-RAS) ONCOGENE HOMOLOG (RRAS), MRNA." |
| AK001674 | 0.67 | "*HOMO SAPIENS* CDNA FLJ10812 FIS, CLONE NT2RP4000975" |
| NM_001980 | 0.67 | "*HOMO SAPIENS* EPIMORPHIN (EPIM), MRNA." |
| AF125158 | 0.67 | "HUMAN ZINC FINGER DNA BINDING PROTEIN 99 (ZNF281) MRNA, COMPLETE CDS." |
| NM_032310 | 0.67 | "*HOMO SAPIENS* HYPOTHETICAL PROTEIN MGC11115 (MGC11115), MRNA" |
| NM_020423 | 0.67 | "*HOMO SAPIENS* HYPOTHETICAL PROTEIN LOC57147 (LOC57147), MRNA" |
| NM_001694 | 0.67 | "*HOMO SAPIENS* ATPASE, H+ TRANSPORTING, LYSOSOMAL (VACUOLAR PROTON PUMP) 16 KD (ATP6L), MRNA." |
| NM_014547 | 0.67 | "*HOMO SAPIENS* TROPOMODULIN 3 (UBIQUITOUS) (TMOD3), MRNA" |
| NM_024874 | 0.67 | "*HOMO SAPIENS* HYPOTHETICAL PROTEIN FLJ14225 (FLJ14225), MRNA" |
| AF244812 | 0.67 | "*HOMO SAPIENS* SCAN DOMAIN-CONTAINING PROTEIN 2 (SCAND2) GENE, COMPLETE CDS, ALTERNATIVELY SPLICED" |
| NM_024070 | 0.67 | "*HOMO SAPIENS* HYPOTHETICAL PROTEIN MGC2463 (MGC2463), MRNA" |

That which is claimed is:

1. A method of screening molecules to determine those which are capable of binding to a farnesoid X receptor (FXR) molecule, said method comprising:
    a) modeling, on a computer, a test molecule that potentially interacts with the ligand binding domain of said FXR molecule, said ligand binding domain comprising amino acid residues 248-476 of SEQ ID NO: 1, wherein said ligand binding domain is further defined by the structure coordinates set forth in Appendix 1;
    b) determining whether there is repulsive electrostatic interaction between said test molecule and said FXR molecule; and
    c) selecting those test molecules which lack repulsive electrostatic interaction with said FXR molecule in their bound state as compounds that are capable of binding to the FXR molecule.

2. A method according to claim 1, wherein said test molecule is developed using a computer algorithm to predict a three-dimensional representation of said test molecule interacting with a FXR molecule based upon a three-dimensional representation of a FXR molecule.

3. A method of screening molecules to determine those that modulate farnesoid X receptor (FXR) molecule activity, said method comprising:
    a) modeling, on a computer, a test compound that potentially interacts with the ligand binding domain of said FXR molecule, said ligand binding domain comprising amino acid residues 248-476 of SEQ ID NO: 1, wherein said ligand binding domain is further defined by the structure coordinates set forth in Appendix 1;
    b) determining the ability of said test compound to modulate the activity of said FXR molecule activity in the optional presence of a known FXR agonist; and
    c) selecting those test compounds which modulate the activity of the FXR molecule.

* * * * *

UNITED STATES PATENT AND TRADEMARK OFFICE
CERTIFICATE OF CORRECTION

PATENT NO.       : 7,647,217 B2                                    Page 1 of 1
APPLICATION NO. : 10/535042
DATED            : January 12, 2010
INVENTOR(S)      : Downes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 860 days.

Signed and Sealed this

Twenty-eighth Day of December, 2010

David J. Kappos
*Director of the United States Patent and Trademark Office*